US012690596B2

(12) United States Patent (10) Patent No.: US 12,690,596 B2
Killmer et al. (45) Date of Patent: Jul. 28, 2026

(54) METHODS AND COMPOSITIONS FOR MICROBIAL DELIVERY OF DOUBLE STRANDED RNA

(71) Applicant: RNAISSANCE AG LLC, Shawnee Mission, KS (US)

(72) Inventors: John L. Killmer, St. Louis, MO (US); Anil Kumar, St. Louis, MO (US)

(73) Assignee: RNAISSANCE AG LLC, Shawnee Mission, KS (US)

( * ) Notice: Subject to any disclaimer, the term of this patent is extended or adjusted under 35 U.S.C. 154(b) by 902 days.

(21) Appl. No.: 17/615,516

(22) PCT Filed: May 29, 2020

(86) PCT No.: PCT/US2020/035339
§ 371 (c)(1),
(2) Date: Nov. 30, 2021

(87) PCT Pub. No.: WO2020/243580
PCT Pub. Date: Dec. 3, 2020

(65) Prior Publication Data
US 2022/0304315 A1 Sep. 29, 2022

Related U.S. Application Data

(60) Provisional application No. 62/854,831, filed on May 30, 2019.

(51) Int. Cl.
| | |
|---|---|
| *A01N 63/60* | (2020.01) |
| *A01N 63/20* | (2020.01) |
| *A01N 63/50* | (2020.01) |
| *A01P 7/04* | (2006.01) |
| *C12N 1/20* | (2006.01) |
| *C12N 15/113* | (2010.01) |
| *C12N 15/70* | (2006.01) |

(52) U.S. Cl.
CPC ............ *A01N 63/60* (2020.01); *A01N 63/20* (2020.01); *A01N 63/50* (2020.01); *A01P 7/04* (2021.08); *C12N 1/20* (2013.01); *C12N 15/113* (2013.01); *C12N 15/70* (2013.01); *C12N 2310/14* (2013.01); *C12N 2310/531* (2013.01); *C12N 2795/18022* (2013.01); *C12N 2795/18023* (2013.01); *C12N 2795/18042*
(2013.01); *C12N 2795/18122* (2013.01); *C12N 2795/18123* (2013.01); *C12N 2795/18142* (2013.01)

(58) Field of Classification Search
CPC ........... C12N 2795/18142; C12N 2795/18123; C12N 2795/18122; C12N 2795/18042; C12N 2795/18023; C12N 2795/18022; C12N 2310/531; C12N 2310/14; C12N 15/70; C12N 15/113; C12N 1/20; A01P 7/04; A01N 63/20; A01N 63/50; A01N 63/60
See application file for complete search history.

(56) References Cited

U.S. PATENT DOCUMENTS

| | | | | |
|---|---|---|---|---|
| 2009/0263364 | A1* | 10/2009 | Bogaert ................ | C12N 15/111 435/254.2 |
| 2017/0035056 | A1* | 2/2017 | Baum .................... | C12N 15/67 |

FOREIGN PATENT DOCUMENTS

| | | | | |
|---|---|---|---|---|
| WO | 2017106171 | A1 | 6/2017 | |
| WO | WO-2017116644 | A1 * | 7/2017 | ............. A01N 63/00 |
| WO | 2017136353 | A1 | 8/2017 | |
| WO | WO-2017160600 | A1 * | 9/2017 | ........... C07K 14/005 |

OTHER PUBLICATIONS

Cagliari D., et al., "Nontransformative Strategies for RNAi in Crop Protection," Modulating Gene Expression, uploaded on Dec. 6, 2018, 20 pages.
Extended European Search Report for Application No. 20812975.9, dated Sep. 27, 2023, 6 Pages.
International Search Report and Written Opinion mailed Oct. 8, 2020 for corresponding International Patent Application No. PCT/US2020/035339.

* cited by examiner

*Primary Examiner* — Robert J Yamasaki
*Assistant Examiner* — Trevor Kane
(74) *Attorney, Agent, or Firm* — Polsinelli PC

(57) ABSTRACT

Methods and materials for improved delivery of dsRNA are presented. In particular, methods for controlling an insect pest by stably delivering large quantities of dsRNA to the insect pest are provided. Compositions comprising a bacterium containing a large quantity of dsRNA targeting an insect gene in which the dsRNA exhibits increased stability and activity are also provided.

12 Claims, 7 Drawing Sheets

Specification includes a Sequence Listing.

FIG. 2

METHODS AND COMPOSITIONS FOR MICROBIAL DELIVERY OF DOUBLE STRANDED RNA

CROSS-REFERENCE TO RELATED APPLICATIONS

This application is a U.S. National Stage Application of International Application No. PCT/US2020/035339, filed May 29, 2020, which claims priority from U.S. Provisional Patent Application No. 62/854,831, filed May 30, 2019, the entire contents of which are hereby incorporated by reference in their entirety.

REFERENCE TO SEQUENCE LISTING

This application contains a Sequence Listing that has been submitted in ASCII format via EFS-Web and is hereby incorporated by reference in its entirety. The ASCII copy, created on Mar. 20, 2020, is named US2020035339.txt, and is 408 KB in size.

FIELD OF THE INVENTION

The present invention relates to methods and compositions for delivering double-stranded RNA to an insect that provide enhanced environmental stability of the dsRNA. The methods comprise contacting an insect with a composition comprising a bacterial cell comprising a dsRNA molecule which specifically inhibits expression of a target gene in the insect.

BACKGROUND OF THE INVENTION

RNA intereference (RNAi) induced through double stranded RNA (dsRNA) has been used to study gene function in insects. Recently, gene knockdown by RNAi has shown promise in managing insect pests and is advantageous over chemical pesticides due to its ability to selectively target only pest species and spare beneficial insects.

To activate the RNAi pathway, dsRNA can be fed to insects and absorbed in the cells that line the midgut. Exogenous dsRNA is usually processed into 20-30 nucleotide duplexes by the ribonuclease III enzyme DICER. These nucleotide duplexes are incorporated into the RNA induced silencing complex (RISC) by the catalytic component ARGONAUTE. The two strands of RNA are unwound and one strand is used as a guide strand. The guide strand binds to complementary mRNAs and the RISC complex mediates degradation or suppression of the endogenous transcript. Targeting endogenous transcripts that code for critical genes in the insect pest enables the population to be controlled.

Delivery of intact dsRNA into insect cells, however, remains problematic. Transgenic plants expressing dsRNAs have been used to control plant viral pathogens; however, the use of RNAi in insect pest control has lagged behind following years of unsuccessful attempts. Recently, transgenic plants have been engineered to express insect dsRNAs to target insect pests. Alternatively, dsRNA has been synthesized in vitro and sprayed onto plant parts.

Attempts have been made to utilize yeast as a delivery system for dsRNA; however, although some gene knockdown has been shown using that system, gel-based evidence of dsRNA stability in that system has never been shown, likely because the dsRNA is degraded very rapidly into very short (e.g. 21mer to 30mer) sequences and/or the quantity of dsRNA produced is miniscule.

Despite these advances, microorganisms such as bacteria have not been shown to be useful as a delivery vehicle for dsRNA due to the high concentrations of dsRNA required to initiate the RNAi pathway and due to the environmental instability of dsRNA. In particular, delivery of dsRNA to members of the order Lepidoptera is particularly problematic as they are generally more refractive to RNAi than members of the order Coleoptera.

SUMMARY OF THE INVENTION

The invention described in the following embodiments provides methods and compositions for delivering large quantities of dsRNA to an insect pest in order to control the insect pest. In some aspects, the compositions comprise a bacterial cell (killed or living) comprising a large quantity of dsRNA that specifically inhibits expression of a target gene in an insect pest, wherein the dsRNA exhibits increased stability over time compared to the same dsRNA in a different composition or compared to the same dsRNA when "naked". In some aspects, dsRNA in the composition remains environmentally stable over a period of at least 7 days in, e.g. insect saliva, puddle water, pond water and/or on the surface of a leaf. In some aspects, the methods comprise contacting an insect pest with a composition comprising a bacterial cell comprising a large quantity of dsRNA that specifically inhibits expression of a target gene in an insect pest, thereby controlling the insect pest.

The bacterial cell can be any bacteria capable of transformation. In some aspects, the bacterial cell lacks double-strand specific RNase III and/or contains an inducible T7 RNA polymerase gene. In some aspects, the bacterial cell is a gram negative bacterial cell, such as an *E. coli* strain, representative examples of which include K12 strains and derivatives thereof (e.g. MG1655, HT115 (DE3)) and B strains (e.g. BL21 (DE3), REL606). In some aspects, the bacterial cell is a gram positive bacterial cell. In a preferred aspect, the gram-positive bacterial cell is from the genus *Corynebacterium*, more preferably is *Corynebacterium glutamicum*.

Delivery of dsRNA should induce a lethal phenotype in the insect pest. Suitable genes to be targeted by dsRNA in the insect pest include midgut or non-midgut genes. Representative non-limiting examples of suitable insect genes that can be targeted by dsRNA include tubulin, vATPase, acetyl choline esterase, chitin synthase gene A, beta-actin, and genes coding for inhibitors of apoptosis (e.g. IAP).

The term "insect" should be understood to refer not only to insects but to their immature forms and larvae.

In some embodiments, the insect pest to be controlled is selected from the orders Coleoptera, Diptera, Hymenoptera, Lepidoptera, Mallophaga, Homoptera, Orthoptera, Thysanoptera, Dermaptera, Isoptera, Anoplura, Siphonaptera, and Trichoptera. In preferred embodiments, the insect pest to be controlled is a member of the order Coleoptera or Lepidoptera.

Larvae and adults of the order Lepidoptera include, but are not limited to, armyworms, cutworms, loopers and heliothines Larvae of the order Lepidoptera include, but are not limited to, armyworms, cutworms, loopers, and heliothines in the family Noctuidae *Spodoptera frugiperda* JE Smith (fall armyworm); *S. exigua*. Hubner (beet armyworm)/*S. litura* Fabricius (tobacco cutworm, cluster caterpillar) *Mamestra* configurata Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Ala-*

*bama argillacea* Hubner (cotton leaf worm); *Trichoplusia ni* Hubner (cabbage looper); *Pseudoplusia includens* Walker (soybean looper); *Anticarsia gemmatalis* Hubner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messona* Harris (darksided cutworm); *Earias insulana* Boisduval (spiny bollworm); *E. vittella* Fabricius (spotted bollworm) *Helicoverpa armigera* Hubner (American bollworm); *H. zea* Boddie (corn earworm or cotton bollworm); *Melanchra picta* Harris (zebra caterpillar); *Egira* (Xylomyges) *curialis* Grote (citrus cutworm); borers, casebearers, webworms, coneworms, and skeletonizers from the family Pyralidae *Ostrinia nubilalis* Hubner (European corn borer); *Amyelois transitella* Walker (naval orangeworm); Anagasta *kuehniella* Zeller (Mediterranean flour moth); Cadra cautella Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hubner (grape leaffolder); *Diaphania* hyalinata Linnaeus (melon worm); *D. nitidalis* Stoll (pickleworm); *Diatraea grandiosella* Dyar (southwestern corn borer); *D. saccharalis* Fabricius (surgarcane borer) *Eoreuma loftini* Dyar (Mexican rice borer); Ephestia elutella Hubner (tobacco (cacao) moth) *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia* gnsella Fabricius (lesser wax moth); *Loxostege sticticalis* Linnaeus (beet webworm); *Orthaga thyrisalis* Walker (tea tree web moth); *Maruca* testulalis Geyer (bean pod borer); Plodia interpunctella Hubner (Indian meal moth); Scirpophaga incertulas Walker (yellow stem borer); *Udea rubigalis* Guenee (celery leaftier); and leafrollers, budworms, seed worms, and fruit worms in the family Tortricidae Acleris gloverana Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rosslerstamm (summer fruit *tortrix* moth); *Cochylis hospes* Walsingham (banded sunflower moth); *Cydia latiferreana* Walsingham (filbertworm); *C. pomonella* Linnaeus (coding moth); Platynota flavedana Clemens (variegated leafroller); *P. stultana* Walsingham (omnivorous leafroller); *Lobesia botrana* Denis & Schiffermiiller (European grape vine moth); Spilonota ocellana Denis & Schiffermiiller (eyespotted bud moth); *Endopiza viteana* Clemens (grape berry moth); *Eupoecilia ambiguella* Hubner (vine moth); *Bonagota* salubncola Meyrick (Brazilian apple leafroller); *Grapholita molesta* Busck (oriental fruit moth); *Suleima helianthana* Riley (sunflower bud moth); *Argyrotaenia* spp.; *Choristoneura* spp. Alsophila pometaria Harris (fall cankerworm); *Anarsia lineatella* Zeller (peach twig borer); *Anisota* senatoria J. E. Smith (orange striped oakworm); Antheraea pernyi Guerin-Meneville (Chinese Oak Tussah Moth); *Bombyx mori* Linnaeus (Silkworm); Bucculatfix thurbefiella Busck (cotton leaf perforator); Colias eurytheme Boisduval (alfalfa caterpillar); Datana *integerrima* Grote & Robinson (walnut caterpillar); *Dendrolimus sibiricus* Tschetwerikov (Siberian silk moth), *Ennomos subsignaria* Hubner (elm spanworm); *Erannis tiliaria* Harris (linden looper); *Euproctis chrysorrhoea* Linnaeus (browntail moth); *Harrisina americana* Guerin-Meneville (grape-leaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria* Hulst (Eastern hemlock looper); *L. fiscellaria* 1.ugubrosa Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia* carduidactyla Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenee (omnivorous looper); Schizura *concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenee; *Malacosoma* spp. and *Orgyia* spp. Tenebhonidae.

Larvae and adults of the order Coleoptera include weevils from the families Anthribidae, Bruchidae, and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); Cylindrocopturus adspersus LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug); flea beetles, cucumber beetles, rootworms, leaf beetles, potato beetles, and leafminers in the family Chrysomelidae (including, but not limited to: *Leptinotarsa decemlineata* Say (Colorado potato beetle); *Diabrotica virgifera* LeConte (western corn rootworm); *D. barberi* Smith & Lawrence (northern corn rootwormj; *D. undecimpunctata* howardi Barber (southern corn rootworm); *Chaetocnema pulicaria* Melsheimer (corn flea beetle); *Phyllotreta* cruciferae Goeze (corn flea beetle); *Colaspis brunnea* Fabricius (grape *colaspis*); *Oulema melanopus* Linnaeus (cereal leaf beetle); Zygogramma *exclamationis* Fabricius (sunflower beetle)); beetles from the family Coccinellidae (including, but not limited to: *Epilachna* vailvestis Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)), carpet beetles from the family Dermestidae; wireworms from the family Elatehdae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebhonidae.

In some other embodiments, the insect pest to be controlled is a member of the order Hymenoptera such as an ant, sawfly, wasp or bee. In related aspects, the insect pest to be controlled is an ant, preferably selected from *Solenopsis invicta* (fire ants), *Camponotus pennsylvanicus* and *Camponotus floridanus* (carpenter ants), *Linepithema humile* (Argentine ants), *Tapinoma sessile* (odorous ants), *Tetramorium caespitum* (pavement ants), and *Monomorium pharaonis* (pharaoh ants).

In other embodiments, the insect pest to be controlled is a member of the order Diptera such as a mosquito or fly, e.g. *A. gambiae* (malaria mosquito) or *Ae. aegypti* (yellow fever mosquito).

In other embodiments, the insect pest to be controlled is a member of the order Acari (e.g. ticks), Blattodea (cockroach), Dermaptera (earwigs), Heteroptera (e.g. bed bug), Isoptera (termite), Siphonaptera (flea), Sternorrhyncha (aphids), or Zygentoma (silverfish)

RNAi strategies for reducing or inhibiting expression of a target gene are known in the art and employ genetic constructs that encode double-stranded RNA (dsRNA). Typically, such constructs comprise sense and anti-sense sequences which are placed in regions flanking an intron sequence in proper splicing orientation with donor and acceptor splicing sites. Alternatively, spacer sequences of various lengths can be employed to separate self-complementary regions of sequence in the construct. During processing of the gene construct transcript, intron sequences can be spliced-out, allowing sense and anti-sense sequences, as well as splice junction sequences, to bind forming double-stranded RNA.

The RNAi polynucleotide can hybridize with the full length mRNA encoded by the target gene or hybridize to a fragment of the target RNA or DNA (the target sequence). The target sequence is typically between 1 and 500 nucleotides in length. In some embodiments, the target sequence and/or the dsRNA sequence is between about 50 and 400 nucleotides in length, preferably between 100 and 300 nucleotides in length. Typically, the sequence of the dsRNA used for RNAi is 100% identical to the target sequence of the target gene, but can be at least 70%, 80%, 90%, 95%, 98% or 99% or more identical to the target sequence.

In some embodiments, compositions for delivering large quantities of dsRNA to an insect pest in order to control the insect pest comprise a bacterial cell containing (i) a gene encoding a self-complementary stretch of sequence separated by non-complementary sequence such that upon hybridization of the complementary sequences a stem-loop structure is formed, wherein the stem portion of the molecule functions as an RNAi precursor when introduced into the target insect pest and (ii) a bacteriophage coat protein gene encoding a capsid protein. Expression of the dsRNA gene and the coat protein gene results in increased accumulation of un-degraded dsRNA and capsid protein, wherein the dsRNA exhibits surprisingly increased stability over time compared to the same dsRNA in a different composition or compared to the same dsRNA when "naked". In some aspects, stability of the dsRNA is maintained in an environment selected from insect saliva, puddle water, rain water and a leaf surface.

In some embodiments, a composition comprising a bacterial cell comprising dsRNA targeting an insect gene is provided, wherein the dsRNA is stable (i.e. substantially undegraded) for a period of at least 7 days, at least 8 days, at least 9 days, at least 10 days, at least 11 days, at least 12 days, at least 13 days, at least 2 weeks, at least 3 weeks, at least 4 weeks or more. In some aspects, a composition comprising a bacterial cell comprising dsRNA targeting an insect gene is provided wherein the dsRNA exhibits increased stability relative to the same dsRNA when "naked". In other aspects, a bacterial cell comprising dsRNA targeting an insect gene is provided, wherein at least 50%, at least 60%, at least 70%, at least 80%, at least 90%, at least 95% or more of the dsRNA remains undegraded after a period of 7, 8, 9, 10, 11, 12, 13, 14, 15, 16, 17, 18, 19, 20, 21, 22, 23, 24, 25, 26, 27, 28, 29, 30 or more days.

In related embodiments, a composition comprising a bacterial cell comprising dsRNA targeting an insect gene is provided wherein the dsRNA maintains at least 50%, at least 60%, at least 70%, at least 80%, at least 90%, at least 95% or more of its original RNAi activity for a period of at least 7 days, at least 8 days, at least 9 days, at least 10 days, at least 11 days, at least 12 days, at least 13 days, at least 2 weeks, at least 3 weeks, at least 4 weeks or more.

In one embodiment the bacteriophage capsid protein is encoded by the coat protein gene of a species of leviviridae. In a preferred embodiment the coat protein gene encodes the capsid protein of bacteriophage MS2. In another preferred embodiment the coat protein gene encodes the capsid protein of bacteriophage Qbeta.

In an embodiment the capsid protein comprises the N-terminus of the MS2 capsid protein. In another embodiment the capsid protein comprises the N-terminal 41, 35, 25, 21 or 12 amino acids of the MS2 capsid protein. In an embodiment the capsid protein comprises the N-terminus of the Qbeta capsid protein. In another embodiment the capsid protein comprises the N-terminal 41, 35, 25, 21 or 12 amino acids of the Qbeta capsid protein.

In an embodiment the gene encoding the dsRNA may be associated with and expressed from an inducible transcriptional promoter. The coat protein gene may be associated with and expressed from a constitutive or inducible transcriptional promoter. The inducible transcriptional promoter associated with expression of the dsRNA may be the same inducible transcriptional promoter or a different transcriptional promoter from a transcriptional promoter associated with expression of the coat protein gene. In one embodiment the inducible transcriptional promoter associated with expression of the coat protein gene is induced before induction of the inducible transcriptional promoter associated with expression of the dsRNA to allow accumulation of capsid protein prior to production of dsRNA. In another embodiment the transcriptional promoter associated with expression of the coat protein gene is a constitutive transcriptional promoter.

In an embodiment the gene encoding the dsRNA and the coat protein gene encoding the capsid protein are present on a plasmid or extrachromosomal element. The gene encoding the dsRNA and the coat protein gene may be present on the same plasmid or extrachromosomal element or may be present on separate plasmids or extrachromosomal elements. In another embodiment one or both of the genes encoding the dsRNA and the coat protein may be present on the microbial host cell chromosome or chromosomes.

DESCRIPTION OF THE DRAWINGS

FIG. 2 depicts a single strand (sense) sequence flanked on each side by a pac-site hairpin sequence.

DETAILED DESCRIPTION OF THE INVENTION

The present invention comprises compositions and methods for delivering large quantities of dsRNA to an insect pest in order to activate the RNAi pathway in the insect. In some aspects, a composition is provided comprising a bacterium that co-expresses a bacteriophage capsid protein, or a portion thereof, in conjunction with the desired dsRNA for a period of time sufficient to allow accumulation of the dsRNA in the bacterium and optionally delivering the composition to an insect pest.

Table 1 outlines a number of permutations of RNA structure and coat protein to optimize the yield of dsRNA produced by the bacterial host. The leftmost column of Table 1 refer to individual figures representing cartoon depiction of the predicted RNA structure produced from each of the listed plasmid constructs. In each figure "S" represents the sense strand, "AS" represents antisense strand, and the small hairpin structures represent pac site sequences). The table also lists the coat protein (if any) and the yields of dsRNA (or ssRNA, as indicated) associated with each of the listed plasmid constructs.

TABLE 1

Production of RNA by *E. coli* HT115(DE3) as a function of variation in RNA structure and the presence or absence of coat protein and coat protein variants (n.a. = not applicable; n.d. = not determined).

Figure 1:
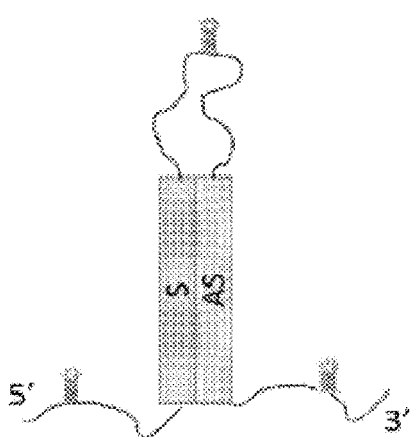
FIG. 1 depicts an RNA stem-loop structure with three pac-site hairpin sequences, one located 5' of the stem-loop structure, one within the loop of the stem-loop structure, and the other 3' of the stem-loop structure.
Figure 2:
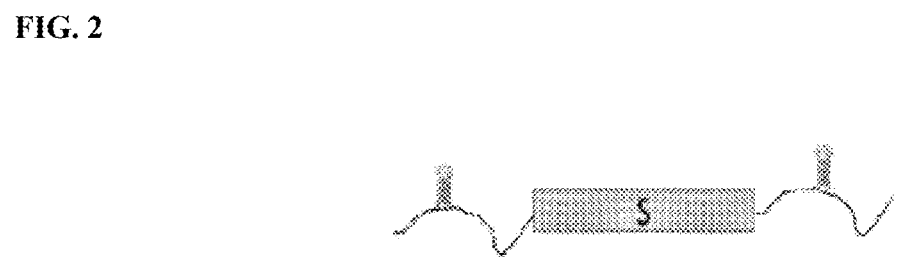
Figure 3:
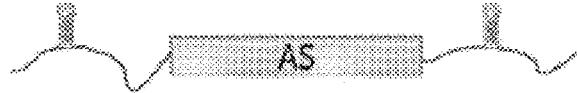
FIG. 3 depicts a single strand (antisense) sequence flanked on each side by a pac-site hairpin sequence.
Figure 4:
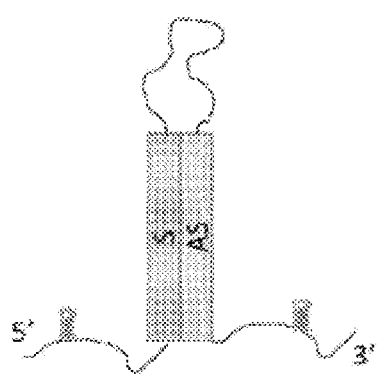
FIG. 4 depicts an RNA stem-loop structure with two pac-site hairpin sequences. one located 5' of the stern-loop structure and the other 3' of the stern-loop structure.
Figure 5:
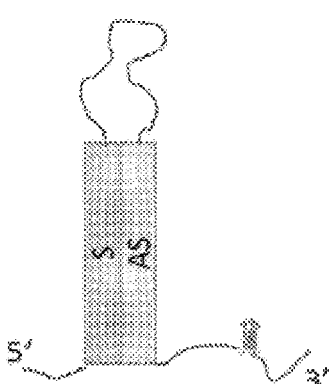
FIG. 5 depicts an RNA stem-loop structure with a single pac-site hairpin sequence located 3' of the stem-loop structure.
Figure 6:
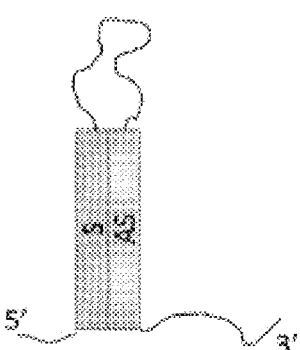
FIG. 6 depicts an RNA stem loop structure lacking any pac site hairpin sequences.

| RNA Structure as depicted in | Plasmid | Loop size (bases) | Stem size (bp) | Stem sequence | Coat protein | RNA encapsid (mg/L) | RNA excapsid (mg/L) |
|---|---|---|---|---|---|---|---|
| FIG. 1 | pAPSE10180 | 139 | 180 | ErkA | MS2 | <2 | 75-90 |
| FIG. 1 | pAPSE10181 | 139 | 180 | ErkA | none | n.a | <2. |
| FIG. 2 | pAPSE10189 | n.a. | n.a. | beta actin | MS2 | 20 | <2 |
| FIG. 3 | pAPSE10190 | n.a. | n.a. | beta actin | MS2 | 20 | <2 |
| FIG. 2 | pAPSE10274 | n.a. | n.a. | beta actin | none | n.a. | <2 |
| FIG. 3 | pAPSE10275 | n.a. | n.a. | beta actin | none | n.a. | <2 |
| FIG. 1 | pAPSE10269 | 166 | 294 | beta actin | MS2 | 2-10 | 200 |
| FIG. 1 | pAPSE10306 | 166 | 294 | beta actin | none | n.a. | 3 |
| FIG. 4 | pAPSE10216 | 166 | 294 | beta actin | MS2 | 5-20 | 50-250 |
| FIG. 4 | pAPSE10305 | 166 | 294 | beta actin | none | n.a. | 4 |
| FIG. 5 | pAPSE10219 | 166 | 294 | beta actin | MS2 | 5-20 | 30-60 |
| FIG. 5 | pAPSE10304 | 166 | 294 | beta actin | none | n.a. | 3 |
| FIG. 6 | pAPSE10279 | 166 | 294 | beta actin | MS2 | 4 | 65 |
| FIG. 6 | pAPSE10303 | 166 | 294 | beta actin | none | n.a. | 4 |
| FIG. 4 | pAPSE10270 | 116 | 294 | beta actin | MS2 | 2-10 | 200 |
| FIG. 4 | pAPSE10271 | 136 | 294 | beta actin | MS2 | 2-10 | 200 |
| FIG. 4 | pAPSE10272 | 156 | 294 | beta actin | MS2 | 2-10 | 200 |
| FIG. 4 | pAPSE10292 | 131 | 294 | beta actin | MS2 | 2-10 | 150 |
| FIG. 4 | pAPSE10291 | 142 | 294 | beta actin | MS2 | 2-10 | 160 |
| FIG. 4 | pAPSE10276 | 166 | 50 | beta actin | MS2 | 5-10 | 80-120 |
| FIG. 4 | pAPSE10277 | 166 | 75 | beta actin | MS2 | 20-30 | 200-250 |
| FIG. 4 | pAPSE10366 | 166 | 294 | beta actin | none (eGFP) | n.a. | <2 |
| FIG. 4 | pAPSE10181 and pAPSE10149 | 139 | 180 | ErkA | MS2 in trans | n. d. | 200 |
| FIG. 1 | pAPSE10359 | 166 | 294 | beta actin | Qbeta | n.d. | n.d. |
| FIG. 4 | pAPSE10357 | 166 | 294 | beta actin | none (U1A) | n.d. | n.a. |
| FIG. 1 | pAPSE10372 | 139 | 180 | ErkA | none (MS2 N-term fragment) | n.a. | 75 |

A. Definitions

As used herein, the term "capsid protein" or "capsid" refers to the coat protein of bacteriophage MS2 or Qβ, capable of binding the bacteriophage RNA pac site with high affinity and assembling into a complex hollow tertiary structure in which the bacteriophage RNA is entirely encapsidated within the hollow tertiary structure. In a VLP, the capsid protein forms a hollow tertiary structure in which the heterologous RNA is entirely encapsidated. The term "capsid" also refers to the hollow tertiary structure formed by assembly of individual capsid proteins.

As used herein "ssRNA" and "dsRNA" refer to "single-stranded RNA and double stranded RNA, respectively. An ssRNA is comprised of an RNA sequence of any length that lacks sufficient internal homology to form any significant secondary structures such as hairpins or other structures dependent on hybridization of internal complementary sequences with one another via Watson-Crick base pairing of nucleotide bases between the complementary sequences. In contrast, a dsRNA comprises RNA sequences with sufficient internal homology to form significant secondary structures such as hairpins due to hybridization of internal complementary sequences with one another via Watson-Crick base pairing of nucleotide bases within the complementary sequences. Significant secondary structures generally involve stretches of homology greater than approximately nine bases, but the exact length depends to some extent on context and on whether such secondary structures impart any biological function to the molecule.

As used herein "plasmid" or "extrachromosomal element" refers to any extrachromosomal episome capable of replication or stable maintenance within the host cell. Specifically embraced by this definition are plasmids such as pBR322, pCG1, and pACYC184 which represent the backbones of the described plasmids. Those of ordinary skill in the art will recognize that other plasmids or stably maintained viral episomes can provide the same required functions of maintenance, expression and selection and that alternatives to the basic plasmids described herein may be generated from such other plasmids or stably maintained viral episomes without undue experimentation. A key feature of the present invention is the ability to express the genes encoding a dsRNA and a capsid protein, not specific modes of replication, expression or the selective markers found on episomes containing the genes encoding the dsRNA and capsid protein.

"Substantially similar sequence" refers to sequence variants of the claimed capsid proteins that retain the ability to facilitate accumulation of dsRNA in a microbial host cell as described herein. Such substantially similar sequences include sequences with at least 26% identity and 47% similarity as shown by the differences between MS2 and Qbeta capsid protein sequences (as determined by blastp). Consequentially, substantially similar sequences encompass conserved and homologous substitutions allowing sequence variants with as little as 95%, 90%, 80%, 70%, 60%, 50%, 40%, 30% or 25% identity to, and 95%, 90%, 80%, 70%, 60%, 50% or 40% similarity to, MS2 or Qbeta capsid protein sequences to facilitate accumulation of dsRNA in a microbial host.

B. Common Materials and Methods

Routine microbial and molecular cloning methods and tools, including those for generating and purifying DNA, RNA, and proteins, and for transforming host organisms and expressing recombinant proteins and nucleic acids as described herein, are fully within the capabilities of a person of ordinary skill in the art and are well described in the literature. See, e.g., Sambrook, et al., Molecular Cloning: A Laboratory Manual, 2nd ed., Cold Spring Harbor Laboratory Press, Cold Spring Harbor, N.Y. (1989); Davis, et al., Basic Methods in Molecular Biology, Elsevier Science Publishing Co., Inc., N.Y. (1986); and Ausubel, et al, Current Protocols in Molecular Biology, Greene Publ. Assoc., Wiley-Interscience, NY (1995). The disclosures in each of which are herein incorporated by reference.

Each of the recombinant DNA constructs described in further detail below are based on a common plasmid vector series derived from plasmid pBR322. The first of this plasmid vector series contains a custom synthetic DNA fragment (produced by PCR GenScript, Piscataway, NJ) comprising a T7 promoter sequence capable of driving transcription of a single copy of the bacteriophage MS2 capsid gene followed by a T7 terminator. This synthetic sequence was inserted as a BamHl-Sphl restriction fragment into the corresponding sites of pBR322 to form plasmid pAPSE10118. A second synthetic sequence comprising a T7 promoter sequence followed by an MS2 pac site sequence, a multi-cloning site containing, in order (5' to 3') AsiSI-Pmel-Ascl-Rsrll-Notl-Pacl restriction sites, a second high affinity variant MS2 pac type sequence (C-pac), a T7 terminator and an SphI restriction site was synthesized (PCR Genscript, Piscataway, NJ) and inserted into the EcoRV site of pAPSE10118 to form pAPSE10136. The two are oriented such that the T7 promoters direct transcription of the same strand of pAPSE10136 (clockwise on the standard pBR322 map) but are separated from one another by a single T7 terminator.

A 180 nucleotide fragment of the ErkA gene of *Drosophila melanogaster* (corresponding to the sequence of GenBank Accession NM 001300706 between nucleotides 156-335) was amplified by PCR incorporating AsiSI and Pmel restriction sites on the 5' and 3' sides, respectively. Insertion of this ErkA gene fragment into the corresponding sites of pAPSE10136 produced pAPSE10169. A second, complimentary copy of the ErkA gene fragment sequence was generated by PCR amplification incorporating a Pmel restriction site on the 5' end, followed by a synthetic loop sequence containing an additional MS2 pac sequence, followed by a Nod restriction site, followed by the complementary (anti-sense) ErkA gene fragment sequence and a Pad restriction site on the 3' end of the PCR fragment. The synthetic loop sequence comprises random sequence incapable of hybridizing with the ErkA gene fragment sequences. This complementary (anti-sense) copy of the ErkA gene fragment is inserted into the Pmel and Pad restriction sites of pAPSE10136 to form pAPSE10180 (SEQ ID NO: 1). A second series of plasmid vectors, lacking the MS2 capsid protein is derived from pAPSE10180 by deleting the MS2 capsid expression sequences by SphI restriction digestion and re-ligation to produce pAPSE 10181 (SEQ ID NO: 2).

Plasmids pAPSE10180 and pAPSE10181 represent the basic platform for expression of the RNA constructs discussed herein. Transcription of the ErkA cassette in these plasmids is predicted to produce an RNA transcript capable of forming a large stem-loop structure comprising a 180 base pair stem and a 139 base loop with 3 individual MS2 pac sequences located 5' and 3' of the stem and within the loop itself. One of ordinary skill in the art will understand that substitution of the ErkA gene fragment sequences by other sequences can be easily accomplished by standard cloning and sub-cloning methods.

Transformation of plasmids pAPSE10180 or pAPSE10181, or any of their derivatives, into host cells capable of inducible expression of T7 polymerase produces cell lines capable of expressing RNA transcripts. All such strains inducibly producing RNA transcripts are referred to generally herein as "expression strains". Unless otherwise indicated, each of the plasmids described herein was electroporated into E. coli strain HT115 (DE3) with genotype F. mcrA,mcrB, IN (rrnD-rrnE) 1, rnc14::Tn10 (Lambda DE3 lysogen: lacUV 5 promoter-T7 polymerase)) and the resulting recombinant transformants were selected on LB agar plates containing 12 µg/ml tetracycline and/or 100 µg/ml ampicillin. Single colonies were isolated, the presence of intact plasmid confirmed by restriction enzyme analysis and the confirmed transformed cells archived for future use.

Standard expression studies comprised inoculating transformed cells into 100 ml of Super Broth containing 0.1% glucose, 0.4% lactose, 100 µg/ml ampicillin and/or 12.5 µg/ml tetracycline and incubating the cultures with vigorous shaking at 37° C. Expression of the T7 polymerase was achieved by auto-induction by depletion of the available glucose and the presence of the lactose inducer. This ensures that all cultures are induced at the same growth stage. Cells were harvested twelve to eighteen hours post-induction (late stationary phase) by centrifugation at 3,000 g at 4° C. for 30 minutes and stored on ice until lysis.

RNA was isolated from harvested cells by resuspending a 5 ml equivalent of cell culture of harvested cells in sonication buffer comprising Tris-HCl pH 7, 10 mM NaCl and sonicating the suspended cells on ice for 3 minutes. Cell debris was removed by centrifugation at 16,000 g the supernatant (cleared lysate) was immediately processed to recover RNA and VLPs as described. RNA was recovered from half of the cleared lysate using the commercial Purelink RNA Mini Kit method (Ambion® Cat. No. 12183018A, Thermo Fisher Scientific® Inc., Waltham, MA) according to the manufacturer's instructions.

VLPs were purified from the remaining half of the cleared lysate which were diluted to a total volume of 1 ml and treated with 100 units of Benzonase® Nuclease (Sigma Aldrich®, St. Louis, MO) at 37° C. for two hours. Subsequently, 0.15 mg of Proteinase K was added and the enzymatically treated cleared lysate incubated at 37° C. for an additional three hours. The VLPS were recovered from the enzymatically treated cleared lysate by fractional precipitation. A saturated ammonium sulfate solution was prepared by adding ammonium sulfate to water until it reached saturation (approximately 4.1 M). Fifty microliters of the saturated ammonium sulfate solution was added to the enzymatically treated cleared lysate and the mixture placed on ice and incubated for two hours. Unwanted precipitate was removed from the mixture by centrifugation at 16,000 g and the aqueous solution transferred to a clean Eppendorf tube. The aqueous solution was then subjected to a second precipitation by the addition of 0.171 g of dry ammonium sulfate directly to the aqueous solution. The aqueous solution was vortexed and incubated on ice for two hours. The precipitate was spun down at 16,000 g the aqueous phase discarded and the solid precipitate representing purified VLPs resuspended in 100 microliters of sonication buffer.

RNA was recovered from the resuspended purified VLPs by adding 3 volumes of TRIzol™ LS Reagent (Ambion® Cat. No. 10296028, Thermo Fisher Scientific® Inc.), vigorously vortexing the mixture, adding 1 ml of chloroform, further vortexing the mixture before pulse centrifugation to separate the aqueous and organic phases of the mixture. The aqueous phase was placed in a clean Eppendorf tube and the RNA purified with a commercial RNA Clean & Concentrator™ kit (Cat. No. R1018, Zymo Research®, Irvine, CA) according to the manufacturer's instructions.

RNA from bacterial and VLP samples were dissolved in 50 µl of nuclease-free water. To determine the concentration of dsRNA in a sample, the samples were treated with RNAse A (Invitrogen® Cat. No. AM2274, Thermo Fisher Scientific® Inc.) to degrade single stranded RNA under the manufacturers recommended conditions, the concentration of dsRNA was determined spectrophotmetrically by measuring OD260 and 1 jig loaded onto Novex® 6% TBE-urea gels (Invitrogen®, Thermo Fisher Scientific® Inc.). One lane of each gel was loaded with dsDNA size markers of known concentration and the samples were electrophoresed, the gel was stained with ethidium bromide and each band quantitated by densitometry using the dsDNA markers as a standard curve.

RNA yields from constructs producing ssRNA were determined by annealing the sense or anti-sense strand recovered from the induced cells or VLPs with an excess of the cognate strand. The annealed mixture was then treated with RNAse A and the amount of dsRNA incorporating the ssRNA of interest measured as described above.

Little or no differences in final cell densities were observed between any of the cultures from which the samples were harvested and in all cases the cultures appear to have reached stationary phase prior to harvest. To allow direct sample to sample comparison of RNA yields, all dsRNA and ssRNA concentrations are reported as the amount of such RNA present in a 1 L equivalent of culture.

Northern blot analysis was used to verify the identity of bands containing the dsRNA transcripts using a DNA oligonucleotide probe against the random sequence comprising the loop of each dsRNA construct (5'-GGCCGGCGTCT-ATTAGTAGATGCC-3', SEQ ID NO 3). RNA from the 6% polyacrylamide denaturing Urea-TBE gel was transferred to a positively-charged BrightStar—Plus nylon membrane (Ambion® Cat. No. 10102, Thermo Fisher Scientific® Inc.) using the semi-dry Trans-Blot® SD transfer apparatus (Bio-Rad®, Hercules, CA) for 1 hour at constant current of 0.3 A. RNA was fixed on the membrane by the SpectroLinker™ XL-1500 UV crosslinking apparatus (Spectronics® Corporation, Westbury, NY) using the "optimal crosslink" setting. The membrane was briefly rinsed with water and prehybridized in 50 ml of SXSSC, 0.1% SDS buffer at 45° C. with gentle shaking. Probe hybridization was carried out overnight at 45° C. in 3 ml of prehybridization buffer with gentle shaking. The oligonucleotide probe targeting the hairpin RNA loop was conjugated with TAMRA. Three washes (for 2 minutes each) with 100 ml of water were completed at room temperature and the blot with a ChemiDoc™ MP imaging system (BioRad®, Hercules, CA), using the rhodamine channel.

C. Preferred Embodiments

The following are among the preferred embodiments of the invention.

One embodiment of the present invention comprises a bacterial host cell containing a plasmid encoding both a gene for the desired dsRNA and a bacteriophage capsid protein gene, such that the dsRNA and the capsid protein genes are transcribed so that the desired dsRNA is produced and the capsid protein gene translated to produce capsid protein and wherein, after a suitable period of time, unencapsidated dsRNA accumulates within the cell to a much higher degree than in the absence of capsid protein. In other embodiments the dsRNA gene and the capsid protein gene may be present on separate compatible plasmids, autonomously maintained phage or other epigenetic elements, or one or both genes may be present within the chromosome of the bacterial host cell.

In an embodiment the dsRNA gene and the capsid protein gene are each transcribed from a transcriptional promoter. The transcriptional promoter may be inducible. In one embodiment the transcriptional promoters are identical; in other embodiments the promoters are different. In still other embodiments the transcriptional promoters may be differentially induced. In such differentially inducible embodiments it may be preferable to induce expression of the capsid protein prior to inducing expression of the dsRNA.

In another embodiment the capsid protein and the dsRNA may be transcribed as a single transcript from a single promoter. The promoter may be inducible. In such embodiments the dsRNA is cleaved from the initial RNA transcript containing the capsid protein coding sequence by post transcriptional processing, such post transcriptional processing may depend on bacterial host cell processes or may be directed by other RNA processing systems such as ribozymes or specific ribonucleases.

In one embodiment one or both of the dsRNA and the capsid protein genes are inducibly transcribed from a transcriptional promoter and transcription is terminated by a transcriptional terminator. In an embodiment the inducible transcriptional promoter is the bacteriophage T7 gene 1 promoter. In other embodiments the inducible transcriptional promoter may be the bacteriophage Lambda PL or PR promoters, the lac operon, tip operon, or synthetic tac promoter, or bacteriophage T5 promoter. Other transcription promoters, both constitutive and inducible, known to those of ordinary skill in the art, may also be used in some embodiments. In an embodiment the transcriptional terminator is the bacteriophage T7 late terminator. Other transcription terminators, both rho-dependent and rho-independent, known to those of ordinary skill in the art may also be used in some embodiments.

In an embodiment the coat protein gene encodes a leviviral capsid protein. The coat protein gene may be the MS2 coat protein gene encoding the MS2 capsid protein or substantially similar sequences retaining the ability to allow accumulation of dsRNA in a microbial host cell. The coat protein gene may encode the Qbeta coat protein gene encoding the Qbeta capsid protein or substantially similar sequences retaining the ability to allow accumulation of dsRNA in a microbial host cell.

In an embodiment the bacterial host comprising the dsRNA is delivered to an insect pest as described herein.

EXAMPLES

Example 1

Unencapsidated dsRNAs are Produced at Higher Levels in the Presence of Capsid Protein than in the Absence of Capsid Protein Expression strains containing pAPSE10180 and pAPSE10181 were constructed and dsRNA production induced by the standard expression procedure described above. The amount of encapsidated and unencapsidated dsRNA each strain produced was measured as described.

The initial impetus for this experiment was to determine whether an RNA molecule with a 180 base pair double-stranded stem structure could be packed within a VLP. A 180 bp dsRNA stem is approximately 60 nm in length, whereas the interior diameter of an MS2 capsid is approximately 20 nm. Based on this geometric limitation, little or no encapsidation was expected and, due to host nuclease activity, little or no unencapsidated dsRNA was expected to be recoverable from the cell lysates. As expected only small amounts of encapsidated dsRNA (en capsid) were recovered (<2 mg/L) from the pAPSE10180 expression cells. In contrast, surprisingly large amounts of unencapsidated dsRNA (ex capsid) were recovered (75-90 mg/L) from the pAPSE10180 expression cells. Even more surprisingly, virtually no unencapsidated dsRNA was recovered from the pAPSE 10181 expression cells.

To determine whether accumulation of RNA is a specific property of the ErkA sequence, or is a more general property of expressing dsRNA in the presence of capsid protein, a series of expression constructs expressing a 294 base sequence from the beta actin gene of the Colorado potato beetle (*Leptinotarsa decemlineata* strain Freeville, GenBank Accession NM 001300706 between nucleotides 156-335) were produced and tested.

Initially, plasmids expressing the 294 base beta actin sequence from Colorado potato beetle in the sense and the anti-sense orientation were constructed from pAPSE10180 by replacing the ErkA sequences, to produce pAPSE10189 (SEQ ID NO: 4 and pAPSE10190 (SEQ ID NO: 5) respectively. The beta actin sense and antisense strand sequences were amplified by PCR (Accuprime Pfx, Invitrogen Cat. No. 12344040, Thermo Fisher Scientific Inc.) from a gBlock template using primers that introduce the AsiSI and PmeI restriction sites at the 5' and 3' ends respectively (gBlock template DNA and PCR primers were synthesized by Integrated DNA Technologies, Coralville IA; all restriction endonucleases were from New England BioLabs, Beverly, MA). Restriction digest of pAPSE 10180 and the beta actin sense and antisense PCR fragment with AsiSI and PmeI resulted in DNA fragments that could be ligated together in the desired manner. The pAPSE10180 plasmid backbone lacking the ErkA sequence was gel purified and the sense and antisense beta actin sequences were ligated into the gel purified vector to produce pAPSE 10189 and pAPSE 10190, respectively. When transformed into a suitable expression host, such as HT115 (DE3) the cells containing pAPSE10189 produces a ssRNA transcript comprising 294 bases of the sense strand of the beta actin gene flanked by pac sequences as well as co-express MS2 capsid protein, when cultured and induced as described above. Likewise, cells containing pAPSE10190 produces a ssRNA transcript comprising 294 bases of the anti-sense strand of the same region of the beta actin gene flanked by pac sequences as well as co-express MS2 capsid protein when transformed into a suitable expression host, cultured and induced as described. A second set of plasmids, lacking the ability to express MS2 capsid protein were also produced by replacing the ErkA sequences of pAPSE10181 with the sense and anti-sense 294 base fragments of the beta actin gene as described above. These plasmids, pASPE10274 (SEQ ID NO: 6) and pAPSE10275 (SEQ ID NO: 7) respectively, were transformed into HT115 (DE3) and cultured and induced as described.

Analysis of un-encapsidated RNA recovered from the cells whether co-expressed with capsid protein (as with pAPSE10189 and pAPSE10190) or not (pAPSE 10274 and pAPSE10275) showed that virtually no ssRNA can be recovered. However, VLPs recovered from pAPSE10189 and pAPSE10190 yield at least 20 mg/L of ssRNA of sense or anti-sense sequence respectively. This confirms that the plasmid expression systems are capable of producing ssRNA and capsid protein as expected.

A dsRNA expression cassette comprising the 294 base Colorado potato beetle beta actin genes was constructed by a process similar to that described for the dsRNA ErkA expression cassette. In this case, the random DNA sequence comprising the loop between the sense and anti-sense strands of the beta actin sequences comprised 166 bases, including the same internal pac site sequence as found in pAPSE10180 and 10181. This beta actin expression cassette was cloned into pAPSE10180 replacing the ErkA related stem loop sequence to form plasmid pAPSE10269 (SEQ ID NO: 8), and into pAPSE10181 to form plasmid pAPSE10306 (SEQ ID NO: 9). The plasmids were transformed into HT115 (DE3), cultured, and induced as described. Analysis of the encapsidated dsRNA produced by the cells containing pAPSE10269 strain showed that 2-10 mg/L dsRNA could be recovered from VLPs. However, much higher levels of the beta actin dsRNA could be recovered from the cells containing pAPSE10269 in unencapsidated form (200 mg/L). Strikingly, analysis of the RNA produced by the pAPSE10306 strain showed that in the absence of co-expressed capsid protein only about 3 mg/L of dsRNA could be recovered.

Thus, the high levels of unencapsidated dsRNA are consistent with a model in which such dsRNA are not packaged efficiently, but for some reason appear to be present within cells co-expressing capsid protein with the dsRNA at much higher levels than in cells which lack capsid protein. One model to account for this observation is that binding of capsid protein to the pac sites inhibits degradation by host cell nucleases.

Example 2

Specific Pac Site-Capsid Protein Interaction is not Required for High Level Production of dsRNA To test whether capsid protein bound to pac sites in the dsRNA results in the observed increase in dsRNA production in cells co-expressing capsid protein, perhaps inhibiting endogenous host nuclease degradation of the bound dsRNA, a series of constructs comprising the basic beta actin dsRNA described above were produced with varying numbers and locations of pac sites. Plasmids pAPSE10216 (SEQ ID NO: 10) and pAPSE10305 (SEQ ID NO: 11), are identical to pAPSE10269 and pAPSE10306 respectively, except they lack the internal loop pac site. Plasmids pAPSE10219 (SEQ ID NO: 12) and pAPSE10304 (SEQ ID NO: 13) are identical to pAPSE10217 and pAPSE10306 respectively, except they have only a single pac site located on the 3' end of the stem of the dsRNA. Plasmids pAPSE10279 (SEQ ID NO: 14) and pAPSE10303 (SEQ ID NO: 15) are identical to pAPSE10216 and pAPSE 10306 except they lack all pac site sequences entirely. Each of these plasmids was transformed into *E. coli* HT115 (DE3), cultured and induced as described. Analysis of the encapsidated RNA recovered from VLPs of each of pAPSE10216 and pAPSE10219 show that 5-20 mg/L of dsRNA is encapsidated. Strikingly, even the strain containing pAPSE10279 entirely lacking pac sites produced 4 mg/L of encapsidated dsRNA, indicating that this level of encapsidation may represent non-specific entrainment of dsRNA present in the cells at the time the capsids were formed. Furthermore, the strain containing pAPSE10216 produced as much as 250 mg/L of unencapsidated dsRNA in the presence of capsid protein. The strains containing pAPSE10219 and pAPSE10279 produced 30-60 mg/L and 65 mg/L of unencapsidated dsRNA, respectively in the presence of capsid protein. All of the strains containing plasmids comprising the expression cassettes without co-expression of capsid protein produced <4 mg/L of dsRNA.

Together, these results indicate that the ability of capsid protein to increase the amount of unencapsidated dsRNA that can be recovered from cell lysates is not dependent on the specific binding of capsid protein to its cognate pac site sequence. Although the highest levels of unencapsidated dsRNA are recovered from constructs containing at least 5' and 3' flanking pac sites (approximately 200 mg/L), significant amounts of unencapsidated dsRNA are produced by constructs having only a single 3' flanking pac site, or lacking pac sites entirely. Cells containing plasmids producing dsRNA lacking pac sites altogether produce significantly higher amounts of dsRNA (65 mg/L) when capsid protein is co-expressed with the dsRNA relative to the cell lines lacking capsid protein altogether (3-4 mg/L). The approximately 16× increase in recoverable dsRNA between cells co-expressing capsid protein and those lacking capsid protein (65 mg/L versus 3-4 mg/L) is much more than the approximately 3×-4× increase due to the presence of pac sites (65 mg/L versus 200-250 mg/L). The effect of capsid protein co-expression appears to involve something other than mere binding to cognate pac site sequences that may (or may not) be present on the dsRNA.

Example 3

Loop Size and Structure are Irrelevant to High Level Production of dsRNA

To test what effect, if any, differences in loop sequence might exert on the production of dsRNA in the presence and absence of co-expressed capsid protein, a series of constructs with different lengths of internal non-homologous loop sequences were inserted between each of the 294 base sense and anti-sense beta actin sequences of pAPSE10269.

Plasmids pAPSE10270 (SEQ ID NO: 16), pAPSE10271 (SEQ ID NO: 17), pAPSE10272 (SEQ ID NO: 18) and pAPSE10292 (SEQ ID NO: 19) have non-homologous loop sizes of 116 bases, 136 bases, 156 bases and 166 bases respectively. Each of these loop sequences has very little propensity for any secondary structure as determined by the m-fold structure prediction program (Zucker and Stiegler (1981) *Optimal computer folding of large RNA sequences using thermodynamics and auxiliary information* Nucl. Acids. Res. 9 (1): 133-48). In addition, the 139 base loop sequence found associated with the ErkA stem sequences in pAPSE 10180 and having a slightly higher propensity for structural interactions within the loop was also placed between the sense and anti-sense beta actin sequences of pAPSE10269, to form pAPSE10292. Additionally, pAPSE10291 (SEQ ID NO: 20) comprising a 142 base loop sequence with a high degree of propensity for forming secondary structure based on internal homology was synthesized and constructed as described.

Each of the plasmids described in this Example were transformed into *E. coli* expression strain HT115 (DE3), cultured and induced and the amount of encapsidated and unencapsidated dsRNA determined as described. In each case 2-10 mg/L of dsRNA was recovered from the VLPs produced by inducing expression of the plasmid, indicating that loop size or structure had little or no effect on the ability of VLPs to encapsidate the dsRNA. Likewise, expression from each of the plasmids produced between 100 and 200 mg/L unencapsidated dsRNA, indicating that loop size or structure had little or no effect on overall production of unencapsidated dsRNA in the presence of capsid protein.

Example 4

Stem Size is Irrelevant to High Level Production of dsRNA

Differences in stem sequence derived from the *Drosophila melanogaster* ErkA gene sequences expressed from pAPSE10180 and the Colorado potato beetle beta actin gene sequences expressed from pAPSE 10269 do not make a significant difference in the ability in expression strains to produce large quantities of unencapsidated dsRNA (75-90 mg/L from pAPSE10180 versus 200 mg/L from pAPSE10269). Nor does the length of the dsRNA stem (180 base pairs in the dsRNA produced from pAPSE10180 and 294 base pairs in dsRNA from pAPSE10269). To more systematically test what affect, if any, differences stem sequence length might exert on the production of dsRNA in the presence and absence of co-expressed capsid protein, a series of expression constructs with different lengths of stem sequences were substituted for each of the 294 base stem forming sense and anti-sense beta actin sequences of pAPSE10269.

Plasmids pAPSE10276 (SEQ ID NO: 21) and pAPSE10277 (SEQ ID NO: 22) encode dsRNA with potential double-stranded stems of 50 and 75 base pairs respectively. The dsRNA expressed by both plasmids comprise 166 bases of non-homologous loop sequence. Although these dsRNA structures are significantly shorter than those in dsRNA from the corresponding ErkA and beta actin constructs, they still exceed the interior diameter of the MS2 VLP.

When transformed into the *E. coli* expression strain HT115 (DE3), cultured and induced as described, pAPSE 10276 produces 5-10 mg/L of encapsidated dsRNA and 80-120 mg/L of unencapsidated dsRNA. Plasmid pAPSE 10277 produces 20-30 mg/L encapsidated dsRNA and 200-250 mg/L unencapsidated dsRNA. These values are similar to those observed for pAPSE10180 and pAPSE10269 described earlier in this Example, indicating that differences in stem length and sequence do not play a major role in producing dsRNA in cells co-expressing capsid protein.

Example 5

Capsid Protein is Required for High Level Production of dsRNA

To confirm the requirement for capsid protein, plasmid pAPSE10216, which produces a dsRNA product at high levels in the presence of capsid protein, was altered to replace the MS2 coat protein gene with eGFP. A gBlock template comprising the T7 promoter to T7 terminator sequences of pAPSE10216 (spanning the sequences between the unique BarHl and Sall sites of the plasmid) in which the coding sequence of MS2 coat protein was replaced with the coding sequence of eGFP was designed, produced and amplified with primers encompassing the BamHl site on the 5' side and the Sall site on the 3' side. The resulting 1 kb fragment was digested with BamHl and Sall and then ligated into BamHl-Sall digested pAPSE10216 to form pAPSE10366 (SEQ ID NO: 24). Plasmid pAPSE10366 was confirmed by restriction digest and transformed into the *E. coli* expression strain HT115 (DE3), cultured and induced as described, pAPSE 10366 produces <2 mg/L of unencapsidated dsRNA, in contrast to the 200 mg/L produced by pAPSE10216. In addition, the cells expressed high amounts of eGFP as evidenced by the intense fluorescence produced on induction (data not shown) confirming that the basic dual expression plasmid used throughout these studies performs as expected. This result further demonstrates that capsid protein is necessary for accumulation of unencapsidated dsRNA in cells expressing the target RNA gene that otherwise accumulate unencapsidated dsRNA in the presence of capsid protein.

To further confirm that the presence of capsid protein is essential to the high levels of unencapsidated dsRNA production a plasmid compatible with pAPSE 10181 and capable of inducible expression of the MS2 capsid protein is constructed. pAPSE10149 (SEQ ID NO: 23) is based on pACYC184. This plasmid comprises a PISA origin of replication that is not excluded by the colE1 based origin of replication of pAPSE10181 and a chloramphenicol acetyl transferase antibiotic marker to allow selection of co-transformants containing both pAPSE10181 (encoding ampicillin resistance) and pAPSE10149 (encoding chloramphenicol resistance). Plasmid pAPSE10149 also comprises the same T7 promoter sequence capable of driving transcription of a single copy of the bacteriophage MS2 capsid gene followed by a T7 terminator as found in pAPSE10118 cloned into the BamHI and Sphl sites of pACYC184. Plasmid pAPSE10149 is transformed into expression strains already containing pAPSE10181 to produce ampicillin and chloramphenicol resistant double transformants. Expression studies of such double transformants show that co-expression of the capsid protein from pAPSE10149 in conjunction with pAPSE10181 produces 200 mg/L of unencapsidated dsRNA whereas cells containing pAPSE10181 alone produce <2 mg/L of unencapsidated dsRNA (see Example 1). This demonstrates that providing capsid protein in trans is sufficient to facilitate production of high levels of unencapsidated dsRNA to host cells containing a plasmid expressing the dsRNA target that otherwise fail to accumulate unencapsidated dsRNA in the absence of capsid protein.

Example 6

Other Capsid Proteins can Induce High Level Production of dsRNA

To test whether the accumulation of unencapsidated dsRNA is a unique property of bacteriophage MS2 capsid protein, or whether other capsid proteins share this property, a plasmid expression system analogous to pAPSE10216 was constructed. This plasmid, pAPSE10359 (SEQ ID NO: 25) comprises a Qbeta capsid protein and Qbeta pac sites at the 5' and 3' ends of the beta actin dsRNA expression cassette, but is in all other aspects similar to pAPSE10216.

Briefly, the Qbeta coat protein gene sequence (Genebank Accession NC_001890 between nucleotides 1343 and 1744) was synthesized as a gBlock fragment by Integrated DNA Technologies, Coralville, IA. The synthetic fragment was amplified with PCR with primers that introduced a BamHI restriction site followed by a T7 promoter sequence upstream of the Qbeta coat protein gene followed by a T7 terminator and a Sphl restriction site. The amplified synthetic fragment and plasmid pBR322 were digested with BamHI and Sphl and ligated together to form intermediate plasmid pAPSE10358. The beta actin dsRNA sequence of pAPSE10269 was amplified by PCR with primers that introduced an EcoRI restriction site followed by a Qbeta pac sequence followed by the beta actin dsRNA sequence followed by a second copy of the Qbeta pac sequence followed by a BamHI restriction site. This amplified beta actin containing sequence and plasmid pAPSE10358 were digested with EcoRI and BamHl and ligated together to form pAPSE10374. Plasmids pAPSE10374 and pAPSE10216 were digested with AsiSI and NotI. This cleaves pAPSE10374 into two fragments of 4,713 and 113 base pairs and pAPSE10216 into two fragments of 5,204 and 786 base pairs. The 4,713 and 786 base pair fragments were isolated and ligated together to produce pAPSE10359.

When transformed into the E. coli expression strain HT115 (DE3), cultured and induced as described, pAPSE10359 will produce a large amount of unencapsidated dsRNA relative to the amount of dsRNA produced from a similar construct lacking capsid protein (pAPSE10305). This pattern, similar to that observed for pAPSE10216 and pAPSE10305 described in Example 1, will confirm that expression of the Qbeta capsid protein, like the MS2 capsid protein, is sufficient to increase the amount of dsRNA produced in vivo.

Example 7

RNA Binding Proteins Other than Capsid Proteins are not Sufficient for High Level Production of dsRNA To test whether the accumulation of unencapsidated dsRNA is a function of general RNA binding or is specific to bacteriophage capsid proteins, a plasmid expression system, pAPSE10357 (SEQ ID NO: 26) was constructed comprising the RNA binding domain of the human U1A protein and its hairpin cognate binding site from human U1 snRNA 5' and 3' of the sense and antisense stem loop structure of the beta actin dsRNA. Plasmid pAPSE10357 is similar to pAPSE10216 with the capsid protein replaced by the human U1A RNA binding protein and U1A binding site sequences at the 5' and 3' ends of the beta actin dsRNA expression cassette, but is in all other aspects similar to pAPSE10216.

The DNA sequence encoding the N-terminal 102 amino acids comprising the RNA binding domain of the human U1A protein was amplified from a cloned copy of the U1A protein (Plasmid pAV105, Professor Kathleen Hall, Washington University, St. Louis, MO) using PCR primers that introduced a BamHI restriction site followed by a T7 promoter sequence upstream of the ULA gene fragment followed by a T7 terminator and a Sphl restriction site. The amplified synthetic fragment and plasmid pBR322 were digested with BamHI and Sphl and ligated together to form intermediate plasmid pAPSE10356. The beta actin dsRNA sequence of pAPSE10269 was amplified by PCR with primers that introduced an EcoRI restriction site followed by the hairpin binding site sequence from human U1 snRNA sequence followed by the beta actin dsRNA sequence followed by a second copy of the hairpin binding site sequence from human U1 snRNA sequence followed by a BamHI restriction site. This amplified beta actin containing sequence and plasmid pAPSE10356 were digested with EcoRI and BamHI and ligated together to form pAPSE10373. Plasmids pAPSE10373 and pAPSE10216 were digested with AsiSl and Notl. This cleaves pAPSE10373 into two fragments of 4,627 and 113 base pairs and pAPSE10216 into two fragments of 5,204 and 786 base pairs. The 4,713 and 786 base pair fragments were isolated and ligated together to produce pAPSE10357.

When transformed into the E. coli expression strain HT115 (DE3), cultured and induced as described, pAPSE10357 will not produce a significant amount of unencapsidated dsRNA relative to the amount of dsRNA produced from a similar construct lacking capsid protein (pAPSE10305). This will confirm that the mere presence of an RNA binding site and binding protein in conjunction with the dsRNA is not sufficient to increase the amount of dsRNA produced in vivo. Alternatively, production of significant amounts of unencapsidated dsRNA will indicate that the presence of RNA binding sites at the 5' and 3' end and the cognate RNA binding protein is sufficient for increasing in vivo production of dsRNA.

Example 8

The N-Terminus of Capsid Protein is Sufficient for High Level Production of dsRNA To examine whether the increased production of dsRNA from plasmids containing both the dsRNA gene and the coat protein gene requires the intact capsid protein or whether only a portion of the protein is required, a frame-shift mutation was introduced into the coat protein gene sequence of pAPSE10180. Double digestion of pAPSE10180 with the restriction enzymes StuI and Pm1I produces two restriction fragments, a large fragment of 5,485 base pairs and a small thirteen base pair fragment comprising about 4 codons of the capsid protein CDS about 40 codons from the coat protein start codon of pAPSE10180. The restriction enzymes produce blunt-ended termini and the larger fragment was religated to produce plasmid pAPSE10372 (SEQ ID NO: 27), which, in addition to producing an intact inducible dsRNA ErkA-specific sequence, also comprises an inducible frame-shifted protein that includes the N-term 41 codons of the MS2 coat protein followed by 27 codons of frame-shifted sequence before terminating at a stop codon (SEQ ID NO: 28). When pAPSE 10372 was transformed into E. coli expression strain HTE115 (DE3) and cultured and induced as described, 75 mg/L of dsRNA was produced. This indicates that the N terminus of the capsid protein alone is sufficient to increase production of dsRNA as well as the intact capsid protein (compare yields from pAPSE10180 and pAPSE 10372 in Table 1).

The N-terminus of the MS2 capsid protein forms a distinctive three-dimensional structure comprised of four separate beta sheets (D. Peabody, The RNA binding site of bacteriophage MS2 coat protein, The EMBO Journal 12 (2) 595-600 (1993)). Each of these sheets, 3D from amino acids 31-35, (3C from amino acids 2225, 13B from amino acids 19-21 and OA amino acids 8-11 may play a role in the ability of the N-terminus capsid protein fragment to improve dsRNA production. Note that the nomenclature is that of Peabody and the numbering includes the N-terminal methionine omitted by Peabody. Progressive deletion of each of these structural motifs can determine the minimum sequence requirement for improving dsRNA production.

Example 9

Fed Batch Fermentation Produces Very High Level Production of dsRNA

To determine whether quantities of dsRNA could be increased by improving the microbial growth conditions, glucose fed batch fermentations were conducted. Briefly, fed-batch fermentations were carried out in an Eppendorf BioFlo 115 fermenter at 37° C. The pH was controlled by automatic addition of 30% ammonium hydroxide. The dissolved oxygen probe was calibrated to 0% by unplugging the DO probe and to 100% with air saturation. The vessel was aerated at 2 vvm and dissolved oxygen maintained at 30% by cascade control of agitation. An overnight culture of HT115 (DE3) containing pAPSE10379 was grown in LB containing 100 ug/ul of ampicillin and 12.5 ug/ul of tetracycline at 37° C. to inoculate the seed medium. The seed media is a defined media consisting of 5.68 g/L Na2HPO4, 1.34 g/L KH₂PO4, 6.6 g/L (NH4)2SO4, 10 g/L glucose, 1× trace metal and 1× vitamin solutions maintained at a pH of 7.0. To ensure plasmid stability antibiotics are added at 100 ug/ul ampicillin and 12.5 ug/ul tetracycline. At saturation (OD600 3-5) the seed cultures are used to provide 10% inoculum for the fermenter.

During fed batch-cultures a 50% (w/v) solution of glucose was added according to a carbon limiting DO stat feeding strategy. The basal medium consists of 6 g/L K2HPO4, 3 g/L NaHPO4, 10 g/L (NH4) 2SO4, 1 g/L MgSO4, 1× trace metal solution with antibiotics added at 100 ug/ul of ampicillin and 12.5 ug/ul of tetracycline. Upon exhaustion of the initial carbon source provided by the glucose the feed solution is added automatically in a manner that maintains the DO level at 30% of saturation.

Once the cell culture has reached an OD600 of 60 the cells are induced with 1 mM IPTG or a feed of 20 g/L of lactose by switching the glucose feed to a lactose feed. After induction 1 mL samples are taken at different times post induction. The samples are lysed by sonication of the cell pellet into 20 mM Tris-HCl at pH 7. Total RNA from the cell pellet is purified using well-known Trizol extraction procedures. Briefly 1 volume of cell lysate is added to 1 volumes of Trizol RNA extraction reagent. Addition of 1 volume of chloroform results in the RNA partitioning to the aqueous layer leaving the protein and DNA contaminants behind.

To analyze the yield of dsRNA the total RNA sample is diluted to 1 ug/ul and subjected to RNAseA treatment. The reaction is carried out in 20 mM Tris at pH 7.0 and 37° C. for 40 minutes. Once this is done proteinase K is added to the reaction to remove the nuclease and is allowed to react at 37° C. for 40 minutes. Upon completion of this step the dsRNA remaining is diluted in half, quarters and eighths in order to determine the concentration of the dsRNA using gel densitometry.

Quantification of dsRNA yield by gel densitometry was performed by comparing the intensity of dsRNA bands versus dsDNA bands of known mass and weight on a 1.5% agarose gel containing ethidium bromide. The lambda 100 bp quantifiable DNA marker was used and a standard curve was generated to determine the range in which the dsRNA from the fermentation can be reliably quantified. The computer program calculates the amount of dsRNA in the amount of sample loaded on the gel and a back calculation that considers the dilution steps is performed. Yields of dsRNA at levels as high as 3 g/L have been calculated with both IPTG and lactose as inducers under these conditions. These results indicate that further increases in dsRNA production are possible by improving fermentation conditions.

Example 10

Compositions and Methods for dsRNA Production in Tram Positive Bacteria

The ability of gram-positive bacteria to produce increased levels of dsRNA by co-expression of capsid proteins can be examined in the following manner. *Corynebacterium glutamicum* MB001 (DE3) strain DSM 102071, containing an inducible T7 RNA polymerase gene (described in Kortmann, et al., *A chromosomally encoded T7 RNA polymerase-dependent gene expression system for Corynebacterium glutamicum; construction and comparative evaluation at the single cell level*. Microb Technol. 8 (2): 253-65. March 2015) is modified to knockout the me gene homolog encoding RNAse III. Briefly, PCR primers capable of amplifying a 1.2 kb sequence homologous to the sequence present in *C. glutamicum* strain MB001 (DE3) immediately upstream of the me gene and PCR primers capable of amplifying a 1.5 kb sequence homologous to the sequence immediately downstream of the me gene are synthesized. A PCR amplification reaction using *C. glutamicum* strain MB001 (DE3) genomic DNA and said primers results in a single DNA fragment comprising the 1.2 kb and 1.5 kb target sequences joined together (by standard overlap PCR methods) to produce an approximately 2.7 kb SalI-BamHI synthetic DNA fragment. This SalI-BamHI DNA fragment and plasmid pK18mobsacB (ATCC 87097, described by Schafer, et al., *Small mobilizable multi purpose cloning vectors derived from the Escherichia coli plasmids pK18 and pK19: selection of defined deletions in the chromosome of Corynebacterium glutamicum*. Gene 145:69-73) are digested with SalI and BamHI and the products ligated together to produce plasmid pAPSE10429 (SEQ ID NO: 29). Plasmid pAPSE 10429 is transformed into *C. glutamicum* strain MB001 and transformants selected on kanamycin containing solid LB medium to identify chromosomal integrants. Kanamycin resistant clones are transferred to a solid LB medium containing 20% sucrose. Conversion of sucrose by the sacB gene product is toxic to *C. glutamicum* strain MB001 so only those chromosomal integrants that subsequently delete the sacB gene from the chromosome can survive on such media. Surviving colonies are grown up and screened by PCR to confirm concomitant loss of the rnc locus from the chromosome. The desired strain is designated *C. glutamicum* MB001 (DE3) rnc. This strain possesses an inducible T7 RNA polymerase and lacks the rnc gene and is suitable for testing the efficacy of dsRNA production in the presence and absence of capsid protein.

A shuttle vector capable of expression of capsid coat protein and dsRNA in both *E. coli* and *C. glutamicum* is constructed by synthesizing a DNA comprising the origin of replication of the gram-positive plasmid pCG1 (GeneBank Accession No. AB027714; described by Trautwetter and Blanco, Structural organization of the *Corynebacterium* glutamicum plasmid pCG100. J. Gen. Microbiol. 137:2093-101 1991) and the kanamycin resistance gene of pK18mobsacB. This synthetic DNA (SEQ ID NO: 30) is ligated into the previously described dsRNA containing plasmids at the unique NruI restriction site to allow testing whether the presence of capsid protein in gram-positive *C. glutamicum* MB001 (DE3) rnc strain produces dsRNA at high levels as described below.

Insertion of the synthetic DNA comprising the pCG1 origin of replication and the kanamycin resistance gene is accomplished by digesting pAPSE10279 with NruI and ligating the phosphorylated synthetic DNA into the plasmid to produce plasmid pAPSE10430 (SEQ ID NO: 31). Plasmid pAPSE10430 contains the kanamycin resistance gene, the bacteriophage MS2 coat protein, and the dsRNA construct based on the previously described 294 base sense and antisense sequences homologous to the Colorado potato beetle beta actin gene separated by a 166 base non-homologous loop and entirely lacking any pac sequences. In similar fashion, the synthetic DNA comprising the pCG1 origin of replication and the kanamycin resistance gene is also ligated into Nrul digested pAPSE10303 to produce pAPSE10431 (SEQ ID NO: 32). Plasmid pAPSE10431 contains resistance genes to ampicillin and kanamycin, as well as the same inducible dsRNA construct as pAPSE10430. However, pAPSE10431 lacks the inducible MS2 coat protein gene of pAPSE10430. The relevant features of pAPSE10430 and pAPSE10431 are presented in Table 2 and the relationship between these two plasmids and their parental plasmids, pAPSE 10279 and pAPSE10303, respectively, can be determined by comparing Table 2 and Table 1.

Additional plasmids containing one, two, and three pac sites, with and without MS2 coat protein, are constructed using the same procedure. Plasmid pAPSE10432 (SEQ ID NO: 33) containing a single pac site 3' of the beta actin stem loop structure and encoding the MS2 coat protein gene is produced by ligating the synthetic DNA fragment into the Nrul site of pAPSE10219. Plasmid pAPSE10433 (SEQ ID NO: 34) is produced by ligating the synthetic DNA fragment into the Nrul site of pAPSE10304. Plasmid pAPSE10433 is identical to pAPSE10432 except it lacks an inducible MS2 coat protein gene. Plasmid pAPSE10434 (SEQ ID NO: 35) containing two pac site sequences located one on either side of the beta actin stem loop and encoding the MS2 coat protein is produced by ligating the synthetic DNA fragment into the Nrul site of pAPSE10216. Plasmid pAPSE10435 (SEQ ID NO: 36) is produced by ligating the synthetic DNA fragment into the Nrul site of pAPSE10305. Plasmid pAPSE10435 is identical to pAPSE10434 except it lacks an inducible MS2 coat protein gene. Plasmid pAPSE10436 (SEQ ID NO: 37) containing three pac site sequences with one each 5' and 3' of the beta actin stem loop and one within the loop sequence itself (as depicted in FIG. 1) and encoding the MS2 coat protein is produced by ligating the synthetic DNA fragment into the Nrul site of pAPSE10269. Plasmid pAPSE10437 (SEQ ID NO: 38) is produced by ligating the synthetic DNA fragment into the Nrul site of pAPSE10306. Plasmid pAPSE10437 is identical to pAPSE104360 except it lacks an inducible MS2 coat protein gene.

In each case, following ligation of the synthetic DNA fragment into the Nrul site of the target plasmid, transforthe dsRNA precursor in the plasmids lacking coat protein. The induced cultures are allowed to grow for at least 4 hours post-induction to allow sufficient time for accumulation of the MS2 coat protein and dsRNA target. Cells are collected by centrifugation at 3,000 g at 4 C. Each pellet is stored at 4° C. until processing.

The dsRNA is purified by re-suspending each pellet in approximately 0.1 volume of 20 mM Tris-HCl, pH 7.0, containing 10 mM NaCl and sonicated to lyse the cells. Cell debris is removed by centrifugation at 16,000 g. The resulting lysate is mixed with 3 volumes of Trizol (Ambion Life Technologies) and the RNA is extracted by adding 1 volume of chloroform. Addition of NaCl to a final concentration of 500 mM to the aqueous layer and subsequent ethanol precipitation results in a pellet containing the 294 bp siRNA precursor and RNA from the C. glutamicum host.

To determine the amount of dsRNA produced by the C. glutamicum transformed with plasmids containing various pac site configurations, with and without MS2 coat protein, the ethanol pellets are resuspended and treated with RNAseA for 1 hour at 37° C. followed by Proteinase K digestion for 1 hour at 37° C. Quantification of the dsRNA is accomplished by gel densitometry using a BioRad ChemiDoc MP Imaging System. Several dilutions of the treated dsRNA are run on a 1.5% agarose gel containing 0.001% ethidium bromide. A 100 bp quantifiable dsDNA ladder (QuantiBP DNA ladder Lambda) is used as the standard curve and the dsRNA is quantified at the concentration that falls within the linear range of the standard curve. Software such as Image Lab 4.1 determines the concentration of the dsRNA loaded on the gel and a final yield of dsRNA is determined by accounting for the dilutions associated with the dsRNA samples present on the gel.

Table 2 summarizes the predicted results of the dsRNA yield determination of the Colorado potato beetle beta actin dsRNA produced by C. glutamicum MB001 (DE3) me and the various plasmids described above. Such results confirm that gram positive hosts such as C. glutamicum produce large quantities of dsRNA by co-expression of the MS2 coat gene and a dsRNA target of interest.

TABLE 2

Predicted production of dsRNA by C. glutamicum MB001(DE3) me as a function of variation in dsRNA structure and the presence or absence of coat protein.

| RNA Structure as depicted in | Plasmid | Loop size (bases) | Stem size (bp) | Stem sequence | Coat protein | dsRNA (mg/L) |
|---|---|---|---|---|---|---|
| FIG. 6 | pAPSE10430 | 166 | 294 | beta actin | MS2 | ~60 |
| FIG. 6 | pAPSE10431 | 166 | 294 | beta actin | none | ~4 |
| FIG. 5 | pAPSE10432 | 166 | 294 | beta actin | MS2 | ~120 |
| FIG. 5 | pAPSE10433 | 166 | 294 | beta actin | none | ~4 |
| FIG. 4 | pAPSE10434 | 166 | 294 | beta actin | MS2 | ~250 |
| FIG. 4 | pAPSE10435 | 166 | 294 | beta actin | none | ~4 |
| FIG. 1 | pAPSE10436 | 166 | 294 | beta actin | MS2 | ~250 |
| FIG. 1 | pAPSE10437 | 166 | 294 | beta actin | none | 4 | mants the ligation reactions are desalted and transformed in to C. glutamicum MB001 (DE3) rnc and selected for resistance to kanamycin. The selected clones are subsequently grown at 32° C. in 100 ml of LB media containing kanamycin until the culture reaches OD600 0.8, at which time isopropyl I3-D-thiogalactopyranoside is added to a final concentration of 1 mM to induce T7 polymerase directed transcription of the MS2 coat protein and the dsRNA, or just Example 11

Compositions and Methods for dsRNA Production in Yeast

To create a Saccharomyces cerevisiae production host suitable for dsRNA accumulation utilizing the MS2 bacteriophage coat protein, the Rntl gene of S. cerevisiae YPH 500 (ATCC 7662.6) is knocked out according to the procedure of Gardenr and Jasperson (Gardner, J M and Jaspersen, S L, *Manipulating the yeast genome: deletion, mutation and tagging by PCR*. Methods Mol Biol. 1205:45-78, 2014). The KanMx4 gene is amplified from pML104-KanMx4 plasmid (Laughery, et al., *New vectors for simple and streamlined CRISPR-Cas9 genome editing in Saccharomyces cerevisiae*. Yeast 32 (12): 711-20 Sep. 21, 2015) with PCR primers including 60 base pair (bp) upstream (forward primer) and 60 bp downstream (reverse primer) regions of the *S. cerevisiae* Rntl gene. The resulting PCR product is introduced into chemically competent *S. cerevisiae* cells following the established *S. cerevisiae* transformation protocol. The transformed cells are incubated overnight without selection marker to allow for homologous recombination to occur, where in the kanMx4 gene carrying 60 bp upstream and downstream regions of Rntl replaced the Rntl gene. Following overnight incubation, the transformed cells are plated on YPD plates carrying G418 as selection marker. G418 resistant colonies are screened by PCR to confirm presence of kanMx4 gene and deletion of Rntl gene in the YPH 500 genome.

*S. cerevisiae* expression vectors pESC-His, pESC-Leu, pESC-Ura and pESC-Trp are widely used for recombinant protein expression in *S. cerevisiae*. Each of the pESC vectors (Agilent Technologies, Santa Clara CA) contains one of four different yeast-selectable markers (HIS3, TRP1, LEU2, or URA3) in the same vector backbone, which allows expression of two different genes in a single yeast cell. The pESC series vectors are used with *S. cerevisiae* strain YPH 500 (M_ATaura3-52 lys2-801 amber ade2-101 ochre trpl-A63 his3-A200 leu2-A1). In this example, the pESC-Trp vector is selected for expression of MS2 coat protein and target dsRNA sequence inside *S. cerevisiae*, although any of the other pESC vectors could be employed using similar methods since these vectors can replicate in *S. cerevisiae* as well as *E. coli*, which facilitates molecular manipulations necessary to produce dsRNA.

The pESC-Trp vector is modified by cloning a 50-base pair multi-cloning site linker containing BamHI, Swat, AsiSI, Notl, SacII and Nhel sites, downstream of the GAL1 promoter into the existing BamHI and Nhel sites. Following this, the beta actin stem loop sequence (dsRNA) of pAPSE10279 is excised as an AsiSI/Notl fragment and ligated into the AsiSI/Notl sites of the modified pESC-Trp vector. Expression of the dsRNA in this plasmid is under the control of galactose inducible promoter GAL1. The new vector is named pAPSE10439 (SEQ ID NO: 39). Another plasmid, pAPSE10440 (SEQ ID NO: 40), which is identical to pAPSE10439, but also includes the MS2 coat protein. Plasmid pAPSE10440 is constructed by PCR amplifying the MS2 coat protein expression sequences of pAPSE10279 with a forward primer carrying an EcoRI restriction site on the 5' end and the reverse primer carrying Sacl site on the 3' end. The PCR product is digested with EcoRI and Sacl and cloned into the cognate sites of pAPSE10439. Thus, pAPSE10439 inducibly expresses the dsRNA from the GAL1 promoter, whereas pAPSE 10440 inducibly expresses the dsRNA sequence from the GAL1 promoter and the MS2 coat protein from the GAL10 promoter, Similar plasmid pairs are constructed using this technique. Plasmids pAPSE10441 (SEQ ID NO: 41) and pAPSE10442 (SEQ ID NO: 42) are produced by digesting pAPSE10439 and pAPSE10440 with AsiSI and Noll and isolating the vector fragment. Plasmid pAPSE10219 is also digested with AsiSI and Notl and the dsRNA sequence is isolated. The isolated dsRNA sequence is ligated into the pAPSE10439 vector to form pAPSE10441 and the isolated dsRNA sequence is ligated into the pAPSE10440 vector to form pAPSE10442. Plasmids pAPSE10443 (SEQ ID NO: 43) and pAPSE10444 (SEQ ID NO: 44) are produced by digesting pAPSE10439 and pAPSE10440 with AsiSI and Notl and isolating the vector fragment. Plasmid pAPSE10216 is also digested with AsiSI and Noll and the dsRNA sequence is isolated. The isolated dsRNA sequence is ligated into the pAPSE10439 vector to form pAPSE10443 and the isolated dsRNA sequence is ligated into the pAPSE10440 vector to form pAPSE10444. Plasmids pAPSE10445 (SEQ ID NO: 45) and pAPSE10446 (SEQ ID NO: 46) are produced by digesting pAPSE10439 and pAPSE 10440 with AsiSI and Notl and isolating the vector fragment. Plasmid pAPSE 10269 is also digested with AsiSI and Notl and the dsRNA sequence is isolated. The isolated dsRNA sequence is ligated into the pAPSE10439 vector to form pAPSE10445 and the isolated dsRNA sequence is ligated into the pAPSE10440 vector to form pAPSE10446.

Chemically competent YPH 500 DRnt1 cells are transformed with each of the above mentioned plasmids (pAPSE10439-46) separately and individual clones selected on synthetic dextrose minimal (SD) tryptophan (trp) drop out plates. After inoculating the 100 ml SD-Trp drop out broth the cultures are grown for 12 to 16 hours. The cells from the culture are then harvested by centrifugation at 3000 g for 5 minutes, the cell pellet is washed once with sterile water and the cells re-suspended in synthetic galactose minimal broth (SG) lacking tryptophan. The cells are grown in the SG-trp drop out broth overnight to induce production and accumulation of dsRNA and MS2 coat protein (where appropriate). Cells are harvested by centrifugation at 3,000 g at 4 C. Each pellet is stored at −20° C. until processing.

The dsRNA is purified by re-suspending each pellet (10 ml culture) in approximately 1.0 ml of yeast cell lysis buffer (Sigma C4482). The resulting lysate is mixed with 3 volumes of Trizol (Ambion Life Technologies) and the RNA extracted by adding 1 volume of chloroform. Addition of NaCl to a final concentration of 500 mM to the aqueous layer and subsequent ethanol precipitation results in a pellet containing the dsRNA and RNA from the *S. cerevisiae* host. The resulting RNA pellet is dissolved in 20 mM Tris HCl pH 7.0 and RNA concentration of the sample determined. To determine the amount of dsRNA produced by the *S. cerevisiae* strains, a known amount of RNA (10 ug) from each RNA sample from pAPSE10439-pAPSE10446) are digested with RNAseA for 1 hour at 37° C. followed by Proteinase K digestion for 1 hour at 37° C. The resulting samples contain only the dsRNA target. Quantification of the dsRNA is done by gel densitometry using a BioRad ChemiDoc MP Imaging System. Several dilutions of the RNAse A reaction are run on a gel that contains 1.5% agarose and 0.001% ethidium bromide. A 100 bp quantifiable dsDNA ladder (QuantiBP DNA ladder Lambda) is used as the standard curve and the dsRNA is quantified at the concentration that falls within the linear range of the standard curve. Using Image Lab 4.1 software, the concentration of the dsRNA loaded on the gel is determine and a final yield of dsRNA calculated by accounting for the dilutions of the dsRNA loaded on the gel.

Table 2 summarizes the predicted results of the dsRNA yield determination of the Colorado potato beetle beta actin dsRNA produced by *S. cerevisiae* YPH-500 and the various plasmids described above. Such results confirm that yeasts such as *S. cerevisiae* produce large quantities of dsRNA by co-expression of the MS2 coat gene and a dsRNA target of interest.

TABLE 2

Predicted production of dsRNA by *S. cerevisiae*
YPH 500 as a function of variation in
dsRNA structure and the presence or absence of coat protein.

| RNA Structure as depicted in | Plasmid | Loop size (bases) | Stem size (bp) | Stem sequence | Coat protein | dsRNA (mg/L) |
|---|---|---|---|---|---|---|
| FIG. 6 | pAPSE 10440 | 166 | 294 | beta actin | MS2 | ~60 |
| FIG. 6 | pAPSE 10439 | 166 | 294 | beta actin | none | ~4 |
| FIG. 5 | pAPSE 10442 | 166 | 294 | beta actin | MS2 | ~120 |
| FIG. 5 | pAPSE 10441 | 166 | 294 | beta actin | none | ~4 |
| FIG. 4 | pAPSE 10444 | 166 | 294 | beta actin | MS2 | ~250 |
| FIG. 4 | pAPSE 10443 | 166 | 294 | beta actin | none | ~4 |
| FIG. 1 | pAPSE 10446 | 166 | 294 | beta actin | MS2 | ~250 |
| FIG. 1 | pAPSE 10445 | 166 | 294 | beta actin | none | 4 |

Example 12

Delivery of dsRNA to Colorado Potato Beetle
Larvae

The superior environmental stability and delivery of dsRNA according to the present invention is demonstrated by delivering naked dsRNA targeting a gene of interest or *Corynebacterium glutamicum* comprising dsRNA targeting a gene of interest ("test substances") to mixed sex, seven-day old Colorado potato beetle larvae of similar size. The test substances are provided as a solution and contain a silicone surfactant to enhance spreading and prevent roll off form the leaf surface.

Briefly, a 10 µl droplet of each test substance is added to the surface of a potato leaf disc. The solution is spread with the pipette tip to cover at least the central half of the leaf disc, with the assumption that the larvae will devour all of the leaf tissue without veins. The pipette is discarded after applying test solution to a leaf disc to prevent the leaf's RNAse's from contaminating the test solution.

The test substance is allowed to dry on the leaf surface prior to test initiation. At day 0, the CPB larvae is starved for 12 hours and then placed on to the treated leaf disc in the petri dish. The larvae is allowed to feed on the treated leaf disc until leaf tissue is devoured (only leaf veins are remaining).

Once the treated leaf discs are completely consumed, the remaining veins are removed and discarded and the larvae is placed on a maintenance diet of potato leaves. Following treatment, larvae is maintained for 15 days on the maintenance diet.

During the test period the test individuals are observed daily to record mortality. The test is preferably carried out with 4 replications with 5 larvae/replication.

Example 13

Delivery of dsRNA to Diamond Back Moths

The test is preferably conducted with four replications and includes appropriate controls, including a non-specific RNA control.

Second-instar larvae of diamond back moths are used for the test. Test individuals are starved for 12 hours prior to testing. Each test substance ("naked" dsRNA" targeting inhibitor of apoptosis gene or *Corynebacterium glutamicum* comprising dsRNA targeting inhibitor of apoptosis gene) will contain a silicone surfactant to enhance spreading and prevent roll off from the leaf surface. Each application to a 1 cm² leaf disc will be made in 10 ml volume. Tubes containing each test substance is vortexed prior to use.

After application of each test substance to the leaf disc, the disposable pipette tip is used, if necessary, to help spreading of the liquid on the leaf surface. A new pipette tip is used for each application to prevent RNAses from the leaf surface destroying the RNA in the treatment solutions.

The test substances are allowed to dry on the leaf surface prior to initiating the test. The treated cabbage leaf disc is placed in a petri dish (each petri dish serves as a replication for a treatment). DBM larvae (10 second instar larvae replication) is applied to the dried leaf surface. After allowing the larvae to feed on the treated leaf discs for 48 hours (or before, if all of the leaf disc has been consumed), larvae is shifted to untreated leaves to observe larvae survival/mortality. The larvae are considered alive if they move in response to touch during the observation period. During the test, the temperature should be maintained at 26 C.

A significant increase in mortality is demonstrated with the *Corynebacterium glutamicum* comprising dsRNA compared to the "naked" dsRNA.

Example 14

Environmental Stability of dsRNA in
*Corynebacterium* glutamicum

The environmental stability of dsRNA in *Corynebacterium glutamicum* was assessed in several pertinent environments. Briefly, *Corynebacterium glutamicum* comprising an expression cassette encoding a dsRNA of about 350 base pairs of inhibitor of apoptosis gene in Diamondback moths, were incubated under appropriate conditions to produce a significant amount of dsRNA.

Briefly, 650 µl of concentrated host cells carrying the target dsRNA were centrifuged and the supernatant (around 350 µl) was removed and replaced with 350 µl of tap water, pond water or puddle water ("rain water collected in a pot hole") in separate tubes. The tubes were then incubated at room temperature for the following time periods: (i) tap water for 168 hours (ii) pond water for 72, 96 or 168 hours and (iii) puddle water for 72, 96 or 168 hours. The amount of dsRNA in each case was assessed by collecting 100 µl of host cells at the specified time periods and extracting dsRNA. 500 ng of total RNA (RNaseA/ProtK treated), as assessed by nanodrop reading, were loaded on a gel for each sample and the amount of target dsRNA was quantified. The amount of dsRNA at 0 hours (i.e. the starting amount of dsRNA) served as a control.

For "naked" dsRNA, in each case, 1.0 ug of dsRNA in 5 µl+95 µl water of puddle, pond or tap water were incubated at room temperature. Aliquots were collected at the specified time points and assessed on gel as described above.

As shown in Table 3 below, after 7 days of incubation at room temperature in water from different sources, about 64% of the target dsRNA was recovered from the host cells. In stark contrast, substantially all of the "naked" dsRNA was degraded over the same time periods in the identical environments. The ability of *Corynebacterium glutamicum* cells to protect dsRNA for more than 7 days in pond water (which contains various microbes and RNAses) indicates that *Corynebacterium glutamicum* can be used to deliver target dsRNA to insect pests in particularly relevant environments for insect pest control, such as puddle water, pond water and a leaf surface. Further, this experimental data is very strong evidence for the use of the present methods to stably delivery dsRNA to e.g. mosquito larvae in standing water.

Notably, some initial degradation of dsRNA within the *C. glutamicum* host occurs within the first 24 hours, which seems to be due to internal RNAses. As such, dsRNA stability may be further increased in killed host cells.

TABLE 3

Figure 7:
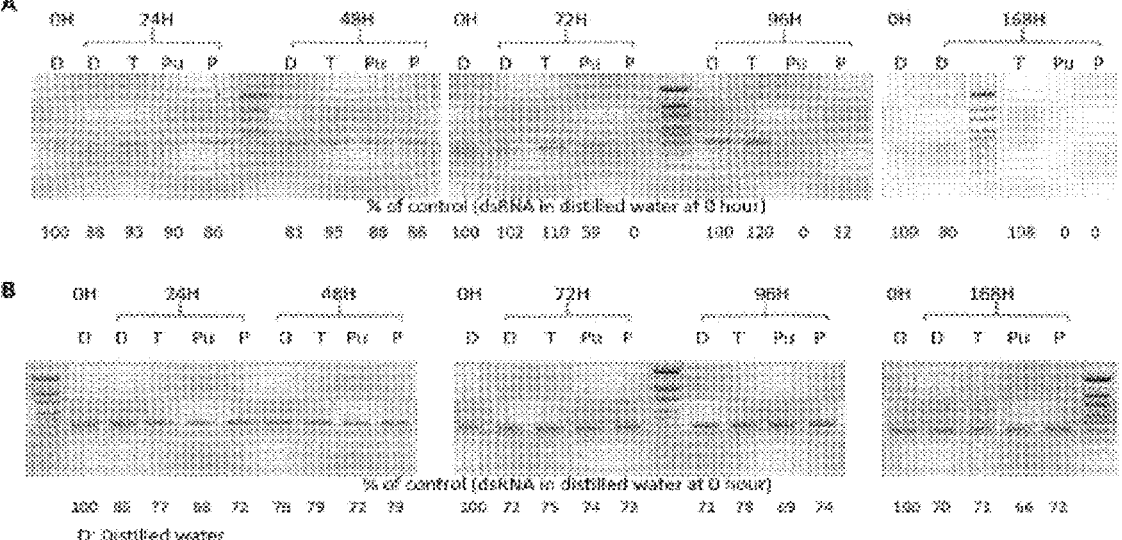
FIG. 7 depicts gels demonstrating stability of dsRNA contained inside *C. glutamicum* (C.g) cells vs naked dsRNA upon exposure to water from different environments over the specified time periods. A: depicts gels demonstrating stability of naked dsRNA in water from different environments over the specified time periods. B: depicts gels demonstrating stability of dsRNA contained inside *C. glutamicum* (C.g) cells in water from different environments over the specified time periods. The amount of dsRNA seen in different lanes of the gels was quantitated using the AzureSpot 2.0 software. The amount of dsRNA quantitated at zero hour (0 H) in distilled water (D) was used as control for each gel to calculate the percentage of dsRNA remaining at specified time periods in different environments for both naked dsRNA and the dsRNA contained inside *C. glutamicum* in that gel. D=Distilled water; T=Tap water; Pu=Puddle water; P=Pond water.

Environmental stability of naked dsRNA vs dsRNA in bacterial host.
Data summarized from FIG. 7.

| Water | Percentage of Control (dsRNA at 0 Hr in Distilled Water) | | | | | | | | | |
| | 24 Hr | | 48 Hr | | 72 Hr | | 96 Hr | | 168 Hr | |
| Treatment | Naked | C. glutamicum | Naked | C. glutamicum | Naked | C. glutamicum | Naked | C. glutamicum | Naked | C. glutamicum |
|---|---|---|---|---|---|---|---|---|---|---|
| Distilled | 88 | 81.8 | 91 | 77.9 | 102 | 72 | 100 | 71.3 | 80 | 70.3 |
| Tap | 93 | 76.8 | 95 | 79.5 | 110 | 74.6 | 120 | 77.6 | 108 | 71.3 |
| Puddle | 93 | 68 | 38 | 72.2 | 59 | 73.6 | 0 | 69.3 | | 66 |
| Pond | 86 | 72 | 96 | 79.5 | 0 | 72.6 | 12 | 73.5 | | 71.3 |

Example 15

Environmental Stability of dsRNA in *Corynebacterium* Glutamicum

The environmental stability of dsRNA in *Corynebacterium glutamicum* is assessed on a leaf surface. Briefly, naked dsRNA targeting an insect gene and C.g. host cells containing the same dsRNA are placed on a plant leaf for 1, 3 and 6 days at room temperature. At each time point, the amount of dsRNA in each case is assessed by washing off the host cells, extracting dsRNA and quantifying the amount of dsRNA targeting an insect gene by gel, with the amount of dsRNA at 0 hours serving as a control.

What is claimed is:

1. A method for controlling an insect pest, the method comprising: contacting the insect pest in a body of water or insect saliva with a composition comprising a microorganism comprising:

(i) a promoter operably linked to a DNA sequence encoding a dsRNA molecule that specifically inhibits expression of a target gene in an insect pest, wherein the target gene is selected from extracellular signal-regulated kinase 1 (erkA), tubulin, vATPase, acetyl choline esterase, chitin synthase gene A, beta-actin, and genes coding for inhibitors of apoptosis; and (ii) a promoter operably linked to a DNA sequence comprising a coat protein gene encoding a capsid protein or N-terminus of the capsid protein coding sequence (CDS); and wherein the dsRNA in the composition comprising the microorganism exhibits at least 60% undegraded dsRNA for at least 7 days in the body of water or insect saliva relative to the dsRNA when isolated.

2. The method according to claim 1, wherein the capsid protein is encoded by a leviviridae coat protein gene.

3. The method according to claim 1, wherein the capsid protein is encoded by the coat protein gene of bacteriophage MS2 or bacteriophage Qβ.

4. The method according to claim 1, wherein the DNA sequence encoding the dsRNA and the DNA sequence of the coat protein gene encoding the capsid protein are present on one plasmid or extrachromosomal element within the micro-organism.

5. The method according to claim 4, wherein the plasmid or extrachromosomal element is pAPSE10180 encoded by SEQ ID NO: 1, pAPSE10269 encoded by SEQ ID NO: 8, pAPSE10216 encoded by SEQ ID NO: 10, pAPSE10219 encoded by SEQ ID NO: 12, pAPSE10279 encoded by SEQ ID NO: 14, pAPSE10270 encoded by SEQ ID NO: 16, pAPSE10271 encoded by SEQ ID NO: 17, pAPSE10272 encoded by SEQ ID NO: 18, pAPSE10292 encoded by SEQ ID NO: 19, pAPSE10291 encoded by SEQ ID NO: 20, pAPSE10359 encoded by SEQ ID NO: 25, pAPSE10372 encoded by SEQ ID NO: 27, pAPSE10429 encoded by SEQ ID NO: 29, pAPSE10430 encoded by SEQ ID NO: 31, pAPSE10431 encoded by SEQ ID NO: 32, pAPSE10432 encoded by SEQ ID NO: 33, pAPSE10434 encoded by SEQ ID NO: 35, pAPSE10436 encoded by SEQ ID NO: 37, pAPSE10440 encoded by SEQ ID NO: 40, pAPSE10442 encoded by SEQ ID NO: 42, pAPSE10444 encoded by SEQ ID NO: 44, or pAPSE10445 encoded by SEQ ID NO: 45.

6. The method according to claim 1, wherein the micro-organism is an *Escherichia coli* strain.

7. The method according to claim 1, wherein the micro-organism is a *Corynebacterium glutamicum* strain.

8. The method according to claim 1, wherein the target gene is beta-actin or the genes coding for inhibitors of apoptosis.

9. The method according to claim 1 wherein the micro-organism is alive or is killed.

10. The method according to claim 1, wherein the insect pest is a member of the order Lepidoptera, the order Cole-optera, the order Hymenoptera, or the order Diptera.

11. The method according to claim 1, wherein the insect pest is a diamond back moth or a Colorado potato beetle.

12. The method of claim 1, wherein the body of water is selected from puddle water and pond water.

* * * * *

```
                    SEQUENCE LISTING

<160> NUMBER OF SEQ ID NOS: 46

<210> SEQ ID NO 1
<211> LENGTH: 5498
<212> TYPE: DNA
<213> ORGANISM: Artificial Sequence
<220> FEATURE:
<223> OTHER INFORMATION: Recombinant plasmid pAPSE10180; ErkA stem
      loop + capsid protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (127)..(145)
<223> OTHER INFORMATION: bacteriophage MS2 pac sequence
<220> FEATURE:
<221> NAME/KEY: misc_feature
<222> LOCATION: (175)..(182)
<223> OTHER INFORMATION: restriction endonuclease AsiSI recognition site
<220> FEATURE:
<221> NAME/KEY: misc_feature
<222> LOCATION: (179)..(384)
<223> OTHER INFORMATION: ErkA sense strand gene fragment
<220> FEATURE:
<221> NAME/KEY: misc_feature
<222> LOCATION: (436)..(454)
<223> OTHER INFORMATION: bacteriophage MS2 pac sequence
<220> FEATURE:
<221> NAME/KEY: misc_feature
<222> LOCATION: (504)..(511)
<223> OTHER INFORMATION: restriction endonuclease NotI recognition site
<220> FEATURE:
<221> NAME/KEY: misc_feature
<222> LOCATION: (505)..(696)
<223> OTHER INFORMATION: ErkA antisense strand gene fragment
<220> FEATURE:
<221> NAME/KEY: misc_feature
<222> LOCATION: (692)..(699)
<223> OTHER INFORMATION: restriction endonuclease PacI recognition site
<220> FEATURE:
<221> NAME/KEY: misc_feature
<222> LOCATION: (709)..(727)
<223> OTHER INFORMATION: bacteriophage MS2 pac sequence
<220> FEATURE:
<221> NAME/KEY: terminator
<222> LOCATION: (743)..(790)
<223> OTHER INFORMATION: bacteriophage T7 transcription terminator
<220> FEATURE:
```

```
<221> NAME/KEY: promoter
<222> LOCATION: (1116)..(1134)
<223> OTHER INFORMATION: bacteriophage T7 gene 1 promoter
<220> FEATURE:
<221> NAME/KEY: gene
<222> LOCATION: (1207)..(1596)
<223> OTHER INFORMATION: bacteriophage MS2 coat protein gene
<220> FEATURE:
<221> NAME/KEY: terminator
<222> LOCATION: (1448)..(1495)
<223> OTHER INFORMATION: bacteriophage T7 transcription terminator

<400> SEQUENCE: 1
ttcagatctc gatcccgcga aattaatacg actcactata gggagaccac aacggtttcc      60
ctctagatca caagtttgta caaaaaagca ggctaagaag gagatataca tacgccggcc     120
attcaaacat gaggattacc catgtaacct aaggccggtg tccaggcgcg ctccgcgatc     180
gcacgcggac aaagttcctc aatctaatgc tgaagttata aggggacaaa tatttgaagt     240
tggtcctagg tatattaaac tcgcctatat aggtgaagga gcttatggca tggttgtgtc     300
tgcggatgac acgctaacaa accaaagagt tgcaataaaa aaaatatcgc cctttgaaca     360
ccaaacttat tgctactaca gtttaaacgc aatcgcagca aactccggca tctactaata     420
gacgccggcc attcaacatg aggattaccc atgtaaccta agaagacaac aaagaagttc     480
aactctttat gtattgatct tccgcggccg ccaataagtt tggtgttcaa agggcgatat     540
tttttttatt gcaactcttt ggtttgttag cgtgtcatcc gcagacacaa ccatgccata     600
agctccttca cctatatagg cgagtttaat atacctagga ccaacttcaa atatttgtcc     660
ccttataact tcagcattag attgaggaac tttaattaag gagttcaaac atgaggatca     720
cccatgtcga agctcccaca ccctagcata accccttggg gcctctaaac gggtcttgag     780
gggttttttg ctgaaaggag gaactatatc cggatatcca caggacgggt gtggtcgcca     840
tgatcgcgta gtcgatagtg gctccaagta gcgaagcgag caggactggg cggcgggcat     900
gcatcgtcca ttccgacagc atcgccagtc actatggcgt gctgctagcg ctatatgcgt     960
tgatgcaatt tctatgcgca cccgttctcg gagcactgtc cgaccgcttt ggccgccgcc    1020
cagtcctgct cgcttcgcta cttggagcca ctatcgacta cgcgatcatg gcgaccacac    1080
ccgtcctgtg gatccagatc tcgatcccgc gaaattaata cgactcacta tagggagacc    1140
acaacggttt ccctctagat cacaagtttg tacaaaaaag caggctaaga aggagatata    1200
catatggcgt ctaactttac ccaattcgtt ctggttgata acggcggtac gggtgacgtt    1260
accgtagctc cgtccaactt cgccaacggt gttgcggaat ggattagctc taacagccgc    1320
tctcaggcct acaaagtcac gtgctccgtt cgtcagtcta gcgcgcagaa tcgcaaatac    1380
accatcaaag ttgaagtacc gaaagtcgca acgcagaccg taggcggcgt agaactccca    1440
gttgcggcct ggcgctctta cctcaacatg gaactgacta ttccgatttt tgcgacgaac    1500
tccgactgcg aactgattgt taaggcaatg cagggcctgc tgaaagacgg taatccgatc    1560
ccatctgcaa tcgctgctaa ctctggcatt tactaataag cggacgcgct gccaccgctg    1620
agcaataact agcataaccc cttggggcct ctaaacgggt cttgaggggt tttttgctga    1680
aaggaggaac tatatccggc atgcaccatt ccttgcggcg gcggtgctca acggcctcaa    1740
cctactactg ggctgcttcc taatgcagga gtcgcataag ggagagcgtc gaccgatgcc    1800
cttgagagcc ttcaacccag tcagctcctt ccggtgggcg cggggcatga ctatcgtcgc    1860
cgcacttatg actgtcttct ttatcatgca actcgtagga caggtgccgg cagcgctctg    1920
ggtcattttc ggcgaggacc gctttcgctg gagcgcgacg atgatcggcc tgtcgcttgc    1980
```

-continued

```
ggtattcgga atcttgcacg ccctcgctca agccttcgtc actggtcccg ccaccaaacg    2040
tttcggcgag aagcaggcca ttatcgccgg catggcggcc gacgcgctgg gctacgtctt    2100
gctggcgttc gcgacgcgag gctggatggc cttccccatt atgattcttc tcgcttccgg    2160
cggcatcggg atgcccgcgt tgcaggccat gctgtccagg caggtagatg acgaccatca    2220
gggacagctt caaggatcgc tcgcggctct taccagccta acttcgatca ttggaccgct    2280
gatcgtcacg gcgatttatg ccgcctcggc gagcacatgg aacgggttgg catggattgt    2340
aggcgccgcc ctataccttg tctgcctccc cgcgttgcgt cgcggtgcat ggagccgggc    2400
cacctcgacc tgaatggaag ccggcggcac ctcgctaacg gattcaccac tccaagaatt    2460
ggagccaatc aattcttgcg gagaactgtg aatgcgcaaa ccaacccttg gcagaacata    2520
tccatcgcgt ccgccatctc cagcagccgc acgcggcgca tctcgggcag cgttgggtcc    2580
tggccacggg tgcgcatgat cgtgctcctg tcgttgagga cccggctagg ctggcggggt    2640
tgccttactg gttagcagaa tgaatcaccg atacgcgagc gaacgtgaag cgactgctgc    2700
tgcaaaacgt ctgcgacctg agcaacaaca tgaatggtct tcggtttccg tgtttcgtaa    2760
agtctggaaa cgcggaagtc agcgccctgc accattatgt tccggatctg catcgcagga    2820
tgctgctggc taccctgtgg aacacctaca tctgtattaa cgaagcgctg gcattgaccc    2880
tgagtgattt ttctctggtc ccgccgcatc cataccgcca gttgtttacc ctcacaacgt    2940
tccagtaacc gggcatgttc atcatcagta acccgtatcg tgagcatcct ctctcgtttc    3000
atcggtatca ttaccccat gaacagaaat cccccttaca cggaggcatc agtgaccaaa    3060
caggaaaaaa ccgcccttaa catggcccgc tttatcagaa gccagacatt aacgcttctg    3120
gagaaactca acgagctgga cgcggatgaa caggcagaca tctgtgaatc gcttcacgac    3180
cacgctgatg agctttaccg cagctgcctc gcgcgtttcg gtgatgacgg tgaaaacctc    3240
tgacacatgc agctcccgga gacggtcaca gcttgtctgt aagcggatgc cgggagcaga    3300
caagcccgtc agggcgcgtc agcgggtgtt ggcgggtgtc ggggcgcagc catgacccag    3360
tcacgtagcg atagcggagt gtatactggc ttaactatgc ggcatcagag cagattgtac    3420
tgagagtgca ccatatgcgg tgtgaaatac cgcacagatg cgtaaggaga aaataccgca    3480
tcaggcgctc ttccgcttcc tcgctcactg actcgctgcg ctcggtcgtt cggctgcggc    3540
gagcggtatc agctcactca aaggcggtaa tacggttatc cacagaatca ggggataacg    3600
caggaaagaa catgtgagca aaaggccagc aaaaggccag gaaccgtaaa aaggccgcgt    3660
tgctggcgtt tttccatagg ctccgccccc ctgacgagca tcacaaaaat cgacgctcaa    3720
gtcagaggtg gcgaaacccg acaggactat aaagatacca ggcgtttccc cctggaagct    3780
ccctcgtgcg ctctcctgtt ccgaccctgc cgcttaccgg atacctgtcc gcctttctcc    3840
cttcgggaag cgtggcgctt tctcatagct cacgctgtag gtatctcagt tcggtgtagg    3900
tcgttcgctc caagctgggc tgtgtgcacg aaccccccgt tcagcccgac cgctgcgcct    3960
tatccggtaa ctatcgtctt gagtccaacc cggtaagaca cgacttatcg ccactggcag    4020
cagccactgg taacaggatt agcagagcga ggtatgtagg cggtgctaca gagttcttga    4080
agtggtggcc taactacggc tacactagaa ggacagtatt tggtatctgc gctctgctga    4140
agccagttac cttcggaaaa agagttggta gctcttgatc cggcaaacaa accaccgctg    4200
gtagcggtgt tttttttgtt tgcaagcagc agattacgcg cagaaaaaaa ggatctcaag    4260
aagatccttt gatcttttct acggggtctg acgctcagtg gaacgaaaac tcacgttaag    4320
```

-continued

```
ggattttggt catgagatta tcaaaaagga tcttcaccta gatccttta aattaaaaat    4380 gaagttttaa atcaatctaa agtatatatg agtaaacttg gtctgacagt taccaatgct    4440
taatcagtga ggcacctatc tcagcgatct gtctatttcg ttcatccata gttgcctgac    4500
tccccgtcgt gtagataact acgatacggg agggcttacc atctggcccc agtgctgcaa    4560
tgataccgcg agacccacgc tcaccggctc cagatttatc agcaataaac cagccagccg    4620
gaagggccga gcgcagaagt ggtcctgcaa ctttatccgc ctccatccag tctattaatt    4680
gttgccggga agctagagta agtagttcgc cagttaatag tttgcgcaac gttgttgcca    4740
ttgctgcagg catcgtggtg tcacgctcgt cgtttggtat ggcttcattc agctccggtt    4800
cccaacgatc aaggcgagtt acatgatccc ccatgttgtg caaaaaagcg gttagctcct    4860
tcggtcctcc gatcgttgtc agaagtaagt tggccgcagt gttatcactc atggttatgg    4920
cagcactgca taattctctt actgtcatgc catccgtaag atgcttttct gtgactggtg    4980
agtactcaac caagtcattc tgagaatagt gtatgcggcg accgagttgc tcttgcccgg    5040
cgtcaacacg ggataatacc gcgccacata gcagaacttt aaaagtgctc atcattggaa    5100
aacgttcttc ggggcgaaaa ctctcaagga tcttaccgct gttgagatcc agttcgatgt    5160
aacccactcg tgcacccaac tgatcttcag catcttttac tttcaccagc gtttctgggt    5220
gagcaaaaac aggaaggcaa aatgccgcaa aaaagggaat aagggcgaca cggaaatgtt    5280
gaatactcat actcttcctt tttcaatatt attgaagcat ttatcagggt tattgtctca    5340
tgagcggata catatttgaa tgtatttaga aaaataaaca ataggggtt ccgcgcacat    5400 ttccccgaaa agtgccacct gacgtctaag aaaccattat tatcatgaca ttaacctata    5460
aaaataggcg tatcacgagg cccttttcgtc ttcaagaa                          5498
```

```
<210> SEQ ID NO 2
<211> LENGTH: 4696
<212> TYPE: DNA
<213> ORGANISM: Artificial Sequence
<220> FEATURE:
<223> OTHER INFORMATION: Recombinant plasmid pAPSE10181; ErkA stem
      loop - coat protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (127)..(145)
<223> OTHER INFORMATION: bacteriophage MS2 pac sequence
<220> FEATURE:
<221> NAME/KEY: misc_feature
<222> LOCATION: (175)..(182)
<223> OTHER INFORMATION: restriction endonuclease AsiSI recognition site
<220> FEATURE:
<221> NAME/KEY: misc_feature
<222> LOCATION: (179)..(384)
<223> OTHER INFORMATION: ErkA sense strand gene fragment
<220> FEATURE:
<221> NAME/KEY: misc_feature
<222> LOCATION: (436)..(454)
<223> OTHER INFORMATION: bacteriophage MS2 pac sequence
<220> FEATURE:
<221> NAME/KEY: misc_feature
<222> LOCATION: (504)..(511)
<223> OTHER INFORMATION: restriction endonuclease NotI recognition site
<220> FEATURE:
<221> NAME/KEY: misc_feature
<222> LOCATION: (505)..(696)
<223> OTHER INFORMATION: ErkA antisense strand gene fragment
<220> FEATURE:
<221> NAME/KEY: misc_feature
<222> LOCATION: (692)..(699)
```

-continued

<223> OTHER INFORMATION: restriction endonuclease PacI recognition site
<220> FEATURE:
<221> NAME/KEY: misc_feature
<222> LOCATION: (709)..(727)
<223> OTHER INFORMATION: bacteriophage MS2 pac sequence
<220> FEATURE:
<221> NAME/KEY: terminator
<222> LOCATION: (743)..(790)
<223> OTHER INFORMATION: bacteriophage T7 transcription terminator
<220> FEATURE:
<221> NAME/KEY: misc_feature
<222> LOCATION: (897)..(902)
<223> OTHER INFORMATION: restriction endonuclease SphI recognition site

<400> SEQUENCE: 2

```
ttcagatctc gatcccgcga aattaatacg actcactata gggagaccac aacggtttcc      60
ctctagatca caagtttgta caaaaaagca ggctaagaag gagatataca tacgccggcc     120
attcaaacat gaggattacc catgtaacct aaggccggtg tccaggcgcg ctccgcgatc     180
gcacgcggac aaagttcctc aatctaatgc tgaagttata aggggacaaa tatttgaagt     240
tggtcctagg tatattaaac tcgcctatat aggtgaagga gcttatggca tggttgtgtc     300
tgcggatgac acgctaacaa accaaagagt tgcaataaaa aaaatatcgc cctttgaaca     360
ccaaacttat tgctactaca gtttaaacgc aatcgcagca aactccggca tctactaata     420
gacgccggcc attcaacatg aggattaccc atgtaaccta agaagacaac aaagaagttc     480
aactctttat gtattgatct tccgcggccg ccaataagtt tggtgttcaa agggcgatat     540
tttttttatt gcaactcttt ggtttgttag cgtgtcatcc gcagacacaa ccatgccata     600
agctccttca cctatatagg cgagtttaat atacctagga ccaacttcaa atatttgtcc     660
ccttataact tcagcattag attgaggaac tttaattaag gagttcaaac atgaggatca     720
cccatgtcga agctcccaca ccctagcata accccttggg gcctctaaac gggtcttgag     780
gggttttttg ctgaaaggag gaactatatc cggatatcca caggacgggt gtggtcgcca     840
tgatcgcgta gtcgatagtg gctccaagta gcgaagcgag caggactggg cggcgggcat     900
gcaccattcc ttgcggcggc ggtgctcaac ggcctcaacc tactactggg ctgcttccta     960
atgcaggagt cgcataaggg agagcgtcga ccgatgccct tgagagcctt caacccagtc    1020
agctccttcc ggtgggcgcg gggcatgact atcgtcgccg cacttatgac tgtcttcttt    1080
atcatgcaac tcgtaggaca ggtgccggca gcgctctggg tcattttcgg cgaggaccgc    1140
tttcgctgga gcgcgacgat gatcggcctg tcgcttgcgg tattcggaat cttgcacgcc    1200
ctcgctcaag ccttcgtcac tggtcccgcc accaaacgtt tcggcgagaa gcaggccatt    1260
atcgccggca tggcggccga cgcgctgggc tacgtcttgc tggcgttcgc gacgcgaggc    1320
tggatggcct tccccattat gattcttctc gcttccggcg gcatcgggat gcccgcgttg    1380
caggccatgc tgtccaggca ggtagatgac gaccatcagg acagcttca aggatcgctc    1440 gcggctctta ccagcctaac ttcgatcatt ggaccgctga tcgtcacggc gatttatgcc    1500
gcctcggcga gcacatggaa cgggttggca tggattgtag gcgccgccct ataccttgtc    1560
tgcctccccg cgttgcgtcg cggtgcatgg agccgggcca cctcgacctg aatggaagcc    1620
ggcggcacct cgctaacgga ttcaccactc caagaattgg agccaatcaa ttcttgcgga    1680
gaactgtgaa tgcgcaaacc aacccttggc agaacatatc catcgcgtcc gccatctcca    1740
gcagccgcac gcggcgcatc tcgggcagcg ttgggtcctg ccacgggtg cgcatgatcg    1800 tgctcctgtc gttgaggacc cggctaggct ggcggggttg ccttactggt tagcagaatg    1860
aatcaccgat acgcgagcga acgtgaagcg actgctgctg caaaacgtct gcgacctgag    1920
```

-continued

```
caacaacatg aatggtcttc ggtttccgtg tttcgtaaag tctggaaacg cggaagtcag   1980
cgccctgcac cattatgttc cggatctgca tcgcaggatg ctgctggcta ccctgtggaa   2040
cacctacatc tgtattaacg aagcgctggc attgaccctg agtgatttt ctctggtccc    2100 gccgcatcca taccgccagt tgtttaccct cacaacgttc cagtaaccgg gcatgttcat   2160
catcagtaac ccgtatcgtg agcatcctct ctcgtttcat cggtatcatt accccatga    2220 acagaaatcc cccttacacg gaggcatcag tgaccaaaca ggaaaaaacc gcccttaaca   2280
tggcccgctt tatcagaagc cagacattaa cgcttctgga gaaactcaac gagctggacg   2340
cggatgaaca ggcagacatc tgtgaatcgc ttcacgacca cgctgatgag ctttaccgca   2400
gctgcctcgc gcgtttcggt gatgacggtg aaaacctctg acacatgcag ctcccggaga   2460
cggtcacagc ttgtctgtaa gcggatgccg ggagcagaca gcccgtcag ggcgcgtcag    2520 cgggtgttgg cgggtgtcgg ggcgcagcca tgacccagtc acgtagcgat agcggagtgt   2580
atactggctt aactatgcgg catcagagca gattgtactg agagtgcacc atatgcggtg   2640
tgaaataccg cacagatgcg taaggagaaa ataccgcatc aggcgctctt ccgcttcctc   2700
gctcactgac tcgctgcgct cggtcgttcg gctgcggcga gcggtatcag ctcactcaaa   2760
ggcggtaata cggttatcca cagaatcagg ggataacgca ggaaagaaca tgtgagcaaa   2820
aggccagcaa aaggccagga accgtaaaaa ggccgcgttg ctggcgtttt tccataggct   2880
ccgcccccct gacgagcatc acaaaaatcg acgctcaagt cagaggtggc gaaacccgac   2940
aggactataa agataccagg cgtttcccc tggaagctcc ctcgtgcgct ctcctgttcc    3000
gaccctgccg cttaccggat acctgtccgc ctttctccct tcgggaagcg tggcgctttc   3060
tcatagctca cgctgtaggt atctcagttc ggtgtaggtc gttcgctcca gctgggctg    3120 tgtgcacgaa ccccccgttc agcccgaccg ctgcgcctta tccggtaact atcgtcttga   3180
gtccaacccg gtaagacacg acttatcgcc actggcagca gccactggta acaggattag   3240
cagagcgagg tatgtaggcg gtgctacaga gttcttgaag tggtggccta actacggcta   3300
cactagaagg acagtatttg gtatctgcgc tctgctgaag ccagttacct tcggaaaaag   3360
agttggtagc tcttgatccg gcaaacaaac caccgctggt agcggtggtt ttttgtttg    3420 caagcagcag attacgcgca gaaaaaaagg atctcaagaa gatcctttga tcttttctac   3480
ggggtctgac gctcagtgga acgaaaactc acgttaaggg attttggtca tgagattatc   3540
aaaaaggatc ttcacctaga tccttttaaa ttaaaaatga agttttaaat caatctaaag   3600
tatatatgag taaacttggt ctgacagtta ccaatgctta atcagtgagg cacctatctc   3660
agcgatctgt ctatttcgtt catccatagt tgcctgactc cccgtcgtgt agataactac   3720
gatacgggag ggcttaccat ctggccccag tgctgcaatg ataccgcgag acccacgctc   3780
accggctcca gatttatcag caataaacca gccagccgga agggccgagc gcagaagtgg   3840
tcctgcaact ttatccgcct ccatccagtc tattaattgt tgccgggaag ctagagtaag   3900
tagttcgcca gttaatagtt tgcgcaacgt tgttgccatt gctgcaggca tcgtggtgtc   3960
acgctcgtcg tttggtatgg cttcattcag ctccggttcc caacgatcaa ggcgagttac   4020
atgatccccc atgttgtgca aaaaagcggt tagctccttc ggtcctccga tcgttgtcag   4080
aagtaagttg gccgcagtgt tatcactcat ggttatggca gcactgcata attctcttac   4140
tgtcatgcca tccgtaagat gctttttctgt gactggtgag tactcaacca agtcattctg   4200
agaatagtgt atgcggcgac cgagttgctc ttgcccggcg tcaacacggg ataataccgc   4260
```

-continued

```
gccacatagc agaactttaa aagtgctcat cattggaaaa cgttcttcgg ggcgaaaact    4320
ctcaaggatc ttaccgctgt tgagatccag ttcgatgtaa cccactcgtg cacccaactg    4380
atcttcagca tcttttactt tcaccagcgt ttctgggtga gcaaaaacag gaaggcaaaa    4440
tgccgcaaaa aagggaataa gggcgacacg gaaatgttga atactcatac tcttcctttt    4500
tcaatattat tgaagcattt atcagggtta ttgtctcatg agcggataca tatttgaatg    4560
tatttagaaa aataaacaaa taggggttcc gcgcacattt ccccgaaaag tgccacctga    4620
cgtctaagaa accattatta tcatgacatt aacctataaa aataggcgta tcacgaggcc    4680
ctttcgtctt caagaa                                                    4696
```

```
<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide probe

<400> SEQUENCE: 3
ggccggcgtc tattagtaga tgcc                                             24

<210> SEQ ID NO 4
<211> LENGTH: 5591
<212> TYPE: DNA
<213> ORGANISM: Artificial Sequence
<220> FEATURE:
<223> OTHER INFORMATION: Recombinant plasmid pAPSE10189; beta actin
      sense strand + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: promoter
<222> LOCATION: (1209)..(1227)
<223> OTHER INFORMATION: bacteriophage T7 gene 1 promoter
<220> FEATURE:
<221> NAME/KEY: gene
<222> LOCATION: (1300)..(1689)
<223> OTHER INFORMATION: bacteriophage MS2 cot protein gene
<220> FEATURE:
<221> NAME/KEY: gene
<222> LOCATION: (1300)..(1689)
<223> OTHER INFORMATION: bacteriophage MS2 coat protein gene
<220> FEATURE:
<221> NAME/KEY: terminator
<222> LOCATION: (1722)..(1769)
```

<223> OTHER INFORMATION: bacteriophage T7 transcription terminator

<400> SEQUENCE: 4

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccegtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaacctttcg gattataaca tcacatctag gcgcgcctga cgatcaacca     720
taccagacgg accgaatacc cggtctgaac gagggcggcc gcggtaccca agaagtactt     780
agagttaatt aaggagttca aacatgagga tcacccatgt cgaagctccc acaccctagc     840
ataacccctt ggggcctcta aacgggtctt gaggggtttt ttgctgaaag gaggaactat     900
atccggatat ccacaggacg ggtgtggtcg ccatgatcgc gtagtcgata gtggctccaa     960
gtagcgaagc gagcaggact gggcggcggg catgcatcgt ccattccgac agcatcgcca    1020
gtcactatgg cgtgctgcta gcgctatatg cgttgatgca atttctatgc gcacccgttc    1080
tcggagcact gtccgaccgc tttggccgcc gcccagtcct gctcgcttcg ctacttggag    1140
ccactatcga ctacgcgatc atggcgacca cacccgtcct gtggatccag atctcgatcc    1200
cgcgaaatta atacgactca ctatagggag accacaacgg tttccctcta gatcacaagt    1260
ttgtacaaaa aagcaggcta agaaggagat atacatatgg cgtctaactt tacccaattc    1320
gttctggttg ataacggcgg tacgggtgac gttaccgtag ctccgtccaa cttcgccaac    1380
ggtgttgcgg aatggattag ctctaacagc cgctctcagg cctacaaagt cacgtgctcc    1440
gttcgtcagt ctagcgcgca gaatcgcaaa tacaccatca aagttgaagt accgaaagtc    1500
gcaacgcaga ccgtaggcgg cgtagaactc ccagttgcgg cctggcgctc ttacctcaac    1560
atggaactga ctattccgat tttttgcgacg aactccgact gcgaactgat tgttaaggca    1620
atgcagggcc tgctgaaaga cggtaatccg atcccatctg caatcgctgc taactctggc    1680
atttactaat aagcggacgc gctgccaccg ctgagcaata actagcataa ccccttgggg    1740
cctctaaacg ggtcttgagg ggttttttgc tgaaaggagg aactatatcc ggcatgcacc    1800
attccttgcg gcggcggtgc tcaacggcct caacctacta ctgggctgct tcctaatgca    1860
ggagtcgcat aagggagagc gtcgaccgat gcccttgaga gccttcaacc cagtcagctc    1920
cttccggtgg gcgcggggca tgactatcgt cgccgcactt atgactgtct ctttatcat     1980 gcaactcgta ggacaggtgc cggcagcgct ctgggtcatt ttcggcgagg accgctttcg    2040
ctggagcgcg acgatgatcg gcctgtcgct tgcggtattc ggaatcttgc acgccctcgc    2100
tcaagccttc gtcactggtc ccgccaccaa acgtttcggc gagaagcagg ccattatcgc    2160
cggcatggcg gccgacgcgc tgggctacgt cttgctggcg ttcgcgacgc gaggctggat    2220
ggccttcccc attatgattc ttctcgcttc cggcggcatc gggatgcccg cgttgcaggc    2280
```

```
catgctgtcc aggcaggtag atgacgacca tcagggacag cttcaaggat cgctcgcggc   2340
tcttaccagc ctaacttcga tcattggacc gctgatcgtc acggcgattt atgccgcctc   2400
ggcgagcaca tggaacgggt tggcatggat tgtaggcgcc gccctatacc ttgtctgcct   2460
ccccgcgttg cgtcgcggtg catggagccg ggccacctcg acctgaatgg aagccggcgg   2520
cacctcgcta acggattcac cactccaaga attggagcca atcaattctt gcggagaact   2580
gtgaatgcgc aaaccaaccc ttggcagaac atatccatcg cgtccgccat ctccagcagc   2640
cgcacgcggc gcatctcggg cagcgttggg tcctggccac gggtgcgcat gatcgtgctc   2700
ctgtcgttga ggacccggct aggctggcgg ggttgcctta ctggttagca gaatgaatca   2760
ccgatacgcg agcgaacgtg aagcgactgc tgctgcaaaa cgtctgcgac ctgagcaaca   2820
acatgaatgg tcttcggttt ccgtgtttcg taaagtctgg aaacgcggaa gtcagcgccc   2880
tgcaccatta tgttccggat ctgcatcgca ggatgctgct ggctaccctg tggaacacct   2940
acatctgtat taacgaagcg ctggcattga ccctgagtga tttttctctg gtcccgccgc   3000
atccataccg ccagttgttt accctcacaa cgttccagta accgggcatg ttcatcatca   3060
gtaacccgta tcgtgagcat cctctctcgt ttcatcggta tcattacccc catgaacaga   3120
aatccccctt acacggaggc atcagtgacc aaacaggaaa aaaccgccct taacatggcc   3180
cgctttatca gaagccagac attaacgctt ctggagaaac tcaacgagct ggacgcggat   3240
gaacaggcag acatctgtga atcgcttcac gaccacgctg atgagcttta ccgcagctgc   3300
ctcgcgcgtt tcggtgatga cggtgaaaac ctctgacaca tgcagctccc ggagacggtc   3360
acagcttgtc tgtaagcgga tgccgggagc agacaagccc gtcagggcgc gtcagcgggt   3420
gttggcgggt gtcggggcgc agccatgacc cagtcacgta gcgatagcgg agtgtatact   3480
ggcttaacta tgcggcatca gagcagattg tactgagagt gcaccatatg cggtgtgaaa   3540
taccgcacag atgcgtaagg agaaaatacc gcatcaggcg ctcttccgct tcctcgctca   3600
ctgactcgct gcgctcggtc gttcggctgc ggcgagcggt atcagctcac tcaaaggcgg   3660
taatacggtt atccacagaa tcaggggata acgcaggaaa gaacatgtga gcaaaaggcc   3720
agcaaaaggc caggaaccgt aaaaaggccg cgttgctggc gtttttccat aggctccgcc   3780
cccctgacga gcatcacaaa aatcgacgct caagtcagag gtggcgaaac ccgacaggac   3840
tataaagata ccaggcgttt cccctggaa gctccctcgt gcgctctcct gttccgaccc    3900
tgccgcttac cggatacctg tccgcctttc tcccttcggg aagcgtggcg ctttctcata   3960
gctcacgctg taggtatctc agttcggtgt aggtcgttcg ctccaagctg ggctgtgtgc   4020
acgaaccccc cgttcagccc gaccgctgcg ccttatccgg taactatcgt cttgagtcca   4080
acccggtaag acacgactta tcgccactgg cagcagccac tggtaacagg attagcagag   4140
cgaggtatgt aggcggtgct acagagttct tgaagtggtg gcctaactac ggctacacta   4200
gaaggacagt atttggtatc tgcgctctgc tgaagccagt taccttcgga aaaagagttg   4260
gtagctcttg atccggcaaa caaaccaccg ctggtagcgg tggttttttt gtttgcaagc   4320
agcagattac gcgcagaaaa aaaggatctc aagaagatcc tttgatcttt tctacggggt   4380
ctgacgctca gtggaacgaa aactcacgtt aagggatttt ggtcatgaga ttatcaaaaa   4440
ggatcttcac ctagatcctt ttaaattaaa aatgaagttt taaatcaatc taaagtatat   4500
atgagtaaac ttggtctgac agttaccaat gcttaatcag tgaggcacct atctcagcga   4560
tctgtctatt tcgttcatcc atagttgcct gactccccgt cgtgtagata actacgatac   4620
```

```
gggagggctt accatctggc cccagtgctg caatgatacc gcgagaccca cgctcaccgg    4680
ctccagattt atcagcaata aaccagccag ccggaagggc cgagcgcaga agtggtcctg    4740
caactttatc cgcctccatc cagtctatta attgttgccg ggaagctaga gtaagtagtt    4800
cgccagttaa tagtttgcgc aacgttgttg ccattgctgc aggcatcgtg gtgtcacgct    4860
cgtcgtttgg tatggcttca ttcagctccg gttcccaacg atcaaggcga gttacatgat    4920
cccccatgtt gtgcaaaaaa gcggttagct ccttcggtcc tccgatcgtt gtcagaagta    4980
agttggccgc agtgttatca ctcatggtta tggcagcact gcataattct cttactgtca    5040
tgccatccgt aagatgcttt tctgtgactg gtgagtactc aaccaagtca ttctgagaat    5100
agtgtatgcg gcgaccgagt tgctcttgcc cggcgtcaac acgggataat accgcgccac    5160
atagcagaac tttaaaagtg ctcatcattg gaaaacgttc ttcggggcga aaactctcaa    5220
ggatcttacc gctgttgaga tccagttcga tgtaacccac tcgtgcaccc aactgatctt    5280
cagcatcttt tactttcacc agcgtttctg ggtgagcaaa aacaggaagg caaaatgccg    5340
caaaaaaggg aataagggcg acacggaaat gttgaatact catactcttc ctttttcaat    5400
attattgaag catttatcag ggttattgtc tcatgagcgg atacatattt gaatgtattt    5460
agaaaaataa acaaataggg gttccgcgca catttccccg aaaagtgcca cctgacgtct    5520
aagaaaccat tattatcatg acattaacct ataaaaatag gcgtatcacg aggccctttc    5580
gtcttcaaga a                                                        5591
```

```
<210> SEQ ID NO 5
<211> LENGTH: 5591
<212> TYPE: DNA
<213> ORGANISM: Artificial Sequence
<220> FEATURE:
<223> OTHER INFORMATION: Recombinant plasmid pAPSE10190; beta actin
      antisense strand + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin antisense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: promoter
<222> LOCATION: (1209)..(1227)
<223> OTHER INFORMATION: bacteriophage T7 gene 1 promoter
<220> FEATURE:
<221> NAME/KEY: gene
<222> LOCATION: (1300)..(1689)
<223> OTHER INFORMATION: bacteriophage MS2 coat protein gene
<220> FEATURE:
```

-continued

```
<221> NAME/KEY: terminator
<222> LOCATION: (1722)..(1769)
<223> OTHER INFORMATION: bacteriophage T7 transcription terminator
```

```
<400> SEQUENCE: 5
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta atacccatg tccaggcgcg      360 ctccgcgatc gctcatccca gttggtgatg ataccgtgtt cgatgggta tttcagggtg      420 aggatacctc ttttgctttg ggcttcatct cctacgtatg agtccttttg tcccataccg     480
accatgactc cttgatgcct tgggcgaccg acgatcgagg ggaagacggc acggggtgcg     540
tcatctcctg cgaaaccggc tttgcacata ccggatccat tgtctacgac aagagccgct     600
acatcgtcgt cacacatgtt gtcttttgag gttggacact gctcactaga cagaaaaacc     660
tcgtgcgttt aaacctttcg gattataaca tcacatctag gcgcgcctga cgatcaacca     720
taccagacgg accgaatacc cggtctgaac gagggcggcc gcggtaccca agaagtactt     780
agagttaatt aaggagttca aacatgagga tcacccatgt cgaagctccc acccctagc      840 ataccccctt ggggcctcta aacgggtctt gaggggtttt ttgctgaaag gaggaactat     900
atccggatat ccacaggacg ggtgtggtcg ccatgatcgc gtagtcgata gtggctccaa     960
gtagcgaagc gagcaggact gggcggcggg catgcatcgt ccattccgac agcatcgcca    1020
gtcactatgg cgtgctgcta gcgctatatg cgttgatgca atttctatgc gcacccgttc    1080
tcggagcact gtccgaccgc tttggccgcc gcccagtcct gctcgcttcg ctacttggag    1140
ccactatcga ctacgcgatc atggcgacca cacccgtcct gtggatccag atctcgatcc    1200
cgcgaaatta atacgactca ctatagggag accacaacgg tttccctcta gatcacaagt    1260
ttgtacaaaa aagcaggcta agaaggagat atacatatgg cgtctaactt tacccaattc    1320
gttctggttg ataacggcgg tacgggtgac gttaccgtag ctccgtccaa cttcgccaac    1380
ggtgttgcgg aatggattag ctctaacagc cgctctcagg cctacaaagt cacgtgctcc    1440
gttcgtcagt ctagcgcgca gaatcgcaaa tacaccatca aagttgaagt accgaaagtc    1500
gcaacgcaga ccgtaggcgg cgtagaactc ccagttgcgg cctggcgctc ttacctcaac    1560
atggaactga ctattccgat ttttgcgacg aactccgact gcgaactgat tgttaaggca    1620
atgcagggcc tgctgaaaga cggtaatccg atcccatctg caatcgctgc taactctggc    1680
atttactaat aagcggacgc gctgccaccg ctgagcaata actagcataa cccccttgggg   1740 cctctaaacg ggtcttgagg ggttttttgc tgaaaggagg aactatatcc ggcatgcacc    1800
attccttgcg gcggcggtgc tcaacggcct caacctacta ctgggctgct tcctaatgca    1860
ggagtcgcat aagggagagc gtcgaccgat gcccttgaga gccttcaacc cagtcagctc    1920
cttccggtgg gcgcggggca tgactatcgt cgccgcactt atgactgtct tctttatcat    1980
gcaactcgta ggacaggtgc cggcagcgct ctgggtcatt ttcggcgagg accgctttcg    2040
ctggagcgcg acgatgatcg gcctgtcgct tgcggtattc ggaatcttgc acgccctcgc    2100
tcaagccttc gtcactggtc ccgccaccaa acgtttcggc gagaagcagg ccattatcgc    2160
cggcatggcg gccgacgcgc tgggctacgt cttgctggcg ttcgcgacgc gaggctggat    2220
```

-continued

```
ggccttcccc attatgattc ttctcgcttc cggcggcatc gggatgcccg cgttgcaggc     2280
catgctgtcc aggcaggtag atgacgacca tcagggacag cttcaaggat cgctcgcggc     2340
tcttaccagc ctaacttcga tcattggacc gctgatcgtc acggcgattt atgccgcctc     2400
ggcgagcaca tggaacgggt tggcatggat tgtaggcgcc gccctatacc ttgtctgcct     2460
ccccgcgttg cgtcgcggtg catggagccg ggccacctcg acctgaatgg aagccggcgg     2520
cacctcgcta acggattcac cactccaaga attggagcca atcaattctt gcggagaact     2580
gtgaatgcgc aaaccaaccc ttggcagaac atatccatcg cgtccgccat ctccagcagc     2640
cgcacgcggc gcatctcggg cagcgttggg tcctggccac gggtgcgcat gatcgtgctc     2700
ctgtcgttga ggacccggct aggctggcgg ggttgcctta ctggttagca gaatgaatca     2760
ccgatacgcg agcgaacgtg aagcgactgc tgctgcaaaa cgtctgcgac ctgagcaaca     2820
acatgaatgg tcttcggttt ccgtgtttcg taaagtctgg aaacgcggaa gtcagcgccc     2880
tgcaccatta tgttccggat ctgcatcgca ggatgctgct ggctaccctg tggaacacct     2940
acatctgtat taacgaagcg ctggcattga ccctgagtga tttttctctg gtcccgccgc     3000
atccataccg ccagttgttt accctcacaa cgttccagta accgggcatg ttcatcatca     3060
gtaacccgta tcgtgagcat cctctctcgt ttcatcggta tcattacccc catgaacaga     3120
aatccccctt acacggaggc atcagtgacc aaacaggaaa aaaccgccct taacatggcc     3180
cgctttatca gaagccagac attaacgctt ctggagaaac tcaacgagct ggacgcggat     3240
gaacaggcag acatctgtga atcgcttcac gaccacgctg atgagcttta ccgcagctgc     3300
ctcgcgcgtt tcggtgatga cggtgaaaac ctctgacaca tgcagctccc ggagacggtc     3360
acagcttgtc tgtaagcgga tgccgggagc agacaagccc gtcagggcgc gtcagcgggt     3420
gttggcgggt gtcggggcgc agccatgacc cagtcacgta gcgatagcgg agtgtatact     3480
ggcttaacta tgcggcatca gagcagattg tactgagagt gcaccatatg cggtgtgaaa     3540
taccgcacag atgcgtaagg agaaaatacc gcatcaggcg ctcttccgct tcctcgctca     3600
ctgactcgct gcgctcggtc gttcggctgc ggcgagcggt atcagctcac tcaaaggcgg     3660
taatacggtt atccacagaa tcaggggata acgcaggaaa gaacatgtga gcaaaaggcc     3720
agcaaaaggc caggaaccgt aaaaaggccg cgttgctggc gtttttccat aggctccgcc     3780
cccctgacga gcatcacaaa aatcgacgct caagtcagag gtggcgaaac ccgacaggac     3840
tataaagata ccaggcgttt ccccctggaa gctccctcgt gcgctctcct gttccgaccc     3900
tgccgcttac cggatacctg tccgcctttc tcccttcggg aagcgtggcg ctttctcata     3960
gctcacgctg taggtatctc agttcggtgt aggtcgttcg ctccaagctg ggctgtgtgc     4020
acgaaccccc cgttcagccc gaccgctgcg ccttatccgg taactatcgt cttgagtcca     4080
acccggtaag acacgactta tcgccactgg cagcagccac tggtaacagg attagcagag     4140
cgaggtatgt aggcggtgct acagagttct tgaagtggtg gcctaactac ggctacacta     4200
gaaggacagt atttggtatc tgcgctctgc tgaagccagt taccttcgga aaaagagttg     4260
gtagctcttg atccggcaaa caaaccaccg ctggtagcgg tggttttttt gtttgcaagc     4320
agcagattac gcgcagaaaa aaaggatctc aagaagatcc tttgatcttt tctacggggt     4380
ctgacgctca gtggaacgaa aactcacgtt aagggatttt ggtcatgaga ttatcaaaaa     4440
ggatcttcac ctagatcctt ttaaattaaa aatgaagttt taaatcaatc taaagtatat     4500
atgagtaaac ttggtctgac agttaccaat gcttaatcag tgaggcacct atctcagcga     4560
```

-continued

```
tctgtctatt tcgttcatcc atagttgcct gactccccgt cgtgtagata actacgatac    4620
gggagggctt accatctggc cccagtgctg caatgatacc gcgagaccca cgctcaccgg    4680
ctccagattt atcagcaata aaccagccag ccggaagggc cgagcgcaga agtggtcctg    4740
caactttatc cgcctccatc cagtctatta attgttgccg ggaagctaga gtaagtagtt    4800
cgccagttaa tagtttgcgc aacgttgttg ccattgctgc aggcatcgtg gtgtcacgct    4860
cgtcgtttgg tatggcttca ttcagctccg gttcccaacg atcaaggcga gttacatgat    4920
cccccatgtt gtgcaaaaaa gcggttagct ccttcggtcc tccgatcgtt gtcagaagta    4980
agttggccgc agtgttatca ctcatggtta tggcagcact gcataattct cttactgtca    5040
tgccatccgt aagatgcttt tctgtgactg gtgagtactc aaccaagtca ttctgagaat    5100
agtgtatgcg gcgaccgagt tgctcttgcc cggcgtcaac acgggataat accgcgccac    5160
atagcagaac tttaaaagtg ctcatcattg gaaaacgttc ttcggggcga aaactctcaa    5220
ggatcttacc gctgttgaga tccagttcga tgtaacccac tcgtgcaccc aactgatctt    5280
cagcatcttt tactttcacc agcgtttctg ggtgagcaaa aacaggaagg caaaatgccg    5340
caaaaaaggg aataagggcg acacggaaat gttgaatact catactcttc ctttttcaat    5400
attattgaag catttatcag ggttattgtc tcatgagcgg atacatattt gaatgtattt    5460
agaaaaataa acaaataggg gttccgcgca catttccccg aaaagtgcca cctgacgtct    5520
aagaaaccat tattatcatg acattaacct ataaaaatag gcgtatcacg aggccctttc    5580
gtcttcaaga a                                                        5591
```

<210> SEQ ID NO 6
<211> LENGTH: 4789
<212> TYPE: DNA
<213> ORGANISM: Artificial Sequence
<220> FEATURE:
<223> OTHER INFORMATION: Recombinant plasmid pAPSE10274; beta actin
      sense strand - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: misc_feature
<222> LOCATION: (990)..(995)
<223> OTHER INFORMATION: restriction endonuclease SphI  recognition site

<400> SEQUENCE: 6

-continued

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaacctttcg gattataaca tcacatctag gcgcgcctga cgatcaacca     720
taccagacgg accgaatacc cggtctgaac gagggcggcc gcggtaccca agaagtactt     780
agagttaatt aaggagttca acatgagga tcacccatgt cgaagctccc acaccctagc     840
ataacccctt ggggcctcta aacgggtctt gaggggtttt ttgctgaaag gaggaactat     900
atccggatat ccacaggacg ggtgtggtcg ccatgatcgc gtagtcgata gtggctccaa     960
gtagcgaagc gagcaggact gggcggcggg catgcaccat tccttgcggc ggcggtgctc    1020
aacggcctca acctactact gggctgcttc ctaatgcagg agtcgcataa gggagagcgt    1080
cgaccgatgc ccttgagagc cttcaaccca gtcagctcct tccggtgggc gcggggcatg    1140
actatcgtcg ccgcacttat gactgtcttc tttatcatgc aactcgtagg acaggtgccg    1200
gcagcgctct gggtcatttt cggcgaggac cgctttcgct ggagcgcgac gatgatcggc    1260
ctgtcgcttg cggtattcgg aatcttgcac gccctcgctc aagccttcgt cactggtccc    1320
gccaccaaac gtttcggcga gaagcaggcc attatcgccg gcatggcggc cgacgcgctg    1380
ggctacgtct tgctggcgtt cgcgacgcga ggctggatgg ccttccccat tatgattctt    1440
ctcgcttccg gcggcatcgg gatgcccgcg ttgcaggcca tgctgtccag gcaggtagat    1500
gacgaccatc agggacagct tcaaggatcg ctcgcggctc ttaccagcct aacttcgatc    1560
attggaccgc tgatcgtcac ggcgatttat gccgcctcgg cgagcacatg gaacgggttg    1620
gcatggattg taggcgccgc cctatacctt gtctgcctcc ccgcgttgcg tcgcggtgca    1680
tggagccggg ccacctcgac ctgaatggaa gccggcggca cctcgctaac ggattcacca    1740
ctccaagaat tggagccaat caattcttgc ggagaactgt gaatgcgcaa accaaccctt    1800
ggcagaacat atccatcgcg tccgccatct ccagcagccg cacgcggcgc atctcgggca    1860
gcgttgggtc ctggccacgg gtgcgcatga tcgtgctcct gtcgttgagg acccggctag    1920
gctggcgggg ttgccttact ggttagcaga atgaatcacc gatacgcgag cgaacgtgaa    1980
gcgactgctg ctgcaaaacg tctgcgacct gagcaacaac atgaatggtc ttcggtttcc    2040
gtgtttcgta aagtctggaa acgcggaagt cagcgccctg caccattatg ttccggatct    2100
gcatcgcagg atgctgctgg ctaccctgtg gaacacctac atctgtatta acgaagcgct    2160
ggcattgacc ctgagtgatt tttctctggt cccgccgcat ccataccgcc agttgtttac    2220
cctcacaacg ttccagtaac cgggcatgtt catcatcagt aacccgtatc gtgagcatcc    2280
tctctcgttt catcggtatc attacccccca tgaacagaaa tccccttac acggaggcat    2340 cagtgaccaa acaggaaaaa accgccctta acatggcccg ctttatcaga agccagacat    2400
```

```
taacgcttct ggagaaactc aacgagctgg acgcggatga acaggcagac atctgtgaat    2460
cgcttcacga ccacgctgat gagctttacc gcagctgcct cgcgcgtttc ggtgatgacg    2520
gtgaaaacct ctgacacatg cagctcccgg agacggtcac agcttgtctg taagcggatg    2580
ccgggagcag acaagcccgt cagggcgcgt cagcgggtgt tggcgggtgt cggggcgcag    2640
ccatgaccca gtcacgtagc gatagcggag tgtatactgg cttaactatg cggcatcaga    2700
gcagattgta ctgagagtgc accatatgcg gtgtgaaata ccgcacagat gcgtaaggag    2760
aaaataccgc atcaggcgct cttccgcttc ctcgctcact gactcgctgc gctcggtcgt    2820
tcggctgcgg cgagcggtat cagctcactc aaaggcggta atacggttat ccacagaatc    2880
aggggataac gcaggaaaga acatgtgagc aaaaggccag caaaaggcca ggaaccgtaa    2940
aaaggccgcg ttgctggcgt ttttccatag gctccgcccc cctgacgagc atcacaaaaa    3000
tcgacgctca agtcagaggt ggcgaaaccc gacaggacta taaagatacc aggcgtttcc    3060
ccctggaagc tccctcgtgc gctctcctgt tccgaccctg ccgcttaccg gatacctgtc    3120
cgcctttctc ccttcgggaa gcgtggcgct ttctcatagc tcacgctgta ggtatctcag    3180
ttcggtgtag gtcgttcgct ccaagctggg ctgtgtgcac gaaccccccg ttcagcccga    3240
ccgctgcgcc ttatccggta actatcgtct tgagtccaac ccggtaagac acgacttatc    3300
gccactggca gcagccactg gtaacaggat tagcagagcg aggtatgtag gcggtgctac    3360
agagttcttg aagtggtggc ctaactacgg ctacactaga aggacagtat ttggtatctg    3420
cgctctgctg aagccagtta ccttcggaaa aagagttggt agctcttgat ccggcaaaca    3480
aaccaccgct ggtagcggtg gtttttttgt ttgcaagcag cagattacgc gcagaaaaaa    3540
aggatctcaa gaagatcctt tgatcttttc tacggggtct gacgctcagt ggaacgaaaa    3600
ctcacgttaa gggattttgg tcatgagatt atcaaaaagg atcttcacct agatcctttt    3660
aaattaaaaa tgaagtttta aatcaatcta agtatatat gagtaaactt ggtctgacag    3720
ttaccaatgc ttaatcagtg aggcacctat ctcagcgatc tgtctatttc gttcatccat    3780
agttgcctga ctccccgtcg tgtagataac tacgatacgg gagggcttac catctggccc    3840
cagtgctgca atgataccgc gagacccacg ctcaccggct ccagatttat cagcaataaa    3900
ccagccagcc ggaagggccg agcgcagaag tggtcctgca actttatccg cctccatcca    3960
gtctattaat tgttgccggg aagctagagt aagtagttcg ccagttaata gtttgcgcaa    4020
cgttgttgcc attgctgcag gcatcgtggt gtcacgctcg tcgtttggta tggcttcatt    4080
cagctccggt tcccaacgat caaggcgagt tacatgatcc cccatgttgt gcaaaaaagc    4140
ggttagctcc ttcggtcctc cgatcgttgt cagaagtaag ttggccgcag tgttatcact    4200
catggttatg gcagcactgc ataattctct tactgtcatg ccatccgtaa gatgcttttc    4260
tgtgactggt gagtactcaa ccaagtcatt ctgagaatag tgtatgcggc gaccgagttg    4320
ctcttgcccg gcgtcaacac gggataatac cgcgccacat agcagaactt taaaagtgct    4380
catcattgga aaacgttctt cggggcgaaa actctcaagg atcttaccgc tgttgagatc    4440
cagttcgatg taacccactc gtgcacccaa ctgatcttca gcatctttta ctttcaccag    4500
cgtttctggg tgagcaaaaa caggaaggca aaatgccgca aaaaagggaa taagggcgac    4560
acggaaatgt tgaatactca tactcttcct ttttcaatat tattgaagca tttatcaggg    4620
ttattgtctc atgagcggat acatatttga atgtatttag aaaaataaac aaataggggt    4680
tccgcgcaca tttccccgaa aagtgccacc tgacgtctaa gaaaccatta ttatcatgac    4740
```

-continued attaacctat aaaaataggc gtatcacgag gcccttttcgt cttcaagaa                    4789

<210> SEQ ID NO 7
<211> LENGTH: 4789
<212> TYPE: DNA
<213> ORGANISM: Artificial Sequence
<220> FEATURE:
<223> OTHER INFORMATION: Recombinant plasmid pAPSE10275; beta actin
      antisense strand - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin antisense strand gene fragment
<220> FEATURE:
<221> NAME/KEY: misc_feature
<222> LOCATION: (667)..(674)
<223> OTHER INFORMATION: restriction endonuclease PmeI recogntion site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: misc_feature
<222> LOCATION: (990)..(995)
<223> OTHER INFORMATION: restriction endonuclease SphI recognition site

<400> SEQUENCE: 7
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gctcatccca gttggtgatg ataccgtgtt cgatgcggta tttcagggtg     420
aggatacctc ttttgctttg ggcttcatct cctacgtatg agtccttttg tcccataccg     480
accatgactc cttgatgcct tgggcgaccg acgatcgagg ggaagacggc acggggtgcg     540
tcatctcctg cgaaaccggc tttgcacata ccggatccat tgtctacgac aagagccgct     600
acatcgtcgt cacacatgtt gtcttttgag gttggacact gctcactaga cagaaaaacc     660
tcgtgcgttt aaacctttcg gattataaca tcacatctag gcgcgcctga cgatcaacca     720
taccagacgg accgaatacc cggtctgaac gagggcggcc gcggtaccca agaagtactt     780
agagttaatt aaggagttca aacatgagga tcacccatgt cgaagctccc acaccctagc     840
ataacccctt ggggcctcta aacgggtctt gaggggtttt ttgctgaaag gaggaactat     900
atccggatat ccacaggacg ggtgtggtcg ccatgatcgc gtagtcgata gtggctccaa     960
gtagcgaagc gagcaggact gggcggcggg catgcaccat tccttgcggc ggcggtgctc    1020

-continued

```
aacggcctca acctactact gggctgcttc ctaatgcagg agtcgcataa gggagagcgt   1080
cgaccgatgc ccttgagagc cttcaaccca gtcagctcct tccggtgggc gcggggcatg   1140
actatcgtcg ccgcacttat gactgtcttc tttatcatgc aactcgtagg acaggtgccg   1200
gcagcgctct gggtcatttt cggcgaggac cgctttcgct ggagcgcgac gatgatcggc   1260
ctgtcgcttg cggtattcgg aatcttgcac gccctcgctc aagccttcgt cactggtccc   1320
gccaccaaac gtttcggcga gaagcaggcc attatcgccg gcatggcggc cgacgcgctg   1380
ggctacgtct tgctggcgtt cgcgacgcga ggctggatgg ccttccccat tatgattctt   1440
ctcgcttccg gcggcatcgg gatgcccgcg ttgcaggcca tgctgtccag gcaggtagat   1500
gacgaccatc agggacagct tcaaggatcg ctcgcggctc ttaccagcct aacttcgatc   1560
attggaccgc tgatcgtcac ggcgatttat gccgcctcgg cgagcacatg gaacgggttg   1620
gcatggattg taggcgccgc cctatacctt gtctgcctcc ccgcgttgcg tcgcggtgca   1680
tggagccggg ccacctcgac ctgaatggaa gccggcggca cctcgctaac ggattcacca   1740
ctccaagaat tggagccaat caattcttgc ggagaactgt gaatgcgcaa accaaccctt   1800
ggcagaacat atccatcgcg tccgccatct ccagcagccg cacgcggcgc atctcgggca   1860
gcgttgggtc ctggccacgg gtgcgcatga tcgtgctcct gtcgttgagg acccggctag   1920
gctggcgggg ttgccttact ggttagcaga atgaatcacc gatacgcgag cgaacgtgaa   1980
gcgactgctg ctgcaaaacg tctgcgacct gagcaacaac atgaatggtc ttcggtttcc   2040
gtgtttcgta aagtctggaa acgcggaagt cagcgccctg caccattatg ttccggatct   2100
gcatcgcagg atgctgctgg ctaccctgtg gaacacctac atctgtatta acgaagcgct   2160
ggcattgacc ctgagtgatt tttctctggt cccgccgcat ccataccgcc agttgtttac   2220
cctcacaacg ttccagtaac cgggcatgtt catcatcagt aacccgtatc gtgagcatcc   2280
tctctcgttt catcggtatc attaccccca tgaacagaaa tcccccttac acggaggcat   2340
cagtgaccaa acaggaaaaa accgccctta acatggcccg ctttatcaga agccagacat   2400
taacgcttct ggagaaactc aacgagctgg acgcggatga acaggcagac atctgtgaat   2460
cgcttcacga ccacgctgat gagctttacc gcagctgcct cgcgcgtttc ggtgatgacg   2520
gtgaaaacct ctgacacatg cagctcccgg agacggtcac agcttgtctg taagcggatg   2580
ccgggagcag acaagcccgt cagggcgcgt cagcgggtgt tggcgggtgt cggggcgcag   2640
ccatgaccca gtcacgtagc gatagcggag tgtatactgg cttaactatg cggcatcaga   2700
gcagattgta ctgagagtgc accatatgcg gtgtgaaata ccgcacagat gcgtaaggag   2760
aaaataccgc atcaggcgct cttccgcttc ctcgctcact gactcgctgc gctcggtcgt   2820
tcggctgcgg cgagcggtat cagctcactc aaaggcggta atacggttat ccacagaatc   2880
aggggataac gcaggaaaga acatgtgagc aaaaggccag caaaaggcca ggaaccgtaa   2940
aaaggccgcg ttgctggcgt ttttccatag gctccgcccc cctgacgagc atcacaaaaa   3000
tcgacgctca agtcagaggt ggcgaaaccc gacaggacta taaagatacc aggcgtttcc   3060
ccctggaagc tccctcgtgc gctctcctgt tccgaccctg ccgcttaccg gatacctgtc   3120
cgcctttctc ccttcgggaa gcgtggcgct ttctcatagc tcacgctgta ggtatctcag   3180
ttcggtgtag gtcgttcgct ccaagctggg ctgtgtgcac gaaccccccg ttcagcccga   3240
ccgctgcgcc ttatccggta actatcgtct tgagtccaac ccggtaagac acgacttatc   3300
gccactggca gcagccactg gtaacaggat tagcagagcg aggtatgtag gcggtgctac   3360
agagttcttg aagtggtggc ctaactacgg ctacactaga aggacagtat ttggtatctg   3420
```

-continued

```
cgctctgctg aagccagtta ccttcggaaa aagagttggt agctcttgat ccggcaaaca    3480
aaccaccgct ggtagcggtg gtttttttgt ttgcaagcag cagattacgc gcagaaaaaa    3540
aggatctcaa gaagatcctt tgatcttttc tacggggtct gacgctcagt ggaacgaaaa    3600
ctcacgttaa gggattttgg tcatgagatt atcaaaaagg atcttcacct agatcctttt    3660
aaattaaaaa tgaagtttta aatcaatcta agtatatat gagtaaactt ggtctgacag    3720
ttaccaatgc ttaatcagtg aggcacctat ctcagcgatc tgtctatttc gttcatccat    3780
agttgcctga ctccccgtcg tgtagataac tacgatacgg gagggcttac catctggccc    3840
cagtgctgca atgataccgc gagacccacg ctcaccggct ccagatttat cagcaataaa    3900
ccagccagcc ggaagggccg agcgcagaag tggtcctgca actttatccg cctccatcca    3960
gtctattaat tgttgccggg aagctagagt aagtagttcg ccagttaata gtttgcgcaa    4020
cgttgttgcc attgctgcag gcatcgtggt gtcacgctcg tcgtttggta tggcttcatt    4080
cagctccggt tcccaacgat caaggcgagt tacatgatcc cccatgttgt gcaaaaaagc    4140
ggttagctcc ttcggtcctc cgatcgttgt cagaagtaag ttggccgcag tgttatcact    4200
catggttatg gcagcactgc ataattctct tactgtcatg ccatccgtaa gatgcttttc    4260
tgtgactggt gagtactcaa ccaagtcatt ctgagaatag tgtatgcggc gaccgagttg    4320
ctcttgcccg gcgtcaacac gggataatac cgcgccacat agcagaactt taaaagtgct    4380
catcattgga aaacgttctt cggggcgaaa actctcaagg atcttaccgc tgttgagatc    4440
cagttcgatg taacccactc gtgcacccaa ctgatcttca gcatctttta ctttcaccag    4500
cgtttctggg tgagcaaaaa caggaaggca aaatgccgca aaaaagggaa taagggcgac    4560
acggaaatgt tgaatactca tactcttcct ttttcaatat tattgaagca tttatcaggg    4620
ttattgtctc atgagcggat acatatttga atgtatttag aaaaataaac aaataggggt    4680
tccgcgcaca tttccccgaa aagtgccacc tgacgtctaa gaaaccatta ttatcatgac    4740
attaacctat aaaaataggc gtatcacgag gccctttcgt cttcaagaa               4789
```

```
<210> SEQ ID NO 8
<211> LENGTH: 3864
<212> TYPE: DNA
<213> ORGANISM: Artificial Sequence
<220> FEATURE:
<223> OTHER INFORMATION: Recombinant plasmid pAPSE10269; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
```

```
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator

<400> SEQUENCE: 8
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatataca     300 tacgccggcc attcaaacat gaggattacc catgtattta atacccatg tccaggcgcg      360 ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccgtgc cgtcttcccc tcgatcgtcg tcgcccaag       540 gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttccctttcc agcgggatgc     720
tttatctaaa cgcaacatga ggatcaccca tgtcgccaca tcgcttccta gttccgctgg     780
gatccatcgt tggcggccga agccgccatt ccatagtgag ttctggcgcg cctcatccca     840
gttggtgatg ataccgtgtt cgatggggta tttcagggtg aggatacctc ttttgctttg     900
ggcttcatct cctacgtatg agtccttttg tcccataccg accatgactc cttgatgcct     960
tgggcgaccg acgatcgagg ggaagacggc acggggtgcg tcatctcctg cgaaaccggc    1020
tttgcacata ccgatccat tgtctacgac aagagccgct acatcgtcgt cacacatgtt     1080
gtcttttgag gttggacact gctcactaga cagaaaaacc tcgtgccgga ccgaataccc    1140
ggtctgaacg agggcggccg cggtacccaa gaagtactta gagttaatta aggagttcaa    1200
acatgaggat cacccatgtc gaagctccca caccctagca taaccccttg gggcctctaa    1260
acgggtcttg aggggttttt tgctgaaagg aggaactata tccggatatc cacaggacgg    1320
gtgtggtcgc catgatcgcg tagtcgatag tggctccaag tagcgaagcg agcaggactg    1380
ggcggcgggc atgcatcgtc cattccgaca gcatcgccag tcactatggc gtgctgctag    1440
cgctatatgc gttgatgcaa tttctatgcg cacccgttct cggagcactg tccgaccgct    1500
ttggccgccg cccagtcctg ctcgcttcgc tacttggagc cactatcgac tacgcgatca    1560
```

-continued

```
tggcgaccac accçgtcctg tggatccaga tctcgatccc gcgaaattaa tacgactcac    1620 tataggggaga ccacaacggt ttccctctag atcacaagtt tgtacaaaaa agcaggctaa    1680
gaaggagata tacatatggc gtctaacttt acccaattcg ttctggttga taacggcggt    1740
acgggtgacg ttaccgtagc tccgtccaac ttcgccaacg gtgttgcgga atggattagc    1800
tctaacagcc gctctcaggc ctacaaagtc acgtgctccg ttcgtcagtc tagcgcgcag    1860
aatcgcaaat acaccatcaa agttgaagta ccgaaagtcg caacgcagac cgtaggcggc    1920
gtagaactcc cagttgcggc ctggcgctct tacctcaaca tggaactgac tattccgatt    1980
tttgcgacga actccgactg cgaactgatt gttaaggcaa tgcagggcct gctgaaagac    2040
ggtaatccga tcccatctgc aatcgctgct aactctggca tttactaata agcggacgcg    2100
ctgccaccgc tgagcaataa ctagcataac cccttggggc ctctaaacgg gtcttgaggg    2160
gttttttgct gaaaggagga actatatccg gcatgcacca ttccttgcgg cggcggtgct    2220
caacggcctc aacctactac tgggctgctt cctaatgcag gagtcgcata agggagagcg    2280
tcgaccgatg cccttgagag ccttcaaccc agtcagctcc ttccggtggg cgcggggcat    2340
gactatcgtc gccgcactta tgactgtctt ctttatcatg caactcgtag gacaggtgcc    2400
ggcagcgctc tgggtcattt tcggcgagga ccgctttcgc tggagcgcga cgatgatcgg    2460
cctgtcgctt gcggtattcg gaatcttgca cgccctcgct caagccttcg tcactggtcc    2520
cgccaccaaa cgtttcggcg agaagcaggc cattatcgcc ggcatggcgg ccgacgcgct    2580
gggctacgtc ttgctggcgt tcgcgacgcg aggctggatg gccttcccca ttatgattct    2640
tctcgcttcc ggcggcatcg ggatgcccgc gttgcaggcc atgctgtcca ggcaggtaga    2700
tgacgaccat cagggacagc ttcaaggatc gctcgcggct cttaccagcc taacttcgat    2760
cattggaccg ctgatcgtca cggcgattta tgccgcctcg gcgagcacat ggaacgggtt    2820
ggcatggatt gtaggcgccg ccctatacct tgtctgcctc cccgcgttgc gtcgcggtgc    2880
atggagccgg gccacctcga cctgaatgga agccggcggc acctcgctaa cggattcacc    2940
actccaagaa ttggagccaa tcaattcttg cggagaactg tgaatgcgca aaccaaccct    3000
tggcagaaca tatccatcgc gtccgccatc tccagcagcc gcacgcggcg catctcgggc    3060
agcgttgggt cctggccacg ggtgcgcatg atcgtgctcc tgtcgttgag gacccggcta    3120
ggctggcggg gttgccttac tggttagcag aatgaatcac cgatacgcga gcgaacgtga    3180
agcgactgct gctgcaaaac gtctgcgacc tgagcaacaa catgaatggt cttcggtttc    3240
cgtgtttcgt aaagtctgga aacgcggaag tcagcgccct gcaccattat gttccggatc    3300
tgcatcgcag gatgctgctg gctaccctgt ggaacaccta catctgtatt aacgaagcgc    3360
tggcattgac cctgagtgat ttttctctgg tcccgccgca tccataccgc cagttgttta    3420
ccctcacaac gttccagtaa ccgggcatgt tcatcatcag taacccgtat cgtgagcatc    3480
ctctctcgtt tcatcggtat cattacccce atgaacagaa atccccctta cacggaggca    3540
tcagtgacca aacaggaaaa aaccgccctt aacatggccc gctttatcag aagccagaca    3600
ttaacgcttc tggagaaact caacgagctg gacgcggatg aacaggcaga catctgtgaa    3660
tcgcttcacg accacgctga tgagctttac cgcagctgcc tcgcgcgttt cggtgatgac    3720
ggtgaaaacc tctgacacat gcagctcccg gagacggtca cagcttgtct gtaagcggat    3780
gccgggagca gacaagcccg tcagggcgcg tcagcgggtg ttggcgggtg tcggggcgca    3840
gccatgaccc agtcacgtag cgat                                          3864
```

```
<210> SEQ ID NO 9
<211> LENGTH: 5375
<212> TYPE: DNA
<213> ORGANISM: Artificial Sequence
<220> FEATURE:
<223> OTHER INFORMATION: Recombinant plasmid pAPSE10306; beta actin stem
      loop - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1389)..(1394)
<223> OTHER INFORMATION: restriction endonuclease SphI recognition site

<400> SEQUENCE: 9
ttctcatgtt tgacagctta tcatcgataa gctttaatgc ggtagtttat cacagttaaa        60
ttgctaacgc agtcaggcac cgtgtatgaa atctaacaat gcgctcatcg tcatcctcgg       120
caccgtcacc ctggatgctg taggcatagg cttggttatg ccggtactgc cgggcctctt       180
gcgggatgaa ttcagatctc gatcccgcga aattaatacg actcactata gggagaccac       240
aacggtttcc ctctagatca caagtttgta caaaaaagca ggctaagaag gagatataca       300
tacgccggcc attcaaacat gaggattacc catgtattta atacccatg tccaggcgcg       360 ctccgcgatc gcgcacgagg tttttctgtc tagtgagcag tgtccaacct caaaagacaa       420
catgtgtgac gacgatgtag cggctcttgt cgtagacaat ggatccggta tgtgcaaagc       480
cggtttcgca ggagatgacg cacccgtgc cgtcttcccc tcgatcgtcg gtcgcccaag       540
gcatcaagga gtcatggtcg gtatgggaca aaaggactca tacgtaggag atgaagccca       600
aagcaaaaga ggtatcctca ccctgaaata ccccatcgaa cacggtatca tcaccaactg       660
ggatgagttt aaaccctcta gctgctttac aaagtactgg ttccctttcc agcgggatgc       720
tttatctaaa cgcaacatga ggatcaccca tgtcgccaca tcgcttccta gttccgctgg       780
gatccatcgt tggcggccga agccgccatt ccatagtgag ttctggcgcg cctcatccca       840
gttggtgatg ataccgtgtt cgatgggta tttcagggtg aggatacctc ttttgctttg       900
```

-continued

```
ggcttcatct cctacgtatg agtccttttg tcccataccg accatgactc cttgatgcct      960
tgggcgaccg acgatcgagg ggaagacggc acggggtgcg tcatctcctg cgaaaccggc     1020
tttgcacata ccggatccat tgtctacgac aagagccgct acatcgtcgt cacacatgtt     1080
gtcttttgag gttggacact gctcactaga cagaaaaacc tcgtgccgga ccgaataccc     1140
ggtctgaacg agggcggccg cggtacccaa gaagtactta gagttaatta aggagttcaa     1200
acatgaggat cacccatgtc gaagctccca caccctagca taaccccttg gggcctctaa      1260
acgggtcttg aggggttttt tgctgaaagg aggaactata tccggatatc cacaggacgg     1320
gtgtggtcgc catgatcgcg tagtcgatag tggctccaag tagcgaagcg agcaggactg     1380
ggcggcgggc atgcatcgtc cattccgaca gcatcgccag tcactatggc gtgctgctag     1440
cgctatatgc gttgatgcaa tttctatgcg cacccgttct cggagcactg tccgaccgct     1500
ttggccgccg cccagtcctg ctcgcttcgc tacttggagc cactatcgac tacgcgatca     1560
tggcgaccac acccgtcctg taccattcct tgcggcggcg gtgctcaacg gcctcaacct     1620
actactgggc tgcttcctaa tgcaggagtc gcataaggga gagcgtcgac cgatgccctt     1680
gagagccttc aacccagtca gctccttccg gtgggcgcgg ggcatgacta tcgtcgccgc     1740
acttatgact gtcttcttta tcatgcaact cgtaggacag gtgccggcag cgctctgggt     1800
cattttcggc gaggaccgct ttcgctggag cgcgacgatg atcggcctgt cgcttgcggt     1860
attcggaatc ttgcacgccc tcgctcaagc cttcgtcact ggtcccgcca ccaaacgttt     1920
cggcgagaag caggccatta tcgccggcat ggcggccgac gcgctgggct acgtcttgct     1980
ggcgttcgcg acgcgaggct ggatggcctt ccccattatg attcttctcg cttccggcgg     2040
catcgggatg cccgcgttgc aggccatgct gtccaggcag gtagatgacg accatcaggg     2100
acagcttcaa ggatcgctcg cggctcttac cagcctaact tcgatcattg gaccgctgat     2160
cgtcacggcg atttatgccg cctcggcgag cacatggaac gggttggcat ggattgtagg     2220
cgccgcccta taccttgtct gcctccccgc gttgcgtcgc ggtgcatgga gccgggccac     2280
ctcgacctga atggaagccg gcggcacctc gctaacggat tcaccactcc aagaattgga     2340
gccaatcaat tcttgcggag aactgtgaat gcgcaaacca acccttggca gaacatatcc     2400
atcgcgtccg ccatctccag cagccgcacg cggcgcatct cgggcagcgt gggtcctgg      2460 ccacgggtgc gcatgatcgt gctcctgtcg ttgaggaccc ggctaggctg gcggggttgc     2520
cttactggtt agcagaatga atcaccgata cgcgagcgaa cgtgaagcga ctgctgctgc     2580
aaaacgtctg cgacctgagc aacaacatga atggtcttcg gtttccgtgt ttcgtaaagt     2640
ctggaaacgc ggaagtcagc gccctgcacc attatgttcc ggatctgcat cgcaggatgc     2700
tgctggctac cctgtggaac acctacatct gtattaacga agcgctggca ttgaccctga     2760
gtgatttttc tctggtcccg ccgcatccat accgccagtt gtttaccctc acaacgttcc     2820
agtaaccggg catgttcatc atcagtaacc cgtatcgtga gcatcctctc tcgtttcatc     2880
ggtatcatta ccccatgaa cagaaatccc ccttacacgg aggcatcagt gaccaaacag       2940
gaaaaaaccg cccttaacat ggcccgcttt atcagaagcc agacattaac gcttctggag     3000
aaactcaacg agctggacgc ggatgaacag gcagacatct gtgaatcgct tcacgaccac     3060
gctgatgagc tttaccgcag ctgcctcgcg cgtttcggtg atgacggtga aaacctctga     3120
cacatgcagc tcccggagac ggtcacagct tgtctgtaag cggatgccgg gagcagacaa     3180
gcccgtcagg gcgcgtcagc gggtgttggc gggtgtcggg gcgcagccat gacccagtca     3240
```

-continued

```
cgtagcgata gcggagtgta tactggctta actatgcggc atcagagcag attgtactga    3300
gagtgcacca tatgcggtgt gaaataccgc acagatgcgt aaggagaaaa taccgcatca    3360
ggcgctcttc cgcttcctcg ctcactgact cgctgcgctc ggtcgttcgg ctgcggcgag    3420
cggtatcagc tcactcaaag gcggtaatac ggttatccac agaatcaggg gataacgcag    3480
gaaagaacat gtgagcaaaa ggccagcaaa aggccaggaa ccgtaaaaag ccgcgttgc     3540 tggcgttttt ccataggctc cgcccccctg acgagcatca caaaaatcga cgctcaagtc    3600
agaggtggcg aaacccgaca ggactataaa gataccaggc gtttccccct ggaagctccc    3660
tcgtgcgctc tcctgttccg accctgccgc ttaccggata cctgtccgcc tttctccctt    3720
cgggaagcgt ggcgctttct catagctcac gctgtaggta tctcagttcg gtgtaggtcg    3780
ttcgctccaa gctgggctgt gtgcacgaac cccccgttca gcccgaccgc tgcgccttat    3840
ccggtaacta tcgtcttgag tccaacccgg taagacacga cttatcgcca ctggcagcag    3900
ccactggtaa caggattagc agagcgaggt atgtaggcgg tgctacagag ttcttgaagt    3960
ggtggcctaa ctacggctac actagaagga cagtatttgg tatctgcgct ctgctgaagc    4020
cagttacctt cggaaaaaga gttggtagct cttgatccgg caaacaaacc accgctggta    4080
gcggtggttt ttttgtttgc aagcagcaga ttacgcgcag aaaaaaagga tctcaagaag    4140
atcctttgat cttttctacg gggtctgacg ctcagtggaa cgaaaactca cgttaaggga    4200
ttttggtcat gagattatca aaaaggatct tcacctagat ccttttaaat taaaaatgaa    4260
gttttaaatc aatctaaagt atatatgagt aaacttggtc tgacagttac caatgcttaa    4320
tcagtgaggc acctatctca gcgatctgtc tatttcgttc atccatagtt gcctgactcc    4380
ccgtcgtgta gataactacg atacgggagg gcttaccatc tggccccagt gctgcaatga    4440
taccgcgaga cccacgctca ccggctccag atttatcagc aataaaccag ccagccggaa    4500
gggccgagcg cagaagtggt cctgcaactt tatccgcctc catccagtct attaattgtt    4560
gccgggaagc tagagtaagt agttcgccag ttaatagttt cgcaacgtt gttgccattg     4620 ctgcaggcat cgtggtgtca cgctcgtcgt ttggtatggc ttcattcagc tccggttccc    4680
aacgatcaag gcgagttaca tgatccccca tgttgtgcaa aaaagcggtt agctccttcg    4740
gtcctccgat cgttgtcaga agtaagttgg ccgcagtgtt atcactcatg gttatggcag    4800
cactgcataa ttctcttact gtcatgccat ccgtaagatg cttttctgtg actggtgagt    4860
actcaaccaa gtcattctga gaatagtgta tgcggcgacc gagttgctct tgcccggcgt    4920
caacacggga taataccgcg ccacatagca gaactttaaa agtgctcatc attggaaaac    4980
gttcttcggg gcgaaaactc tcaaggatct taccgctgtt gagatccagt tcgatgtaac    5040
ccactcgtgc acccaactga tcttcagcat cttttacttt caccagcgtt tctgggtgag    5100
caaaaacagg aaggcaaaat gccgcaaaaa agggaataag ggcgacacgg aaatgttgaa    5160
tactcatact cttccttttt caatattatt gaagcattta tcagggttat tgtctcatga    5220
gcggatacat atttgaatgt atttagaaaa ataaacaaat aggggttccg cgcacatttc    5280
cccgaaaagt gccacctgac gtctaagaaa ccattattat catgacatta acctataaaa    5340
ataggcgtat cacgaggccc tttcgtcttc aagaa                              5375
```

<210> SEQ ID NO 10
<211> LENGTH: 5990
<212> TYPE: DNA
<213> ORGANISM: Artificial Sequence
<220> FEATURE:
<223> OTHER INFORMATION: Recombinant plasmid pAPSE10216; beta actin stem

```
        loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator

<400> SEQUENCE: 10
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatatacca     300
tacgccggcc attcaaacat gaggattacc catgtattta aatacccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttccctttcc agcgggatgc     720
tttatctaaa cgcaatgaga gaggtattcc tcaggccaca tcgcttccta gttccgctgg     780
gatccatcgt tggcggccga agccgccatt ccatagtgag ttctggcgcg cctcatccca     840
gttggtgata taccgtgtt cgatgggggta tttcaggggtg aggatacctc ttttgctttg     900
ggcttcatct cctacgtatg agtccttttg tcccataccg accatgactc cttgatgcct     960
```

```
tgggcgaccg acgatcgagg ggaagacggc acggggtgcg tcatctcctg cgaaaccggc     1020
tttgcacata ccggatccat tgtctacgac aagagccgct acatcgtcgt cacacatgtt     1080
gtcttttgag gttggacact gctcactaga cagaaaaacc tcgtgccgga ccgaataccc     1140
ggtctgaacg agggcggccg cggtacccaa gaagtactta gagttaatta aggagttcaa     1200
acatgaggat cacccatgtc gaagctccca caccctagca taaccccttg gggcctctaa     1260
acgggtcttg aggggttttt tgctgaaagg aggaactata tccggatatc cacaggacgg     1320
gtgtggtcgc catgatcgcg tagtcgatag tggctccaag tagcgaagcg agcaggactg     1380
ggcggcgggc atgcatcgtc cattccgaca gcatcgccag tcactatggc gtgctgctag     1440
cgctatatgc gttgatgcaa tttctatgcg cacccgttct cggagcactg tccgaccgct     1500
ttggccgccg cccagtcctg ctcgcttcgc tacttggagc cactatcgac tacgcgatca     1560
tggcgaccac acccgtcctg tggatccaga tctcgatccc gcgaaattaa tacgactcac     1620
tatagggaga ccacaacggt ttccctctag atcacaagtt tgtacaaaaa agcaggctaa     1680
gaaggagata tacatatggc gtctaacttt acccaattcg ttctggttga taacggcggt     1740
acgggtgacg ttaccgtagc tccgtccaac ttcgccaacg gtgttgcgga atggattagc     1800
tctaacagcc gctctcaggc ctacaaagtc acgtgctccg ttcgtcagtc tagcgcgcag     1860
aatcgcaaat acaccatcaa agttgaagta ccgaaagtcg caacgcagac cgtaggcggc     1920
gtagaactcc cagttgcggc ctggcgctct tacctcaaca tggaactgac tattccgatt     1980
tttgcgacga actccgactg cgaactgatt gttaaggcaa tgcagggcct gctgaaagac     2040
ggtaatccga tcccatctgc aatcgctgct aactctggca tttactaata agcggacgcg     2100
ctgccaccgc tgagcaataa ctagcataac cccttggggc tctaaacggt gtcttgaggg     2160
gttttttgct gaaaggagga actatatccg gcatgcacca ttccttgcgg cggcggtgct     2220
caacggcctc aacctactac tgggctgctt cctaatgcag gagtcgcata agggagagcg     2280
tcgaccgatg cccttgagag ccttcaaccc agtcagctcc ttccggtggg cgcggggcat     2340
gactatcgtc gccgcactta tgactgtctt ctttatcatg caactcgtag gacaggtgcc     2400
ggcagcgctc tgggtcattt tcggcgagga ccgctttcgc tggagcgcga cgatgatcgg     2460
cctgtcgctt gcggtattcg gaatcttgca cgccctcgct caagccttcg tcactggtcc     2520
cgccaccaaa cgtttcggcg agaagcaggc cattatcgcc ggcatggcgg ccgacgcgct     2580
gggctacgtc ttgctggcgt cgcgacgcg aggctggatg gccttcccca ttatgattct     2640
tctcgcttcc ggcggcatcg ggatgcccgc gttgcaggcc atgctgtcca ggcaggtaga     2700
tgacgaccat cagggacagc ttcaaggatc gctcgcggct cttaccagcc taacttcgat     2760
cattggaccg ctgatcgtca cggcgattta tgccgcctcg cgagcacat ggaacgggtt     2820 ggcatggatt gtaggcgccg ccctatacct tgtctgcctc cccgcgttgc gtcgcggtgc     2880
atggagccgg gccacctcga cctgaatgga agccggcggc acctcgctaa cggattcacc     2940
actccaagaa ttggagccaa tcaattcttg cggagaactg tgaatgcgca aaccaaccct     3000
tggcagaaca tatccatcgc gtccgccatc tccagcagcc gcacgcggcg catctcgggc     3060
agcgttgggt cctggccacg ggtgcgcatg atcgtgctcc tgtcgttgag gacccggcta     3120
ggctggcggg gttgccttac tggttagcag aatgaatcac cgatacgcga gcgaacgtga     3180
agcgactgct gctgcaaaac gtctgcgacc tgagcaacaa catgaatggt cttcggtttc     3240
cgtgtttcgt aaagtctgga aacgcggaag tcagcgccct gcaccattat gttccggatc     3300
```

-continued

```
tgcatcgcag gatgctgctg gctaccctgt ggaacaccta catctgtatt aacgaagcgc    3360
tggcattgac cctgagtgat ttttctctgg tcccgccgca tccataccgc cagttgttta    3420
ccctcacaac gttccagtaa ccgggcatgt tcatcatcag taacccgtat cgtgagcatc    3480
ctctctcgtt tcatcggtat cattaccccc atgaacagaa atccccctta cacggaggca    3540
tcagtgacca aacaggaaaa aaccgccctt aacatggccc gctttatcag aagccagaca    3600
ttaacgcttc tggagaaact caacgagctg gacgcggatg aacaggcaga catctgtgaa    3660
tcgcttcacg accacgctga tgagctttac cgcagctgcc tcgcgcgttt cggtgatgac    3720
ggtgaaaacc tctgacacat gcagctcccg gagacggtca cagcttgtct gtaagcggat    3780
gccgggagca gacaagcccg tcagggcgcg tcagcgggtg ttggcgggtg tcggggcgca    3840
gccatgaccc agtcacgtag cgatagcgga gtgtatactg gcttaactat gcggcatcag    3900
agcagattgt actgagagtg caccatatgc ggtgtgaaat accgcacaga tgcgtaagga    3960
gaaaataccg catcaggcgc tcttccgctt cctcgctcac tgactcgctg cgctcggtcg    4020
ttcggctgcg gcgagcggta tcagctcact caaaggcggt aatacggtta tccacagaat    4080 cagggggataa cgcaggaaag aacatgtgag caaaaggcca gcaaaaggcc aggaaccgta    4140
aaaaggccgc gttgctggcg tttttccata ggctccgccc ccctgacgag catcacaaaa    4200
atcgacgctc aagtcagagg tggcgaaacc cgacaggact ataaagatac caggcgtttc    4260
cccctggaag ctccctcgtg cgctctcctg ttccgaccct gccgcttacc ggatacctgt    4320
ccgcctttct cccttcggga agcgtggcgc tttctcatag ctcacgctgt aggtatctca    4380
gttcggtgta ggtcgttcgc tccaagctgg gctgtgtgca cgaacccccc gttcagcccg    4440
accgctgcgc cttatccggt aactatcgtc ttgagtccaa cccggtaaga cacgacttat    4500
cgccactggc agcagccact ggtaacagga ttagcagagc gaggtatgta ggcggtgcta    4560
cagagttctt gaagtggtgg cctaactacg gctacactag aaggacagta tttggtatct    4620
gcgctctgct gaagccagtt accttcggaa aaagagttgg tagctcttga tccggcaaac    4680
aaaccaccgc tggtagcggt ggtttttttg tttgcaagca gcagattacg cgcagaaaaa    4740
aaggatctca agaagatcct ttgatctttt ctacggggtc tgacgctcag tggaacgaaa    4800
actcacgtta agggattttg gtcatgagat tatcaaaaag gatcttcacc tagatccttt    4860
taaattaaaa atgaagtttt aaatcaatct aaagtatata tgagtaaact tggtctgaca    4920
gttaccaatg cttaatcagt gaggcaccta tctcagcgat ctgtctattt cgttcatcca    4980
tagttgcctg actccccgtc gtgtagataa ctacgatacg ggagggctta ccatctggcc    5040
ccagtgctgc aatgataccg cgagacccac gctcaccggc tccagattta tcagcaataa    5100
accagccagc cggaagggcc gagcgcagaa gtggtcctgc aactttatcc gcctccatcc    5160
agtctattaa ttgttgccgg gaagctagag taagtagttc gccagttaat agtttgcgca    5220
acgttgttgc cattgctgca ggcatcgtgg tgtcacgctc gtcgtttggt atggcttcat    5280
tcagctccgg ttcccaacga tcaaggcgag ttacatgatc ccccatgttg tgcaaaaaag    5340
cggttagctc cttcggtcct ccgatcgttg tcagaagtaa gttggccgca gtgttatcac    5400
tcatggttat ggcagcactg cataattctc ttactgtcat gccatccgta agatgctttt    5460
ctgtgactgg tgagtactca accaagtcat tctgagaata gtgtatgcgg cgaccgagtt    5520
gctcttgccc ggcgtcaaca cgggataata ccgcgccaca tagcagaact ttaaaagtgc    5580
tcatcattgg aaaacgttct tcggggcgaa aactctcaag gatcttaccg ctgttgagat    5640
ccagttcgat gtaacccact cgtgcaccca actgatcttc agcatctttt actttcacca    5700
```

-continued

```
gcgtttctgg gtgagcaaaa acaggaaggc aaaatgccgc aaaaaaggga ataagggcga    5760
cacggaaatg ttgaatactc atactcttcc tttttcaata ttattgaagc atttatcagg    5820
gttattgtct catgagcgga tacatatttg aatgtattta gaaaaataaa caaatagggg    5880
ttccgcgcac atttcccga aaagtgccac ctgacgtcta agaaaccatt attatcatga     5940
cattaaccta taaaaatagg cgtatcacga ggccctttcg tcttcaagaa               5990
```

```
<210> SEQ ID NO 11
<211> LENGTH: 5188
<212> TYPE: DNA
<213> ORGANISM: Artificial Sequence
<220> FEATURE:
<223> OTHER INFORMATION: Recombinant plasmid pAPSE10305; beta actin stem
      loop - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophageT7 transcription terminator
<220> FEATURE:
<221> NAME/KEY: misc_feature
<222> LOCATION: (1389)..(1394)
<223> OTHER INFORMATION: restriction endonuclease SphI recognition site

<400> SEQUENCE: 11
```

```
ttctcatgtt tgacagctta tcatcgataa gctttaatgc ggtagtttat cacagttaaa    60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatgaa ttcagatctc gatcccgcga aattaatacg actcactata gggagaccac    240
aacggtttcc ctctagatca caagtttgta caaaaaagca ggctaagaag gagatataca    300
tacgccggcc attcaaacat gaggattacc catgtattta atacccatg tccaggcgcg     360 ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttcccttcc agcgggatgc      720 tttatctaaa cgcaatgaga gaggtattcc tcaggccaca tcgcttccta gttccgctgg    780
```

-continued

```
gatccatcgt tggcggccga agccgccatt ccatagtgag ttctggcgcg cctcatccca      840
gttggtgatg ataccgtgtt cgatggggta tttcagggtg aggatacctc ttttgctttg      900
ggcttcatct cctacgtatg agtccttttg tcccataccg accatgactc cttgatgcct      960
tgggcgaccg acgatcgagg ggaagacggc acggggtgcg tcatctcctg cgaaaccggc     1020
tttgcacata ccggatccat tgtctacgac aagagccgct acatcgtcgt cacacatgtt     1080
gtcttttgag gttggacact gctcactaga cagaaaaacc tcgtgccgga ccgaataccc     1140
ggtctgaacg agggcggccg cggtacccaa gaagtactta gagttaatta aggagttcaa     1200
acatgaggat cacccatgtc gaagctccca caccctagca taaccccttg gggcctctaa     1260
acgggtcttg aggggttttt tgctgaaagg aggaactata tccggatatc cacaggacgg     1320
gtgtggtcgc catgatcgcg tagtcgatag tggctccaag tagcgaagcg agcaggactg     1380
ggcggcgggc atgcaccatt ccttgcggcg gcggtgctca acggcctcaa cctactactg     1440
ggctgcttcc taatgcagga gtcgcataag ggagagcgtc gaccgatgcc cttgagagcc     1500
ttcaacccag tcagctcctt ccggtgggcg cggggcatga ctatcgtcgc cgcacttatg     1560
actgtcttct ttatcatgca actcgtagga caggtgccgg cagcgctctg ggtcattttc     1620
ggcgaggacc gctttcgctg gagcgcgacg atgatcggcc tgtcgcttgc ggtattcgga     1680
atcttgcacg ccctcgctca agccttcgtc actggtcccg ccaccaaacg tttcggcgag     1740
aagcaggcca ttatcgccgg catggcggcc gacgcgctgg gctacgtctt gctggcgttc     1800
gcgacgcgag gctggatggc cttccccatt atgattcttc tcgcttccgg cggcatcggg     1860
atgcccgcgt tgcaggccat gctgtccagg caggtagatg acgaccatca gggacagctt     1920
caaggatcgc tcgcggctct taccagccta acttcgatca ttggaccgct gatcgtcacg     1980
gcgatttatg ccgcctcggc gagcacatgg aacgggttgg catggattgt aggcgccgcc     2040
ctataccttg tctgcctccc cgcgttgcgt cgcggtgcat ggagccgggc cacctcgacc     2100
tgaatggaag ccggcggcac ctcgctaacg gattcaccac tccaagaatt ggagccaatc     2160
aattcttgcg gagaactgtg aatgcgcaaa ccaacccttg gcagaacata tccatcgcgt     2220
ccgccatctc cagcagccgc acgcggcgca tctcgggcag cgttgggtcc tggccacggg     2280
tgcgcatgat cgtgctcctg tcgttgagga cccggctagg ctggcggggt tgccttactg     2340
gttagcagaa tgaatcaccg atacgcgagc gaacgtgaag cgactgctgc tgcaaaacgt     2400
ctgcgacctg agcaacaaca tgaatggtct tcggtttccg tgtttcgtaa agtctggaaa     2460
cgcggaagtc agcgccctgc accattatgt tccggatctg catcgcagga tgctgctggc     2520
taccctgtgg aacacctaca tctgtattaa cgaagcgctg gcattgaccc tgagtgattt     2580
ttctctggtc ccgccgcatc cataccgcca gttgtttacc ctcacaacgt tccagtaacc     2640
gggcatgttc atcatcagta acccgtatcg tgagcatcct ctctcgtttc atcggtatca     2700
ttacccccat gaacagaaat cccccttaca cggaggcatc agtgaccaaa caggaaaaaa     2760
ccgcccttaa catggcccgc tttatcagaa gccagacatt aacgcttctg gagaaactca     2820
acgagctgga cgcggatgaa caggcagaca tctgtgaatc gcttcacgac cacgctgatg     2880
agctttaccg cagctgcctc gcgcgtttcg gtgatgacg tgaaaacctc tgacacatgc     2940
agctcccgga gacggtcaca gcttgtctgt aagcggatgc cgggagcaga caagcccgtc     3000
agggcgcgtc agcgggtgtt ggcgggtgtc ggggcgcagc catgacccag tcacgtagcg     3060
atagcggagt gtatactggc ttaactatgc ggcatcagag cagattgtac tgagagtgca     3120
```

-continued

```
ccatatgcgg tgtgaaatac cgcacagatg cgtaaggaga aaataccgca tcaggcgctc      3180
ttccgcttcc tcgctcactg actcgctgcg ctcggtcgtt cggctgcggc gagcggtatc      3240
agctcactca aaggcggtaa tacggttatc cacagaatca ggggataacg caggaaagaa      3300
catgtgagca aaaggccagc aaaaggccag gaaccgtaaa aaggccgcgt tgctggcgtt      3360
tttccatagg ctccgccccc ctgacgagca tcacaaaaat cgacgctcaa gtcagaggtg      3420
gcgaaacccg acaggactat aaagatacca ggcgtttccc cctggaagct ccctcgtgcg      3480
ctctcctgtt ccgaccctgc cgcttaccgg atacctgtcc gcctttctcc cttcgggaag      3540
cgtggcgctt tctcatagct cacgctgtag gtatctcagt tcggtgtagg tcgttcgctc      3600
caagctgggc tgtgtgcacg aaccccccgt tcagcccgac cgctgcgcct tatccggtaa      3660
ctatcgtctt gagtccaacc cggtaagaca cgacttatcg ccactggcag cagccactgg      3720
taacaggatt agcagagcga ggtatgtagg cggtgctaca gagttcttga agtggtggcc      3780
taactacggc tacactagaa ggacagtatt tggtatctgc gctctgctga gccagttac       3840 cttcggaaaa agagttggta gctcttgatc cggcaaacaa accaccgctg gtagcggtgg      3900
tttttttgtt tgcaagcagc agattacgcg cagaaaaaaa ggatctcaag aagatccttt      3960
gatcttttct acggggtctg acgctcagtg gaacgaaaac tcacgttaag ggattttggt      4020
catgagatta tcaaaaagga tcttcaccta gatcctttta aattaaaaat gaagttttaa      4080
atcaatctaa agtatatatg agtaaacttg gtctgacagt taccaatgct taatcagtga      4140
ggcacctatc tcagcgatct gtctatttcg ttcatccata gttgcctgac tccccgtcgt      4200
gtagataact acgatacggg agggcttacc atctggcccc agtgctgcaa tgataccgcg      4260
agacccacgc tcaccggctc cagatttatc agcaataaac cagccagccg gaagggccga      4320
gcgcagaagt ggtcctgcaa ctttatccgc ctccatccag tctattaatt gttgccggga      4380
agctagagta agtagttcgc cagttaatag tttgcgcaac gttgttgcca ttgctgcagg      4440
catcgtggtg tcacgctcgt cgtttggtat ggcttcattc agctccggtt cccaacgatc      4500
aaggcgagtt acatgatccc ccatgttgtg caaaaaagcg gttagctcct tcggtcctcc      4560
gatcgttgtc agaagtaagt tggccgcagt gttatcactc atggttatgg cagcactgca      4620
taattctctt actgtcatgc catccgtaag atgcttttct gtgactggtg agtactcaac      4680
caagtcattc tgagaatagt gtatgcggcg accgagttgc tcttgcccgg cgtcaacacg      4740
ggataatacc gcgccacata gcagaacttt aaaagtgctc atcattggaa aacgttcttc      4800
ggggcgaaaa ctctcaagga tcttaccgct gttgagatcc agttcgatgt aacccactcg      4860
tgcacccaac tgatcttcag catctttac tttcaccagc gtttctgggt gagcaaaaac       4920
aggaaggcaa aatgccgcaa aaaagggaat aaggcgaca cggaaatgtt gaatactcat        4980
actcttcctt tttcaatatt attgaagcat ttatcagggt tattgtctca tgagcggata      5040
catatttgaa tgtatttaga aaataaaca aataggggtt ccgcgcacat ttccccgaaa        5100
agtgccacct gacgtctaag aaaccattat tatcatgaca ttaacctata aaaataggcg      5160
tatcacgagg cccttttcgtc ttcaagaa                                        5188
```

<210> SEQ ID NO 12
<211> LENGTH: 5657
<212> TYPE: DNA
<213> ORGANISM: Artificial Sequence
<220> FEATURE:
<223> OTHER INFORMATION: Recombinant plasmid pAPSE10219; beta actin stem
        loop + coat protein
<220> FEATURE:

```
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
      sequence
<220> FEATURE:
<221> NAME/KEY: misc_feature
<222> LOCATION: (40)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI recognition site
<220> FEATURE:
<221> NAME/KEY: misc_feature
<222> LOCATION: (497)..(791)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: promoter
<222> LOCATION: (1275)..(1293)
<223> OTHER INFORMATION: bacteriophage T7 gene 1 promoter
<220> FEATURE:
<221> NAME/KEY: gene
<222> LOCATION: (1366)..(1755)
<223> OTHER INFORMATION: bacteriophage MS2 coat protein gene
<220> FEATURE:
<221> NAME/KEY: terminator
<222> LOCATION: (1788)..(1835)
<223> OTHER INFORMATION: bacteriophage T7 transcription terminator

<400> SEQUENCE: 12
ttccgaaatt aatacgactc actataggga ggcgatcgcg cacgaggttt ttctgtctag        60
tgagcagtgt ccaacctcaa aagacaacat gtgtgacgac gatgtagcgg ctcttgtcgt       120
agacaatgga tccggtatgt gcaaagccgg tttcgcagga gatgacgcac cccgtgccgt       180
cttcccctcg atcgtcggtc gcccaaggca tcaaggagtc atggtcggta tgggacaaaa       240
ggactcatac gtaggagatg aagcccaaag caaaagaggt atcctcaccc tgaaataccc       300
catcgaacac ggtatcatca ccaactggga tgagtttaaa ccctctagct gctttacaaa       360
gtactggttc cctttccagc gggatgcttt atctaaacgc aatgagagag gtattcctca       420
ggccacatcg cttcctagtt ccgctgggat ccatcgttgg cggccgaagc cgccattcca       480
tagtgagttc tggcgcgcct catcccagtt ggtgatgata ccgtgttcga tggggtattt       540
cagggtgagg atacctcttt tgctttgggc ttcatctcct acgtatgagt ccttttgtcc       600
cataccgacc atgactcctt gatgccttgg gcgaccgacg atcgagggga agacggcacg       660
gggtgcgtca tctcctgcga aaccggcttt gcacataccg gatccattgt ctacgacaag       720
agccgctaca tcgtcgtcac acatgttgtc ttttgaggtt ggacactgct cactagacag       780
aaaaacctcg tgccggaccg aatacccggt ctgaacgagg gcggccgcgg tacccaagaa       840
gtacttagag ttaattaagg agttcaaaca tgaggatcac ccatgtcgaa gctcccacac       900
cctagcataa cccctttgggg cctctaaacg ggtcttgagg ggttttttgc tgaaaggagg       960
aactatatcc ggatatccac aggacgggtg tggtcgccat gatcgcgtag tcgatagtgg      1020
ctccaagtag cgaagcgagc aggactgggc ggcgggcatg catcgtccat tccgacagca      1080
```

-continued

```
tcgccagtca ctatggcgtg ctgctagcgc tatatgcgtt gatgcaattt ctatgcgcac      1140
ccgttctcgg agcactgtcc gaccgctttg gccgccgccc agtcctgctc gcttcgctac      1200
ttggagccac tatcgactac gcgatcatgg cgaccacacc cgtcctgtgg atccagatct      1260
cgatcccgcg aaattaatac gactcactat agggagacca caacggtttc cctctagatc      1320
acaagtttgt acaaaaaagc aggctaagaa ggagatatac atatggcgtc taactttacc      1380
caattcgttc tggttgataa cggcggtacg ggtgacgtta ccgtagctcc gtccaacttc      1440
gccaacggtg ttgcggaatg gattagctct aacagccgct ctcaggccta caaagtcacg      1500
tgctccgttc gtcagtctag cgcgcagaat cgcaaataca ccatcaaagt tgaagtaccg      1560
aaagtcgcaa cgcagaccgt aggcggcgta gaactcccag ttgcggcctg gcgctcttac      1620
ctcaacatgg aactgactat tccgattttt gcgacgaact ccgactgcga actgattgtt      1680
aaggcaatgc agggcctgct gaaagacggt aatccgatcc catctgcaat cgctgctaac      1740
tctggcattt actaataagc ggacgcgctg ccaccgctga gcaataacta gcataacccc      1800
ttggggcctc taaacgggtc ttgaggggtt ttttgctgaa aggaggaact atatccggca      1860
tgcaccattc cttgcggcgg cggtgctcaa cggcctcaac ctactactgg gctgcttcct      1920
aatgcaggag tcgcataagg gagagcgtcg accgatgccc ttgagagcct caacccagt       1980 cagctccttc cggtgggcgc ggggcatgac tatcgtcgcc gcacttatga ctgtcttctt      2040
tatcatgcaa ctcgtaggac aggtgccggc agcgctctgg gtcattttcg gcgaggaccg      2100
ctttcgctgg agcgcgacga tgatcggcct gtcgcttgcg gtattcggaa tcttgcacgc      2160
cctcgctcaa gccttcgtca ctggtcccgc caccaaacgt ttcggcgaga gcaggccat       2220 tatcgccggc atggcggccg acgcgctggg ctacgtcttg ctggcgttcg cgacgcgagg      2280
ctggatggcc ttccccatta tgattcttct cgcttccggc ggcatcggga tgcccgcgtt      2340
gcaggccatg ctgtccaggc aggtagatga cgaccatcag ggacagcttc aaggatcgct      2400
cgcggctctt accagcctaa cttcgatcat tggaccgctg atcgtcacgg cgatttatgc      2460
cgcctcggcg agcacatgga acgggttggc atggattgta ggcgccgccc tataccttgt      2520
ctgcctcccc gcgttgcgtc gcggtgcatg gagccgggcc acctcgacct gaatggaagc      2580
cggcggcacc tcgctaacgg attcaccact ccaagaattg gagccaatca attcttgcgg      2640
agaactgtga atgcgcaaac caaccccttgg cagaacatat ccatcgcgtc cgccatctcc      2700
agcagccgca cgcggcgcat ctcgggcagc gttgggtcct ggccacgggt gcgcatgatc      2760
gtgctcctgt cgttgaggac ccggctaggc tggcgggggtt gccttactgg ttagcagaat      2820
gaatcaccga tacgcgagcg aacgtgaagc gactgctgct gcaaaacgtc tgcgacctga      2880
gcaacaacat gaatggtctt cggtttccgt gtttcgtaaa gtctggaaac gcggaagtca      2940
gcgccctgca ccattatgtt ccggatctgc atcgcaggat gctgctggct accctgtgga      3000
acacctacat ctgtattaac gaagcgctgg cattgaccct gagtgatttt tctctggtcc      3060
cgccgcatcc ataccgccag ttgtttaccc tcacaacgtt ccagtaaccg gcatgttca       3120 tcatcagtaa cccgtatcgt gagcatcctc tctcgtttca tcggtatcat taccccatg       3180 aacagaaatc ccccttacac ggaggcatca gtgaccaaac aggaaaaaac cgcccttaac      3240
atggcccgct ttatcagaag ccagacatta acgcttctgg agaaactcaa cgagctggac      3300
gcggatgaac aggcagacat ctgtgaatcg cttcacgacc acgctgatga gctttaccgc      3360
agctgcctcg cgcgtttcgg tgatgacggt gaaaacctct gacacatgca gctcccggag      3420
acggtcacag cttgtctgta agcggatgcc gggagcagac aagcccgtca gggcgcgtca      3480
```

```
gcgggtgttg gcgggtgtcg gggcgcagcc atgacccagt cacgtagcga tagcggagtg      3540
tatactggct taactatgcg gcatcagagc agattgtact gagagtgcac catatgcggt      3600
gtgaaatacc gcacagatgc gtaaggagaa aataccgcat caggcgctct tccgcttcct      3660
cgctcactga ctcgctgcgc tcggtcgttc ggctgcggcg agcggtatca gctcactcaa      3720
aggcggtaat acggttatcc acagaatcag gggataacgc aggaaagaac atgtgagcaa      3780
aaggccagca aaaggccagg aaccgtaaaa aggccgcgtt gctggcgttt ttccataggc      3840
tccgcccccc tgacgagcat cacaaaaatc gacgctcaag tcagaggtgg cgaaacccga      3900
caggactata aagataccag gcgtttcccc ctggaagctc cctcgtgcgc tctcctgttc      3960
cgaccctgcc gcttaccgga tacctgtccg cctttctccc ttcgggaagc gtggcgcttt      4020
ctcatagctc acgctgtagg tatctcagtt cggtgtaggt cgttcgctcc aagctgggct      4080
gtgtgcacga acccccgtt cagcccgacc gctgcgcctt atccggtaac tatcgtcttg       4140
agtccaaccc ggtaagacac gacttatcgc cactggcagc agccactggt aacaggatta      4200
gcagagcgag gtatgtaggc ggtgctacag agttcttgaa gtggtggcct aactacggct      4260
acactagaag gacagtattt ggtatctgcg ctctgctgaa gccagttacc ttcggaaaaa      4320
gagttggtag ctcttgatcc ggcaaacaaa ccaccgctgg tagcggtggt ttttttgttt      4380
gcaagcagca gattacgcgc agaaaaaaag gatctcaaga agatcctttg atcttttcta      4440
cggggtctga cgctcagtgg aacgaaaact cacgttaagg gattttggtc atgagattat      4500
caaaaaggat cttcacctag atccttttaa attaaaaatg aagttttaaa tcaatctaaa      4560
gtatatatga gtaaacttgg tctgacagtt accaatgctt aatcagtgag gcacctatct      4620
cagcgatctg tctatttcgt tcatccatag ttgcctgact ccccgtcgtg tagataacta      4680
cgatacggga gggcttacca tctggcccca gtgctgcaat gataccgcga gacccacgct      4740
caccggctcc agatttatca gcaataaacc agccagccgg aagggccgag cgcagaagtg      4800
gtcctgcaac tttatccgcc tccatccagt ctattaattg ttgccgggaa gctagagtaa      4860
gtagttcgcc agttaatagt ttgcgcaacg ttgttgccat tgctgcaggc atcgtggtgt      4920
cacgctcgtc gtttggtatg gcttcattca gctccggttc ccaacgatca aggcgagtta      4980
catgatcccc catgttgtgc aaaaaagcgg ttagctcctt cggtcctccg atcgttgtca      5040
gaagtaagtt ggccgcagtg ttatcactca tggttatggc agcactgcat aattctctta      5100
ctgtcatgcc atccgtaaga tgcttttctg tgactggtga gtactcaacc aagtcattct      5160
gagaatagtg tatgcggcga ccgagttgct cttgcccggc gtcaacacgg gataataccg      5220
cgccacatag cagaacttta aaagtgctca tcattggaaa acgttcttcg gggcgaaaac      5280
tctcaaggat cttaccgctg ttgagatcca gttcgatgta acccactcgt gcacccaact      5340
gatcttcagc atcttttact ttcaccagcg tttctgggtg agcaaaaaca ggaaggcaaa      5400
atgccgcaaa aaagggaata agggcgcac ggaaatgttg aatactcata ctcttccttt        5460
ttcaatatta ttgaagcatt tatcagggtt attgtctcat gagcggatac atatttgaat      5520
gtatttagaa aaataaacaa ataggggttc cgcgcacatt tccccgaaaa gtgccacctg      5580
acgtctaaga aaccattatt atcatgacat taacctataa aaataggcgt atcacgaggc      5640
cctttcgtct tcaagaa                                                       5657
```

<210> SEQ ID NO 13
<211> LENGTH: 4855
<212> TYPE: DNA

-continued

```
<213> ORGANISM: Artificial Sequence
<220> FEATURE:
<223> OTHER INFORMATION: Recombinant plasmid pAPSE10304; beta actin stem
      loop - coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (40)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI recognition site
<220> FEATURE:
<221> NAME/KEY: misc_feature
<222> LOCATION: (497)..(791)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: misc_feature
<222> LOCATION: (1056)..(1061)
<223> OTHER INFORMATION: restriction endonuclease SphI recognition site

<400> SEQUENCE: 13
ttccgaaatt aatacgactc actataggga ggcgatcgcg cacgaggttt ttctgtctag       60
tgagcagtgt ccaacctcaa aagacaacat gtgtgacgac gatgtagcgg ctcttgtcgt      120
agacaatgga tccggtatgt gcaaagccgg tttcgcagga gatgacgcac cccgtgccgt      180
cttcccctcg atcgtcggtc gcccaaggca tcaaggagtc atggtcggta tgggacaaaa      240
ggactcatac gtaggagatg aagcccaaag caaaagaggt atcctcaccc tgaaataccc      300
catcgaacac ggtatcatca ccaactggga tgagtttaaa ccctctagct gctttacaaa      360
gtactggttc cctttccagc gggatgcttt atctaaacgc aatgagagag gtattcctca      420
ggccacatcg cttcctagtt ccgctgggat ccatcgttgg cggccgaagc cgccattcca      480
tagtgagttc tggcgcgcct catcccagtt ggtgatgata ccgtgttcga tggggtattt      540
cagggtgagg atacctcttt tgctttgggc ttcatctcct acgtatgagt cctttttgtcc      600 cataccgacc atgactcctt gatgccttgg gcgaccgacg atcgagggga agacggcacg      660
gggtgcgtca tctcctgcga aaccggcttt gcacataccg gatccattgt ctacgacaag      720
agccgctaca tcgtcgtcac acatgttgtc ttttgaggtt ggacactgct cactagacag      780
aaaaacctcg tgccggaccg aatacccggt ctgaacgagg gcggccgcgg tacccaagaa      840
gtacttagag ttaattaagg agttcaaaca tgaggatcac ccatgtcgaa gctcccacac      900
cctagcataa ccccttgggg cctctaaacg ggtcttgagg ggttttttgc tgaaaggagg      960
aactatatcc ggatatccac aggacgggtg tggtcgccat gatcgcgtag tcgatagtgg     1020
ctccaagtag cgaagcgagc aggactgggc ggcgggcatg caccattcct tgcggcggcg     1080
gtgctcaacg gcctcaacct actactgggc tgcttcctaa tgcaggagtc gcataaggga     1140
gagcgtcgac cgatgccctt gagagccttc aacccagtca gctccttccg gtgggcgcgg     1200
```

```
ggcatgacta tcgtcgccgc acttatgact gtcttcttta tcatgcaact cgtaggacag    1260
gtgccggcag cgctctgggt cattttcggc gaggaccgct ttcgctggag cgcgacgatg    1320
atcggcctgt cgcttgcggt attcggaatc ttgcacgccc tcgctcaagc cttcgtcact    1380
ggtcccgcca ccaaacgttt cggcgagaag caggccatta tcgccggcat ggcggccgac    1440
gcgctgggct acgtcttgct ggcgttcgcg acgcgaggct ggatggcctt ccccattatg    1500
attcttctcg cttccggcgg catcgggatg cccgcgttgc aggccatgct gtccaggcag    1560
gtagatgacg accatcaggg acagcttcaa ggatcgctcg cggctcttac cagcctaact    1620
tcgatcattg gaccgctgat cgtcacggcg atttatgccg cctcggcgag cacatggaac    1680
gggttggcat ggattgtagg cgccgcccta taccttgtct gcctccccgc gttgcgtcgc    1740
ggtgcatgga gccgggccac ctcgacctga atggaagccg gcggcacctc gctaacggat    1800
tcaccactcc aagaattgga gccaatcaat tcttgcggag aactgtgaat gcgcaaacca    1860
acccttggca gaacatatcc atcgcgtccg ccatctccag cagccgcacg cggcgcatct    1920
cgggcagcgt tgggtcctgg ccacgggtgc gcatgatcgt gctcctgtcg ttgaggaccc    1980
ggctaggctg gcggggttgc cttactggtt agcagaatga atcaccgata cgcgagcgaa    2040
cgtgaagcga ctgctgctgc aaaacgtctg cgacctgagc aacaacatga atggtcttcg    2100
gtttccgtgt ttcgtaaagt ctggaaacgc ggaagtcagc gccctgcacc attatgttcc    2160
ggatctgcat cgcaggatgc tgctggctac cctgtggaac acctacatct gtattaacga    2220
agcgctggca ttgaccctga gtgatttttc tctggtcccg ccgcatccat accgccagtt    2280
gtttaccctc acaacgttcc agtaaccggg catgttcatc atcagtaacc cgtatcgtga    2340
gcatcctctc tcgtttcatc ggtatcatta cccccatgaa cagaaatccc ccttacacgg    2400
aggcatcagt gaccaaacag gaaaaaaccg cccttaacat ggcccgcttt atcagaagcc    2460
agacattaac gcttctggag aaactcaacg agctggacgc ggatgaacag gcagacatct    2520
gtgaatcgct tcacgaccac gctgatgagc tttaccgcag ctgcctcgcg cgtttcggtg    2580
atgacggtga aaacctctga cacatgcagc tcccggagac ggtcacagct tgtctgtaag    2640
cggatgccgg gagcagacaa gcccgtcagg cgcgtcagc gggtgttggc gggtgtcggg    2700
gcgcagccat gacccagtca cgtagcgata gcggagtgta tactggctta actatgcggc    2760
atcagagcag attgtactga gagtgcacca tatgcggtgt gaaataccgc acagatgcgt    2820
aaggagaaaa taccgcatca ggcgctcttc cgcttcctcg ctcactgact cgctgcgctc    2880
ggtcgttcgg ctgcggcgag cggtatcagc tcactcaaag gcggtaatac ggttatccac    2940
agaatcaggg gataacgcag gaaagaacat gtgagcaaaa ggccagcaaa aggccaggaa    3000
ccgtaaaaag gccgcgttgc tggcgttttt ccataggctc cgcccccctg acgagcatca    3060
caaaaatcga cgctcaagtc agaggtggcg aaacccgaca ggactataaa gataccaggc    3120
gtttccccct ggaagctccc tcgtgcgctc tcctgttccg accctgccgc ttaccggata    3180
cctgtccgcc tttctccctt cgggaagcgt ggcgctttct catagctcac gctgtaggta    3240
tctcagttcg gtgtaggtcg ttcgctccaa gctgggctgt gtgcacgaac ccccgttca     3300 gcccgaccgc tgcgccttat ccggtaacta tcgtcttgag tccaacccgg taagacacga    3360
cttatcgcca ctggcagcag ccactggtaa caggattagc agagcgaggt atgtaggcgg    3420
tgctacagag ttcttgaagt ggtggcctaa ctacggctac actagaagga cagtatttgg    3480
tatctgcgct ctgctgaagc cagttacctt cggaaaaaga gttggtagct cttgatccgg    3540
caaacaaacc accgctggta gcggtggttt ttttgtttgc aagcagcaga ttacgcgcag    3600
```

```
aaaaaaagga tctcaagaag atcctttgat cttttctacg gggtctgacg ctcagtggaa    3660
cgaaaactca cgttaaggga ttttggtcat gagattatca aaaaggatct tcacctagat    3720 cctttaaat  taaaaatgaa gttttaaatc aatctaaagt atatatgagt aaacttggtc    3780
tgacagttac caatgcttaa tcagtgaggc acctatctca gcgatctgtc tatttcgttc    3840
atccatagtt gcctgactcc ccgtcgtgta dataactacg atacgggagg gcttaccatc    3900
tggccccagt gctgcaatga taccgcgaga cccacgctca ccggctccag atttatcagc    3960
aataaaccag ccagccggaa gggccgagcg cagaagtggt cctgcaactt tatccgcctc    4020
catccagtct attaattgtt gccgggaagc tagagtaagt agttcgccag ttaatagttt    4080
gcgcaacgtt gttgccattg ctgcaggcat cgtggtgtca cgctcgtcgt ttggtatggc    4140
ttcattcagc tccggttccc aacgatcaag gcgagttaca tgatccccca tgttgtgcaa    4200
aaaagcggtt agctccttcg gtcctccgat cgttgtcaga agtaagttgg ccgcagtgtt    4260
atcactcatg gttatggcag cactgcataa ttctcttact gtcatgccat ccgtaagatg    4320
cttttctgtg actggtgagt actcaaccaa gtcattctga gaatagtgta tgcggcgacc    4380
gagttgctct tgcccggcgt caacacggga taataccgcg ccacatagca gaactttaaa    4440
agtgctcatc attggaaaac gttcttcggg gcgaaaactc tcaaggatct taccgctgtt    4500
gagatccagt tcgatgtaac ccactcgtgc acccaactga tcttcagcat cttttacttt    4560
caccagcgtt tctgggtgag caaaaacagg aaggcaaaat gccgcaaaaa agggaataag    4620
ggcgacacgg aaatgttgaa tactcatact cttccttttt caatattatt gaagcattta    4680
tcagggttat tgtctcatga gcggatacat atttgaatgt atttagaaaa ataaacaaat    4740
aggggttccg cgcacatttc cccgaaaagt gccacctgac gtctaagaaa ccattattat    4800
catgacatta acctataaaa ataggcgtat cacgaggccc tttcgtcttc aagaa          4855
```

```
<210> SEQ ID NO 14
<211> LENGTH: 5367
<212> TYPE: DNA
<213> ORGANISM: Artificial Sequence
<220> FEATURE:
<223> OTHER INFORMATION: Recombinant plasmid pAPSE10279; beta actin stem
      loop + capsid
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: promoter
<222> LOCATION: (985)..(1003)
<223> OTHER INFORMATION: bacteriophage T7 gene 1 promoter
```

<220> FEATURE:
<221> NAME/KEY: gene
<222> LOCATION: (1076)..(1465)
<223> OTHER INFORMATION: bacteriophage MS2 coat protein gene
<220> FEATURE:
<221> NAME/KEY: terminator
<222> LOCATION: (1498)..(1545)
<223> OTHER INFORMATION: bacteriophage T7 transcription terminator

<400> SEQUENCE: 14

```
ttcttagctc cggcaagcaa ttaagaactt ccgaaattaa tacgactcac tatagggagg    60
cgatcgcgca cgaggttttt ctgtctagtg agcagtgtcc aacctcaaaa gacaacatgt   120
gtgacgacga tgtagcggct cttgtcgtag acaatggatc cggtatgtgc aaagccggtt   180
tcgcaggaga tgacgcaccc cgtgccgtct tcccctcgat cgtcggtcgc ccaaggcatc   240
aaggagtcat ggtcggtatg ggacaaaagg actcatacgt aggagatgaa gcccaaagca   300
aaagaggtat cctcaccctg aaatacccca tcgaacacgg tatcatcacc aactgggatg   360
agtttaaacc ctctagctgc tttacaaagt actggttccc tttccagcgg gatgctttat   420
ctaaacgcaa tgagagaggt attcctcagg ccacatcgct tcctagttcc gctgggatcc   480
atcgttggcg gccgaagccg ccattccata gtgagttctg gcgcgcctca tcccagttgg   540
tgatgatacc gtgttcgatg gggtatttca gggtgaggat acctcttttg ctttgggctt   600
catctcctac gtatgagtcc ttttgtccca taccgaccat gactccttga tgccttgggc   660
gaccgacgat cgaggggaag acggcacggg gtgcgtcatc tcctgcgaaa ccggctttgc   720
acataccgga tccattgtct acgacaagag ccgctacatc gtcgtcacac atgttgtctt   780
ttgaggttgg acactgctca ctagacagaa aaacctcgtg ccggaccgaa tacccggtct   840
gaacgaggtt aattaaggta cccaagaagt acttagaggc ggccgcctag cataacccct   900
tggggcctct aaacgggtct tgaggggttt tttgagaaac ggccgaatac acctgttcgg   960
atccagatct cgatcccgcg aaattaatac gactcactat agggagacca caacggtttc  1020
cctctagatc acaagtttgt acaaaaaagc aggctaagaa ggagatatac atatggcgtc  1080
taactttacc caattcgttc tggttgataa cggcggtacg ggtgacgtta ccgtagctcc  1140
gtccaacttc gccaacggtg ttgcggaatg gattagctct aacagccgct ctcaggccta  1200
caaagtcacg tgctccgttc gtcagtctag cgcgcagaat cgcaaataca ccatcaaagt  1260
tgaagtaccg aaagtcgcaa cgcagaccgt aggcggcgta gaactcccag ttgcggcctg  1320
gcgctcttac ctcaacatgg aactgactat tccgattttt gcgacgaact ccgactgcga  1380
actgattgtt aaggcaatgc agggcctgct gaaagacggt aatccgatcc catctgcaat  1440
cgctgctaac tctggcattt actaataagc ggacgcgctg ccaccgctga gcaataacta  1500
gcataacccc ttggggcctc taaacgggtc ttgaggggtt ttttgctgaa aggaggaact  1560
atatccggca tgcaccattc cttgcggcgg cggtgctcaa cggcctcaac ctactactgg  1620
gctgcttcct aatgcaggag tcgcataagg agagcgtcg accgatgccc ttgagagcct  1680
tcaacccagt cagctccttc cggtgggcgc ggggcatgac tatcgtcgcc gcacttatga  1740
ctgtcttctt tatcatgcaa ctcgtaggac aggtgccggc agcgctctgg gtcattttcg  1800
gcgaggaccg ctttcgctgg agcgcgacga tgatcggcct gtcgcttgcg gtattcggaa  1860
tcttgcacgc cctcgctcaa gccttcgtca ctggtcccgc caccaaacgt ttcggcgaga  1920
agcaggccat tatcgccggc atggcggccg acgcgctggg ctacgtcttg ctggcgttcg  1980
cgacgcgagg ctggatggcc ttccccatta tgattcttct cgcttccggc ggcatcggga  2040
```

-continued

```
tgcccgcgtt gcaggccatg ctgtccaggc aggtagatga cgaccatcag ggacagcttc      2100
aaggatcgct cgcggctctt accagcctaa cttcgatcat tggaccgctg atcgtcacgg      2160
cgatttatgc cgcctcggcg agcacatgga acgggttggc atggattgta ggcgccgccc      2220
tataccttgt ctgcctcccc gcgttgcgtc gcggtgcatg gagccgggcc acctcgacct      2280
gaatggaagc cggcggcacc tcgctaacgg attcaccact ccaagaattg gagccaatca      2340
attcttgcgg agaactgtga atgcgcaaac caacccttgg cagaacatat ccatcgcgtc      2400
cgccatctcc agcagccgca cgcggcgcat ctcgggcagc gttgggtcct ggccacgggt      2460
gcgcatgatc gtgctcctgt cgttgaggac ccggctaggc tggcgggggtt gccttactgg      2520 ttagcagaat gaatcaccga tacgcgagcg aacgtgaagc gactgctgct gcaaaacgtc      2580
tgcgacctga gcaacaacat gaatggtctt cggtttccgt gtttcgtaaa gtctggaaac      2640
gcggaagtca gcgccctgca ccattatgtt ccggatctgc atcgcaggat gctgctggct      2700
accctgtgga acacctacat ctgtattaac gaagcgctgg cattgaccct gagtgatttt      2760
tctctggtcc cgccgcatcc ataccgccag ttgtttaccc tcacaacgtt ccagtaaccg      2820
ggcatgttca tcatcagtaa cccgtatcgt gagcatcctc tctcgtttca tcggtatcat      2880 taccccccatg aacagaaatc ccccttacac ggaggcatca gtgaccaaac aggaaaaaac      2940
cgcccttaac atggcccgct ttatcagaag ccagacatta acgcttctgg agaaactcaa      3000
cgagctggac gcggatgaac aggcagacat ctgtgaatcg cttcacgacc acgctgatga      3060
gctttaccgc agctgcctcg cgcgtttcgg tgatgacggt gaaaacctct gacacatgca      3120
gctcccggag acggtcacag cttgtctgta agcggatgcc gggagcagac aagcccgtca      3180
gggcgcgtca gcgggtgttg gcgggtgtcg gggcgcagcc atgacccagt cacgtagcga      3240
tagcggagtg tatactggct taactatgcg gcatcagagc agattgtact gagagtgcac      3300
catatgcggt gtgaaatacc gcacagatgc gtaaggagaa aataccgcat caggcgctct      3360
tccgcttcct cgctcactga ctcgctgcgc tcggtcgttc ggctgcggcg agcggtatca      3420
gctcactcaa aggcggtaat acggttatcc acagaatcag gggataacgc aggaaagaac      3480
atgtgagcaa aaggccagca aaaggccagg aaccgtaaaa aggccgcgtt gctggcgttt      3540
ttccataggc tccgcccccc tgacgagcat cacaaaaatc gacgctcaag tcagaggtgg      3600
cgaaacccga caggactata aagataccag gcgtttcccc ctggaagctc cctcgtgcgc      3660
tctcctgttc cgaccctgcc gcttaccgga tacctgtccg cctttctccc ttcgggaagc      3720
gtggcgcttt ctcatagctc acgctgtagg tatctcagtt cggtgtaggt cgttcgctcc      3780
aagctgggct gtgtgcacga accccccgtt cagcccgacc gctgcgcctt atccggtaac      3840
tatcgtcttg agtccaaccc ggtaagacac gacttatcgc cactggcagc agccactggt      3900
aacaggatta gcagagcgag gtatgtaggc ggtgctacag agttcttgaa gtggtggcct      3960
aactacggct acactagaag gacagtattt ggtatctgcg ctctgctgaa gccagttacc      4020
ttcggaaaaa gagttggtag ctcttgatcc ggcaaacaaa ccaccgctgg tagcggtggt      4080
ttttttgttt gcaagcagca gattacgcgc agaaaaaaag gatctcaaga agatcctttg      4140
atcttttcta cggggtctga cgctcagtgg aacgaaaact cacgttaagg gattttggtc      4200
atgagattat caaaaaggat cttcacctag atccttttaa attaaaaatg aagttttaaa      4260
tcaatctaaa gtatatatga gtaaacttgg tctgacagtt accaatgctt aatcagtgag      4320
gcacctatct cagcgatctg tctatttcgt tcatccatag ttgcctgact ccccgtcgtg      4380
tagataacta cgatacggga gggcttacca tctggcccca gtgctgcaat gataccgcga      4440
```

```
gacccacgct caccggctcc agatttatca gcaataaacc agccagccgg aagggccgag      4500
cgcagaagtg gtcctgcaac tttatccgcc tccatccagt ctattaattg ttgccgggaa      4560
gctagagtaa gtagttcgcc agttaatagt ttgcgcaacg ttgttgccat tgctgcaggc      4620
atcgtggtgt cacgctcgtc gtttggtatg gcttcattca gctccggttc ccaacgatca      4680
aggcgagtta catgatcccc catgttgtgc aaaaaagcgg ttagctcctt cggtcctccg      4740
atcgttgtca gaagtaagtt ggccgcagtg ttatcactca tggttatggc agcactgcat      4800
aattctctta ctgtcatgcc atccgtaaga tgcttttctg tgactggtga gtactcaacc      4860
aagtcattct gagaatagtg tatgcggcga ccgagttgct cttgcccggc gtcaacacgg      4920
gataataccg cgccacatag cagaacttta aaagtgctca tcattggaaa acgttcttcg      4980
gggcgaaaac tctcaaggat cttaccgctg ttgagatcca gttcgatgta acccactcgt      5040
gcacccaact gatcttcagc atcttttact ttcaccagcg tttctgggtg agcaaaaaca      5100
ggaaggcaaa atgccgcaaa aaagggaata agggcgacac ggaaatgttg aatactcata      5160
ctcttccttt ttcaatatta ttgaagcatt tatcagggtt attgtctcat gagcggatac      5220
atatttgaat gtatttagaa aaataaacaa ataggggttc cgcgcacatt tccccgaaaa      5280
gtgccacctg acgtctaaga aaccattatt atcatgacat taacctataa aaataggcgt      5340
atcacgaggc cctttcgtct tcaagaa                                          5367
```

```
<210> SEQ ID NO 15
<211> LENGTH: 4764
<212> TYPE: DNA
<213> ORGANISM: Artificial Sequence
<220> FEATURE:
<223> OTHER INFORMATION: Recombinant plasmid pAPSE10303; beta actin stem
      loop - coat protein
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator

<400> SEQUENCE: 15
```

```
ttcttagctc cggcaagcaa ttaagaactt ccgaaattaa tacgactcac tatagggagg       60
cgatcgcgca cgaggttttt ctgtctagtg agcagtgtcc aacctcaaaa gacaacatgt      120
gtgacgacga tgtagcggct cttgtcgtag acaatggatc cggtatgtgc aaagccggtt      180
tcgcaggaga tgacgcaccc cgtgccgtct tccctcgat cgtcggtcgc ccaaggcatc       240
aaggagtcat ggtcggtatg ggacaaaagg actcatacgt aggagatgaa gcccaaagca      300
aaagaggtat cctcaccctg aaatacccca tcgaacacgg tatcatcacc aactgggatg      360
```

-continued

```
agtttaaacc ctctagctgc tttacaaagt actggttccc tttccagcgg gatgctttat    420
ctaaacgcaa tgagagaggt attcctcagg ccacatcgct tcctagttcc gctgggatcc    480
atcgttggcg gccgaagccg ccattccata gtgagttctg gcgcgcctca tcccagttgg    540
tgatgatacc gtgttcgatg gggtatttca gggtgaggat acctcttttg ctttgggctt    600
catctcctac gtatgagtcc ttttgtccca taccgaccat gactccttga tgccttgggc    660
gaccgacgat cgaggggaag acggcacggg gtgcgtcatc tcctgcgaaa ccggctttgc    720
acataccgga tccattgtct acgacaagag ccgctacatc gtcgtcacac atgttgtctt    780
ttgaggttgg acactgctca ctagacagaa aaacctcgtg ccggaccgaa tacccggtct    840
gaacgaggtt aattaaggta cccaagaagt acttagaggc ggccgcctag cataacccct    900
tggggcctct aaacgggtct tgaggggttt tttgagaaac ggccgaatac acctgttcgg    960
atccagatcc accattcctt gcggcggcgg tgctcaacgg cctcaaccta ctactgggct   1020
gcttcctaat gcaggagtcg cataagggag agcgtcgacc gatgcccttg agagccttca   1080
acccagtcag ctccttccgg tgggcgcggg gcatgactat cgtcgccgca cttatgactg   1140
tcttctttat catgcaactc gtaggacagg tgccggcagc gctctgggtc attttcggcg   1200
aggaccgctt tcgctggagc gcgacgatga tcggcctgtc gcttgcggta ttcggaatct   1260
tgcacgccct cgctcaagcc ttcgtcactg gtcccgccac caaacgtttc ggcgagaagc   1320
aggccattat cgccggcatg gcggccgacg cgctgggcta cgtcttgctg gcgttcgcga   1380
cgcgaggctg gatggccttc cccattatga ttcttctcgc ttccggcggc atcgggatgc   1440
ccgcgttgca ggccatgctg tccaggcagg tagatgacga ccatcaggga cagcttcaag   1500
gatcgctcgc ggctcttacc agcctaactt cgatcattgg accgctgatc gtcacggcga   1560
tttatgccgc ctcggcgagc acatggaacg ggttggcatg gattgtaggc gccgccctat   1620
accttgtctg cctccccgcg ttgcgtcgcg gtgcatggag ccgggccacc tcgacctgaa   1680
tggaagccgg cggcacctcg ctaacggatt caccactcca agaattggag ccaatcaatt   1740
cttgcggaga actgtgaatg cgcaaaccaa cccttggcag aacatatcca tcgcgtccgc   1800
catctccagc agccgcacgc ggcgcatctc gggcagcgtt gggtcctggc cacgggtgcg   1860
catgatcgtg ctcctgtcgt tgaggacccg gctaggctgg cggggttgcc ttactggtta   1920
gcagaatgaa tcaccgatac gcgagcgaac gtgaagcgac tgctgctgca aaacgtctgc   1980
gacctgagca acaacatgaa tggtcttcgg tttccgtgtt tcgtaaagtc tggaaacgcg   2040
gaagtcagcg ccctgcacca ttatgttccg gatctgcatc gcaggatgct gctggctacc   2100
ctgtggaaca cctacatctg tattaacgaa gcgctggcat tgaccctgag tgattttttct   2160 ctggtcccgc cgcatccata ccgccagttg tttaccctca caacgttcca gtaaccgggc   2220
atgttcatca tcagtaaccc gtatcgtgag catcctctct cgtttcatcg gtatcattac   2280
ccccatgaac agaaatcccc cttacacgga ggcatcagtg accaaacagg aaaaaaccgc   2340
ccttaacatg gcccgcttta tcagaagcca gacattaacg cttctggaga aactcaacga   2400
gctggacgcg gatgaacagg cagacatctg tgaatcgctt cacgaccacg ctgatgagct   2460
ttaccgcagc tgcctcgcgc gtttcggtga tgacggtgaa aacctctgac acatgcagct   2520
cccggagacg gtcacagctt gtctgtaagc ggatgccggg agcagacaag cccgtcaggg   2580
cgcgtcagcg ggtgttggcg ggtgtcgggg cgcagccatg acccagtcac gtagcgatag   2640
cggagtgtat actggcttaa ctatgcggca tcagagcaga ttgtactgag agtgcaccat   2700
```

-continued

```
atgcggtgtg aaataccgca cagatgcgta aggagaaaat accgcatcag gcgctcttcc     2760
gcttcctcgc tcactgactc gctgcgctcg gtcgttcggc tgcggcgagc ggtatcagct     2820
cactcaaagg cggtaatacg gttatccaca gaatcagggg ataacgcagg aaagaacatg     2880
tgagcaaaag gccagcaaaa ggccaggaac cgtaaaaagg ccgcgttgct ggcgtttttc     2940
cataggctcc gcccccctga cgagcatcac aaaaatcgac gctcaagtca gaggtggcga     3000
aacccgacag gactataaag ataccaggcg tttcccctg gaagctccct cgtgcgctct     3060
cctgttccga ccctgccgct taccggatac ctgtccgcct ttctcccttc gggaagcgtg     3120
gcgctttctc atagctcacg ctgtaggtat ctcagttcgg tgtaggtcgt tcgctccaag     3180
ctgggctgtg tgcacgaacc ccccgttcag cccgaccgct gcgccttatc cggtaactat     3240
cgtcttgagt ccaacccggt aagacacgac ttatcgccac tggcagcagc cactggtaac     3300
aggattagca gagcgaggta tgtaggcggt gctacagagt tcttgaagtg gtggcctaac     3360
tacggctaca ctagaaggac agtatttggt atctgcgctc tgctgaagcc agttaccttc     3420
ggaaaaagag ttggtagctc ttgatccggc aaacaaacca ccgctggtag cggtggtttt     3480
tttgtttgca agcagcagat tacgcgcaga aaaaaaggat ctcaagaaga tcctttgatc     3540
ttttctacgg ggtctgacgc tcagtggaac gaaaactcac gttaagggat tttggtcatg     3600
agattatcaa aaaggatctt cacctagatc cttttaaatt aaaaatgaag ttttaaatca     3660
atctaaagta tatatgagta aacttggtct gacagttacc aatgcttaat cagtgaggca     3720
cctatctcag cgatctgtct atttcgttca tccatagttg cctgactccc cgtcgtgtag     3780
ataactacga tacgggaggg cttaccatct ggccccagtg ctgcaatgat accgcgagac     3840
ccacgctcac cggctccaga tttatcagca ataaaccagc cagccggaag ggccgagcgc     3900
agaagtggtc ctgcaacttt atccgcctcc atccagtcta ttaattgttg ccgggaagct     3960
agagtaagta gttcgccagt taatagtttg cgcaacgttg ttgccattgc tgcaggcatc     4020
gtggtgtcac gctcgtcgtt tggtatggct tcattcagct ccggttccca acgatcaagg     4080
cgagttacat gatcccccat gttgtgcaaa aaagcggtta gctccttcgg tcctccgatc     4140
gttgtcagaa gtaagttggc cgcagtgtta tcactcatgg ttatggcagc actgcataat     4200
tctcttactg tcatgccatc cgtaagatgc ttttctgtga ctggtgagta ctcaaccaag     4260
tcattctgag aatagtgtat gcggcgaccg agttgctctt gcccggcgtc aacacgggat     4320
aataccgcgc cacatagcag aactttaaaa gtgctcatca ttggaaaacg ttcttcgggg     4380
cgaaaactct caaggatctt accgctgttg agatccagtt cgatgtaacc cactcgtgca     4440
cccaactgat cttcagcatc ttttactttc accagcgttt ctgggtgagc aaaaacagga     4500
aggcaaaatg ccgcaaaaaa gggaataagg gcgacacgga atgttgaat actcatactc     4560 ttcctttttc aatattattg aagcatttat cagggttatt gtctcatgag cggatacata     4620
tttgaatgta tttagaaaaa taaacaaata ggggttccgc gcacatttcc ccgaaaagtg     4680
ccacctgacg tctaagaaac cattattatc atgacattaa cctataaaaa taggcgtatc     4740
acgaggccct ttcgtcttca agaa                                            4764
```

<210> SEQ ID NO 16
<211> LENGTH: 5940
<212> TYPE: DNA
<213> ORGANISM: Artificial Sequence
<220> FEATURE:
<223> OTHER INFORMATION: Recombinant plasmid pAPSE10270; beta actin stem
      loop + coat protein
<220> FEATURE:

-continued

```
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (782)..(1076)
<223> OTHER INFORMATION: beta actin antisense gene fragment
<220> FEATURE:
<221> NAME/KEY: misc_feature
<222> LOCATION: (1151)..(1169)
<223> OTHER INFORMATION: Bacteriophage MS2 pac sequence
<220> FEATURE:
<221> NAME/KEY: terminator
<222> LOCATION: (1185)..(1232)
<223> OTHER INFORMATION: bacteriophage T7 transcription terminator
<220> FEATURE:
<221> NAME/KEY: promoter
<222> LOCATION: (1558)..(1576)
<223> OTHER INFORMATION: bacteriophage T7 gene 1 promoter
<220> FEATURE:
<221> NAME/KEY: gene
<222> LOCATION: (1649)..(2038)
<223> OTHER INFORMATION: bacteriophage MS2 coat protein gene
<220> FEATURE:
<221> NAME/KEY: terminator
<222> LOCATION: (2071)..(2118)
<223> OTHER INFORMATION: bacteriophage T7 transcription terminator

<400> SEQUENCE: 16
ttctcatgtt tgacagctta tcatcgataa gctttaatgc ggtagtttat cacagttaaa       60
ttgctaacgc agtcaggcac cgtgtatgaa atctaacaat gcgctcatcg tcatcctcgg      120
caccgtcacc ctggatgctg taggcatagg cttggttatg ccggtactgc cgggcctctt      180
gcgggatgaa ttcagatctc gatcccgcga aattaatacg actcactata gggagaccac      240
aacggtttcc ctctagatca caagtttgta caaaaaagca ggctaagaag gagatataca      300
tacgccggcc attcaaacat gaggattacc catgtattta atacccatg tccaggcgcg       360 ctccgcgatc gcgcacgagg tttttctgtc tagtgagcag tgtccaacct caaaagacaa      420
catgtgtgac gacgatgtag cggctcttgt cgtagacaat ggatccggta tgtgcaaagc      480
cggtttcgca ggagatgacg cacccgtgc cgtcttcccc tcgatcgtcg tcgcccaag       540 gcatcaagga gtcatggtcg gtatgggaca aaaggactca tacgtaggag atgaagccca      600
aagcaaaaga ggtatcctca ccctgaaata ccccatcgaa cacggtatca tcaccaactg      660
ggatgagttt aaaccctcta gctgctttac aaagtactgg ttccctttcc agcgggatgc      720
tttatctaaa cgcaatgaga gaggtattcc tcaggccaca tcgcttccta gttcggcgcg      780
cctcatccca gttggtgatg ataccgtgtt cgatggggta tttcagggtg aggatacctc      840
ttttgctttg ggcttcatct cctacgtatg agtccttttg tcccataccg accatgactc      900
cttgatgcct tgggcgaccg acgatcgagg ggaagacggc acggggtgcg tcatctcctg      960
cgaaaccggc tttgcacata ccggatccat tgtctacgac aagagccgct acatcgtcgt     1020
cacacatgtt gtcttttgag gttggacact gctcactaga cagaaaaacc tcgtgccgga     1080
ccgaataccc ggtctgaacg agggcggccg cggtacccaa gaagtactta gagttaatta    1140
```

-continued

```
aggagttcaa acatgaggat cacccatgtc gaagctccca cacccctagca taacccccttg    1200 gggcctctaa acgggtcttg aggggttttt tgctgaaagg aggaactata tccggatatc    1260
cacaggacgg gtgtggtcgc catgatcgcg tagtcgatag tggctccaag tagcgaagcg    1320
agcaggactg ggcggcgggc atgcatcgtc cattccgaca gcatcgccag tcactatggc    1380
gtgctgctag cgctatatgc gttgatgcaa tttctatgcg cacccgttct cggagcactg    1440
tccgaccgct ttggccgccg cccagtcctg ctcgcttcgc tacttggagc cactatcgac    1500
tacgcgatca tggcgaccac acccgtcctg tggatccaga tctcgatccc gcgaaattaa    1560
tacgactcac tatagggaga ccacaacggt ttccctctag atcacaagtt tgtacaaaaa    1620
agcaggctaa gaaggagata tacatatggc gtctaacttt acccaattcg ttctggttga    1680
taacggcggt acgggtgacg ttaccgtagc tccgtccaac ttcgccaacg gtgttgcgga    1740
atggattagc tctaacagcc gctctcaggc ctacaaagtc acgtgctccg ttcgtcagtc    1800
tagcgcgcag aatcgcaaat acaccatcaa agttgaagta ccgaaagtcg caacgcagac    1860
cgtaggcggc gtagaactcc cagttgcggc ctggcgctct tacctcaaca tggaactgac    1920
tattccgatt tttgcgacga actccgactg cgaactgatt gttaaggcaa tgcagggcct    1980
gctgaaagac ggtaatccga tcccatctgc aatcgctgct aactctggca tttactaata    2040
agcggacgcg ctgccaccgc tgagcaataa ctagcataac cccttggggc ctctaaacgg    2100
gtcttgaggg gttttttgct gaaaggagga actatatccg gcatgcacca ttccttgcgg    2160
cggcggtgct caacggcctc aacctactac tgggctgctt cctaatgcag gagtcgcata    2220
agggagagcg tcgaccgatg cccttgagag ccttcaaccc agtcagctcc ttccggtggg    2280
cgcggggcat gactatcgtc gccgcactta tgactgtctt ctttatcatg caactcgtag    2340
gacaggtgcc ggcagcgctc tgggtcattt tcggcgagga ccgctttcgc tggagcgcga    2400
cgatgatcgg cctgtcgctt gcggtattcg gaatcttgca cgccctcgct caagccttcg    2460
tcactggtcc cgccaccaaa cgtttcggcg agaagcaggc cattatcgcc ggcatggcgg    2520
ccgacgcgct gggctacgtc ttgctggcgt cgcgacgcg aggctggatg gccttccccca    2580 ttatgattct tctcgcttcc ggcggcatcg ggatgcccgc gttgcaggcc atgctgtcca    2640
ggcaggtaga tgacgaccat cagggacagc ttcaaggatc gctcgcggct cttaccagcc    2700
taacttcgat cattggaccg ctgatcgtca cggcgattta tgccgcctcg gcgagcacat    2760
ggaacgggtt ggcatggatt gtaggcgccg ccctatacct tgtctgcctc cccgcgttgc    2820
gtcgcggtgc atggagccgg gccacctcga cctgaatgga agccggcggc acctcgctaa    2880
cggattcacc actccaagaa ttggagccaa tcaattcttg cggagaactg tgaatgcgca    2940
aaccaaccct tggcagaaca tatccatcgc gtccgccatc tccagcagcc gcacgcggcg    3000
catctcgggc agcgttgggt cctggccacg ggtgcgcatg atcgtgctcc tgtcgttgag    3060
gacccggcta ggctggcggg gttgccttac tggttagcag aatgaatcac cgatacgcga    3120
gcgaacgtga agcgactgct gctgcaaaac gtctgcgacc tgagcaacaa catgaatggt    3180
cttcggtttc cgtgtttcgt aaagtctgga aacgcggaag tcagcgccct gcaccattat    3240
gttccggatc tgcatcgcag gatgctgctg gctaccctgt ggaacaccta catctgtatt    3300
aacgaagcgc tggcattgac cctgagtgat ttttctctgg tcccgccgca tccataccgc    3360
cagttgttta ccctcacaac gttccagtaa ccgggcatgt tcatcatcag taacccgtat    3420
cgtgagcatc ctctctcgtt tcatcggtat cattacccccc atgaacagaa atccccctta    3480
```

-continued

```
cacggaggca tcagtgacca aacaggaaaa aaccgccctt aacatggccc gctttatcag   3540
aagccagaca ttaacgcttc tggagaaact caacgagctg gacgcggatg aacaggcaga   3600
catctgtgaa tcgcttcacg accacgctga tgagctttac cgcagctgcc tcgcgcgttt   3660
cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggcgca gccatgaccc agtcacgtag cgatagcgga gtgtatactg gcttaactat   3840
gcggcatcag agcagattgt actgagagtg caccatatgc ggtgtgaaat accgcacaga   3900
tgcgtaagga gaaaataccg catcaggcgc tcttccgctt cctcgctcac tgactcgctg   3960
cgctcggtcg ttcggctgcg gcgagcggta tcagctcact caaaggcggt aatacggtta   4020
tccacagaat caggggataa cgcaggaaag aacatgtgag caaaaggcca gcaaaaggcc   4080
aggaaccgta aaaaggccgc gttgctggcg tttttccata ggctccgccc ccctgacgag   4140
catcacaaaa atcgacgctc aagtcagagg tggcgaaacc cgacaggact ataaagatac   4200
caggcgtttc cccctggaag ctccctcgtg cgctctcctg ttccgaccct gccgcttacc   4260
ggatacctgt ccgcctttct cccttcggga agcgtggcgc tttctcatag ctcacgctgt   4320
aggtatctca gttcggtgta ggtcgttcgc tccaagctgg gctgtgtgca cgaacccccc   4380
gttcagcccg accgctgcgc cttatccggt aactatcgtc ttgagtccaa cccggtaaga   4440
cacgacttat cgccactggc agcagccact ggtaacagga ttagcagagc gaggtatgta   4500
ggcggtgcta cagagttctt gaagtggtgg cctaactacg gctacactag aaggacagta   4560
tttggtatct gcgctctgct gaagccagtt accttcggaa aaagagttgg tagctcttga   4620
tccggcaaac aaaccaccgc tggtagcggt ggtttttttg tttgcaagca gcagattacg   4680
cgcagaaaaa aaggatctca agaagatcct ttgatctttt ctacggggtc tgacgctcag   4740
tggaacgaaa actcacgtta agggattttg gtcatgagat tatcaaaaag gatcttcacc   4800
tagatccttt taaattaaaa atgaagtttt aaatcaatct aaagtatata tgagtaaact   4860
tggtctgaca gttaccaatg cttaatcagt gaggcaccta tctcagcgat ctgtctattt   4920
cgttcatcca tagttgcctg actccccgtc gtgtagataa ctacgatacg ggagggctta   4980
ccatctggcc ccagtgctgc aatgataccg cgagacccac gctcaccggc tccagattta   5040
tcagcaataa accagccagc cggaagggcc gagcgcagaa gtggtcctgc aactttatcc   5100
gcctccatcc agtctattaa ttgttgccgg gaagctagag taagtagttc gccagttaat   5160
agtttgcgca acgttgttgc cattgctgca ggcatcgtgg tgtcacgctc gtcgtttggt   5220
atggcttcat tcagctccgg ttcccaacga tcaaggcgag ttacatgatc ccccatgttg   5280
tgcaaaaaag cggttagctc cttcggtcct ccgatcgttg tcagaagtaa gttggccgca   5340
gtgttatcac tcatggttat ggcagcactg cataattctc ttactgtcat gccatccgta   5400
agatgctttt ctgtgactgg tgagtactca accaagtcat tctgagaata gtgtatgcgg   5460
cgaccgagtt gctcttgccc ggcgtcaaca cgggataata ccgcgccaca tagcagaact   5520
ttaaaagtgc tcatcattgg aaaacgttct cggggcgaa aactctcaag gatcttaccg   5580
ctgttgagat ccagttcgat gtaacccact cgtgcaccca actgatcttc agcatctttt   5640
actttcacca gcgtttctgg gtgagcaaaa acaggaaggc aaaatgccgc aaaaaaggga   5700
ataagggcga cacggaaatg ttgaatactc atactcttcc ttttcaata ttattgaagc   5760 atttatcagg gttattgtct catgagcgga tacatatttg aatgtattta gaaaaataaa   5820 caaataggg ttccgcgcac atttccccga aaagtgccac ctgacgtcta agaaaccatt   5880
```
attatcatga cattaaccta taaaaatagg cgtatcacga ggcccctttcg tcttcaagaa      5940

<210> SEQ ID NO 17
<211> LENGTH: 5960
<212> TYPE: DNA
<213> ORGANISM: Artificial Sequence
<220> FEATURE:
<223> OTHER INFORMATION: Recombinant plasmid pAPSE10271; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (802)..(1096)
<223> OTHER INFORMATION: beta actin antisense gene fragment
<220> FEATURE:
<221> NAME/KEY: misc_feature
<222> LOCATION: (1171)..(1189)
<223> OTHER INFORMATION: bacteriophage MS2 pac sequence
<220> FEATURE:
<221> NAME/KEY: terminator
<222> LOCATION: (1205)..(1252)
<223> OTHER INFORMATION: bacteriophage T7 transcription terminator
<220> FEATURE:
<221> NAME/KEY: promoter
<222> LOCATION: (1578)..(1596)
<223> OTHER INFORMATION: bacteriophage T7 gene 1 promoter
<220> FEATURE:
<221> NAME/KEY: gene
<222> LOCATION: (1669)..(2058)
<223> OTHER INFORMATION: bacteriophage MS2 coat protein gene
<220> FEATURE:
<221> NAME/KEY: terminator
<222> LOCATION: (2091)..(2138)
<223> OTHER INFORMATION: bacteriophage T7 transcription terminator

<400> SEQUENCE: 17
ttctcatgtt tgacagctta tcatcgataa gctttaatgc ggtagtttat cacagttaaa       60
ttgctaacgc agtcaggcac cgtgtatgaa atctaacaat gcgctcatcg tcatcctcgg      120
caccgtcacc ctggatgctg taggcatagg cttggttatg ccggtactgc cgggcctctt      180
gcgggatgaa ttcagatctc gatcccgcga aattaatacg actcactata gggagaccac      240
aacggtttcc ctctagatca caagtttgta caaaaaagca ggctaagaag gagatataca      300
tacgccggcc attcaaacat gaggattacc catgtattta aatacccatg tccaggcgcg      360
ctccgcgatc gcgcacgagg tttttctgtc tagtgagcag tgtccaacct caaaagacaa      420
catgtgtgac gacgatgtag cggctcttgt cgtagacaat ggatccggta tgtgcaaagc      480
cggtttcgca ggagatgacg caccccgtgc cgtcttcccc tcgatcgtcg gtcgcccaag      540
gcatcaagga gtcatggtcg gtatgggaca aaaggactca tacgtaggag atgaagccca      600
aagcaaaaga ggtatcctca ccctgaaata ccccatcgaa cacggtatca tcaccaactg      660
ggatgagttt aaaccctcta gctgctttac aaagtactgg ttccctttcc agcgggatgc      720
tttatctaaa cgcaatgaga gaggtattcc tcaggccaca tcgcttccta gttccgctgg      780

```
gatccatcgt tggcggcgcg cctcatccca gttggtgatg ataccgtgtt cgatggggta      840
tttcagggtg aggatacctc ttttgctttg ggcttcatct cctacgtatg agtccttttg      900
tcccataccg accatgactc cttgatgcct tgggcgaccg acgatcgagg ggaagacggc      960
acggggtgcg tcatctcctg cgaaaccggc tttgcacata ccggatccat tgtctacgac     1020
aagagccgct acatcgtcgt cacacatgtt gtcttttgag gttggacact gctcactaga     1080
cagaaaaacc tcgtgccgga ccgaataccc ggtctgaacg agggcggccg cggtacccaa     1140
gaagtactta gagttaatta aggagttcaa acatgaggat cacccatgtc gaagctccca     1200
caccctagca taacccttg gggcctctaa acgggtcttg aggggttttt tgctgaaagg     1260
aggaactata tccggatatc cacaggacgg gtgtggtcgc catgatcgcg tagtcgatag     1320
tggctccaag tagcgaagcg agcaggactg ggcggcgggc atgcatcgtc cattccgaca     1380
gcatcgccag tcactatggc gtgctgctag cgctatatgc gttgatgcaa tttctatgcg     1440
cacccgttct cggagcactg tccgaccgct ttggccgccg cccagtcctg ctcgcttcgc     1500
tacttggagc cactatcgac tacgcgatca tggcgaccac acccgtcctg tggatccaga     1560
tctcgatccc gcgaaattaa tacgactcac tataggagga ccacaacggt ttccctctag     1620
atcacaagtt tgtacaaaaa agcaggctaa gaaggagata tacatatggc gtctaacttt     1680
acccaattcg ttctggttga taacggcggt acgggtgacg ttaccgtagc tccgtccaac     1740
ttcgccaacg gtgttgcgga atggattagc tctaacagcc gctctcaggc ctacaaagtc     1800
acgtgctccg ttcgtcagtc tagcgcgcag aatcgcaaat acaccatcaa agttgaagta     1860
ccgaaagtcg caacgcagac cgtaggcggc gtagaactcc cagttgcggc ctggcgctct     1920
tacctcaaca tggaactgac tattccgatt tttgcgacga actccgactg cgaactgatt     1980
gttaaggcaa tgcagggcct gctgaaagac ggtaatccga tcccatctgc aatcgctgct     2040
aactctggca tttactaata agcggacgcg ctgccaccgc tgagcaataa ctagcataac     2100
cccttggggc ctctaaacgg gtcttgaggg gttttttgct gaaaggagga actatatccg     2160
gcatgcacca ttccttgcgg cggcggtgct caacggcctc aacctactac tgggctgctt     2220
cctaatgcag gagtcgcata agggagagcg tcgaccgatg cccttgagag ccttcaaccc     2280
agtcagctcc ttccggtggg cgcggggcat gactatcgtc gccgcactta tgactgtctt     2340
ctttatcatg caactcgtag gacaggtgcc ggcagcgctc tgggtcattt tcggcgagga     2400
ccgctttcgc tggagcgcga cgatgatcgg cctgtcgctt gcggtattcg gaatcttgca     2460
cgccctcgct caagccttcg tcactggtcc cgccaccaaa cgtttcggcg agaagcaggc     2520
cattatcgcc ggcatggcgg ccgacgcgct gggctacgtc ttgctggcgt cgcgacgcg      2580 aggctggatg gccttcccca ttatgattct tctcgcttcc ggcggcatcg ggatgcccgc     2640
gttgcaggcc atgctgtcca ggcaggtaga tgacgaccat cagggacagc ttcaaggatc     2700
gctcgcggct cttaccagcc taacttcgat cattggaccg ctgatcgtca cggcgattta     2760
tgccgcctcg gcgagcacat ggaacgggtt ggcatggatt gtaggcgccg ccctatacct     2820
tgtctgcctc cccgcgttgc gtcgcggtgc atggagccgg gccacctcga cctgaatgga     2880
agccggcggc acctcgctaa cggattcacc actccaagaa ttggagccaa tcaattcttg     2940
cggagaactg tgaatgcgca aaccaaccct tggcagaaca tatccatcgc gtccgccatc     3000
tccagcagcc gcacgcggcg catctcgggc agcgttgggt cctggccacg ggtgcgcatg     3060
atcgtgctcc tgtcgttgag gacccggcta ggctggcggg gttgccttac tggttagcag     3120
```

-continued

```
aatgaatcac cgatacgcga gcgaacgtga agcgactgct gctgcaaaac gtctgcgacc     3180
tgagcaacaa catgaatggt cttcggtttc cgtgtttcgt aaagtctgga aacgcggaag     3240
tcagcgccct gcaccattat gttccggatc tgcatcgcag gatgctgctg ctaccctgt      3300 ggaacaccta catctgtatt aacgaagcgc tggcattgac cctgagtgat ttttctctgg     3360
tcccgccgca tccataccgc cagttgttta ccctcacaac gttccagtaa ccgggcatgt     3420
tcatcatcag taacccgtat cgtgagcatc ctctctcgtt tcatcggtat cattacccc      3480 atgaacagaa atcccccatta cacggaggca tcagtgacca aacaggaaaa aaccgccctt     3540
aacatggccc gctttatcag aagccagaca ttaacgcttc tggagaaact caacgagctg     3600
gacgcggatg aacaggcaga catctgtgaa tcgcttcacg accacgctga tgagctttac     3660
cgcagctgcc tcgcgcgttt cggtgatgac ggtgaaaacc tctgacacat gcagctcccg     3720
gagacggtca cagcttgtct gtaagcggat gccgggagca gacaagcccg tcagggcgcg     3780
tcagcgggtg ttggcgggtg tcggggcgca gccatgaccc agtcacgtag cgatagcgga     3840
gtgtatactg gcttaactat gcggcatcag agcagattgt actgagagtg caccatatgc     3900
ggtgtgaaat accgcacaga tgcgtaagga gaaaataccg catcaggcgc tcttccgctt     3960
cctcgctcac tgactcgctg cgctcggtcg ttcggctgcg gcgagcggta tcagctcact     4020
caaaggcggt aatacggtta tccacagaat caggggataa cgcaggaaag aacatgtgag     4080
caaaaggcca gcaaaaggcc aggaaccgta aaaaggccgc gttgctggcg tttttccata     4140
ggctccgccc ccctgacgag catcacaaaa atcgacgctc aagtcagagg tggcgaaacc     4200
cgacaggact ataaagatac caggcgtttc cccctggaag ctccctcgtg cgctctcctg     4260
ttccgaccct gccgcttacc ggatacctgt ccgcctttct cccttcggga agcgtggcgc     4320
tttctcatag ctcacgctgt aggtatctca gttcggtgta ggtcgttcgc tccaagctgg     4380
gctgtgtgca cgaacccccc gttcagcccg accgctgcgc cttatccggt aactatcgtc     4440
ttgagtccaa cccggtaaga cacgacttat cgccactggc agcagccact ggtaacagga     4500
ttagcagagc gaggtatgta ggcggtgcta cagagttctt gaagtggtgg cctaactacg     4560
gctacactag aaggacagta tttggtatct gcgctctgct gaagccagtt accttcggaa     4620
aaagagttgg tagctcttga tccggcaaac aaaccaccgc tggtagcggt ggtttttttg     4680
tttgcaagca gcagattacg cgcagaaaaa aaggatctca agaagatcct ttgatctttt     4740
ctacggggtc tgacgctcag tggaacgaaa actcacgtta agggattttg gtcatgagat     4800
tatcaaaaag gatcttcacc tagatccttt taaattaaaa atgaagtttt aaatcaatct     4860
aaagtatata tgagtaaact tggtctgaca gttaccaatg cttaatcagt gaggcaccta     4920
tctcagcgat ctgtctattt cgttcatcca tagttgcctg actccccgtc gtgtagataa     4980
ctacgatacg ggagggctta ccatctggcc ccagtgctgc aatgataccg cgagacccac     5040
gctcaccggc tccagattta tcagcaataa accagccagc cggaagggcc gagcgcagaa     5100
gtggtcctgc aactttatcc gcctccatcc agtctattaa ttgttgccgg gaagctagag     5160
taagtagttc gccagttaat agtttgcgca acgttgttgc cattgctgca ggcatcgtgg     5220
tgtcacgctc gtcgtttggt atggcttcat tcagctccgg ttcccaacga tcaaggcgag     5280
ttacatgatc ccccatgttg tgcaaaaaag cggttagctc cttcggtcct ccgatcgttg     5340
tcagaagtaa gttggccgca gtgttatcac tcatggttat ggcagcactg cataattctc     5400
ttactgtcat gccatccgta agatgctttt ctgtgactgg tgagtactca accaagtcat     5460
tctgagaata gtgtatgcgg cgaccgagtt gctcttgccc ggcgtcaaca cgggataata     5520
```

```
ccgcgccaca tagcagaact ttaaaagtgc tcatcattgg aaaacgttct tcggggcgaa      5580
aactctcaag gatcttaccg ctgttgagat ccagttcgat gtaacccact cgtgcaccca      5640
actgatcttc agcatctttt actttcacca gcgtttctgg gtgagcaaaa acaggaaggc      5700
aaaatgccgc aaaaaaggga ataagggcga cacggaaatg ttgaatactc atactcttcc      5760
tttttcaata ttattgaagc atttatcagg gttattgtct catgagcgga tacatatttg      5820
aatgtattta gaaaaataaa caaatagggg ttccgcgcac atttccccga aaagtgccac      5880
ctgacgtcta agaaaccatt attatcatga cattaaccta taaaaatagg cgtatcacga      5940
ggccctttcg tcttcaagaa                                                  5960
```

```
<210> SEQ ID NO 18
<211> LENGTH: 5980
<212> TYPE: DNA
<213> ORGANISM: Artificial Sequence
<220> FEATURE:
<223> OTHER INFORMATION: Recombinant plasmid pAPSE10272; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_features
<222> LOCATION: (317)..(335)
<223> OTHER INFORMATION: bacteriophage MS2 pac sequence
<220> FEATURE:
<221> NAME/KEY: misc_features
<222> LOCATION: (365)..(372)
<223> OTHER INFORMATION: restriction endonuclease AsiSI recognition site
<220> FEATURE:
<221> NAME/KEY: misc_features
<222> LOCATION: (372)..(666)
<223> OTHER INFORMATION: beta actin sense gene fragment
<220> FEATURE:
<221> NAME/KEY: misc_features
<222> LOCATION: (822)..(1116)
<223> OTHER INFORMATION: beta actin antisense gene fragment
<220> FEATURE:
<221> NAME/KEY: misc_feature
<222> LOCATION: (1191)..(1209)
<223> OTHER INFORMATION: bacteriophage MS2 pac sequence
<220> FEATURE:
<221> NAME/KEY: terminator
<222> LOCATION: (1225)..(1272)
<223> OTHER INFORMATION: bacteriophage T7 transcription terminator
<220> FEATURE:
<221> NAME/KEY: promoter
<222> LOCATION: (1598)..(1616)
<223> OTHER INFORMATION: bacteriophage T7 gene 1 promoter
<220> FEATURE:
<221> NAME/KEY: gene
<222> LOCATION: (1689)..(2078)
<223> OTHER INFORMATION: bacteriophage MS2 coat protein gene
<220> FEATURE:
<221> NAME/KEY: terminator
<222> LOCATION: (2111)..(2158)
<223> OTHER INFORMATION: bacteriophage T7 transcription terminator

<400> SEQUENCE: 18
ttctcatgtt tgacagctta tcatcgataa gctttaatgc ggtagtttat cacagttaaa       60
ttgctaacgc agtcaggcac cgtgtatgaa atctaacaat gcgctcatcg tcatcctcgg      120
caccgtcacc ctggatgctg taggcatagg cttggttatg ccggtactgc cgggcctctt      180
gcgggatgaa ttcagatctc gatcccgcga aattaatacg actcactata gggagaccac      240
aacggtttcc ctctagatca caagtttgta caaaaaagca ggctaagaag gagatataca      300
tacgccggcc attcaaacat gaggattacc catgtattta atacccatg tccaggcgcg      360
```

-continued

```
ctccgcgatc gcgcacgagg tttttctgtc tagtgagcag tgtccaacct caaaagacaa      420
catgtgtgac gacgatgtag cggctcttgt cgtagacaat ggatccggta tgtgcaaagc      480
cggtttcgca ggagatgacg cacccgtgc cgtcttcccc tcgatcgtcg gtcgcccaag       540
gcatcaagga gtcatggtcg gtatgggaca aaaggactca tacgtaggag atgaagccca      600
aagcaaaaga ggtatcctca ccctgaaata ccccatcgaa cacggtatca tcaccaactg      660
ggatgagttt aaaccctcta gctgctttac aaagtactgg ttccctttcc agcgggatgc      720
tttatctaaa cgcaatgaga gaggtattcc tcaggccaca tcgcttccta gttccgctgg      780
gatccatcgt tggcggccga agccgccatt ccatggcgcg cctcatccca gttggtgatg      840
ataccgtgtt cgatggggta tttcaggggtg aggatacctc ttttgctttg ggcttcatct     900
cctacgtatg agtccttttg tcccataccg accatgactc cttgatgcct tgggcgaccg      960
acgatcgagg ggaagacggc acgggggtgcg tcatctcctg cgaaaccggc tttgcacata    1020
ccggatccat tgtctacgac aagagccgct acatcgtcgt cacacatgtt gtcttttgag     1080
gttggacact gctcactaga cagaaaaacc tcgtgccgga ccgaataccc ggtctgaacg     1140
agggcggccg cggtacccaa gaagtactta gagttaatta aggagttcaa acatgaggat     1200
cacccatgtc gaagctccca caccctagca taaccccttg gggcctctaa acgggtcttg     1260
aggggttttt tgctgaaagg aggaactata tccggatatc cacaggacgg gtgtggtcgc     1320
catgatcgcg tagtcgatag tggctccaag tagcgaagcg agcaggactg ggcggcgggc     1380
atgcatcgtc cattccgaca gcatcgccag tcactatggc gtgctgctag cgctatatgc     1440
gttgatgcaa tttctatgcg cacccgttct cggagcactg tccgaccgct ttggccgccg    1500
cccagtcctg ctcgcttcgc tacttggagc cactatcgac tacgcgatca tggcgaccac    1560
acccgtcctg tggatccaga tctcgatccc gcgaaattaa tacgactcac tatagggaga    1620
ccacaacggt ttccctctag atcacaagtt tgtacaaaaa agcaggctaa gaaggagata    1680
tacatatggc gtctaacttt acccaattcg ttctggttga taacggcggt acgggtgacg    1740
ttaccgtagc tccgtccaac ttcgccaacg gtgttgcgga atggattagc tctaacagcc    1800
gctctcaggc ctacaaagtc acgtgctccg ttcgtcagtc tagcgcgcag aatcgcaaat    1860
acaccatcaa agttgaagta ccgaaagtcg caacgcagac cgtaggcggc gtagaactcc    1920
cagttgcggc ctggcgctct tacctcaaca tggaactgac tattccgatt tttgcgacga    1980
actccgactg cgaactgatt gttaaggcaa tgcagggcct gctgaaagac ggtaatccga    2040
tcccatctgc aatcgctgct aactctggca tttactaata agcggacgcg ctgccaccgc    2100
tgagcaataa ctagcataac cccttggggc ctctaaacgg tcttgaggg gttttttgct     2160 gaaaggagga actatatccg gcatgcacca ttccttgcgg cggcggtgct caacggcctc     2220
aacctactac tgggctgctt cctaatgcag gagtcgcata agggagagcg tcgaccgatg    2280
cccttgagag ccttcaaccc agtcagctcc ttccggtggg cgcggggcat gactatcgtc     2340
gccgcactta tgactgtctt ctttatcatg caactcgtag gacaggtgcc ggcagcgctc    2400
tgggtcattt tcggcgagga ccgctttcgc tggagcgcga cgatgatcgg cctgtcgctt    2460
gcggtattcg gaatcttgca cgccctcgct caagccttcg tcactggtcc cgccaccaaa    2520
cgtttcggcg agaagcaggc cattatcgcc ggcatggcgg ccgacgcgct gggctacgtc    2580
ttgctggcgt tcgcgacgcg aggctggatg gccttcccca ttatgattct tctcgcttcc    2640
ggcggcatcg ggatgcccgc gttgcaggcc atgctgtcca ggcaggtaga tgacgaccat    2700
```

-continued

```
cagggacagc ttcaaggatc gctcgcggct cttaccagcc taacttcgat cattggaccg    2760
ctgatcgtca cggcgattta tgccgcctcg gcgagcacat ggaacgggtt ggcatggatt    2820
gtaggcgccg ccctatacct tgtctgcctc cccgcgttgc gtcgcggtgc atggagccgg    2880
gccacctcga cctgaatgga agccggcggc acctcgctaa cggattcacc actccaagaa    2940
ttggagccaa tcaattcttg cggagaactg tgaatgcgca aaccaaccct tggcagaaca    3000
tatccatcgc gtccgccatc tccagcagcc gcacgcggcg catctcgggc agcgttgggt    3060
cctggccacg ggtgcgcatg atcgtgctcc tgtcgttgag gacccggcta ggctggcggg    3120
gttgccttac tggttagcag aatgaatcac cgatacgcga gcgaacgtga agcgactgct    3180
gctgcaaaac gtctgcgacc tgagcaacaa catgaatggt cttcggtttc cgtgtttcgt    3240
aaagtctgga aacgcggaag tcagcgccct gcaccattat gttccggatc tgcatcgcag    3300
gatgctgctg gctaccctgt ggaacaccta catctgtatt aacgaagcgc tggcattgac    3360
cctgagtgat ttttctctgg tcccgccgca tccataccgc cagttgttta ccctcacaac    3420
gttccagtaa ccgggcatgt tcatcatcag taacccgtat cgtgagcatc ctctctcgtt    3480
tcatcggtat cattacccccc atgaacagaa atcccccctta cacggaggca tcagtgacca    3540
aacaggaaaa aaccgccctt aacatggccc gctttatcag aagccagaca ttaacgcttc    3600
tggagaaact caacgagctg gacgcggatg aacaggcaga catctgtgaa tcgcttcacg    3660
accacgctga tgagctttac cgcagctgcc tcgcgcgttt cggtgatgac ggtgaaaacc    3720
tctgacacat gcagctcccg gagacggtca cagcttgtct gtaagcggat gccgggagca    3780
gacaagcccg tcagggcgcg tcagcgggtg ttggcgggtg tcgggcgca gccatgaccc    3840 agtcacgtag cgatagcgga gtgtatactg gcttaactat gcggcatcag agcagattgt    3900
actgagagtg caccatatgc ggtgtgaaat accgcacaga tgcgtaagga gaaaataccg    3960
catcaggcgc tcttccgctt cctcgctcac tgactcgctg cgctcggtcg ttcggctgcg    4020
gcgagcggta tcagctcact caaaggcggt aatacggtta tccacagaat cagggggataa    4080 cgcaggaaag aacatgtgag caaaaggcca gcaaaaggcc aggaaccgta aaaaggccgc    4140
gttgctggcg tttttccata ggctccgccc ccctgacgag catcacaaaa atcgacgctc    4200
aagtcagagg tggcgaaacc cgacaggact ataaagatac caggcgtttc cccctggaag    4260
ctccctcgtg cgctctcctg ttccgaccct gccgcttacc ggatacctgt ccgcctttct    4320
cccttcggga agcgtggcgc tttctcatag ctcacgctgt aggtatctca gttcggtgta    4380
ggtcgttcgc tccaagctgg gctgtgtgca cgaacccccc gttcagcccg accgctgcgc    4440
cttatccggt aactatcgtc ttgagtccaa cccggtaaga cacgacttat cgccactggc    4500
agcagccact ggtaacagga ttagcagagc gaggtatgta ggcggtgcta cagagttctt    4560
gaagtggtgg cctaactacg gctacactag aaggacagta tttggtatct gcgctctgct    4620
gaagccagtt accttcggaa aaagagttgg tagctcttga tccggcaaac aaaccaccgc    4680
tggtagcggt ggtttttttg tttgcaagca gcagattacg cgcagaaaaa aaggatctca    4740
agaagatcct ttgatctttt ctacggggtc tgacgctcag tggaacgaaa actcacgtta    4800
agggattttg gtcatgagat tatcaaaaag gatcttcacc tagatccttt taaattaaaa    4860
atgaagtttt aaatcaatct aaagtatata tgagtaaact tggtctgaca gttaccaatg    4920
cttaatcagt gaggcaccta tctcagcgat ctgtctattt cgttcatcca tagttgcctg    4980
actccccgtc gtgtagataa ctacgatacg ggagggctta ccatctggcc ccagtgctgc    5040
aatgataccg cgagacccac gctcaccggc tccagattta tcagcaataa accagccagc    5100
```

-continued

```
cggaagggcc gagcgcagaa gtggtcctgc aactttatcc gcctccatcc agtctattaa    5160
ttgttgccgg gaagctagag taagtagttc gccagttaat agtttgcgca acgttgttgc    5220
cattgctgca ggcatcgtgg tgtcacgctc gtcgtttggt atggcttcat tcagctccgg    5280
ttcccaacga tcaaggcgag ttacatgatc ccccatgttg tgcaaaaaag cggttagctc    5340
cttcggtcct ccgatcgttg tcagaagtaa gttggccgca gtgttatcac tcatggttat    5400
ggcagcactg cataattctc ttactgtcat gccatccgta agatgctttt ctgtgactgg    5460
tgagtactca accaagtcat tctgagaata gtgtatgcgg cgaccgagtt gctcttgccc    5520
ggcgtcaaca cgggataata ccgcgccaca tagcagaact ttaaaagtgc tcatcattgg    5580
aaaacgttct cggggcgaa aactctcaag gatcttaccg ctgttgagat ccagttcgat    5640
gtaacccact cgtgcaccca actgatcttc agcatctttt actttcacca gcgtttctgg    5700
gtgagcaaaa acaggaaggc aaaatgccgc aaaaaaggga ataagggcga cacggaaatg    5760
ttgaatactc atactcttcc tttttcaata ttattgaagc atttatcagg gttattgtct    5820
catgagcgga tacatatttg aatgtattta gaaaaataaa caaatagggg ttccgcgcac    5880
atttccccga aaagtgccac ctgacgtcta agaaaccatt attatcatga cattaaccta    5940
taaaaatagg cgtatcacga ggccctttcg tcttcaagaa                          5980
```

```
<210> SEQ ID NO 19
<211> LENGTH: 6005
<212> TYPE: DNA
<213> ORGANISM: Artificial Sequence
<220> FEATURE:
<223> OTHER INFORMATION: Recombinant plasmid pAPSE10292; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (797)..(1091)
<223> OTHER INFORMATION: beta actin antisense gene fragment
<220> FEATURE:
<221> NAME/KEY: misc_feature
<222> LOCATION: (1166)..(1184)
<223> OTHER INFORMATION: bacteriophage MS2 pac sequence
<220> FEATURE:
<221> NAME/KEY: terminator
<222> LOCATION: (1200)..(1247)
<223> OTHER INFORMATION: bacteriophage T7 transcription terminator
<220> FEATURE:
<221> NAME/KEY: promoter
<222> LOCATION: (1573)..(1591)
<223> OTHER INFORMATION: bacteriophage T7 gene 1 promoter
<220> FEATURE:
<221> NAME/KEY: gene
<222> LOCATION: (1664)..(2053)
<223> OTHER INFORMATION: bacteriophage MS2 coat protein gene
<220> FEATURE:
<221> NAME/KEY: terminator
<222> LOCATION: (2086)..(2133)
<223> OTHER INFORMATION: bacteriophage T7 transcription terminator
```

-continued

<400> SEQUENCE: 19

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaacgcaatc gcagcaaact ccggcatcta ctaatagacg ccggccattc     720
aacatgagga ttacccatgt aacctaagaa gacaacaaag aagttcaact ctttatgtat     780
tgatcttccg gcgcgcctca tcccagttgg tgatgatacc gtgttcgatg gggtatttca     840
gggtgaggat acctcttttg ctttgggctt catctcctac gtatgagtcc ttttgtccca     900
taccgaccat gactccttga tgccttgggc gaccgacgat cgaggggaag acggcacggg     960
gtgcgtcatc tcctgcgaaa ccggctttgc acataccgga tccattgtct acgacaagag    1020
ccgctacatc gtcgtcacac atgttgtctt ttgaggttgg acactgctca ctagacagaa    1080
aaacctcgtg ccggaccgaa tacccggtct gaacgagggc ggccgcggta cccaagaagt    1140
acttagagtt aattaaggag ttcaaacatg aggatcaccc atgtcgaagc tcccacaccc    1200
tagcataacc ccttgggcc tctaaacggg tcttgagggg tttttgctg aaaggaggaa    1260 ctatatccgg atatccacag gacgggtgtg tcgccatga tcgcgtagtc gatagtggct    1320
ccaagtagcg aagcgagcag gactgggcgg cgggcatgca tcgtccattc cgacagcatc    1380
gccagtcact atggcgtgct gctagcgcta tatgcgttga tgcaatttct atgcgcaccc    1440
gttctcggag cactgtccga ccgctttggc cgccgcccag tcctgctcgc ttcgctactt    1500
ggagccacta tcgactacgc gatcatggcg accacacccg tcctgtggat ccagatctcg    1560
atcccgcgaa attaatacga ctcactatag ggagaccaca acggtttccc tctagatcac    1620
aagtttgtac aaaaaagcag gctaagaagg agatatacat atggcgtcta actttaccca    1680
attcgttctg gttgataacg gcggtacggg tgacgttacc gtagctccgt ccaacttcgc    1740
caacggtgtt gcggaatgga ttagctctaa cagccgctct caggcctaca aagtcacgtg    1800
ctccgttcgt cagtctagcg cgcagaatcg caaatacacc atcaaagttg aagtaccgaa    1860
agtcgcaacg cagaccgtag cggcgtaga actcccagtt gcggcctggc gctcttacct    1920
caacatggaa ctgactattc cgattttttgc gacgaactcc gactgcgaac tgattgttaa    1980
ggcaatgcag ggcctgctga aagacggtaa tccgatccca tctgcaatcg ctgctaactc    2040
tggcatttac taataagcgg acgcgctgcc accgctgagc aataactagc ataacccctt    2100
ggggcctcta aacgggtctt gaggggtttt ttgctgaaag gaggaactat atccggcatg    2160
caccattcct tgcggcggcg gtgctcaacg gcctcaacct actactgggc tgcttcctaa    2220
tgcaggagtc gcataaggga gagcgtcgac cgatgccctt gagagccttc aacccagtca    2280
```

-continued

```
gctccttccg gtgggcgcgg ggcatgacta tcgtcgccgc acttatgact gtcttcttta   2340
tcatgcaact cgtaggacag gtgccggcag cgctctgggt cattttcggc gaggaccgct   2400
ttcgctggag cgcgacgatg atcggcctgt cgcttgcggt attcggaatc ttgcacgccc   2460
tcgctcaagc cttcgtcact ggtcccgcca ccaaacgttt cggcgagaag caggccatta   2520
tcgccggcat ggcggccgac gcgctgggct acgtcttgct ggcgttcgcg acgcgaggct   2580
ggatggcctt ccccattatg attcttctcg cttccggcgg catcgggatg cccgcgttgc   2640
aggccatgct gtccaggcag gtagatgacg accatcaggg acagcttcaa ggatcgctcg   2700
cggctcttac cagcctaact tcgatcattg gaccgctgat cgtcacggcg atttatgccg   2760
cctcggcgag cacatggaac gggttggcat ggattgtagg cgccgccta taccttgtct   2820 gcctccccgc gttgcgtcgc ggtgcatgga gccgggccac ctcgacctga atggaagccg   2880
gcggcacctc gctaacggat tcaccactcc aagaattgga gccaatcaat tcttgcggag   2940
aactgtgaat gcgcaaacca acccttggca gaacatatcc atcgcgtccg ccatctccag   3000
cagccgcacg cggcgcatct cgggcagcgt tgggtcctgg ccacgggtgc gcatgatcgt   3060
gctcctgtcg ttgaggaccc ggctaggctg gcggggttgc cttactggtt agcagaatga   3120
atcaccgata cgcgagcgaa cgtgaagcga ctgctgctgc aaaacgtctg cgacctgagc   3180
aacaacatga atggtcttcg gtttccgtgt ttcgtaaagt ctggaaacgc ggaagtcagc   3240
gccctgcacc attatgttcc ggatctgcat cgcaggatgc tgctggctac cctgtggaac   3300
acctacatct gtattaacga agcgctggca ttgaccctga gtgattttc tctggtcccg   3360 ccgcatccat accgccagtt gtttaccctc acaacgttcc agtaaccggg catgttcatc   3420
atcagtaacc cgtatcgtga gcatcctctc tcgtttcatc ggtatcatta cccccatgaa   3480
cagaaatccc ccttacacgg aggcatcagt gaccaaacag gaaaaaaccg cccttaacat   3540
ggcccgcttt atcagaagcc agacattaac gcttctggag aaactcaacg agctggacgc   3600
ggatgaacag gcagacatct gtgaatcgct tcacgaccac gctgatgagc tttaccgcag   3660
ctgcctcgcg cgtttcggtg atgacggtga aaacctctga cacatgcagc tcccggagac   3720
ggtcacagct tgtctgtaag cggatgccgg gagcagacaa gcccgtcagg gcgcgtcagc   3780
gggtgttggc gggtgtcggg gcgcagccat gacccagtca cgtagcgata gcggagtgta   3840
tactggctta actatgcggc atcagagcag attgtactga gagtgcacca tatgcggtgt   3900
gaaataccgc acagatgcgt aaggagaaaa taccgcatca ggcgctcttc cgcttcctcg   3960
ctcactgact cgctgcgctc ggtcgttcgg ctgcggcgag cggtatcagc tcactcaaag   4020
gcggtaatac ggttatccac agaatcaggg gataacgcag gaaagaacat gtgagcaaaa   4080
ggccagcaaa aggccaggaa ccgtaaaaag gccgcgttgc tggcgttttt ccataggctc   4140
cgcccccctg acgagcatca caaaaatcga cgctcaagtc agaggtggcg aaacccgaca   4200
ggactataaa gataccaggc gtttccccct ggaagctccc tcgtgcgctc tcctgttccg   4260
accctgccgc ttaccggata cctgtccgcc tttctccctt cgggaagcgt ggcgctttct   4320
catagctcac gctgtaggta tctcagttcg gtgtaggtcg ttcgctccaa gctgggctgt   4380
gtgcacgaac cccccgttca gcccgaccgc tgcgccttat ccggtaacta tcgtcttgag   4440
tccaacccgg taagacacga cttatcgcca ctggcagcag ccactggtaa caggattagc   4500
agagcgaggt atgtaggcgg tgctacagag ttcttgaagt ggtggcctaa ctacggctac   4560
actagaagga cagtatttgg tatctgcgct ctgctgaagc cagttacctt cggaaaaaga   4620
gttggtagct cttgatccgg caaacaaacc accgctggta gcggtggttt ttttgtttgc   4680
```

-continued

```
aagcagcaga ttacgcgcag aaaaaaagga tctcaagaag atcctttgat cttttctacg   4740
gggtctgacg ctcagtggaa cgaaaactca cgttaaggga ttttggtcat gagattatca   4800
aaaaggatct tcacctagat cctttttaaa taaaaatgaa gttttaaatc aatctaaagt   4860
atatatgagt aaacttggtc tgacagttac caatgcttaa tcagtgaggc acctatctca   4920
gcgatctgtc tatttcgttc atccatagtt gcctgactcc ccgtcgtgta gataactacg   4980
atacgggagg gcttaccatc tggccccagt gctgcaatga taccgcgaga cccacgctca   5040
ccggctccag atttatcagc aataaaccag ccagccggaa gggccgagcg cagaagtggt   5100
cctgcaactt tatccgcctc catccagtct attaattgtt gccgggaagc tagagtaagt   5160
agttcgccag ttaatagttt gcgcaacgtt gttgccattg ctgcaggcat cgtggtgtca   5220
cgctcgtcgt ttggtatggc ttcattcagc tccggttccc aacgatcaag gcgagttaca   5280
tgatccccca tgttgtgcaa aaaagcggtt agctccttcg gtcctccgat cgttgtcaga   5340
agtaagttgg ccgcagtgtt atcactcatg gttatggcag cactgcataa ttctcttact   5400
gtcatgccat ccgtaagatg cttttctgtg actggtgagt actcaaccaa gtcattctga   5460
gaatagtgta tgcggcgacc gagttgctct tgcccggcgt caacacggga taataccgcg   5520
ccacatagca gaactttaaa agtgctcatc attggaaaac gttcttcggg gcgaaaactc   5580
tcaaggatct taccgctgtt gagatccagt tcgatgtaac ccactcgtgc acccaactga   5640
tcttcagcat cttttacttt caccagcgtt tctgggtgag caaaaacagg aaggcaaaat   5700
gccgcaaaaa agggaataag ggcgacacgg aaatgttgaa tactcatact cttccttttt   5760
caatattatt gaagcattta tcagggttat tgtctcatga gcggatacat atttgaatgt   5820
atttagaaaa ataaacaaat aggggttccg cgcacatttc cccgaaaagt gccacctgac   5880
gtctaagaaa ccattattat catgacatta acctataaaa ataggcgtat cacgaggccc   5940
tttcgtcttc aagaacatta acctataaaa ataggcgtat cacgaggccc tttcgtcttc   6000
aagaa                                                                6005
```

<210> SEQ ID NO 20
<211> LENGTH: 5966
<212> TYPE: DNA
<213> ORGANISM: Artificial Sequence
<220> FEATURE:
<223> OTHER INFORMATION: Recombinant plasmid pAPSE10291; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (808)..(1102)
<223> OTHER INFORMATION: beta actin antisense gene fragment
<220> FEATURE:
<221> NAME/KEY: misc_feature
<222> LOCATION: (1177)..(1195)
<223> OTHER INFORMATION: bacteriophage MS2 pac sequence

```
<220> FEATURE:
<221> NAME/KEY: terminator
<222> LOCATION: (1211)..(1258)
<223> OTHER INFORMATION: bacteriophage T7 transcription terminator
<220> FEATURE:
<221> NAME/KEY: promoter
<222> LOCATION: (1584)..(1602)
<223> OTHER INFORMATION: bacteriophage T7 gene 1 promoter
<220> FEATURE:
<221> NAME/KEY: gene
<222> LOCATION: (1675)..(2064)
<223> OTHER INFORMATION: bacteriophage MS2 coat protein gene
<220> FEATURE:
<221> NAME/KEY: terminator
<222> LOCATION: (2097)..(2144)
<223> OTHER INFORMATION: bacteriophage T7 transcription terminator

<400> SEQUENCE: 20
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatatataca    300 tacgccggcc attcaaacat gaggattacc catgtattta atacccatg tccaggcgcg     360 ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaacttaagc ggaacaccag gcggaacgaa gaggagatag agaactagat     720
tgattagaat caaatactag aactactaaa tcgaatcgat acgctaacga aaggacctgg     780
acacgtcgac gagccgctgg ggcgcgcctc atcccagttg gtgatgatac cgtgttcgat     840
ggggtatttc agggtgagga tacctctttt gctttgggct tcatctccta cgtatgagtc     900
cttttgtccc ataccgacca tgactccttg atgccttggg cgaccgacga tcgaggggaa     960
gacggcacgg ggtgcgtcat ctcctgcgaa accggctttg cacataccgg atccattgtc    1020
tacgacaaga gccgctacat cgtcgtcaca catgttgtct tttgaggttg gacactgctc    1080
actagacaga aaaacctcgt gccggaccga atacccggtc tgaacgaggg cggccgcggt    1140
acccaagaag tacttagagt taattaagga gttcaaacat gaggatcacc catgtcgaag    1200
ctcccacacc ctagcataac cccttggggc ctctaaacgg tcttgaggg gttttttgct     1260 gaaaggagga actatatccg gatatccaca ggacgggtgt ggtcgccatg atcgcgtagt    1320
cgatagtggc tccaagtagc gaagcgagca ggactgggcg gcgggcatgc atcgtccatt    1380
ccgacagcat cgccagtcac tatggcgtgc tgctagcgct atatgcgttg atgcaatttc    1440
tatgcgcacc cgttctcgga gcactgtccg accgctttgg ccgccgccca gtcctgctcg    1500
cttcgctact tggagccact atcgactacg cgatcatggc gaccacaccc gtcctgtgga    1560
tccagatctc gatcccgcga aattaatacg actcactata gggagaccac aacggtttcc    1620
ctctagatca caagtttgta caaaaaagca ggctaagaag agatataca tatggcgtct     1680 aactttaccc aattcgttct ggttgataac ggcggtacgg gtgacgttac cgtagctccg    1740
tccaacttcg ccaacggtgt tgcggaatgg attagctcta acagccgctc tcaggcctac    1800
```

-continued

```
aaagtcacgt gctccgttcg tcagtctagc gcgcagaatc gcaaatacac catcaaagtt   1860
gaagtaccga aagtcgcaac gcagaccgta ggcggcgtag aactcccagt tgcggcctgg   1920
cgctcttacc tcaacatgga actgactatt ccgatttttg cgacgaactc cgactgcgaa   1980
ctgattgtta aggcaatgca gggcctgctg aaagacggta atccgatccc atctgcaatc   2040
gctgctaact ctggcattta ctaataagcg gacgcgctgc caccgctgag caataactag   2100
cataacccct tggggcctct aaacgggtct tgaggggttt tttgctgaaa ggaggaacta   2160
tatccggcat gcaccattcc ttgcggcggc ggtgctcaac ggcctcaacc tactactggg   2220
ctgcttccta atgcaggagt cgcataaggg agagcgtcga ccgatgccct tgagagcctt   2280
caacccagtc agctccttcc ggtgggcgcg gggcatgact atcgtcgccg cacttatgac   2340
tgtcttcttt atcatgcaac tcgtaggaca ggtgccggca gcgctctggg tcattttcgg   2400
cgaggaccgc tttcgctgga gcgcgacgat gatcggcctg tcgcttgcgg tattcggaat   2460
cttgcacgcc ctcgctcaag ccttcgtcac tggtcccgcc accaaacgtt tcggcgagaa   2520
gcaggccatt atcgccggca tggcggccga cgcgctgggc tacgtcttgc tggcgttcgc   2580
gacgcgaggc tggatggcct tccccattat gattcttctc gcttccggcg gcatcgggat   2640
gcccgcgttg caggccatgc tgtccaggca ggtagatgac gaccatcagg gacagcttca   2700
aggatcgctc gcggctctta ccagcctaac ttcgatcatt ggaccgctga tcgtcacggc   2760
gatttatgcc gcctcggcga gcacatggaa cgggttggca tggattgtag gcgccgccct   2820
ataccttgtc tgcctccccg cgttgcgtcg cggtgcatgg agccgggcca cctcgacctg   2880
aatggaagcc ggcggcacct cgctaacgga ttcaccactc caagaattgg agccaatcaa   2940
ttcttgcgga gaactgtgaa tgcgcaaacc aacccttggc agaacatatc catcgcgtcc   3000
gccatctcca gcagccgcac gcggcgcatc tcgggcagcg ttgggtcctg gccacgggtg   3060
cgcatgatcg tgctcctgtc gttgaggacc cggctaggct ggcggggttg ccttactggt   3120
tagcagaatg aatcaccgat acgcgagcga acgtgaagcg actgctgctg caaaacgtct   3180
gcgacctgag caacaacatg aatggtcttc ggtttccgtg tttcgtaaag tctggaaacg   3240
cggaagtcag cgccctgcac cattatgttc cggatctgca tcgcaggatg ctgctggcta   3300
ccctgtggaa cacctacatc tgtattaacg aagcgctggc attgaccctg agtgattttt   3360
ctctggtccc gccgcatcca taccgccagt tgtttaccct cacaacgttc cagtaaccgg   3420
gcatgttcat catcagtaac ccgtatcgtg agcatcctct ctcgtttcat cggtatcatt   3480
acccccatga acagaaatcc cccttacacg gaggcatcag tgaccaaaca ggaaaaaacc   3540
gcccttaaca tggcccgctt tatcagaagc cagacattaa cgcttctgga gaaactcaac   3600
gagctggacg cggatgaaca ggcagacatc tgtgaatcgc ttcacgacca cgctgatgag   3660
ctttaccgca gctgcctcgc gcgtttcggt gatgacggtg aaaacctctg acacatgcag   3720
ctcccggaga cggtcacagc ttgtctgtaa gcggatgccg ggagcagaca gcccgtcag   3780 ggcgcgtcag cgggtgttgg cgggtgtcgg ggcgcagcca tgacccagtc acgtagcgat   3840
agcggagtgt atactggctt aactatgcgg catcagagca gattgtactg agagtgcacc   3900
atatgcggtg tgaaataccg cacagatgcg taaggagaaa ataccgcatc aggcgctctt   3960
ccgcttcctc gctcactgac tcgctgcgct cggtcgttcg gctgcggcga gcggtatcag   4020
ctcactcaaa ggcggtaata cggttatcca cagaatcagg ggataacgca ggaaagaaca   4080
tgtgagcaaa aggccagcaa aaggccagga accgtaaaaa ggccgcgttg ctggcgtttt   4140
tccataggct ccgcccccct gacgagcatc acaaaaatcg acgctcaagt cagaggtggc   4200
```

-continued

```
gaaacccgac aggactataa agataccagg cgtttccccc tggaagctcc ctcgtgcgct    4260
ctcctgttcc gaccctgccg cttaccggat acctgtccgc ctttctccct tcgggaagcg    4320
tggcgctttc tcatagctca cgctgtaggt atctcagttc ggtgtaggtc gttcgctcca    4380
agctgggctg tgtgcacgaa ccccccgttc agcccgaccg ctgcgcctta ccggtaact    4440 atcgtcttga gtccaacccg gtaagacacg acttatcgcc actggcagca gccactggta    4500
acaggattag cagagcgagg tatgtaggcg gtgctacaga gttcttgaag tggtggccta    4560
actacggcta cactagaagg acagtatttg gtatctgcgc tctgctgaag ccagttacct    4620
tcggaaaaag agttggtagc tcttgatccg gcaaacaaac caccgctggt agcggtggtt    4680
tttttgtttg caagcagcag attacgcgca gaaaaaaagg atctcaagaa gatcctttga    4740
tcttttctac ggggtctgac gctcagtgga acgaaaactc acgttaaggg attttggtca    4800
tgagattatc aaaaaggatc ttcacctaga tccttttaaa ttaaaaatga agttttaaat    4860
caatctaaag tatatatgag taaacttggt ctgacagtta ccaatgctta atcagtgagg    4920
cacctatctc agcgatctgt ctatttcgtt catccatagt tgcctgactc cccgtcgtgt    4980
agataactac gatacgggag ggcttaccat ctggccccag tgctgcaatg ataccgcgag    5040
acccacgctc accggctcca gatttatcag caataaacca gccagccgga agggccgagc    5100
gcagaagtgg tcctgcaact ttatccgcct ccatccagtc tattaattgt tgccgggaag    5160
ctagagtaag tagttcgcca gttaatagtt tgcgcaacgt tgttgccatt gctgcaggca    5220
tcgtggtgtc acgctcgtcg tttggtatgg cttcattcag ctccggttcc caacgatcaa    5280
ggcgagttac atgatccccc atgttgtgca aaaaagcggt tagctccttc ggtcctccga    5340
tcgttgtcag aagtaagttg gccgcagtgt tatcactcat ggttatggca gcactgcata    5400
attctcttac tgtcatgcca tccgtaagat gcttttctgt gactggtgag tactcaacca    5460
agtcattctg agaatagtgt atgcggcgac cgagttgctc ttgcccggcg tcaacacggg    5520
ataataccgc gccacatagc agaactttaa aagtgctcat cattggaaaa cgttcttcgg    5580
ggcgaaaact ctcaaggatc ttaccgctgt tgagatccag ttcgatgtaa cccactcgtg    5640
cacccaactg atcttcagca tcttttactt tcaccagcgt ttctgggtga gcaaaaacag    5700
gaaggcaaaa tgccgcaaaa aagggaataa gggcgacacg gaaatgttga atactcatac    5760
tcttcctttt tcaatattat tgaagcattt atcagggtta ttgtctcatg agcggataca    5820
tatttgaatg tatttagaaa ataaacaaa taggggttcc gcgcacattt ccccgaaaag    5880
tgccacctga cgtctaagaa accattatta tcatgacatt aacctataaa aataggcgta    5940
tcacgaggcc ctttcgtctt caagaa                                          5966
```

```
<210> SEQ ID NO 21
<211> LENGTH: 5502
<212> TYPE: DNA
<213> ORGANISM: Artificial Sequence
<220> FEATURE:
<223> OTHER INFORMATION: Recombinant plasmid pAPSE10276; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
```

-continued

<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(422)
<223> OTHER INFORMATION: beta actin sense gene fragment
<220> FEATURE:
<221> NAME/KEY: misc_feature
<222> LOCATION: (588)..(638)
<223> OTHER INFORMATION: beta actin antisense gene fragment
<220> FEATURE:
<221> NAME/KEY: misc_feature
<222> LOCATION: (713)..(731)
<223> OTHER INFORMATION: bacteriophage MS2 pac sequence
<220> FEATURE:
<221> NAME/KEY: terminator
<222> LOCATION: (747)..(794)
<223> OTHER INFORMATION: bacteriophage T7 transcription terminator
<220> FEATURE:
<221> NAME/KEY: promoter
<222> LOCATION: (1120)..(1138)
<223> OTHER INFORMATION: bacteriophage T7 gene 1 promoter
<220> FEATURE:
<221> NAME/KEY: gene
<222> LOCATION: (1211)..(1600)
<223> OTHER INFORMATION: bacteriophage MS2 coat protein gene
<220> FEATURE:
<221> NAME/KEY: terminator
<222> LOCATION: (1633)..(1680)
<223> OTHER INFORMATION: bacteriophage T7 transcription terminator

<400> SEQUENCE: 21

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta atacccatg tccaggcgcg      360 ctccgcgatc gcgcacgagg tttttctgtc tagtgagcag tgtccaacct caaaagacaa     420
cagtttaaac cctctagctg ctttacaaag tactggttcc cttttccagcg ggatgcttta    480 tctaaacgca atgagagagg tattcctcag gccacatcgc ttcctagttc cgctgggatc     540
catcgttggc ggccgaagcc gccattccat agtgagttct ggcgcgcctg ttgtcttttg     600
aggttggaca ctgctcacta gacagaaaaa cctcgtgccg gaccgaatac ccggtctgaa     660
cgagggcggc cgcggtaccc aagaagtact tagagttaat taaggagttc aaacatgagg     720
atcacccatg tcgaagctcc cacaccctag cataacccct tggggcctct aaacgggtct     780
tgaggggttt tttgctgaaa ggaggaacta tatccggata tccacaggac gggtgtggtc     840
gccatgatcg cgtagtcgat agtggctcca agtagcgaag cgagcaggac tgggcggcgg     900
gcatgcatcg tccattccga cagcatcgcc agtcactatg gcgtgctgct agcgctatat     960
gcgttgatgc aatttctatg cgcacccgtt ctcggagcac tgtccgaccg ctttggccgc    1020
cgcccagtcc tgctcgcttc gctacttgga gccactatcg actacgcgat catggcgacc    1080
acacccgtcc tgtggatcca gatctcgatc ccgcgaaatt aatacgactc actatagggga   1140 gaccacaacg gtttccctct agatcacaag tttgtacaaa aaagcaggct aagaaggaga    1200
tatacatatg gcgtctaact ttacccaatt cgttctggtt gataacggcg gtacgggtga    1260
cgttaccgta gctccgtcca acttcgccaa cggtgttgcg gaatggatta gctctaacag    1320
ccgctctcag gcctacaaag tcacgtgctc cgttcgtcag tctagcgcgc agaatcgcaa    1380
```

-continued

```
atacaccatc aaagttgaag taccgaaagt cgcaacgcag accgtaggcg gcgtagaact   1440
cccagttgcg gcctggcgct cttacctcaa catggaactg actattccga tttttgcgac   1500
gaactccgac tgcgaactga ttgttaaggc aatgcagggc ctgctgaaag acggtaatcc   1560
gatcccatct gcaatcgctg ctaactctgg catttactaa taagcggacg cgctgccacc   1620
gctgagcaat aactagcata acccettggg gcctctaaac gggtcttgag gggttttttg   1680
ctgaaaggag gaactatatc cggcatgcac cattccttgc ggcggcggtg ctcaacggcc   1740
tcaacctact actgggctgc ttcctaatgc aggagtcgca taagggagag cgtcgaccga   1800
tgcccttgag agccttcaac ccagtcagct ccttccggtg ggcgcggggc atgactatcg   1860
tcgccgcact tatgactgtc ttctttatca tgcaactcgt aggacaggtg ccggcagcgc   1920
tctgggtcat tttcggcgag gaccgctttc gctggagcgc gacgatgatc ggcctgtcgc   1980
ttgcggtatt cggaatcttg cacgccctcg ctcaagcctt cgtcactggt cccgccacca   2040
aacgtttcgg cgagaagcag gccattatcg ccggcatggc ggccgacgcg ctgggctacg   2100
tcttgctggc gttcgcgacg cgaggctgga tggccttccc cattatgatt cttctcgctt   2160
ccggcggcat cgggatgccc gcgttgcagg ccatgctgtc caggcaggta gatgacgacc   2220
atcagggaca gcttcaagga tcgctcgcgg ctcttaccag cctaacttcg atcattggac   2280
cgctgatcgt cacggcgatt tatgccgcct cggcgagcac atggaacggg ttggcatgga   2340
ttgtaggcgc cgccctatac cttgtctgcc tccccgcgtt gcgtcgcggt gcatggagcc   2400
gggccacctc gacctgaatg gaagccggcg gcacctcgct aacggattca ccactccaag   2460
aattggagcc aatcaattct tgcggagaac tgtgaatgcg caaaccaacc cttggcagaa   2520
catatccatc gcgtccgcca tctccagcag ccgcacgcgg cgcatctcgg gcagcgttgg   2580
gtcctggcca cgggtgcgca tgatcgtgct cctgtcgttg aggacccggc taggctggcg   2640
gggttgcctt actggttagc agaatgaatc accgatacgc gagcgaacgt gaagcgactg   2700
ctgctgcaaa acgtctgcga cctgagcaac aacatgaatg gtcttcggtt tccgtgtttc   2760
gtaaagtctg gaaacgcgga agtcagcgcc ctgcaccatt atgttccgga tctgcatcgc   2820
aggatgctgc tggctaccct gtggaacacc tacatctgta ttaacgaagc gctggcattg   2880
accctgagtg attttttctct ggtcccgccg catccatacc gccagttgtt taccctcaca   2940
acgttccagt aaccgggcat gttcatcatc agtaacccgt atcgtgagca tcctctctcg   3000
tttcatcggt atcattaccc ccatgaacag aaatccccct tacacggagg catcagtgac   3060
caaacaggaa aaaaccgccc ttaacatggc ccgctttatc agaagccaga cattaacgct   3120
tctggagaaa ctcaacgagc tggacgcgga tgaacaggca gacatctgtg aatcgcttca   3180
cgaccacgct gatgagcttt accgcagctg cctcgcgcgt ttcggtgatg acggtgaaaa   3240
cctctgacac atgcagctcc cggagacggt cacagcttgt ctgtaagcgg atgccgggag   3300
cagacaagcc cgtcagggcg cgtcagcggg tgttggcggg tgtcggggcg cagccatgac   3360
ccagtcacgt agcgatagcg gagtgtatac tggcttaact atgcggcatc agagcagatt   3420
gtactgagag tgcaccatat gcggtgtgaa ataccgcaca gatgcgtaag gagaaaatac   3480
cgcatcaggc gctcttccgc ttcctcgctc actgactcgc tgcgctcggt cgttcggctg   3540
cggcgagcgg tatcagctca ctcaaaggcg gtaatacggt tatccacaga atcaggggat   3600
aacgcaggaa agaacatgtg agcaaaaggc cagcaaaagg ccaggaaccg taaaaaggcc   3660
gcgttgctgg cgtttttcca taggctccgc cccctgacg agcatcacaa aaatcgacgc   3720
tcaagtcaga ggtggcgaaa cccgacagga ctataaagat accaggcgtt tccccctgga   3780
```

```
agctccctcg tgcgctctcc tgttccgacc ctgccgctta ccggatacct gtccgccttt    3840
ctcccttcgg gaagcgtggc gctttctcat agctcacgct gtaggtatct cagttcggtg    3900
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaaggacag tatttggtat ctgcgctctg    4140
ctgaagccag ttaccttcgg aaaaagagtt ggtagctctt gatccggcaa acaaaccacc    4200
gctggtagcg gtggtttttt tgtttgcaag cagcagatta cgcgcagaaa aaaggatct    4260 caagaagatc ctttgatctt ttctacgggg tctgacgctc agtggaacga aaactcacgt    4320
taagggattt tggtcatgag attatcaaaa aggatcttca cctagatcct tttaaattaa    4380
aaatgaagtt ttaaatcaat ctaaagtata tatgagtaaa cttggtctga cagttaccaa    4440
tgcttaatca gtgaggcacc tatctcagcg atctgtctat ttcgttcatc catagttgcc    4500
tgactccccg tcgtgtagat aactacgata cgggagggct taccatctgg ccccagtgct    4560
gcaatgatac cgcgagaccc acgctcaccg gctccagatt tatcagcaat aaaccagcca    4620
gccggaaggg ccgagcgcag aagtggtcct gcaactttat ccgcctccat ccagtctatt    4680
aattgttgcc gggaagctag agtaagtagt tcgccagtta atagtttgcg caacgttgtt    4740
gccattgctg caggcatcgt ggtgtcacgc tcgtcgtttg gtatggcttc attcagctcc    4800
ggttcccaac gatcaaggcg agttacatga tcccccatgt tgtgcaaaaa agcggttagc    4860
tccttcggtc ctccgatcgt tgtcagaagt aagttggccg cagtgttatc actcatggtt    4920
atggcagcac tgcataattc tcttactgtc atgccatccg taagatgctt ttctgtgact    4980
ggtgagtact caaccaagtc attctgagaa tagtgtatgc ggcgaccgag ttgctcttgc    5040
ccggcgtcaa cacgggataa taccgcgcca catagcagaa ctttaaaagt gctcatcatt    5100
ggaaaacgtt cttcggggcg aaaactctca aggatcttac cgctgttgag atccagttcg    5160
atgtaaccca ctcgtgcacc caactgatct tcagcatctt ttactttcac cagcgtttct    5220
gggtgagcaa aaacaggaag gcaaaatgcc gcaaaaaagg aataagggc gacacggaaa    5280 tgttgaatac tcatactctt cctttttcaa tattattgaa gcatttatca gggttattgt    5340
ctcatgagcg gatacatatt tgaatgtatt tagaaaaata aacaaatagg ggttccgcgc    5400
acatttcccc gaaaagtgcc acctgacgtc taagaaacca ttattatcat gacattaacc    5460
tataaaaata ggcgtatcac gaggccctttt cgtcttcaag aa    5502
```

<210> SEQ ID NO 22
<211> LENGTH: 5552
<212> TYPE: DNA
<213> ORGANISM: Artificial Sequence
<220> FEATURE:
<223> OTHER INFORMATION: Recombinant plasmid pAPSE10277; beta actin stem
     loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site -continued

```
<220> FEATURE:
<221> NAME/KEY: misc_feature
<222> LOCATION: (372)..(447)
<223> OTHER INFORMATION: beta actin sense gene fragment
<220> FEATURE:
<221> NAME/KEY: misc_feature
<222> LOCATION: (613)..(688)
<223> OTHER INFORMATION: beta actin antisense gene fragment
<220> FEATURE:
<221> NAME/KEY: misc_feature
<222> LOCATION: (763)..(781)
<223> OTHER INFORMATION: bacteriophage MS2 pac sequence
<220> FEATURE:
<221> NAME/KEY: terminator
<222> LOCATION: (797)..(844)
<223> OTHER INFORMATION: bacteriophage T7 transcription terminator
<220> FEATURE:
<221> NAME/KEY: promoter
<222> LOCATION: (1170)..(1188)
<223> OTHER INFORMATION: bacteriophage T7 gene 1 promoter
<220> FEATURE:
<221> NAME/KEY: gene
<222> LOCATION: (1261)..(1650)
<223> OTHER INFORMATION: bacteriophage MS2 coat protein gene
<220> FEATURE:
<221> NAME/KEY: terminator
<222> LOCATION: (1683)..(1730)
<223> OTHER INFORMATION: bacteriophage T7 transcription terminator

<400> SEQUENCE: 22
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta atacccatg tccaggcgcg      360 ctccgcgatc gcgcacgagg tttttctgtc tagtgagcag tgtccaacct caaaagacaa     420
catgtgtgac gacgatgtag cggctctgtt taaaccctct agctgcttta caaagtactg     480
gttccctttc cagcgggatg ctttatctaa acgcaatgag agaggtattc ctcaggccac     540
atcgcttcct agttccgctg ggatccatcg ttggcggccg aagccgccat tccatagtga     600
gttctggcgc gccagagccg ctacatcgtc gtcacacatg ttgtcttttg aggttggaca     660
ctgctcacta gacagaaaaa cctcgtgccg gaccgaatac ccggtctgaa cgagggcggc     720
cgcggtaccc aagaagtact tagagttaat taaggagttc aaacatgagg atcacccatg     780
tcgaagctcc cacaccctag cataaccct tggggcctct aaacgggtct tgaggggttt      840
tttgctgaaa ggaggaacta tatccggata tccacaggac gggtgtggtc gccatgatcg     900
cgtagtcgat agtggctcca agtagcgaag cgagcaggac tgggcggcgg catgcatcg      960 tccattccga cagcatcgcc agtcactatg gcgtgctgct agcgctatat cgttgatgc     1020 aatttctatg cgcacccgtt ctcggagcac tgtccgaccg ctttggccgc cgcccagtcc    1080
tgctcgcttc gctacttgga gccactatcg actacgcgat catggcgacc acaccgtcc     1140 tgtggatcca gatctcgatc ccgcgaaatt aatacgactc actatagggga gaccacaacg   1200 gtttccctct agatcacaag tttgtacaaa aaagcaggct aagaaggaga tatacatatg    1260
gcgtctaact ttacccaatt cgttctggtt gataacggcg gtacgggtga cgttaccgta    1320
gctccgtcca acttcgccaa cggtgttgcg gaatggatta gctctaacag ccgctctcag    1380
gcctacaaag tcacgtgctc cgttcgtcag tctagcgcgc agaatcgcaa atacaccatc    1440
```

```
aaagttgaag taccgaaagt cgcaacgcag accgtaggcg gcgtagaact cccagttgcg      1500
gcctggcgct cttacctcaa catggaactg actattccga tttttgcgac gaactccgac      1560
tgcgaactga ttgttaaggc aatgcagggc ctgctgaaag acggtaatcc gatcccatct      1620
gcaatcgctg ctaactctgg catttactaa taagcggacg cgctgccacc gctgagcaat      1680
aactagcata accccttggg gcctctaaac gggtcttgag gggttttttg ctgaaaggag      1740
gaactatatc cggcatgcac cattccttgc ggcggcggtg ctcaacggcc tcaacctact      1800
actgggctgc ttcctaatgc aggagtcgca taagggagag cgtcgaccga tgcccttgag      1860
agccttcaac ccagtcagct ccttccggtg ggcgcggggc atgactatcg tcgccgcact      1920
tatgactgtc ttctttatca tgcaactcgt aggacaggtg ccggcagcgc tctgggtcat      1980
tttcggcgag gaccgctttc gctggagcgc gacgatgatc ggcctgtcgc ttgcggtatt      2040
cggaatcttg cacgccctcg ctcaagcctt cgtcactggt cccgccacca aacgtttcgg      2100
cgagaagcag gccattatcg ccggcatggc ggccgacgcg ctgggctacg tcttgctggc      2160
gttcgcgacg cgaggctgga tggccttccc cattatgatt cttctcgctt ccggcggcat      2220
cgggatgccc gcgttgcagg ccatgctgtc caggcaggta gatgacgacc atcagggaca      2280
gcttcaagga tcgctcgcgg ctcttaccag cctaacttcg atcattggac cgctgatcgt      2340
cacggcgatt tatgccgcct cggcgagcac atggaacggg ttggcatgga ttgtaggcgc      2400
cgccctatac cttgtctgcc tccccgcgtt gcgtcgcggt gcatggagcc gggccacctc      2460
gacctgaatg gaagccggcg gcacctcgct aacggattca ccactccaag aattggagcc      2520
aatcaattct tgcggagaac tgtgaatgcg caaaccaacc cttggcagaa catatccatc      2580
gcgtccgcca tctccagcag ccgcacgcgg cgcatctcgg gcagcgttgg gtcctggcca      2640
cgggtgcgca tgatcgtgct cctgtcgttg aggacccggc taggctggcg gggttgcctt      2700
actggttagc agaatgaatc accgatacgc gagcgaacgt gaagcgactg ctgctgcaaa      2760
acgtctgcga cctgagcaac aacatgaatg gtcttcggtt tccgtgtttc gtaaagtctg      2820
gaaacgcgga agtcagcgcc ctgcaccatt atgttccgga tctgcatcgc aggatgctgc      2880
tggctaccct gtggaacacc tacatctgta ttaacgaagc gctggcattg accctgagtg      2940 attttttctct ggtcccgccg catccatacc gccagttgtt taccctcaca acgttccagt      3000
aaccgggcat gttcatcatc agtaacccgt atcgtgagca tcctctctcg tttcatcggt      3060
atcattaccc ccatgaacag aaatccccct tacacggagg catcagtgac caaacaggaa      3120
aaaaccgccc ttaacatggc ccgctttatc agaagccaga cattaacgct tctggagaaa      3180
ctcaacgagc tggacgcgga tgaacaggca gacatctgtg aatcgcttca cgaccacgct      3240
gatgagcttt accgcagctg cctcgcgcgt ttcggtgatg acggtgaaaa cctctgacac      3300
atgcagctcc cggagacggt cacagcttgt ctgtaagcgg atgccgggag cagacaagcc      3360
cgtcagggcg cgtcagcggg tgttggcggg tgtcggggcg cagccatgac ccagtcacgt      3420
agcgatagcg gagtgtatac tggcttaact atgcggcatc agagcagatt gtactgagag      3480
tgcaccatat gcggtgtgaa ataccgcaca gatgcgtaag gagaaaatac cgcatcaggc      3540
gctcttccgc ttcctcgctc actgactcgc tgcgctcggt cgttcggctg cggcgagcgg      3600
tatcagctca ctcaaaggcg gtaatacggt tatccacaga atcaggggat aacgcaggaa      3660
agaacatgtg agcaaaaggc cagcaaaagg ccaggaaccg taaaaaggcc gcgttgctgg      3720
cgtttttcca taggctccgc cccctgacg agcatcacaa aaatcgacgc tcaagtcaga      3780
ggtggcgaaa cccgacagga ctataaagat accaggcgtt cccccctgga agctccctcg      3840
```

```
tgcgctctcc tgttccgacc ctgccgctta ccggatacct gtccgccttt ctcccttcgg      3900
gaagcgtggc gctttctcat agctcacgct gtaggtatcc cagttcggtg taggtcgttc      3960
gctccaagct gggctgtgtg cacgaacccc ccgttcagcc cgaccgctgc gccttatccg      4020
gtaactatcg tcttgagtcc aacccggtaa gacacgactt atcgccactg gcagcagcca      4080
ctggtaacag gattagcaga gcgaggtatg taggcggtgc tacagagttc ttgaagtggt      4140
ggcctaacta cggctacact agaaggacag tatttggtat ctgcgctctg ctgaagccag      4200
ttaccttcgg aaaaagagtt ggtagctctt gatccggcaa acaaaccacc gctggtagcg      4260
gtggtttttt tgtttgcaag cagcagatta cgcgcagaaa aaaaggatct caagaagatc      4320
ctttgatctt ttctacgggg tctgacgctc agtggaacga aaactcacgt taagggattt      4380
tggtcatgag attatcaaaa aggatcttca cctagatcct tttaaattaa aaatgaagtt      4440
ttaaatcaat ctaaagtata tatgagtaaa cttggtctga cagttaccaa tgcttaatca      4500
gtgaggcacc tatctcagcg atctgtctat ttcgttcatc catagttgcc tgactccccg      4560
tcgtgtagat aactacgata cgggagggct taccatctgg ccccagtgct gcaatgatac      4620
cgcgagaccc acgctcaccg gctccagatt tatcagcaat aaaccagcca gccggaaggg      4680
ccgagcgcag aagtggtcct gcaactttat ccgcctccat ccagtctatt aattgttgcc      4740
gggaagctag agtaagtagt tcgccagtta atagtttgcg caacgttgtt gccattgctg      4800
caggcatcgt ggtgtcacgc tcgtcgtttg gtatggcttc attcagctcc ggttcccaac      4860
gatcaaggcg agttacatga tcccccatgt tgtgcaaaaa agcggttagc tccttcggtc      4920
ctccgatcgt tgtcagaagt aagttggccg cagtgttatc actcatggtt atggcagcac      4980
tgcataattc tcttactgtc atgccatccg taagatgctt ttctgtgact ggtgagtact      5040
caaccaagtc attctgagaa tagtgtatgc ggcgaccgag ttgctcttgc ccggcgtcaa      5100
cacgggataa taccgcgcca catagcagaa ctttaaaagt gctcatcatt ggaaaacgtt      5160
cttcggggcg aaaactctca aggatcttac cgctgttgag atccagttcg atgtaaccca      5220
ctcgtgcacc caactgatct tcagcatctt ttactttcac cagcgtttct gggtgagcaa      5280
aaacaggaag gcaaaatgcc gcaaaaaagg gaataagggc gacacggaaa tgttgaatac      5340
tcatactctt cctttttcaa tattattgaa gcatttatca gggttattgt ctcatgagcg      5400
gatacatatt tgaatgtatt tagaaaaata aacaaatagg ggttccgcgc acatttcccc      5460
gaaaagtgcc acctgacgtc taagaaacca ttattatcat gacattaacc tataaaaata      5520
ggcgtatcac gaggcccttt cgtcttcaag aa                                     5552
```

```
<210> SEQ ID NO 23
<211> LENGTH: 4667
<212> TYPE: DNA
<213> ORGANISM: Artificial Sequence
<220> FEATURE:
<223> OTHER INFORMATION: Recombinant plasmid pAPSE10149; coat protein
<220> FEATURE:
<221> NAME/KEY: promoter
<222> LOCATION: (1896)..(1914)
<223> OTHER INFORMATION: bacteriophage T7 gene 1 promoter
<220> FEATURE:
<221> NAME/KEY: gene
<222> LOCATION: (1987)..(2376)
<223> OTHER INFORMATION: bacteriophage MS2 coat protein
<220> FEATURE:
<221> NAME/KEY: terminator
<222> LOCATION: (2409)..(2456)
<223> OTHER INFORMATION: bacteriophage T7 transcription terminator
```

-continued

```
<400> SEQUENCE: 23
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttatttta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aacccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttctaga tttcagtgca    1440
atttatctct tcaaatgtag cacctgaagt cagccccata cgatataagt tgtaattctc    1500
atgtttgaca gcttatcatc gataagcttt aatgcggtag tttatcacag ttaaattgct    1560
aacgcagtca ggcaccgtgt atgaaatcta acaatgcgct catcgtcatc ctcggcaccg    1620
tcaccctgga tgctgtaggc ataggcttgg ttatgccggt actgccgggc ctcttgcggg    1680
atatcgtcca ttccgacagc atcgccagtc actatggcgt gctgctagcg ctatatgcgt    1740
tgatgcaatt tctatgcgca cccgttctcg gagcactgtc cgaccgcttt ggccgccgcc    1800
cagtcctgct cgcttcgcta cttggagcca ctatcgacta cgcgatcatg gcgaccacac    1860
ccgtcctgtg gatccagatc tcgatcccgc gaaattaata cgactcacta tagggagacc    1920
acaacggttt ccctctagat cacaagtttg tacaaaaaag caggctaaga aggagatata    1980
catatggcgt ctaactttac ccaattcgtt ctggttgata acggcggtac gggtgacgtt    2040
accgtagctc cgtccaactt cgccaacggt gttgcggaat ggattagctc taacagccgc    2100
tctcaggcct acaaagtcac gtgctccgtt cgtcagtcta gcgcgcagaa tcgcaaatac    2160
accatcaaag ttgaagtacc gaaagtcgca acgcagaccg taggcggcgt agaactccca    2220
gttgcggcct ggcgctctta cctcaacatg gaactgacta ttccgatttt tgcgacgaac    2280
tccgactgcg aactgattgt taaggcaatg cagggcctgc tgaaagacgg taatccgatc    2340
```

-continued

```
ccatctgcaa tcgctgctaa ctctggcatt tactaataag cggacgcgct gccaccgctg      2400
agcaataact agcataaccc cttggggcct ctaaacgggt cttgaggggt tttttgctga      2460
aaggaggaac tatatccggc atgcaccatt ccttgcggcg gcggtgctca acggcctcaa      2520
cctactactg ggctgcttcc taatgcagga gtcgcataag ggagagcgtc gaccgatgcc      2580
cttgagagcc ttcaacccag tcagctcctt ccggtgggcg cggggcatga ctatcgtcgc      2640
cgcacttatg actgtcttct ttatcatgca actcgtagga caggtgccgg cagcgctctg      2700
ggtcattttc ggcgaggacc gctttcgctg gagcgcgacg atgatcggcc tgtcgcttgc      2760
ggtattcgga atcttgcacg ccctcgctca agccttcgtc actggtcccg ccaccaaacg      2820
tttcggcgag aagcaggcca ttatcgccgg catggcggcc gacgcgctgg gctacgtctt      2880
gctggcgttc gcgacgcgag gctggatggc cttccccatt atgattcttc tcgcttccgg      2940
cggcatcggg atgcccgcgt tgcaggccat gctgtccagg caggtagatg acgaccatca      3000
gggacagctt caaggatcgc tcgcggctct taccagccta acttcgatca ttggaccgct      3060
gatcgtcacg gcgatttatg ccgcctcggc gagcacatgg aacgggttgg catggattgt      3120
aggcgccgcc ctataccttg tctgcctccc cgcgttgcgt cgcggtgcat ggagccgggc      3180
cacctcgacc tgaatggaag ccggcggcac ctcgctaacg gattcaccac tccaagaatt      3240
ggagccaatc aattcttgcg gagaactgtg aatgcgcaaa ccaacccttg gcagaacata      3300
tccatcgcgt ccgccatctc cagcagccgc acgcggcgca tctcgggcag cgttgggtcc      3360
tggccacggg tgcgcatgat cgtgctcctg tcgttgagga cccggctagg ctggcggggt      3420
tgccttactg gttagcagaa tgaatcaccg atacgcgagc gaacgtgaag cgactgctgc      3480
tgcaaaacgt ctgcgacctg agcaacaaca tgaatggtct tcggtttccg tgtttcgtaa      3540
agtctggaaa cgcggaagtc ccctacgtgc tgctgaagtt gcccgcaaca gagagtggaa      3600
ccaaccggtg ataccacgat actatgactg agagtcaacg ccatgagcgg cctcatttct      3660
tattctgagt tacaacagtc cgcaccgctg tccggtagct ccttccggtg ggcgcggggc      3720
atgactatcg tcgccgcact tatgactgtc ttctttatca tgcaactcgt aggacaggtg      3780
ccggcagcgc ccaacagtcc cccggccacg gggcctgcca ccatacccac gccgaaacaa      3840
gcgccctgca ccattatgtt ccggatctgc atcgcaggat gctgctggct accctgtgga      3900
acacctacat ctgtattaac gaagcgctaa ccgtttttat caggctctgg gaggcagaat      3960
aaatgatcat atcgtcaatt attacctcca cggggagagc ctgagcaaac tggcctcagg      4020
catttgagaa gcacacggtc acactgcttc cggtagtcaa taaaccggta aaccagcaat      4080
agacataagc ggctatttaa cgaccctgcc ctgaaccgac gaccgggtcg aatttgcttt      4140
cgaatttctg ccattcatcc gcttattatc acttattcag gcgtagcacc aggcgtttaa      4200
gggcaccaat aactgcctta aaaaaattac gccccgccct gccactcatc gcagtactgt      4260
tgtaattcat taagcattct gccgacatgg aagccatcac agacggcatg atgaacctga      4320
atcgccagcg gcatcagcac cttgtcgcct tgcgtataat atttgcccat ggtgaaaacg      4380
ggggcgaaga agttgtccat attggccacg tttaaatcaa aactggtgaa actcacccag      4440
ggattggctg agacgaaaaa catattctca ataaaccctt tagggaaata ggccaggttt      4500
tcaccgtaac acgccacatc ttgcgaatat atgtgtagaa actgccggaa atcgtcgtgg      4560
tattcactcc agagcgatga aaacgtttca gtttgctcat ggaaaacggt gtaacaaggg      4620
tgaacactat cccatatcac cagctcaccg tctttcattg ccatacg                    4667
```

<210> SEQ ID NO 24
<211> LENGTH: 6228
<212> TYPE: DNA
<213> ORGANISM: Artificial Sequence
<220> FEATURE:
<223> OTHER INFORMATION: Recombinant plasmid pAPSE10366; beta actin stem
      loop + eGFP protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1696)..(2415)
<223> OTHER INFORMATION: bacteriophage MS2 coat protein gene
<220> FEATURE:
<221> NAME/KEY: terminator
<222> LOCATION: (2448)..(2495)
<223> OTHER INFORMATION: bacteriophage T7 transcription terminator

<400> SEQUENCE: 24
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccgtgc cgtcttcccc tcgatcgtcg gtcgcccaag      540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttccctttcc agcgggatgc     720
tttatctaaa cgcaatgaga gaggtattcc tcaggccaca tcgcttccta gttccgctgg     780
gatccatcgt tggcggccga agccgccatt ccatagtgag ttctggcgcg cctcatccca     840

-continued

```
gttggtgatg ataccgtgtt cgatgggta tttcagggtg aggatacctc tttttgctttg      900 ggcttcatct cctacgtatg agtccttttg tcccataccg accatgactc cttgatgcct      960
tgggcgaccg acgatcgagg ggaagacggc acggggtgcg tcatctcctg cgaaaccggc     1020
tttgcacata ccggatccat tgtctacgac aagagccgct acatcgtcgt cacacatgtt     1080
gtcttttgag gttggacact gctcactaga cagaaaaacc tcgtgccgga ccgaataccc     1140
ggtctgaacg agggcggccg cggtacccaa gaagtactta gagttaatta aggagttcaa     1200
acatgaggat cacccatgtc gaagctccca caccctagca taaccccttg gggcctctaa     1260
acgggtcttg aggggttttt tgctgaaagg aggaactata tccggatatc cacaggacgg     1320
gtgtggtcgc catgatcgcg tagtcgatag tggctccaag tagcgaagcg agcaggactg     1380
ggcggcgggc atgcatcgtc cattccgaca gcatcgccag tcactatggc gtgctgctag     1440
cgctatatgc gttgatgcaa tttctatgcg cacccgttct cggagcactg tccgaccgct     1500
ttggccgccg cccagtcctg ctcgcttcgc tacttggagc cactatcgac tacgcgatca     1560
tggcgaccac acccgtcctg tggatccaga tctcgatccc gcgaaattaa tacgactcac     1620
tataggagga ccacaacggt ttccctctag atcacaagtt tgtacaaaaa agcaggctaa     1680
gaaggagata tacatatggt gagcaagggc gaggagctgt tcaccggggt ggtgcccatc     1740
ctggtcgagc tggacggcga cgtaaacggc cacaagttca gcgtgtccgg cgagggcgag     1800
ggcgatgcca cctacggcaa gctgaccctg aagttcatct gcaccaccgg caagctgccc     1860
gtgccctggc ccaccctcgt gaccaccctg acctacggcg tgcagtgctt cagccgctac     1920
cccgaccaca tgaagcagca cgacttcttc aagtccgcca tgcccgaagg ctacgtccag     1980
gagcgcacca tcttcttcaa ggacgacggc aactacaaga cccgcgccga ggtgaagttc     2040
gagggcgaca ccctggtgaa ccgcatcgag ctgaagggca tcgacttcaa ggaggacggc     2100
aacatcctgg ggcacaagct ggagtacaac tacaacagcc acaacgtcta tatcatggcc     2160
gacaagcaga agaacggcat caaggtgaac ttcaagatcc gccacaacat cgaggacggc     2220
agcgtgcagc tcgccgacca ctaccagcag aacacccca tcggcgacgg ccccgtgctg     2280
ctgcccgaca accactacct gagcacccag tccgccctga gcaaagaccc caacgagaag     2340
cgcgatcaca tggtcctgct ggagttcgtg accgccgccg ggatcactct cggcatggac     2400
gagctgtaca gtaataaagc ggacgcgctg ccaccgctga gcaataacta gcataacccc     2460
ttggggcctc taaacgggtc ttgaggggtt ttttgctgaa aggaggaact atatccggtc     2520
gaccgatgcc cttgagagcc ttcaacccag tcagctcctt ccggtgggcg cggggcatga     2580
ctatcgtcgc cgcacttatg actgtcttct ttatcatgca actcgtagga caggtgccgg     2640
cagcgctctg ggtcatttttc ggcgaggacc gctttcgctg gagcgcgacg atgatcggcc     2700
tgtcgcttgc ggtattcgga atcttgcacg ccctcgctca agccttcgtc actggtcccg     2760
ccaccaaacg tttcggcgag aagcaggcca ttatcgccgg catggcggcc gacgcgctgg     2820
gctacgtctt gctggcgttc gcgacgcgag gctggatggc cttccccatt atgattcttc     2880
tcgcttccgg cggcatcggg atgcccgcgt tgcaggccat gctgtccagg caggtagatg     2940
acgaccatca gggacagctt caaggatcgc tcgcggctct taccagccta acttcgatca     3000
ttggaccgct gatcgtcacg gcgatttatg ccgcctcggc gagcacatgg aacgggttgg     3060
catggattgt aggcgccgcc ctataccttg tctgcctccc cgcgttgcgt cgcggtgcat     3120
ggagccgggc cacctcgacc tgaatggaag ccggcggcac ctcgctaacg gattcaccac     3180
tccaagaatt ggagccaatc aattcttgcg gagaactgtg aatgcgcaaa ccaacccttg     3240
```

-continued

```
gcagaacata tccatcgcgt ccgccatctc cagcagccgc acgcggcgca tctcgggcag      3300
cgttgggtcc tggccacggg tgcgcatgat cgtgctcctg tcgttgagga cccggctagg      3360
ctggcggggt tgccttactg gttagcagaa tgaatcaccg atacgcgagc gaacgtgaag      3420
cgactgctgc tgcaaaacgt ctgcgacctg agcaacaaca tgaatggtct tcggtttccg      3480
tgtttcgtaa agtctggaaa cgcggaagtc agcgccctgc accattatgt tccggatctg      3540
catcgcagga tgctgctggc taccctgtgg aacacctaca tctgtattaa cgaagcgctg      3600
gcattgaccc tgagtgattt ttctctggtc ccgccgcatc cataccgcca gttgtttacc      3660
ctcacaacgt tccagtaacc gggcatgttc atcatcagta acccgtatcg tgagcatcct      3720
ctctcgtttc atcggtatca ttacccccat gaacagaaat cccccttaca cggaggcatc      3780
agtgaccaaa caggaaaaaa ccgcccttaa catggcccgc tttatcagaa gccagacatt      3840
aacgcttctg gagaaactca acgagctgga cgcggatgaa caggcagaca tctgtgaatc      3900
gcttcacgac cacgctgatg agctttaccg cagctgcctc gcgcgtttcg gtgatgacgg      3960
tgaaaacctc tgacacatgc agctcccgga cacggtcaca gcttgtctgt aagcggatgc      4020
cgggagcaga caagcccgtc agggcgcgtc agcgggtgtt ggcgggtgtc ggggcgcagc      4080
catgacccag tcacgtagcg atagcggagt gtatactggc ttaactatgc ggcatcagag      4140
cagattgtac tgagagtgca ccatatgcgg tgtgaaatac cgcacagatg cgtaaggaga      4200
aaataccgca tcaggcgctc ttccgcttcc tcgctcactg actcgctgcg ctcggtcgtt      4260
cggctgcggc gagcggtatc agctcactca aaggcggtaa tacggttatc cacagaatca      4320
ggggataacg caggaaagaa catgtgagca aaaggccagc aaaaggccag gaaccgtaaa      4380
aaggccgcgt tgctggcgtt tttccatagg ctccgccccc ctgacgagca tcacaaaaat      4440
cgacgctcaa gtcagaggtg gcgaaacccg acaggactat aaagatacca ggcgtttccc      4500
cctggaagct ccctcgtgcg ctctcctgtt ccgaccctgc cgcttaccgg atacctgtcc      4560
gcctttctcc cttcgggaag cgtggcgctt tctcatagct cacgctgtag gtatctcagt      4620
tcggtgtagg tcgttcgctc caagctgggc tgtgtgcacg aaccccccgt tcagcccgac      4680
cgctgcgcct tatccggtaa ctatcgtctt gagtccaacc cggtaagaca cgacttatcg      4740
ccactggcag cagccactgg taacaggatt agcagagcga ggtatgtagg cggtgctaca      4800
gagttcttga gtggtggcc taactacggc tacactagaa ggacagtatt tggtatctgc      4860
gctctgctga agccagttac cttcggaaaa agagttggta gctcttgatc cggcaaacaa      4920
accaccgctg gtagcggtgg tttttttgtt tgcaagcagc agattacgcg cagaaaaaaa      4980
ggatctcaag aagatccttt gatcttttct acggggtctg acgctcagtg gaacgaaaac      5040
tcacgttaag ggattttggt catgagatta tcaaaaagga tcttcaccta gatccttttra      5100 aattaaaaat gaagttttaa atcaatctaa agtatatatg agtaaacttg gtctgacagt      5160
taccaatgct taatcagtga ggcacctatc tcagcgatct gtctatttcg ttcatccata      5220
gttgcctgac tccccgtcgt gtagataact acgatacggg agggcttacc atctggcccc      5280
agtgctgcaa tgataccgcg agacccacgc tcaccggctc cagatttatc agcaataaac      5340
cagccagccg gaagggccga gcgcagaagt ggtcctgcaa ctttatccgc ctccatccag      5400
tctattaatt gttgccggga agctagagta agtagttcgc cagttaatag tttgcgcaac      5460
gttgttgcca ttgctgcagg catcgtggtg tcacgctcgt cgtttggtat ggcttcattc      5520
agctccggtt cccaacgatc aaggcgagtt acatgatccc ccatgttgtg caaaaaagcg      5580
```

```
gttagctcct tcggtcctcc gatcgttgtc agaagtaagt tggccgcagt gttatcactc      5640
atggttatgg cagcactgca taattctctt actgtcatgc catccgtaag atgcttttct      5700
gtgactggtg agtactcaac caagtcattc tgagaatagt gtatgcggcg accgagttgc      5760
tcttgcccgg cgtcaacacg ggataatacc gcgccacata gcagaacttt aaaagtgctc      5820
atcattggaa aacgttcttc ggggcgaaaa ctctcaagga tcttaccgct gttgagatcc      5880
agttcgatgt aacccactcg tgcacccaac tgatcttcag catcttttac tttcaccagc      5940
gtttctgggt gagcaaaaac aggaaggcaa aatgccgcaa aaaagggaat aagggcgaca      6000
cggaaatgtt gaatactcat actcttcctt tttcaatatt attgaagcat ttatcagggt      6060
tattgtctca tgagcggata catatttgaa tgtatttaga aaaataaaca aataggggtt      6120
ccgcgcacat ttccccgaaa agtgccacct gacgtctaag aaaccattat tatcatgaca      6180
ttaacctata aaaataggcg tatcacgagg ccctttcgtc ttcaagaa                   6228
```

```
<210> SEQ ID NO 25
<211> LENGTH: 5499
<212> TYPE: DNA
<213> ORGANISM: Artificial Sequence
<220> FEATURE:
<223> OTHER INFORMATION: Recombinant plasmid pAPSE10359; beta actin stem
      loop + Qbeta coat protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (46)..(65)
<223> OTHER INFORMATION: bacteriophage Qbeta pac sequence
<220> FEATURE:
<221> NAME/KEY: misc_feature
<222> LOCATION: (66)..(73)
<223> OTHER INFORMATION: restriction endonuclease AsiSI recognition site
<220> FEATURE:
<221> NAME/KEY: misc_feature
<222> LOCATION: (74)..(367)
<223> OTHER INFORMATION: beta actin sense strand gene fragment
<220> FEATURE:
<221> NAME/KEY: misc_feature
<222> LOCATION: (534)..(827)
<223> OTHER INFORMATION: beta actin antisense strand gene fragment
<220> FEATURE:
<221> NAME/KEY: misc_feature
<222> LOCATION: (872)..(891)
<223> OTHER INFORMATION: bacteriophage Qbeta pac sequence
<220> FEATURE:
<221> NAME/KEY: terminator
<222> LOCATION: (907)..(954)
<223> OTHER INFORMATION: bacteriophage T7 transcription terminator
<220> FEATURE:
<221> NAME/KEY: promoter
<222> LOCATION: (1108)..(1126)
<223> OTHER INFORMATION: bacteriophage T7 gene 1 promoter
<220> FEATURE:
<221> NAME/KEY: gene
<222> LOCATION: (1196)..(1597)
<223> OTHER INFORMATION: bacteriophage Qbeta coat protein
<220> FEATURE:
<221> NAME/KEY: terminator
<222> LOCATION: (1630)..(1677)
<223> OTHER INFORMATION: bacteriophage T7 transcription terminator

<400> SEQUENCE: 25
ttcagatctc gatcccgcga aattaatacg actcactata gggagatgca tgtctaagac       60
agcatgcgat cgcgcacgag gttttttctgt ctagtgagca gtgtccaacc tcaaaagaca      120
acatgtgtga cgacgatgta gcggctcttg tcgtagacaa tggatccggt atgtgcaaag      180
```

```
ccggtttcgc aggagatgac gcaccccgtg ccgtcttccc ctcgatcgtc ggtcgcccaa      240
ggcatcaagg agtcatggtc ggtatgggac aaaaggactc atacgtagga gatgaagccc      300
aaagcaaaag aggtatcctc accctgaaat accccatcga acacggtatc atcaccaact      360
gggatgagtt taaaccctct agctgcttta caaagtactg gttccctttc cagcgggatg      420
ctttatctaa acgcaatgag agaggtattc ctcaggccac atcgcttcct agttccgctg      480
ggatccatcg ttggcggccg aagccgccat tccatagtga gttctggcgc gcctcatccc      540
agttggtgat gataccgtgt tcgatggggt atttcagggt gaggatacct cttttgcttt      600
gggcttcatc tcctacgtat gagtcctttt gtcccatacc gaccatgact ccttgatgcc      660
ttgggcgacc gacgatcgag gggaagacgg cacggggtgc gtcatctcct gcgaaaccgg      720
ctttgcacat accggatcca ttgtctacga caagagccgc tacatcgtcg tcacacatgt      780
tgtcttttga ggttggacac tgctcactag acagaaaaac ctcgtgccgg accgaatacc      840
cggtctgaac gagggcggcc gcggagttca aatgcatgtc taagacagca tcgaagctcc      900
cacaccctag cataacccct tggggcctct aaacgggtct tgaggggttt tttgctgaaa      960
ggaggaacta tatccggata tccacaggac gggtgtggtc gccatgatcg cgtagtcgat     1020
agtggctcca agtagcgaag cgagcaggac tgggcggcgg gcatgcgcct ccgcctttag     1080
gggatccaga tctcgatccc gcgaaattaa tacgactcac tataggggaga ccacaacggt     1140 ttccctctag atcacaagtt tgtacaaaaa agcaggctaa gaaggagata tacatatggc     1200
aaaattagag actgttactt taggtaacat cgggaaagat ggaaaacaaa ctctggtcct     1260
caatccgcgt ggggtaaatc ccactaacgg cgttgcctcg ctttcacaag cgggtgcagt     1320
tcctgcgctg gagaagcgtg ttaccgtttc ggtatctcag ccttctcgca atcgtaagaa     1380
ctacaaggtc caggttaaga tccagaaccc gaccgcttgc actgcaaacg gttcttgtga     1440
cccatccgtt actcgccagg catatgctga cgtgaccttt tcgttcacgc agtatagtac     1500
cgatgaggaa cgagcttttg ttcgtacaga gcttactgct ctgctcgcta gtcctctgct     1560
gatcgatgct attgatcagc tgaacccagc gtattaataa gcggacgcgc tgccaccgct     1620
gagcaataac tagcataacc ccttgggggcc tctaaacggg tcttgagggg ttttttgctg     1680
aaaggaggaa ctatatccgg catgcaccat tccttgcggc ggcggtgctc aacggcctca     1740
acctactact gggctgcttc ctaatgcagg agtcgcataa gggagagcgt cgaccgatgc     1800
ccttgagagc cttcaaccca gtcagctcct tccggtgggc gcggggcatg actatcgtcg     1860
ccgcacttat gactgtcttc tttatcatgc aactcgtagg acaggtgccg gcagcgctct     1920
gggtcatttt cggcgaggac cgctttcgct ggagcgcgac gatgatcggc ctgtcgcttg     1980
cggtattcgg aatcttgcac gccctcgctc aagccttcgt cactggtccc gccaccaaac     2040
gtttcggcga gaagcaggcc attatcgccg gcatggcggc cgacgcgctg ggctacgtct     2100
tgctggcgtt cgcgacgcga ggctggatgg ccttccccat tatgattctt ctcgcttccg     2160
gcggcatcgg gatgcccgcg ttgcaggcca tgctgtccag gcaggtagat gacgaccatc     2220
agggacagct tcaaggatcg ctcgcggctc ttaccagcct aacttcgatc attggaccgc     2280
tgatcgtcac ggcgatttat gccgcctcgg cgagcacatg gaacgggttg gcatggattg     2340
taggcgccgc cctatacctt gtctgcctcc ccgcgttgcg tcgcggtgca tggagccggg     2400
ccacctcgac ctgaatggaa gccggcggca cctcgctaac ggattcacca ctccaagaat     2460
tggagccaat caattcttgc ggagaactgt gaatgcgcaa accaacccctt ggcagaacat     2520 atccatcgcg tccgccatct ccagcagccg cacgcggcgc atctcgggca gcgttgggtc     2580
```

```
ctggccacgg gtgcgcatga tcgtgctcct gtcgttgagg acccggctag gctggcgggg      2640
ttgccttact ggttagcaga atgaatcacc gatacgcgag cgaacgtgaa gcgactgctg      2700
ctgcaaaacg tctgcgacct gagcaacaac atgaatggtc ttcggtttcc gtgtttcgta      2760
aagtctggaa acgcggaagt cagcgccctg caccattatg ttccggatct gcatcgcagg      2820
atgctgctgg ctaccctgtg gaacacctac atctgtatta acgaagcgct ggcattgacc      2880
ctgagtgatt tttctctggt cccgccgcat ccataccgcc agttgtttac cctcacaacg      2940
ttccagtaac cgggcatgtt catcatcagt aacccgtatc gtgagcatcc tctctcgttt      3000
catcggtatc attaccccca tgaacagaaa tcccccttac acggaggcat cagtgaccaa      3060
acaggaaaaa accgcccta acatggcccg ctttatcaga agccagacat taacgcttct      3120
ggagaaactc aacgagctgg acgcggatga acaggcagac atctgtgaat cgcttcacga      3180
ccacgctgat gagctttacc gcagctgcct cgcgcgtttc ggtgatgacg gtgaaaacct      3240
ctgacacatg cagctcccgg agacggtcac agcttgtctg taagcggatg ccgggagcag      3300
acaagcccgt cagggcgcgt cagcgggtgt tggcgggtgt cggggcgcag ccatgaccca      3360
gtcacgtagc gatagcggag tgtatactgg cttaactatg cggcatcaga gcagattgta      3420
ctgagagtgc accatatgcg gtgtgaaata ccgcacagat gcgtaaggag aaaataccgc      3480
atcaggcgct cttccgcttc ctcgctcact gactcgctgc gctcggtcgt tcggctgcgg      3540
cgagcggtat cagctcactc aaaggcggta atacggttat ccacagaatc aggggataac      3600
gcaggaaaga acatgtgagc aaaaggccag caaaaggcca ggaaccgtaa aaaggccgcg      3660
ttgctggcgt ttttccatag gctccgcccc cctgacgagc atcacaaaaa tcgacgctca      3720
agtcagaggt ggcgaaaccc gacaggacta taaagatacc aggcgtttcc ccctggaagc      3780
tccctcgtgc gctctcctgt tccgaccctg ccgcttaccg gatacctgtc cgcctttctc      3840
ccttcgggaa gcgtggcgct ttctcatagc tcacgctgta ggtatctcag ttcggtgtag      3900
gtcgttcgct ccaagctggg ctgtgtgcac gaaccccccg ttcagcccga ccgctgcgcc      3960
ttatccggta actatcgtct tgagtccaac ccggtaagac acgacttatc gccactggca      4020
gcagccactg gtaacaggat tagcagagcg aggtatgtag gcggtgctac agagttcttg      4080
aagtggtggc ctaactacgg ctacactaga aggacagtat ttggtatctg cgctctgctg      4140
aagccagtta ccttcggaaa aagagttggt agctcttgat ccggcaaaca aaccaccgct      4200
ggtagcggtg gtttttttgt ttgcaagcag cagattacgc gcagaaaaaa aggatctcaa      4260
gaagatcctt tgatcttttc tacggggtct gacgctcagt ggaacgaaaa ctcacgttaa      4320
gggattttgg tcatgagatt atcaaaaagg atcttcacct agatcctttt aaattaaaaa      4380
tgaagtttta aatcaatcta aagtatatat gagtaaactt ggtctgacag ttaccaatgc      4440
ttaatcagtg aggcacctat ctcagcgatc tgtctatttc gttcatccat agttgcctga      4500
ctccccgtcg tgtagataac tacgatacgg gagggcttac catctggccc cagtgctgca      4560
atgataccgc gagacccacg ctcaccggct ccagatttat cagcaataaa ccagccagcc      4620
ggaagggccg agcgcagaag tggtcctgca actttatccg cctccatcca gtctattaat      4680
tgttgccggg aagctagagt aagtagttcg ccagttaata gtttgcgcaa cgttgttgcc      4740
attgctgcag gcatcgtggt gtcacgctcg tcgtttggta tggcttcatt cagctccggt      4800
tcccaacgat caaggcgagt tacatgatcc cccatgttgt gcaaaaaagc ggttagctcc      4860
ttcggtcctc cgatcgttgt cagaagtaag ttggccgcag tgttatcact catggttatg      4920
```

-continued

```
gcagcactgc ataattctct tactgtcatg ccatccgtaa gatgcttttc tgtgactggt          4980
gagtactcaa ccaagtcatt ctgagaatag tgtatgcggc gaccgagttg ctcttgcccg          5040
gcgtcaacac gggataatac cgcgccacat agcagaactt taaaagtgct catcattgga          5100
aaacgttctt cggggcgaaa actctcaagg atcttaccgc tgttgagatc cagttcgatg          5160
taacccactc gtgcacccaa ctgatcttca gcatctttta ctttcaccag cgtttctggg          5220
tgagcaaaaa caggaaggca aaatgccgca aaaaagggaa taagggcgac acggaaatgt          5280
tgaatactca tactcttcct ttttcaatat tattgaagca tttatcaggg ttattgtctc          5340
atgagcggat acatatttga atgtatttag aaaaataaac aaataggggt tccgcgcaca          5400
tttccccgaa aagtgccacc tgacgtctaa gaaaccatta ttatcatgac attaacctat          5460
aaaaataggc gtatcacgag gccctttcgt cttcaagaa                                 5499
```

```
<210> SEQ ID NO 26
<211> LENGTH: 5413
<212> TYPE: DNA
<213> ORGANISM: Artificial Sequence
<220> FEATURE:
<223> OTHER INFORMATION: Recombinant plasmid pAPSE10357; beta actin stem
      loop + U1A protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (41)..(66)
<223> OTHER INFORMATION: U1A binding site sequence
<220> FEATURE:
<221> NAME/KEY: misc_feature
<222> LOCATION: (67)..(74)
<223> OTHER INFORMATION: restriction endonuclease AsiSI recognition site
<220> FEATURE:
<221> NAME/KEY: misc_feature
<222> LOCATION: (75)..(368)
<223> OTHER INFORMATION: beta actin sense strand gene fragment
<220> FEATURE:
<221> NAME/KEY: misc_feature
<222> LOCATION: (535)..(828)
<223> OTHER INFORMATION: beta actin antisense strand gene fragment
<220> FEATURE:
<221> NAME/KEY: misc_feature
<222> LOCATION: (873)..(898)
<223> OTHER INFORMATION: U1A binding site sequence
<220> FEATURE:
<221> NAME/KEY: terminator
<222> LOCATION: (914)..(961)
<223> OTHER INFORMATION: bacteriophage T7 transcription terminator
<220> FEATURE:
<221> NAME/KEY: promoter
<222> LOCATION: (1115)..(1133)
<223> OTHER INFORMATION: bacteriophage T7 gene 1 promoter
<220> FEATURE:
<221> NAME/KEY: gene
<222> LOCATION: (1203)..(1511)
<223> OTHER INFORMATION: human U1A protein gene
<220> FEATURE:
<221> NAME/KEY: terminator
<222> LOCATION: (1544)..(1591)
<223> OTHER INFORMATION: bacteriophage T7 transcription terminator

<400> SEQUENCE: 26
ttcagatctc gatcccgcga aattaatacg actcactata gggtatccat tgcactccgg           60
atgcccgcga tcgcgcacga ggtttttctg tctagtgagc agtgtccaac ctcaaaagac          120
aacatgtgtg acgacgatgt agcggctctt gtcgtagaca atggatccgg tatgtgcaaa          180
gccggtttcg caggagatga cgcaccccgt gccgtcttcc cctcgatcgt cggtcgccca          240
```

-continued

```
aggcatcaag gagtcatggt cggtatggga caaaaggact catacgtagg agatgaagcc      300
caaagcaaaa gaggtatcct caccctgaaa taccccatcg aacacggtat catcaccaac      360
tgggatgagt ttaaaccctc tagctgcttt acaaagtact ggttcccttt ccagcgggat      420
gctttatcta aacgcaatga gagaggtatt cctcaggcca catcgcttcc tagttccgct      480
gggatccatc gttggcggcc gaagccgcca ttccatagtg agttctggcg cgcctcatcc      540
cagttggtga tgataccgtg ttcgatgggg tatttcaggg tgaggatacc tcttttgctt      600
tgggcttcat ctcctacgta tgagtccttt tgtcccatac cgaccatgac tccttgatgc      660
cttgggcgac cgacgatcga ggggaagacg gcacggggtg cgtcatctcc tgcgaaaccg      720
gctttgcaca taccggatcc attgtctacg acaagagccg ctacatcgtc gtcacacatg      780
ttgtcttttg aggttggaca ctgctcacta gacagaaaaa cctcgtgccg gaccgaatac      840
ccggtctgaa cgagggcggc cgcggagttc aagggtatcc attgcactcc ggatgccccg      900
aagctcccac accctagcat aacccccttgg ggcctctaaa cgggtcttga ggggtttttt      960
gctgaaagga ggaactatat ccggatatcc acaggacggg tgtggtcgcc atgatcgcgt     1020
agtcgatagt ggctccaagt agcgaagcga gcaggactgg gcggcgggca tgcgcctccg     1080
cctttagggg atccagatct cgatcccgcg aaattaatac gactcactat agggagacca     1140
caacggtttc cctctagatc acaagtttgt acaaaaaagc aggctaagaa ggagatatac     1200
atatggcagt tcccgagacc cgccctaacc acactattta tatcaacaac ctcaatgaga     1260
agatcaagaa ggatgagcta aaaaagtccc tgtacgccat cttctcccag tttggccaga     1320
tcctggatat cctggtatca cggagcctga agatgagggg ccaggccttt gtcatcttca     1380
aggaggtcag cagcgccacc aacgccctgc gctccatgca gggtttccct ttctatgaca     1440
aacctatgcg tatccagtat gccaagaccg actcagatat cattgccaag atgaaaggca     1500
ccttcgtgta ataagcggac gcgctgccac cgctgagcaa taactagcat aaccccttgg     1560
ggcctctaaa cgggtcttga ggggtttttt gctgaaagga ggaactatat ccggcatgca     1620
ccattccttg cggcggcggt gctcaacggc ctcaacctac tactgggctg cttcctaatg     1680
caggagtcgc ataagggaga gcgtcgaccg atgcccttga gagccttcaa cccagtcagc     1740
tccttccggt gggcgcgggg catgactatc gtcgccgcac ttatgactgt cttctttatc     1800
atgcaactcg taggacaggt gccggcagcg ctctgggtca ttttcggcga ggaccgcttt     1860
cgctggagcg cgacgatgat cggcctgtcg cttgcggtat tcggaatctt gcacgccctc     1920
gctcaagcct tcgtcactgg tcccgccacc aaacgtttcg gcgagaagca ggccattatc     1980
gccggcatgg cggccgacgc gctgggctac gtcttgctgg cgttcgcgac gcgaggctgg     2040
atggccttcc ccattatgat tcttctcgct tccggcggca tcgggatgcc cgcgttgcag     2100
gccatgctgt ccaggcaggt agatgacgac catcagggac agcttcaagg atcgctcgcg     2160
gctcttacca gcctaacttc gatcattgga ccgctgatcg tcacggcgat ttatgccgcc     2220
tcggcgagca catggaacgg gttggcatgg attgtaggcg ccgccctata ccttgtctgc     2280
ctccccgcgt tgcgtcgcgg tgcatggagc cgggccacct cgacctgaat ggaagccggc     2340
ggcacctcgc taacggattc accactccaa gaattggagc caatcaattc ttgcggagaa     2400
ctgtgaatgc gcaaaccaac ccttggcaga acatatccat cgcgtccgcc atctccagca     2460
gccgcacgcg cgcatctcg gcagcgttg gtcctggcc acgggtgcgc atgatcgtgc         2520
tcctgtcgtt gaggacccgg ctaggctggc ggggttgcct tactggttag cagaatgaat     2580
caccgatacg cgagcgaacg tgaagcgact gctgctgcaa aacgtctgcg acctgagcaa     2640
```

-continued

```
caacatgaat ggtcttcggt ttccgtgttt cgtaaagtct ggaaacgcgg aagtcagcgc      2700
cctgcaccat tatgttccgg atctgcatcg caggatgctg ctggctaccc tgtggaacac      2760
ctacatctgt attaacgaag cgctggcatt gaccctgagt gattttttctc tggtcccgcc     2820 gcatccatac cgccagttgt ttaccctcac aacgttccag taaccgggca tgttcatcat      2880
cagtaacccg tatcgtgagc atcctctctc gtttcatcgg tatcattacc cccatgaaca      2940
gaaatccccc ttacacggag gcatcagtga ccaaacagga aaaaaccgcc cttaacatgg      3000
cccgctttat cagaagccag acattaacgc ttctggagaa actcaacgag ctggacgcgg      3060
atgaacaggc agacatctgt gaatcgcttc acgaccacgc tgatgagctt taccgcagct      3120
gcctcgcgcg tttcggtgat gacggtgaaa acctctgaca catgcagctc ccggagacgg      3180
tcacagcttg tctgtaagcg gatgccggga gcagacaagc ccgtcagggc gcgtcagcgg      3240
gtgttggcgg gtgtcggggc gcagccatga cccagtcacg tagcgatagc ggagtgtata      3300
ctggcttaac tatgcggcat cagagcagat tgtactgaga gtgcaccata tgcggtgtga      3360
aataccgcac agatgcgtaa ggagaaaata ccgcatcagg cgctcttccg cttcctcgct      3420
cactgactcg ctgcgctcgg tcgttcggct gcggcgagcg gtatcagctc actcaaaggc      3480
ggtaatacgg ttatccacag aatcagggga taacgcagga agaacatgt gagcaaaagg      3540 ccagcaaaag gccaggaacc gtaaaaaggc cgcgttgctg gcgtttttcc ataggctccg      3600
cccccctgac gagcatcaca aaaatcgacg ctcaagtcag aggtggcgaa acccgacagg      3660
actataaaga taccaggcgt ttccccctgg aagctccctc gtgcgctctc ctgttccgac      3720
cctgccgctt accggatacc tgtccgcctt tctcccttcg ggaagcgtgg cgctttctca      3780
tagctcacgc tgtaggtatc tcagttcggt gtaggtcgtt cgctccaagc tgggctgtgt      3840
gcacgaaccc cccgttcagc ccgaccgctg cgccttatcc ggtaactatc gtcttgagtc      3900
caacccggta agacacgact tatcgccact ggcagcagcc actggtaaca ggattagcag      3960
agcgaggtat gtaggcggtg ctacagagtt cttgaagtgg tggcctaact acggctacac      4020
tagaaggaca gtatttggta tctgcgctct gctgaagcca gttaccttcg gaaaaagagt      4080
tggtagctct tgatccggca aacaaaccac cgctggtagc ggtggttttt ttgtttgcaa      4140
gcagcagatt acgcgcagaa aaaaaggatc tcaagaagat cctttgatct tttctacggg      4200
gtctgacgct cagtggaacg aaaactcacg ttaagggatt ttggtcatga gattatcaaa      4260
aaggatcttc acctagatcc ttttaaatta aaaatgaagt tttaaatcaa tctaaagtat      4320
atatgagtaa acttggtctg acagttacca atgcttaatc agtgaggcac ctatctcagc      4380
gatctgtcta tttcgttcat ccatagttgc ctgactcccc gtcgtgtaga taactacgat      4440
acgggagggc ttaccatctg gccccagtgc tgcaatgata ccgcgagacc cacgctcacc      4500
ggctccagat ttatcagcaa taaaccagcc agccggaagg gccgagcgca gaagtggtcc      4560
tgcaacttta tccgcctcca tccagtctat taattgttgc cgggaagcta gagtaagtag      4620
ttcgccagtt aatagtttgc gcaacgttgt tgccattgct gcaggcatcg tggtgtcacg      4680
ctcgtcgttt ggtatggctt cattcagctc cggttcccaa cgatcaaggc gagttacatg      4740
atcccccatg ttgtgcaaaa aagcggttag ctccttcggt cctccgatcg ttgtcagaag      4800
taagttggcc gcagtgttat cactcatggt tatggcagca ctgcataatt ctcttactgt      4860
catgccatcc gtaagatgct tttctgtgac tggtgagtac tcaaccaagt cattctgaga      4920
atagtgtatg cggcgaccga gttgctcttg cccggcgtca acacgggata ataccgcgcc      4980
```

-continued

```
acatagcaga actttaaaag tgctcatcat tggaaaacgt tcttcggggc gaaaactctc      5040
aaggatctta ccgctgttga gatccagttc gatgtaaccc actcgtgcac ccaactgatc      5100
ttcagcatct tttactttca ccagcgtttc tgggtgagca aaaacaggaa ggcaaaatgc      5160
cgcaaaaaag ggaataaggg cgacacggaa atgttgaata ctcatactct tcctttttca      5220
atattattga agcatttatc agggttattg tctcatgagc ggatacatat ttgaatgtat      5280
ttagaaaaat aaacaaatag gggttccgcg cacatttccc cgaaaagtgc cacctgacgt      5340
ctaagaaacc attattatca tgacattaac ctataaaaat aggcgtatca cgaggccctt      5400
tcgtcttcaa gaa                                                        5413
```

```
<210> SEQ ID NO 27
<211> LENGTH: 5504
<212> TYPE: DNA
<213> ORGANISM: Artificial Sequence
<220> FEATURE:
<223> OTHER INFORMATION: Recombinant plasmid pAPSE10372; beta actin stem
      loop + truncated coat protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (127)..(145)
<223> OTHER INFORMATION: bacteriophage MS2 pac sequence
<220> FEATURE:
<221> NAME/KEY: misc_feature
<222> LOCATION: (175)..(182)
<223> OTHER INFORMATION: restriction endonuclease AsiSI recognition site
<220> FEATURE:
<221> NAME/KEY: misc_feature
<222> LOCATION: (179)..(384)
<223> OTHER INFORMATION: ErkA sense strand gene fragment
<220> FEATURE:
<221> NAME/KEY: misc_feature
<222> LOCATION: (436)..(454)
<223> OTHER INFORMATION: bacteriophage MS2 pac sequence
<220> FEATURE:
<221> NAME/KEY: misc_feature
<222> LOCATION: (504)..(511)
<223> OTHER INFORMATION: restriction endonuclease NotI recognition site
<220> FEATURE:
<221> NAME/KEY: misc_feature
<222> LOCATION: (505)..(696)
<223> OTHER INFORMATION: ErkA antisense strand gene fragment
<220> FEATURE:
<221> NAME/KEY: misc_feature
<222> LOCATION: (692)..(699)
<223> OTHER INFORMATION: restriction endonuclease PacI recognition site
<220> FEATURE:
<221> NAME/KEY: misc_feature
<222> LOCATION: (728)..(746)
<223> OTHER INFORMATION: bacteriophage MS2 pac sequence
<220> FEATURE:
<221> NAME/KEY: terminator
<222> LOCATION: (762)..(809)
<223> OTHER INFORMATION: bacteriophage T7 transcription terminator
<220> FEATURE:
<221> NAME/KEY: promoter
<222> LOCATION: (1135)..(1153)
<223> OTHER INFORMATION: bacteriophage T7 gene 1 promoter
<220> FEATURE:
<221> NAME/KEY: misc_feature
<222> LOCATION: (1223)..(1429)
<223> OTHER INFORMATION: bacteriophage MS2 coat protein N-terminal
      fragment
<220> FEATURE:
<221> NAME/KEY: terminator
<222> LOCATION: (1635)..(1682)
<223> OTHER INFORMATION: bacteriophage T7 transcription terminator

<400> SEQUENCE: 27
```

-continued

```
ttcagatctc gatcccgcga aattaatacg actcactata gggagaccac aacggtttcc      60
ctctagatca caagtttgta caaaaaagca ggctaagaag gagatataca tacgccggcc     120
attcaaacat gaggattacc catgtaacct aaggccggtg tccaggcgcg ctccgcgatc     180
gcacgcggac aaagttcctc aatctaatgc tgaagttata aggggacaaa tatttgaagt     240
tggtcctagg tatattaaac tcgcctatat aggtgaagga gcttatggca tggttgtgtc     300
tgcggatgac acgctaacaa accaaagagt tgcaataaaa aaaatatcgc cctttgaaca     360
ccaaacttat tgctactaca gtttaaacgc aatcgcagca aactccggca tctactaata     420
gacgccggcc attcaacatg aggattaccc atgtaaccta agaagacaac aaagaagttc     480
aactctttat gtattgatct tccgcggccg cggtaccggg gcaataagtt tggtgttcaa     540
agggcgatat tttttttatt gcaactcttt ggtttgttag cgtgtcatcc gcagacacaa     600
ccatgccata agctccttca cctatatagg cgagtttaat atacctagga ccaacttcaa     660
atatttgtcc ccttataact tcagcattag attgaggaac tatacgaaaa ttaattaagg     720
agttcaaaca tgaggatcac ccatgtcgaa gctcccacac cctagcataa ccccttgggg     780
cctctaaacg ggtcttgagg ggtttttttgc tgaaaggagg aactatatcc ggatatccac     840
aggacgggtg tggtcgccat gatcgcgtag tcgatagtgg ctccaagtag cgaagcgagc     900
aggactgggc ggcgggcatg catcgtccat tccgacagca tcgccagtca ctatggcgtg     960
ctgctagcgc tatatgcgtt gatgcaattt ctatgcgcac ccgttctcgg agcactgtcc    1020
gaccgctttg gccgccgccc agtcctgctc gcttcgctac ttggagccac tatcgactac    1080
gcgatcatgg cgaccacacc cgtcctgtgg atccagatct cgatcccgcg aaattaatac    1140
gactcactat agggagacca caacggtttc cctctagatc acaagtttgt acaaaaaagc    1200
aggctaagaa ggagatatac atatggcgtc taactttacc caattcgttc tggttgataa    1260
cggcggtacg ggtgacgtta ccgtagctcc gtccaacttc gccaacggtg ttgcggaatg    1320
gattagctct aacagccgct ctcagggtgc tccgttcgtc agtctagcgc gcagaatcgc    1380
aaatacacca tcaaagttga agtaccgaaa gtcgcaacgc agaccgtagg cggcgtagaa    1440
ctcccagttg cggcctggcg ctcttacctc aacatggaac tgactattcc gatttttgcg    1500
acgaactccg actgcgaact gattgttaag gcaatgcagg gcctgctgaa agacggtaat    1560
ccgatcccat ctgcaatcgc tgctaactct ggcatttact aataagcgga cgcgctgcca    1620
ccgctgagca ataactagca taaccccttg gggcctctaa acgggtcttg aggggttttt    1680
tgctgaaagg aggaactata tccggcatgc accattcctt cgcggcggcgg tgctcaacgg    1740 cctcaaccta ctactgggct gcttcctaat gcaggagtcg cataagggag agcgtcgacc    1800
gatgcccttg agagccttca acccagtcag ctccttccgg tgggcgcggg gcatgactat    1860
cgtcgccgca cttatgactg tcttctttat catgcaactc gtaggacagg tgccggcagc    1920
gctctgggtc attttcggcg aggaccgctt tcgctggagc gcgacgatga tcggcctgtc    1980
gcttgcggta ttcggaatct tgcacgccct cgctcaagcc ttcgtcactg gtcccgccac    2040
caaacgtttc ggcgagaagc aggccattat cgccggcatg gcggccgacg cgctgggcta    2100
cgtcttgctg gcgttcgcga cgcgaggctg gatggccttc cccattatga ttcttctcgc    2160
ttccggcggc atcgggatgc ccgcgttgca ggccatgctg tccaggcagg tagatgacga    2220
ccatcaggga cagcttcaag gatcgctcgc ggctcttacc agcctaactt cgatcattgg    2280
accgctgatc gtcacggcga tttatgccgc ctcggcgagc acatggaacg ggttggcatg    2340
```

-continued

```
gattgtaggc gccgccctat accttgtctg cctccccgcg ttgcgtcgcg gtgcatggag    2400
ccgggccacc tcgacctgaa tggaagccgg cggcacctcg ctaacggatt caccactcca    2460
agaattggag ccaatcaatt cttgcggaga actgtgaatg cgcaaaccaa cccttggcag    2520
aacatatcca tcgcgtccgc catctccagc agccgcacgc ggcgcatctc gggcagcgtt    2580
gggtcctggc cacgggtgcg catgatcgtg ctcctgtcgt tgaggacccg gctaggctgg    2640
cggggttgcc ttactggtta gcagaatgaa tcaccgatac gcgagcgaac gtgaagcgac    2700
tgctgctgca aaacgtctgc gacctgagca acaacatgaa tggtcttcgg tttccgtgtt    2760
tcgtaaagtc tggaaacgcg gaagtcagcg ccctgcacca ttatgttccg gatctgcatc    2820
gcaggatgct gctggctacc ctgtggaaca cctacatctg tattaacgaa gcgctggcat    2880
tgaccctgag tgattttct  ctggtcccgc cgcatccata ccgccagttg tttaccctca    2940
caacgttcca gtaaccgggc atgttcatca tcagtaaccc gtatcgtgag catcctctct    3000
cgtttcatcg gtatcattac ccccatgaac agaaatcccc cttacacgga ggcatcagtg    3060
accaaacagg aaaaaaccgc ccttaacatg gcccgcttta tcagaagcca gacattaacg    3120
cttctggaga aactcaacga gctggacgcg gatgaacagg cagacatctg tgaatcgctt    3180
cacgaccacg ctgatgagct ttaccgcagc tgcctcgcgc gtttcggtga tgacggtgaa    3240
aacctctgac acatgcagct cccggagacg gtcacagctt gtctgtaagc ggatgccggg    3300
agcagacaag cccgtcaggg cgcgtcagcg ggtgttggcg ggtgtcgggg cgcagccatg    3360
acccagtcac gtagcgatag cggagtgtat actggcttaa ctatgcggca tcagagcaga    3420
ttgtactgag agtgcaccat atgcggtgtg aaataccgca cagatgcgta aggagaaaat    3480
accgcatcag gcgctcttcc gcttcctcgc tcactgactc gctgcgctcg gtcgttcggc    3540
tgcggcgagc ggtatcagct cactcaaagg cggtaatacg gttatccaca gaatcagggg    3600
ataacgcagg aaagaacatg tgagcaaaag gccagcaaaa ggccaggaac cgtaaaaagg    3660
ccgcgttgct ggcgtttttc cataggctcc gcccccctga cgagcatcac aaaaatcgac    3720
gctcaagtca gaggtggcga aacccgacag gactataaag ataccaggcg tttccccctg    3780
gaagctccct cgtgcgctct cctgttccga ccctgccgct taccggatac ctgtccgcct    3840
ttctcccttc gggaagcgtg gcgctttctc atagctcacg ctgtaggtat ctcagttcgg    3900
tgtaggtcgt tcgctccaag ctgggctgtg tgcacgaacc ccccgttcag cccgaccgct    3960
gcgccttatc cggtaactat cgtcttgagt ccaacccggt aagacacgac ttatcgccac    4020
tggcagcagc cactggtaac aggattagca gagcgaggta tgtaggcggt gctacagagt    4080
tcttgaagtg gtggcctaac tacggctaca ctagaaggac agtatttggt atctgcgctc    4140
tgctgaagcc agttaccttc ggaaaaagag ttggtagctc ttgatccggc aaacaaacca    4200
ccgctggtag cggtggtttt tttgtttgca agcagcagat tacgcgcaga aaaaaggat    4260 ctcaagaaga tcctttgatc ttttctacgg ggtctgacgc tcagtggaac gaaaactcac    4320
gttaagggat tttggtcatg agattatcaa aaaggatctt cacctagatc cttttaaatt    4380
aaaaatgaag ttttaaatca atctaaagta tatatgagta aacttggtct gacagttacc    4440
aatgcttaat cagtgaggca cctatctcag cgatctgtct atttcgttca tccatagttg    4500
cctgactccc cgtcgtgtag ataactacga tacgggaggg cttaccatct ggccccagtg    4560
ctgcaatgat accgcgagac ccacgctcac cggctccaga tttatcagca ataaaccagc    4620 cagccgaag ggccgagcgc agaagtggtc ctgcaacttt atccgcctcc atccagtcta    4680
ttaattgttg ccgggaagct agagtaagta gttcgccagt taatagtttg cgcaacgttg    4740
```

```
ttgccattgc tgcaggcatc gtggtgtcac gctcgtcgtt tggtatggct tcattcagct    4800
ccggttccca acgatcaagg cgagttacat gatcccccat gttgtgcaaa aaagcggtta    4860
gctccttcgg tcctccgatc gttgtcagaa gtaagttggc cgcagtgtta tcactcatgg    4920
ttatggcagc actgcataat tctcttactg tcatgccatc cgtaagatgc ttttctgtga    4980
ctggtgagta ctcaaccaag tcattctgag aatagtgtat gcggcgaccg agttgctctt    5040
gcccggcgtc aacacgggat aataccgcgc cacatagcag aactttaaaa gtgctcatca    5100
ttggaaaacg ttcttcgggg cgaaaactct caaggatctt accgctgttg agatccagtt    5160
cgatgtaacc cactcgtgca cccaactgat cttcagcatc ttttactttc accagcgttt    5220
ctgggtgagc aaaaacagga aggcaaaatg ccgcaaaaaa gggaataagg gcgacacgga    5280
aatgttgaat actcatactc ttcctttttc aatattattg aagcatttat cagggttatt    5340
gtctcatgag cggatacata tttgaatgta tttagaaaaa taaacaaata ggggttccgc    5400
gcacatttcc ccgaaaagtg ccacctgacg tctaagaaac cattattatc atgacattaa    5460
cctataaaaa taggcgtatc acgaggccct ttcgtcttca agaa                     5504
```

```
<210> SEQ ID NO 28
<211> LENGTH: 68
<212> TYPE: PRT
<213> ORGANISM: Artificial Sequence
<220> FEATURE:
<223> OTHER INFORMATION: N-terminus truncated bacteriophage MS2 coat
      protein sequence

<400> SEQUENCE: 28

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Gly Ala Pro Phe Val Ser Leu
        35                  40                  45

Ala Arg Arg Ile Ala Asn Thr Pro Ser Lys Leu Lys Tyr Arg Lys Ser
    50                  55                  60

Gln Arg Arg Pro
65
```

```
<210> SEQ ID NO 29
<211> LENGTH: 8339
<212> TYPE: DNA
<213> ORGANISM: Artificial Sequence
<220> FEATURE:
<223> OTHER INFORMATION: Recombinant plasmid pAPSE10429; C. glutamicum
      rnc deletion plasmid
<220> FEATURE:
<221> NAME/KEY: gene
<222> LOCATION: (346)..(1140)
<223> OTHER INFORMATION: Kanamycin resistance gene
<220> FEATURE:
<221> NAME/KEY: promoter
<222> LOCATION: (1186)..(1631)
<223> OTHER INFORMATION: sacB promoter
<220> FEATURE:
<221> NAME/KEY: gene
<222> LOCATION: (1632)..(3053)
<223> OTHER INFORMATION: sacB gene
<220> FEATURE:
<221> NAME/KEY: misc_feature
<222> LOCATION: (5504)..(5510)
<223> OTHER INFORMATION: restriction endonuclease BamHI recognition site
<220> FEATURE:
<221> NAME/KEY: misc_feature
```

-continued

<222> LOCATION: (5511)..(8136)
<223> OTHER INFORMATION: PCR fragment comprising 1.5 kb of chromosomal
      sequencedownstream of rnc gene (5511-7012) and 1.2 kb of
      chromosomal sequence upstream of rnc gene (7013-8136).
<220> FEATURE:
<221> NAME/KEY: misc_feature
<222> LOCATION: (8136)..(8141)
<223> OTHER INFORMATION: restrcition endonuclease SalI recognition site

<400> SEQUENCE: 29

```
tgccgcaagc actcagggcg caagggctgc taaaggaagc ggaacacgta gaaagccagt      60
ccgcagaaac ggtgctgacc ccggatgaat gtcagctact gggctatctg gacaagggaa     120
aacgcaagcg caaagagaaa gcaggtagct tgcagtgggc ttacatggcg atagctagac     180
tgggcggttt tatggacagc aagcgaaccg gaattgccag ctggggcgcc ctctggtaag     240
gttgggaagc cctgcaaagt aaactggatg gctttcttgc cgccaaggat ctgatggcgc     300
aggggatcaa gatctgatca agagacagga tgaggatcgt ttcgcatgat tgaacaagat     360
ggattgcacg caggttctcc ggccgcttgg gtggagaggc tattcggcta tgactgggca     420
caacagacaa tcggctgctc tgatgccgcc gtgttccggc tgtcagcgca ggggcgcccg     480
gttctttttg tcaagaccga cctgtccggt gccctgaatg aactccaaga cgaggcagcg     540
cggctatcgt ggctggccac gacgggcgtt ccttgcgcag ctgtgctcga cgttgtcact     600
gaagcgggaa gggactggct gctattgggc gaagtgccgg ggcaggatct cctgtcatct     660
caccttgctc ctgccgagaa agtatccatc atggctgatg caatgcggcg gctgcatacg     720
cttgatccgg ctacctgccc attcgaccac caagcgaaac atcgcatcga gcgagcacgt     780
actcggatgg aagccggtct tgtcgatcag gatgatctgg acgaagagca tcaggggctc     840
gcgccagccg aactgttcgc caggctcaag gcgcggatgc ccgacggcga ggatctcgtc     900
gtgacccatg gcgatgcctg cttgccgaat atcatggtgg aaaatggccg cttttctgga     960
ttcatcgact gtggccggct gggtgtggcg gaccgctatc aggacatagc gttggctacc    1020
cgtgatattg ctgaagagct tggcggcgaa tgggctgacc gcttcctcgt gctttacggt    1080
atcgccgctc ccgattcgca gcgcatcgcc ttctatcgcc ttcttgacga gttcttctga    1140
gcgggactct ggggttcgct agaggatcga tcctttttaa cccatcacat atacctgccg    1200
ttcactatta tttagtgaaa tgagatatta tgatattttc tgaattgtga ttaaaaaggc    1260
aactttatgc ccatgcaaca gaaactataa aaaatacaga gaatgaaaag aaacagatag    1320
attttttagt tctttaggcc cgtagtctgc aaatcctttt atgattttct atcaaacaaa    1380
agaggaaaat agaccagttg caatccaaac gagagtctaa tagaatgagg tcgaaaagta    1440
aatcgcgcgg gtttgttact gataaagcag gcaagaccta aaatgtgtaa agggcaaagt    1500
gtatactttg gcgtcacccc ttacatattt taggtctttt tttattgtgc gtaactaact    1560
tgccatcttc aaacaggagg gctggaagaa gcagaccgct aacacagtac ataaaaaagg    1620
agacatgaac gatgaacatc aaaaagtttg caaacaagc aacagtatta acctttacta    1680
ccgcactgct ggcaggaggc gcaactcaag cgtttgcgaa agaaacgaac caaaagccat    1740
ataaggaaac atacggcatt cccatatta cacgccatga tatgctgcaa atccctgaac    1800
agcaaaaaaa tgaaaaatat caagtttctg aatttgattc gtccacaatt aaaaatatct    1860
cttctgcaaa aggcctggac gtttgggaca gctggccatt acaaaacgct gacggcactg    1920
tcgcaaacta tcacggctac cacatcgtct ttgcattagc cggagatcct aaaaatgcgg    1980
atgacacatc gatttacatg ttctatcaaa aagtcggcga aacttctatt gacagctgga    2040
```

-continued

```
aaaacgctgg  ccgcgtcttt  aaagacagcg  acaaattcga  tgcaaatgat  tctatcctaa      2100
aagaccaaac  acaagaatgg  tcaggttcag  ccacatttac  atctgacgga  aaaatccgtt      2160
tattctacac  tgatttctcc  ggtaaacatt  acggcaaaca  aacactgaca  actgcacaag      2220
ttaacgtatc  agcatcagac  agctctttga  acatcaacgg  tgtagaggat  tataaatcaa      2280
tctttgacgg  tgacggaaaa  acgtatcaaa  atgtacagca  gttcatcgat  gaaggcaact      2340
acagctcagg  cgacaaccat  acgctgagag  atcctcacta  cgtagaagat  aaaggccaca      2400
aatacttagt  atttgaagca  aacactggaa  ctgaagatgg  ctaccaaggc  gaagaatctt      2460
tatttaacaa  agcatactat  ggcaaaagca  catcattctt  ccgtcaagaa  agtcaaaaac      2520
ttctgcaaag  cgataaaaaa  cgcacggctg  agttagcaaa  cggcgctctc  ggtatgattg      2580
agctaaacga  tgattacaca  ctgaaaaaag  tgatgaaacc  gctgattgca  tctaacacag      2640
taacagatga  aattgaacgc  gcgaacgtct  ttaaaatgaa  cggcaaatgg  tacctgttca      2700
ctgactcccg  cggatcaaaa  atgacgattg  acggcattac  gtctaacgat  atttacatgc      2760
ttggttatgt  ttctaattct  ttaactggcc  catacaagcc  gctgaacaaa  actggccttg      2820
tgttaaaaat  ggatcttgat  cctaacgatg  taacctttac  ttactcacac  ttcgctgtac      2880
ctcaagcgaa  aggaaacaat  gtcgtgatta  caagctatat  gacaaacaga  ggattctacg      2940
cagacaaaca  atcaacgttt  gcgccgagct  tcctgctgaa  catcaaaggc  aagaaaacat      3000
ctgttgtcaa  agacagcatc  cttgaacaag  gacaattaac  agttaacaaa  taaaaacgca      3060
aaagaaaatg  ccgatgggta  ccgagcgaaa  tgaccgacca  agcgacgccc  aacctgccat      3120
cacgagattt  cgattccacc  gccgccttct  atgaaaggtt  gggcttcgga  atcgtttttc      3180
gggacgccct  cgcggacgtg  ctcatagtcc  acgacgcccg  tgattttgta  gccctggccg      3240
acggccagca  ggtaggccga  caggctcatg  ccggccgccg  ccgccttttc  ctcaatcgct      3300
cttcgttcgt  ctggaaggca  gtacaccttg  ataggtgggc  tgcccttcct  ggttggcttg      3360
gtttcatcag  ccatccgctt  gccctcatct  gttacgccgg  cggtagccgg  ccagcctcgc      3420
agagcaggat  tcccgttgag  caccgccagg  tgcgaataag  ggacagtgaa  gaaggaacac      3480
ccgctcgcgg  gtgggcctac  ttcacctatc  ctgcccggct  gacgccgttg  gatacaccaa      3540
ggaaagtcta  cacgaaccct  ttggcaaaat  cctgtatatc  gtgcgaaaaa  ggatggatat      3600
accgaaaaaa  tcgctataat  gaccccgaag  cagggttatg  cagcggaaaa  gcgctgcttc      3660
cctgctgttt  tgtggaatat  ctaccgactg  gaaacaggca  aatgcaggaa  attactgaac      3720
tgaggggaca  ggcgagagac  gatgccaaag  agctcctgaa  aatctcgata  actcaaaaaa      3780
tacgcccggt  agtgatctta  tttcattatg  gtgaaagttg  gaacctctta  cgtgccgatc      3840
aacgtctcat  tttcgccaaa  agttggccca  gggcttccg  gtatcaacag  ggacaccagg      3900
atttatttat  tctgcgaagt  gatcttccgt  cacaggtatt  tattcggcgc  aaagtgcgtc      3960
gggtgatgct  gccaacttac  tgatttagtg  tatgatggtg  tttttgaggt  gctccagtgg      4020
cttctgtttc  tatcagctcc  tgaaaatctc  gataactcaa  aaaatacgcc  cggtagtgat      4080
cttatttcat  tatggtgaaa  gttggaacct  cttacgtgcc  gatcaacgtc  tcattttcgc      4140
caaaagttgg  cccagggctt  cccggtatca  acagggacac  caggatttat  ttattctgcg      4200
aagtgatctt  ccgtcacagg  tatttattcg  gcgcaaagtg  cgtcgggtga  tgctgccaac      4260
ttactgattt  agtgtatgat  ggtgtttttg  aggtgctcca  gtggcttctg  tttctatcag      4320
ggctggatga  tcctccagcg  cggggatctc  atgctggagt  tcttcgccca  ccccaaaagg      4380
atctaggtga  agatcctttt  tgataatctc  atgaccaaaa  tcccttaacg  tgagttttcg      4440
```

-continued

```
ttccactgag cgtcagaccc cgtagaaaag atcaaaggat cttcttgaga tccttttttt    4500
ctgcgcgtaa tctgctgctt gcaaacaaaa aaaccaccgc taccagcggt ggtttgtttg    4560
ccggatcaag agctaccaac tcttttttccg aaggtaactg gcttcagcag agcgcagata    4620
ccaaatactg ttcttctagt gtagccgtag ttaggccacc acttcaagaa ctctgtagca    4680
ccgcctacat acctcgctct gctaatcctg ttaccagtgg ctgctgccag tggcgataag    4740
tcgtgtctta ccgggttgga ctcaagacga tagttaccgg ataaggcgca gcggtcgggc    4800
tgaacggggg gttcgtgcac acagcccagc ttggagcgaa cgacctacac cgaactgaga    4860
tacctacagc gtgagctatg agaaagcgcc acgcttcccg aagggagaaa ggcggacagg    4920
tatccggtaa gcggcagggt cggaacagga gagcgcacga gggagcttcc aggggggaaac    4980 gcctggtatc tttatagtcc tgtcgggttt cgccacctct gacttgagcg tcgattttttg    5040 tgatgctcgt caggggggcg gagcctatgg aaaaacgcca gcaacgcggc cttttttacgg    5100 ttcctggcct tttgctggcc ttttgctcac atgttctttc ctgcgttatc ccctgattct    5160
gtggataacc gtattaccgc ctttgagtga gctgataccg ctcgccgcag ccgaacgacc    5220
gagcgcagcg agtcagtgag cgaggaagcg gaagagcgcc caatacgcaa accgcctctc    5280
cccgcgcgtt ggccgattca ttaatgcagc tggcacgaca ggtttcccga ctggaaagcg    5340
ggcagtgagc gcaacgcaat taatgtgagt tagctcactc attaggcacc ccaggcttta    5400
cactttatgc ttccggctcg tatgttgtgt ggaattgtga gcggataaca atttcacaca    5460
ggaaacagct atgacatgat tacgaattcg agctcggtac ccgggggatcc caaatccaga    5520 aaagctcata ctgctcccct aatcgatggc ttccccagca agggctttgg aggcgaggcg    5580
ttcttcctca ctgacttccc acacctcgtg agcggcgtgc agtgcgagca gaatgatgaa    5640
acaacctagg atcaaatctg gccatccaga cgtcgtccat gcggtaatta aggccatcat    5700
gatgatggca atgttgatca ggacgtcatt tcgggcggat aggaaggcag cttggccaag    5760
cgagccacca tgttgtcgca ctcgagaaat aatgatggca ctcgcgccgt tgatcacgac    5820
ggcgcccaga gaagcgacga tgatcggaaa cacttcgggc gcttgcggtg cggaaaaccg    5880
ttgaatcgct gcccacgcag caaaagcagc aggtgcaaga atcacaatcg ccataagttt    5940
gcccatcact gcgcgcctcg ccaacggcca tcctagggca atgaaaatga gcaggttgat    6000
ggaggtgtct tcaagaaaat cgacactgtc agccagtaga gaaacggagc ctgcgcttaa    6060
tgcaataaag aattctacaa agaaataagc gaagttaagc agcgcgacgg tgagcacagc    6120
tttgcgcact ttggttgcat caaaagcttc gctcatcagc tagcgccgct tctggcagtt    6180
tgggcagtag tgggagccgc ggttcatgaa actctcccgg atgattaatg ttccgcagcg    6240
tccgcacggc tccccggttt gcgcataagc attcaatgac agcgcaaagt agccggagtt    6300
gccattgacg ttgacataga gcgcgtcgaa agaggtgcca ccttgagcaa gtgctttggt    6360
catcacgtct ttgccagctt gaagaagttc ttccaagcga gctagggaca gtcgatcggc    6420
acgttgcaat gggtgaattt ttgcttgcca gagcatttca tcggcataga tatttccgat    6480 gccgagacg atctcttggt taagcaggag gcgtttgatc tccgatttcc gagatttcaa    6540
attccgcgca atcgcagaga aatcagcaga ctcatccaat acatctgtgg caatgtgaga    6600
gacgcgttcg ggtactccat caactaggtc gccgagccac caataaccga aggtgcgttg    6660
atcgacaaac cacacttcat cgccattatc tagctcgact ttggctcgaa ggtgtggact    6720
aattggtgca tctggttctt tgatgagcat ttgtccactc atcccaaggt gaaccagtag    6780
```

-continued

```
ccctaaatcg ggacgggttt cgccggaggg tgcgtcgata agctcaagcc agaggaattt      6840
gccgcgtcgc ttggcagcgc tgaccctaag ccctgcgatg ttggcctcga tttcggggcc      6900
accgccgagt tgattgcggg ctgcgcgcgg gtgaagcact gtggcggaca cgatggtgtg      6960
gccgaccata tgatcttcta aaccgcggcg caccacctca acttcaggca gtaggaactt      7020
ctccaaacca gcccagcgcg gatcgacctt ttcctcgtct tctacttctt cagagacacc      7080
gtcaggagct ggcgtttcat catcctggca tgcgccgtac ccaagttctt cgcagacagg      7140
gttaaacggc aaggtcagac cagcttcatc aatgacagac tgaagcagat caatctggtc      7200
ttggttaacc attggcagct catcttcgtc atctgctgca tcttcaccag taacaaagtc      7260
tggatcggca gcaaaaacct cagagacgtg cagcgtcttg gttggggtga gttcgcggag      7320
gcagcgggag cactgtccca gaagctgcgc ttcgatatct gcttcgacgg ccaggcctcc      7380
accgagtgga atgatctggg cttctacgat aactttttccg ccctcgggga tcgcgatcat      7440
ttccggacca atgcgggtcg ggcttggacc tgattgggtg aggtgttccg gaagggcact      7500
tccacgaagg agtgcggcga catcaaaaat aaatggagat ttcatgacca ggaagatcct      7560
actcgtacct catcgtgact acatacatca gatgaggatc gctagacgga aaggtgaaaa      7620
agcctaaatg gtttcttgga aactagtagt ctcgatcgtc gcgttcgtag cctcgttcat      7680
aatcacgctc gtagtcccgc tcatattcac cacgcgctgc cggttgctca tcgcgcagct      7740
cgcggccagt agctccagct cctcggcgta gtgcggaacg atcagcagtg acagaacgca      7800
acgtggtgga cagcgaggtt tcaaactctg ccaacttggt atccacgtag tcatcgcatt      7860
cattgcgcag cttgttggag tcagcgtgcg ctgcatccac aatgcggtgt gcttcttccg      7920
tggagcgacg caccacttct gcctcgctga ccaggcgatc ctgctcggcc tggccttcag      7980
caaccgcgcg gcgatacgca tcattgccgg agttgaccag gcgctcagat tcagcctggg      8040
cgcgctcggt gacgctgttt gcttctcgac gagcgtcact cacgatgcga tccgctgtgt      8100
cattagcctt agcaacgaca gaatgcgcat gcttgggtcg acctgcaggc atgcaagctt      8160
ggcactggcc gtcgttttac aacgtcgtga ctgggaaaac cctggcgtta cccaacttaa      8220
tcgccttgca gcacatcccc ctttcgccag ctggcgtaat agcgaagagg cccgcaccga      8280
tcgcccttcc caacagttgc gcagcctgaa tggcgaatgg cgataagcta gcttcacgc       8339
```

```
<210> SEQ ID NO 30
<211> LENGTH: 3343
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (1)..(301)
<223> OTHER INFORMATION: pCG1 origin of replication
<220> FEATURE:
<221> NAME/KEY: gene
<222> LOCATION: (2269)..(3063)
<223> OTHER INFORMATION: kanamycin resistance gene

<400> SEQUENCE: 30
ccatggtcgt cacagagctg gaagcggcag cgagaattat ccgcgatcgt ggcgcggtgc       60
ccgcaggcat gacaaacatc gtaaatgccg cgtttcgtgt ggccgtggcc gcccaggacg      120
tgtcagcgcc gccaccacct gcaccgaatc ggcagcagcg tcgcgcgtcg aaaaagcgca      180
caggcggcaa gaagcgataa gctgcacgaa tacctgaaaa atgttgaacg ccccgtgagc      240
ggtaactcac agggcgtcgg ctaaccccca gtccaaacct gggagaaagc gctcaaaaat      300
```

-continued

```
gactctagcg gattcacgag acattgacac accggcctgg aaattttccg ctgatctgtt      360
cgacacccat cccgagctcg cgctgcgatc acgtggctgg acgagcgaag accgccgcga      420
attcctcgct cacctgggca gagaaaattt ccagggcagc aagacccgcg acttcgccag      480
cgcttggatc aaagacccgg acacgggaga aacacagccg aagttatacc gagttggttc      540
aaaatcgctt gcccggtgcc agtatgttgc tctgacgcac gcgcagcacg cagccgtgct      600
tgtcctggac attgatgtgc cgagccacca ggccggcggg aaaatcgagc acgtaaaccc      660
cgaggtctac gcgattttgg agcgctgggc acgcctggaa aaagcgccag cttggatcgg      720
cgtgaatcca ctgagcggga aatgccagct catctggctc attgatccgg tgtatgccgc      780
agcaggcatg agcagcccga atatgcgcct gctggctgca acgaccgagg aaatgacccg      840
cgttttcggc gctgaccagg ctttttcaca taggctgagc cggtggccac tgcacgtctc      900
cgacgatccc accgcgtacc gctggcatgc ccagcacaat cgcgtggatc gcctagctga      960
tcttatggag gttgctcgca tgatctcagg cacagaaaaa cctaaaaaac gctatgagca     1020 ggagtttttct agcggacggg cacgtatcga agcggcaaga aaagccactg cggaagcaaa     1080
agcacttgcc acgcttgaag caagcctgcc gagcgccgct gaagcgtctg agagctgat      1140 cgacggcgtc cgtgtcctct ggactgctcc agggcgtgcc gcccgtgatg agacggcttt     1200
tcgccacgct ttgactgtgg gataccagtt aaaagcggct ggtgagcgcc taaaagacac     1260
caagatcatc gacgcctacg agcgtgccta caccgtcgct caggcggtcg gagcagacgg     1320
ccgtgagcct gatctgccgc cgatgcgtga ccgccagacg atggcgcgac gtgtgcgcgg     1380
ctacgtcgct aaaggccagc cagtcgtccc tgctcgtcag acagagacgc agagcagccg     1440
agggcgaaaa gctctggcca ctatgggaag acgtggcggt aaaaaggccg cagaacgctg     1500
gaaagaccca aacagtgagt acgcccgagc acagcgagaa aaactagcta agtccagtca     1560
acgacaagct aggaaagcta aaggaaatcg cttgaccatt gcaggttggt ttatgactgt     1620
tgagggagag actggctcgt ggcgacaatc aatgaagcta tgtctgaatt tagcgtgtca     1680
cgtcagaccg tgaatagagc acttaagtct gcgggcattg aacttccacg aggacgccgt     1740
aaagcttccc agtaaatgtg ccatctcgta ggcagaaaac ggttcccccc gtaggggtct     1800
ctctcttggc ctcctttcta ggtcgggctg attgctcttg aagctctcta gggggggctca    1860 caccataggc agataacggt tccccaccgg ctcacctcgt aagcgcacaa ggactgctcc     1920
caatgccgca agcactcagg cgcaagggc tgctaaagga agcggaacac gtagaaagcc     1980
agtccgcaga aacggtgctg accccggatg aatgtcagct actgggctat ctggacaagg     2040
gaaaacgcaa gcgcaaagag aaagcaggta gcttgcagtg ggcttacatg gcgatagcta     2100
gactgggcgg ttttatggac agcaagcgaa ccggaattgc cagctggggc gccctctggt     2160
aaggttggga agccctgcaa agtaaactgg atggctttct tgccgccaag gatctgatgg     2220
cgcaggggat caagatctga tcaagagaca ggatgaggat cgtttcgcat gattgaacaa     2280
gatggattgc acgcaggttc tccggccgct tgggtggaga ggctattcgg ctatgactgg     2340
gcacaacaga caatcggctg ctctgatgcc gccgtgttcc ggctgtcagc gcaggggcgc     2400
ccggttcttt ttgtcaagac cgacctgtcc ggtgccctga tgaactcca agacgaggca     2460 gcgcggctat cgtggctggc cacgacgggc gttccttgcg cagctgtgct cgacgttgtc     2520
actgaagcgg gaagggactg gctgctattg ggcgaagtgc cggggcagga tctcctgtca     2580
tctcaccttg ctcctgccga gaaagtatcc atcatggctg atgcaatgcg gcggctgcat     2640
```

```
acgcttgatc cggctacctg cccattcgac caccaagcga aacatcgcat cgagcgagca      2700
cgtactcgga tggaagccgg tcttgtcgat caggatgatc tggacgaaga gcatcagggg      2760
ctcgcgccag ccgaactgtt cgccaggctc aaggcgcgga tgcccgacgg cgaggatctc      2820
gtcgtgaccc atggcgatgc ctgcttgccg aatatcatgg tggaaaatgg ccgcttttct      2880
ggattcatcg actgtggccg gctgggtgtg gcggaccgct atcaggacat agcgttggct      2940
acccgtgata ttgctgaaga gcttggcggc gaatgggctg accgcttcct cgtgctttac      3000
ggtatcgccg ctcccgattc gcagcgcatc gccttctatc gccttcttga cgagttcttc      3060
tgagcgggac tctggggttc gctagaggat cgatcctttt taacccatca catatacctg      3120
ccgttcacta ttatttagtg aaatgagata ttatgatatt ttctgaattg tgattaaaaa      3180
ggcaacttta tgcccatgca acagaaacta taaaaaatac agagaatgaa aagaaacaga      3240
tagatttttt agttctttag gcccgtagtc tgcaaatcct tttatgattt tctatcaaac      3300
aaaagaggaa aatagaccag ttgcaatcca aacgagagtc taa                        3343
```

<210> SEQ ID NO 31
<211> LENGTH: 8710
<212> TYPE: DNA
<213> ORGANISM: Artificial Sequence
<220> FEATURE:
<223> OTHER INFORMATION: Recombinant plasmid pAPSE10430; beta actin
      hairpin + coat protein
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: promoter
<222> LOCATION: (985)..(1003)
<223> OTHER INFORMATION: bacteriophage T7 gene 1 promoter
<220> FEATURE:
<221> NAME/KEY: gene
<222> LOCATION: (1076)..(1465)
<223> OTHER INFORMATION: bacteriophage MS2 coat protein gene
<220> FEATURE:
<221> NAME/KEY: terminator
<222> LOCATION: (1498)..(1545)
<223> OTHER INFORMATION: bacteriophage T7 transcription terminator
<220> FEATURE:
<221> NAME/KEY: misc_feature
<222> LOCATION: (1981)..(5324)
<223> OTHER INFORMATION: synthetic DNA (SEQ ID NO: 30)

<400> SEQUENCE: 31

```
ttcttagctc cggcaagcaa ttaagaactt ccgaaattaa tacgactcac tatagggagg        60
cgatcgcgca cgaggttttt ctgtctagtg agcagtgtcc aacctcaaaa gacaacatgt       120
```

-continued

```
gtgacgacga tgtagcggct cttgtcgtag acaatggatc cggtatgtgc aaagccggtt      180
tcgcaggaga tgacgcaccc cgtgccgtct tcccctcgat cgtcggtcgc ccaaggcatc      240
aaggagtcat ggtcggtatg ggacaaaagg actcatacgt aggagatgaa gcccaaagca      300
aaagaggtat cctcaccctg aaatacccca tcgaacacgg tatcatcacc aactgggatg      360
agtttaaacc ctctagctgc tttacaaagt actggttccc tttccagcgg gatgctttat      420
ctaaacgcaa tgagagaggt attcctcagg ccacatcgct tcctagttcc gctgggatcc      480
atcgttggcg gccgaagccg ccattccata gtgagttctg gcgcgcctca tcccagttgg      540
tgatgatacc gtgttcgatg gggtatttca gggtgaggat acctcttttg ctttgggctt      600
catctcctac gtatgagtcc ttttgtccca taccgaccat gactccttga tgccttgggc      660
gaccgacgat cgaggggaag acggcacggg gtgcgtcatc tcctgcgaaa ccggctttgc      720
acataccgga tccattgtct acgacaagag ccgctacatc gtcgtcacac atgttgtctt      780
ttgaggttgg acactgctca ctagacagaa aaacctcgtg ccggaccgaa tacccggtct      840
gaacgaggtt aattaaggta cccaagaagt acttagaggc ggccgcctag cataaccct      900 tggggcctct aaacgggtct tgaggggttt tttgagaaac ggccgaatac acctgttcgg      960
atccagatct cgatcccgcg aaattaatac gactcactat agggagacca caacggtttc     1020
cctctagatc acaagtttgt acaaaaaagc aggctaagaa ggagatatac atatggcgtc     1080
taactttacc caattcgttc tggttgataa cggcggtacg ggtgacgtta ccgtagctcc     1140
gtccaacttc gccaacggtg ttgcggaatg gattagctct aacagccgct ctcaggccta     1200
caaagtcacg tgctccgttc gtcagtctag cgcgcagaat cgcaaataca ccatcaaagt     1260
tgaagtaccg aaagtcgcaa cgcagaccgt aggcggcgta gaactcccag ttgcggcctg     1320
gcgctcttac ctcaacatgg aactgactat tccgattttt gcgacgaact ccgactgcga     1380
actgattgtt aaggcaatgc agggcctgct gaaagacggt aatccgatcc catctgcaat     1440
cgctgctaac tctggcattt actaataagc ggacgcgctg ccaccgctga gcaataacta     1500
gcataacccc ttggggcctc taaacgggtc ttgaggggtt ttttgctgaa aggaggaact     1560
atatccggca tgcaccattc cttgcggcgg cggtgctcaa cggcctcaac ctactactgg     1620
gctgcttcct aatgcaggag tcgcataagg agagcgtcg accgatgccc ttgagagcct     1680
tcaacccagt cagctccttc cggtgggcgc ggggcatgac tatcgtcgcc gcacttatga     1740
ctgtcttctt tatcatgcaa ctcgtaggac aggtgccggc agcgctctgg gtcattttcg     1800
gcgaggaccg ctttcgctgg agcgcgacga tgatcggcct gtcgcttgcg gtattcggaa     1860
tcttgcacgc cctcgctcaa gccttcgtca ctggtcccgc caccaaacgt ttcggcgaga     1920
agcaggccat tatcgccggc atggcggccg acgcgctggg ctacgtcttg ctggcgttcg     1980
ccatggtcgt cacagagctg gaagcggcag cgagaattat ccgcgatcgt ggcgcggtgc     2040
ccgcaggcat gacaaacatc gtaaatgccg cgtttcgtgt ggccgtggcc gcccaggacg     2100
tgtcagcgcc gccaccacct gcaccgaatc ggcagcagc tcgcgcgtcg aaaaagcgca     2160
caggcggcaa gaagcgataa gctgcacgaa tacctgaaaa atgttgaacg ccccgtgagc     2220
ggtaactcac agggcgtcgg ctaacccccca gtccaaacct gggagaaagc gctcaaaaat     2280
gactctagcg gattcacgag acattgacac accggcctgg aaattttccg ctgatctgtt     2340
cgacacccat cccgagctcg cgctgcgatc acgtggctgg acgagcgaag accgccgcga     2400
attcctcgct cacctgggca gagaaaattt ccagggcagc aagacccgcg acttcgccag     2460
cgcttggatc aaagacccgg acacgggaga aacacagccg aagttatacc gagttggttc     2520
```

-continued

```
aaaatcgctt gcccggtgcc agtatgttgc tctgacgcac gcgcagcacg cagccgtgct    2580
tgtcctggac attgatgtgc cgagccacca ggccggcggg aaaatcgagc acgtaaaccc    2640
cgaggtctac gcgattttgg agcgctgggc acgcctggaa aaagcgccag cttggatcgg    2700
cgtgaatcca ctgagcggga aatgccagct catctggctc attgatccgg tgtatgccgc    2760
agcaggcatg agcagcccga atatgcgcct gctggctgca acgaccgagg aaatgacccg    2820
cgttttcggc gctgaccagg ctttttcaca taggctgagc cggtggccac tgcacgtctc    2880
cgacgatccc accgcgtacc gctggcatgc ccagcacaat cgcgtggatc gcctagctga    2940
tcttatggag gttgctcgca tgatctcagg cacagaaaaa cctaaaaaac gctatgagca    3000
ggagttttct agcggacggg cacgtatcga agcggcaaga aaagccactg cggaagcaaa    3060
agcacttgcc acgcttgaag caagcctgcc gagcgccgct gaagcgtctg gagagctgat    3120
cgacggcgtc cgtgtcctct ggactgctcc agggcgtgcc gcccgtgatg agacggcttt    3180
tcgccacgct ttgactgtgg gataccagtt aaaagcggct ggtgagcgcc taaaagacac    3240
caagatcatc gacgcctacg agcgtgccta caccgtcgct caggcggtcg gagcagacgg    3300
ccgtgagcct gatctgccgc cgatgcgtga ccgccagacg atggcgcgac gtgtgcgcgg    3360
ctacgtcgct aaaggccagc cagtcgtccc tgctcgtcag acagagacgc agagcagccg    3420
agggcgaaaa gctctggcca ctatgggaag acgtggcggt aaaaaggccg cagaacgctg    3480
gaaagaccca aacagtgagt acgcccgagc acagcgagaa aaactagcta agtccagtca    3540
acgacaagct aggaaagcta aaggaaatcg cttgaccatt gcaggttggt ttatgactgt    3600
tgagggagag actggctcgt ggcgacaatc aatgaagcta tgtctgaatt tagcgtgtca    3660
cgtcagaccg tgaatagagc acttaagtct gcgggcattg aacttccacg aggacgccgt    3720
aaagcttccc agtaaatgtg ccatctcgta ggcagaaaac ggttcccccc gtaggggtct    3780
ctctcttggc ctcctttcta ggtcgggctg attgctcttg aagctctcta gggggggctca   3840 caccataggc agataacggt tccccaccgg ctcacctcgt aagcgcacaa ggactgctcc    3900
caatgccgca agcactcagg gcgcaagggc tgctaaagga agcggaacac gtagaaagcc    3960
agtccgcaga aacggtgctg accccggatg aatgtcagct actgggctat ctggacaagg    4020
gaaaacgcaa gcgcaaagag aaagcaggta gcttgcagtg ggcttacatg gcgatagcta    4080
gactgggcgg ttttatggac agcaagcgaa ccggaattgc cagctggggc gccctctggt    4140
aaggttggga agccctgcaa agtaaactgg atggctttct tgccgccaag gatctgatgg    4200
cgcaggggat caagatctga tcaagagaca ggatgaggat cgtttcgcat gattgaacaa    4260
gatggattgc acgcaggttc tccggccgct tgggtggaga ggctattcgg ctatgactgg    4320
gcacaacaga caatcggctg ctctgatgcc gccgtgttcc ggctgtcagc gcaggggcgc    4380
ccggttcttt ttgtcaagac cgacctgtcc ggtgccctga tgaactccca agacgaggca    4440
gcgcggctat cgtggctggc cacgacgggc gttccttgcg cagctgtgct cgacgttgtc    4500
actgaagcgg gaagggactg gctgctattg ggcgaagtgc cggggcagga tctcctgtca    4560
tctcaccttg ctcctgccga gaaagtatcc atcatggctg atgcaatgcg gcggctgcat    4620
acgcttgatc cggctacctg cccattcgac caccaagcga aacatcgcat cgagcgagca    4680
cgtactcgga tggaagccgg tcttgtcgat caggatgatc tggacgaaga gcatcagggg    4740
ctcgcgccag ccgaactgtt cgccaggctc aaggcgcgga tgcccgacgg cgaggatctc    4800
gtcgtgaccc atggcgatgc ctgcttgccg aatatcatgg tggaaaatgg ccgcttttct    4860
```

-continued

```
ggattcatcg actgtggccg gctgggtgtg gcggaccgct atcaggacat agcgttggct     4920
acccgtgata ttgctgaaga gcttggcggc gaatgggctg accgcttcct cgtgctttac     4980
ggtatcgccg ctcccgattc gcagcgcatc gccttctatc gccttcttga cgagttcttc     5040
tgagcgggac tctgggggttc gctagaggat cgatcctttt taacccatca catatacctg     5100
ccgttcacta ttatttagtg aaatgagata ttatgatatt ttctgaattg tgattaaaaa     5160
ggcaacttta tgcccatgca acagaaacta taaaaaatac agagaatgaa aagaaacaga     5220 tagattttt agttctttag gcccgtagtc tgcaaatcct tttatgattt tctatcaaac      5280
aaaagaggaa aatagaccag ttgcaatcca aacgagagtc taacgacgcg aggctggatg     5340
gccttcccca ttatgattct tctcgcttcc ggcggcatcg ggatgcccgc gttgcaggcc     5400
atgctgtcca ggcaggtaga tgacgaccat cagggacagc ttcaaggatc gctcgcggct     5460
cttaccagcc taacttcgat cattggaccg ctgatcgtca cggcgattta tgccgcctcg     5520
gcgagcacat ggaacgggtt ggcatggatt gtaggcgccg ccctatacct tgtctgcctc     5580
cccgcgttgc gtcgcggtgc atggagccgg gccacctcga cctgaatgga agccggcggc     5640
acctcgctaa cggattcacc actccaagaa ttggagccaa tcaattcttg cggagaactg     5700
tgaatgcgca aaccaaccct tggcagaaca tatccatcgc gtccgccatc tccagcagcc     5760
gcacgcggcg catctcgggc agcgttgggt cctggccacg ggtgcgcatg atcgtgctcc     5820
tgtcgttgag gacccggcta ggctggcggg gttgccttac tggttagcag aatgaatcac     5880
cgatacgcga gcgaacgtga agcgactgct gctgcaaaac gtctgcgacc tgagcaacaa     5940
catgaatggt cttcggtttc cgtgtttcgt aaagtctgga aacgcggaag tcagcgccct     6000
gcaccattat gttccggatc tgcatcgcag gatgctgctg gctaccctgt ggaacaccta     6060
catctgtatt aacgaagcgc tggcattgac cctgagtgat ttttctctgg tcccgccgca     6120
tccataccgc cagttgttta ccctcacaac gttccagtaa ccgggcatgt tcatcatcag     6180
taacccgtat cgtgagcatc ctctctcgtt tcatcggtat cattacccce atgaacagaa     6240 atcccccctta cacggaggca tcagtgacca aacaggaaaa aaccgccctt aacatggccc     6300
gctttatcag aagccagaca ttaacgcttc tggagaaact caacgagctg gacgcggatg     6360
aacaggcaga catctgtgaa tcgcttcacg accacgctga tgagctttac cgcagctgcc     6420
tcgcgcgttt cggtgatgac ggtgaaaacc tctgacacat gcagctcccg gagacggtca     6480
cagcttgtct gtaagcggat gccgggagca gacaagcccg tcagggcgcg tcagcgggtg     6540
ttggcgggtg tcggggcgca gccatgaccc agtcacgtag cgatagcgga gtgtatactg     6600
gcttaactat gcggcatcag agcagattgt actgagagtg caccatatgc ggtgtgaaat     6660
accgcacaga tgcgtaagga gaaaataccg catcaggcgc tcttccgctt cctcgctcac     6720
tgactcgctg cgctcggtcg ttcggctgcg gcgagcggta tcagctcact caaaggcggt     6780
aatacggtta tccacagaat caggggataa cgcaggaaag aacatgtgag caaaaggcca     6840
gcaaaaggcc aggaaccgta aaaaggccgc gttgctggcg tttttccata ggctccgccc     6900
ccctgacgag catcacaaaa atcgacgctc aagtcagagg tggcgaaacc cgacaggact     6960
ataaagatac caggcgtttc cccctggaag ctccctcgtg cgctctcctg ttccgaccct     7020
gccgcttacc ggatacctgt ccgcctttct cccttcggga agcgtggcgc tttctcatag     7080
ctcacgctgt aggtatctca gttcggtgta ggtcgttcgc tccaagctgg gctgtgtgca     7140 cgaaccccce gttcagcccg accgctgcgc cttatccggt aactatcgtc ttgagtccaa     7200
cccggtaaga cacgacttat cgccactggc agcagccact ggtaacagga ttagcagagc     7260
```

-continued

```
gaggtatgta ggcggtgcta cagagttctt gaagtggtgg cctaactacg gctacactag    7320
aaggacagta tttggtatct gcgctctgct gaagccagtt accttcggaa aaagagttgg    7380
tagctcttga tccggcaaac aaaccaccgc tggtagcggt ggtttttttg tttgcaagca    7440
gcagattacg cgcagaaaaa aaggatctca agaagatcct ttgatctttt ctacggggtc    7500
tgacgctcag tggaacgaaa actcacgtta agggattttg gtcatgagat tatcaaaaag    7560
gatcttcacc tagatccttt taaattaaaa atgaagtttt aaatcaatct aaagtatata    7620
tgagtaaact tggtctgaca gttaccaatg cttaatcagt gaggcaccta tctcagcgat    7680
ctgtctattt cgttcatcca tagttgcctg actccccgtc gtgtagataa ctacgatacg    7740
ggagggctta ccatctggcc ccagtgctgc aatgataccg cgagacccac gctcaccggc    7800
tccagattta tcagcaataa accagccagc cggaagggcc gagcgcagaa gtggtcctgc    7860
aactttatcc gcctccatcc agtctattaa ttgttgccgg gaagctagag taagtagttc    7920
gccagttaat agtttgcgca acgttgttgc cattgctgca ggcatcgtgg tgtcacgctc    7980
gtcgtttggt atggcttcat tcagctccgg ttcccaacga tcaaggcgag ttacatgatc    8040
ccccatgttg tgcaaaaaag cggttagctc cttcggtcct ccgatcgttg tcagaagtaa    8100
gttggccgca gtgttatcac tcatggttat ggcagcactg cataattctc ttactgtcat    8160
gccatccgta agatgctttt ctgtgactgg tgagtactca accaagtcat tctgagaata    8220
gtgtatgcgg cgaccgagtt gctcttgccc ggcgtcaaca cgggataata ccgcgccaca    8280
tagcagaact ttaaaagtgc tcatcattgg aaaacgttct tcggggcgaa aactctcaag    8340
gatcttaccg ctgttgagat ccagttcgat gtaacccact cgtgcaccca actgatcttc    8400
agcatctttt actttcacca gcgtttctgg gtgagcaaaa acaggaaggc aaaatgccgc    8460
aaaaaaggga ataagggcga cacggaaatg ttgaatactc atactcttcc tttttcaata    8520
ttattgaagc atttatcagg gttattgtct catgagcgga tacatatttg aatgtattta    8580
gaaaaataaa caaatagggg ttccgcgcac atttccccga aaagtgccac ctgacgtcta    8640
agaaaccatt attatcatga cattaaccta taaaaatagg cgtatcacga ggccctttcg    8700
tcttcaagaa                                                            8710
```

<210> SEQ ID NO 32
<211> LENGTH: 8107
<212> TYPE: DNA
<213> ORGANISM: Artificial Sequence
<220> FEATURE:
<223> OTHER INFORMATION: Recombinant plasmid pAPSE10431; beta actin stem
      loop - coat protein
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: misc_feature
<222> LOCATION: (1378)..(4721)
<223> OTHER INFORMATION: synthetic DNA (SEQ ID NO: 30)

<400> SEQUENCE: 32

```
ttcttagctc cggcaagcaa ttaagaactt ccgaaattaa tacgactcac tatagggagg      60
cgatcgcgca cgaggttttt ctgtctagtg agcagtgtcc aacctcaaaa gacaacatgt     120
gtgacgacga tgtagcggct cttgtcgtag acaatggatc cggtatgtgc aaagccggtt     180
tcgcaggaga tgacgcaccc cgtgccgtct tcccctcgat cgtcggtcgc ccaaggcatc     240
aaggagtcat ggtcggtatg ggacaaaagg actcatacgt aggagatgaa gcccaaagca     300
aaagaggtat cctcaccctg aaataccca tcgaacacgg tatcatcacc aactgggatg     360
agtttaaacc ctctagctgc tttacaaagt actggttccc tttccagcgg gatgctttat     420
ctaaacgcaa tgagagaggt attcctcagg ccacatcgct tcctagttcc gctgggatcc     480
atcgttggcg gccgaagccg ccattccata gtgagttctg gcgcgcctca tcccagttgg     540
tgatgatacc gtgttcgatg gggtatttca gggtgaggat acctcttttg ctttgggctt     600
catctcctac gtatgagtcc ttttgtccca taccgaccat gactccttga tgccttgggc     660
gaccgacgat cgaggggaag acggcacggg gtgcgtcatc tcctgcgaaa ccggctttgc     720
acataccgga tccattgtct acgacaagag ccgctacatc gtcgtcacac atgttgtctt     780
ttgaggttgg acactgctca ctagacagaa aaacctcgtg ccggaccgaa tacccggtct     840
gaacgaggtt aattaaggta cccaagaagt acttagaggc ggccgcctag cataacccct     900
tggggcctct aaacgggtct tgaggggttt tttgagaaac ggccgaatac acctgttcgg     960
atccagatcc accattcctt gcggcggcgg tgctcaacgg cctcaaccta ctactgggct    1020
gcttcctaat gcaggagtcg cataagggag agcgtcgacc gatgcccttg agagccttca    1080
acccagtcag ctccttccgg tgggcgcggg gcatgactat cgtcgccgca cttatgactg    1140
tcttctttat catgcaactc gtaggacagg tgccggcagc gctctgggtc attttcggcg    1200
aggaccgctt tcgctggagc gcgacgatga tcggcctgtc gcttgcggta ttcggaatct    1260
tgcacgccct cgctcaagcc ttcgtcactg gtcccgccac caaacgtttc ggcgagaagc    1320
aggccattat cgccggcatg gcggccgacg cgctgggcta cgtcttgctg gcgttcgcca    1380
tggtcgtcac agagctggaa gcggcagcga gaattatccg cgatcgtggc gcggtgcccg    1440
caggcatgac aaacatcgta aatgccgcgt tcgtgtggc cgtggccgcc caggacgtgt     1500
cagcgccgcc accacctgca ccgaatcggc agcagcgtcg cgcgtcgaaa aagcgcacag    1560
gcggcaagaa gcgataagct gcacgaatac ctgaaaaatg ttgaacgccc cgtgagcggt    1620
aactcacagg gcgtcggcta accccagtc caaacctggg agaaagcgct caaaaatgac    1680
tctagcggat tcacgagaca ttgacacacc ggcctggaaa ttttccgctg atctgttcga    1740
cacccatccc gagctcgcgc tgcgatcacg tggctggacg agcgaagacc gccgcgaatt    1800
cctcgctcac ctgggcagag aaaatttcca gggcagcaag acccgcgact cgccagcgc     1860 ttggatcaaa gacccggaca cgggagaaac acagccgaag ttataccgag ttggttcaaa    1920
atcgcttgcc cggtgccagt atgttgctct gacgcacgcg cagcacgcag ccgtgcttgt    1980
cctggacatt gatgtgccga gccaccaggc cggcgggaaa atcgagcacg taaaccccga    2040
```

```
ggtctacgcg attttggagc gctgggcacg cctggaaaaa gcgccagctt ggatcggcgt   2100
gaatccactg agcgggaaat gccagctcat ctggctcatt gatccggtgt atgccgcagc   2160
aggcatgagc agcccgaata tgcgcctgct ggctgcaacg accgaggaaa tgacccgcgt   2220
tttcggcgct gaccaggctt tttcacatag gctgagccgg tggccactgc acgtctccga   2280
cgatcccacc gcgtaccgct ggcatgccca gcacaatcgc gtggatcgcc tagctgatct   2340
tatggaggtt gctcgcatga tctcaggcac agaaaaacct aaaaaacgct atgagcagga   2400
gttttctagc ggacgggcac gtatcgaagc ggcaagaaaa gccactgcgg aagcaaaagc   2460
acttgccacg cttgaagcaa gcctgccgag cgccgctgaa gcgtctggag agctgatcga   2520
cggcgtccgt gtcctctgga ctgctccagg gcgtgccgcc cgtgatgaga cggcttttcg   2580
ccacgctttg actgtgggat accagttaaa agcggctggt gagcgcctaa aagacaccaa   2640
gatcatcgac gcctacgagc gtgcctacac cgtcgctcag gcggtcggag cagacggccg   2700
tgagcctgat ctgccgccga tgcgtgaccg ccagacgatg gcgcgacgtg tgcgcggcta   2760
cgtcgctaaa ggccagccag tcgtccctgc tcgtcagaca gagacgcaga gcagccgagg   2820
gcgaaaagct ctggccacta tgggaagacg tggcggtaaa aaggccgcag aacgctggaa   2880
agacccaaac agtgagtacg cccgagcaca gcgagaaaaa ctagctaagt ccagtcaacg   2940
acaagctagg aaagctaaag gaaatcgctt gaccattgca ggttggttta tgactgttga   3000
gggagagact ggctcgtggc gacaatcaat gaagctatgt ctgaatttag cgtgtcacgt   3060
cagaccgtga atagagcact taagtctgcg ggcattgaac ttccacgagg acgccgtaaa   3120
gcttcccagt aaatgtgcca tctcgtaggc agaaaacggt tcccccgta ggggtctctc      3180 tcttggcctc ctttctaggt cgggctgatt gctcttgaag ctctctaggg gggctcacac   3240
cataggcaga taacggttcc ccaccggctc acctcgtaag cgcacaagga ctgctcccaa   3300
tgccgcaagc actcagggcg caagggctgc taaaggaagc ggaacacgta gaaagccagt   3360
ccgcagaaac ggtgctgacc ccggatgaat gtcagctact gggctatctg gacaagggaa   3420
aacgcaagcg caaagagaaa gcaggtagct tgcagtgggc ttacatggcg atagctagac   3480
tgggcggttt tatggacagc aagcgaaccg gaattgccag ctggggcgcc ctctggtaag   3540
gttgggaagc cctgcaaagt aaactggatg gctttcttgc cgccaaggat ctgatggcgc   3600
aggggatcaa gatctgatca agagacagga tgaggatcgt ttcgcatgat tgaacaagat   3660
ggattgcacg caggttctcc ggccgcttgg gtggagaggc tattcggcta tgactgggca   3720
caacagacaa tcggctgctc tgatgccgcc gtgttccggc tgtcagcgca ggggcgcccg   3780
gttctttttg tcaagaccga cctgtccggt gccctgaatg aactccaaga cgaggcagcg   3840
cggctatcgt ggctggccac gacgggcgtt ccttgcgcag ctgtgctcga cgttgtcact   3900
gaagcgggaa gggactggct gctattgggc gaagtgccgg gcaggatct cctgtcatct     3960 caccttgctc ctgccgagaa agtatccatc atggctgatg caatgcggcg gctgcatacg   4020
cttgatccgg ctacctgccc attcgaccac caagcgaaac atcgcatcga gcgagcacgt   4080
actcggatgg aagccggtct tgtcgatcag gatgatctgg acgaagagca tcaggggctc   4140
gcgccagccg aactgttcgc caggctcaag gcgcggatgc ccgacggcga ggatctcgtc   4200
gtgacccatg gcgatgcctg cttgccgaat atcatggtgg aaaatggccg cttttctgga   4260
ttcatcgact gtggccggct gggtgtggcg gaccgctatc aggacatagc gttggctacc   4320
cgtgatattg ctgaagagct tggcggcgaa tgggctgacc gcttcctcgt gctttacggt   4380
atcgccgctc ccgattcgca gcgcatcgcc ttctatcgcc ttcttgacga gttcttctga   4440
```

-continued

```
gcgggactct ggggttcgct agaggatcga tcctttttaa cccatcacat atacctgccg    4500
ttcactatta tttagtgaaa tgagatatta tgatattttc tgaattgtga ttaaaaaggc    4560
aactttatgc ccatgcaaca gaaactataa aaaatacaga gaatgaaaag aaacagatag    4620 atttttagt tctttaggcc cgtagtctgc aaatcctttt atgattttct atcaaacaaa     4680
agaggaaaat agaccagttg caatccaaac gagagtctaa cgacgcgagg ctggatggcc    4740
ttccccatta tgattcttct cgcttccggc ggcatcggga tgcccgcgtt gcaggccatg    4800
ctgtccaggc aggtagatga cgaccatcag ggacagcttc aaggatcgct cgcggctctt    4860
accagcctaa cttcgatcat tggaccgctg atcgtcacgg cgatttatgc cgcctcggcg    4920
agcacatgga acgggttggc atggattgta ggcgccgccc tataccttgt ctgcctcccc    4980
gcgttgcgtc gcggtgcatg gagccgggcc acctcgacct gaatggaagc cggcggcacc    5040
tcgctaacgg attcaccact ccaagaattg gagccaatca attcttgcgg agaactgtga    5100
atgcgcaaac caacccttgg cagaacatat ccatcgcgtc cgccatctcc agcagccgca    5160
cgcggcgcat ctcgggcagc gttgggtcct ggccacgggt gcgcatgatc gtgctcctgt    5220
cgttgaggac ccggctaggc tggcggggtt gccttactgg ttagcagaat gaatcaccga    5280
tacgcgagcg aacgtgaagc gactgctgct gcaaaacgtc tgcgacctga gcaacaacat    5340
gaatggtctt cggtttccgt gtttcgtaaa gtctggaaac gcggaagtca gcgccctgca    5400
ccattatgtt ccggatctgc atcgcaggat gctgctggct accctgtgga acacctacat    5460
ctgtattaac gaagcgctgg cattgaccct gagtgatttt tctctggtcc cgccgcatcc    5520
ataccgccag ttgtttaccc tcacaacgtt ccagtaaccg ggcatgttca tcatcagtaa    5580
cccgtatcgt gagcatcctc tctcgtttca tcggtatcat taccccatg aacagaaatc     5640 cccttacac ggaggcatca gtgaccaaac aggaaaaaac cgcccttaac atggcccgct     5700
ttatcagaag ccagacatta acgcttctgg agaaactcaa cgagctggac gcggatgaac    5760
aggcagacat ctgtgaatcg cttcacgacc acgctgatga gctttaccgc agctgcctcg    5820
cgcgtttcgg tgatgacggt gaaaacctct gacacatgca gctcccggag acggtcacag    5880
cttgtctgta agcggatgcc gggagcagac aagcccgtca gggcgcgtca gcgggtgttg    5940
gcgggtgtcg gggcgcagcc atgacccagt cacgtagcga tagcggagtg tatactggct    6000
taactatgcg gcatcagagc agattgtact gagagtgcac catatgcggt gtgaaatacc    6060
gcacagatgc gtaaggagaa aataccgcat caggcgctct tccgcttcct cgctcactga    6120
ctcgctgcgc tcggtcgttc ggctgcggcg agcggtatca gctcactcaa aggcggtaat    6180
acggttatcc acagaatcag gggataacgc aggaaagaac atgtgagcaa aaggccagca    6240
aaaggccagg aaccgtaaaa aggccgcgtt gctggcgttt ttccataggc tccgcccccc    6300
tgacgagcat cacaaaaatc gacgctcaag tcagaggtgg cgaaacccga caggactata    6360
aagataccag gcgtttcccc ctggaagctc cctcgtgcgc tctcctgttc cgaccctgcc    6420
gcttaccgga tacctgtccg cctttctccc ttcgggaagc gtggcgcttt ctcatagctc    6480
acgctgtagg tatctcagtt cggtgtaggt cgttcgctcc aagctgggct gtgtgcacga    6540
accccccgtt cagcccgacc gctgcgcctt atccggtaac tatcgtcttg agtccaaccc    6600
ggtaagacac gacttatcgc cactggcagc agccactggt aacaggatta gcagagcgag    6660
gtatgtaggc ggtgctacag agttcttgaa gtggtggcct aactacggct acactagaag    6720
gacagtattt ggtatctgcg ctctgctgaa gccagttacc ttcggaaaaa gagttggtag    6780
```

```
ctcttgatcc ggcaaacaaa ccaccgctgg tagcggtggt tttttttgttt gcaagcagca      6840 gattacgcgc agaaaaaaag gatctcaaga agatcctttg atctttttcta cggggtctga      6900 cgctcagtgg aacgaaaact cacgttaagg gattttggtc atgagattat caaaaaggat      6960
cttcacctag atcctttttaa attaaaaatg aagtttttaaa tcaatctaaa gtatatatga      7020
gtaaacttgg tctgacagtt accaatgctt aatcagtgag gcacctatct cagcgatctg      7080
tctatttcgt tcatccatag ttgcctgact ccccgtcgtg tagataacta cgatacggga      7140
gggcttacca tctggcccca gtgctgcaat gataccgcga acccacgct caccggctcc       7200 agatttatca gcaataaacc agccagccgg aagggccgag cgcagaagtg gtcctgcaac      7260
tttatccgcc tccatccagt ctattaattg ttgccgggaa gctagagtaa gtagttcgcc      7320
agttaatagt ttgcgcaacg ttgttgccat tgctgcaggc atcgtggtgt cacgctcgtc      7380
gtttggtatg gcttcattca gctccggttc ccaacgatca aggcgagtta catgatcccc      7440
catgttgtgc aaaaaagcgg ttagctcctt cggtcctccg atcgttgtca gaagtaagtt      7500
ggccgcagtg ttatcactca tggttatggc agcactgcat aattctctta ctgtcatgcc      7560
atccgtaaga tgcttttctg tgactggtga gtactcaacc aagtcattct gagaatagtg      7620
tatgcggcga ccgagttgct cttgcccggc gtcaacacgg gataataccg cgccacatag      7680
cagaacttta aaagtgctca tcattggaaa acgttcttcg gggcgaaaac tctcaaggat      7740
cttaccgctg ttgagatcca gttcgatgta acccactcgt gcacccaact gatcttcagc      7800 atctttttact ttcaccagcg tttctgggtg agcaaaaaca ggaaggcaaa atgccgcaaa      7860
aaagggaata agggcgacac ggaaatgttg aatactcata ctcttccttt ttcaatatta      7920
ttgaagcatt tatcagggtt attgtctcat gagcggatac atatttgaat gtatttagaa      7980
aaataaacaa atagggggttc cgcgcacatt tccccgaaaa gtgccacctg acgtctaaga      8040
aaccattatt atcatgacat taacctataa aaataggcgt atcacgaggc cctttcgtct      8100
tcaagaa                                                                8107
```

```
<210> SEQ ID NO 33
<211> LENGTH: 9000
<212> TYPE: DNA
<213> ORGANISM: Artificial Sequence
<220> FEATURE:
<223> OTHER INFORMATION: Recombinant plasmid pAPSE10432; beta actin
      hairpin + coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (41)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI recognition site
<220> FEATURE:
<221> NAME/KEY: misc_feature
<222> LOCATION: (498)..(793)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
```

```
<221> NAME/KEY: terminator
<222> LOCATION: (902)..(949)
<223> OTHER INFORMATION: bacteriophage T7 transcription terminator
<220> FEATURE:
<221> NAME/KEY: promoter
<222> LOCATION: (1275)..(1293)
<223> OTHER INFORMATION: bacteriophage T7 gene 1 promoter
<220> FEATURE:
<221> NAME/KEY: gene
<222> LOCATION: (1366)..(1755)
<223> OTHER INFORMATION: bacteriophage MS2 coat protein gene
<220> FEATURE:
<221> NAME/KEY: terminator
<222> LOCATION: (1788)..(1835)
<223> OTHER INFORMATION: bacteriophage T7 transcription terminator
<220> FEATURE:
<221> NAME/KEY: misc_feature
<222> LOCATION: (2272)..(5614)
<223> OTHER INFORMATION: synthetic DNA (SEQ ID NO: 30)

<400> SEQUENCE: 33
ttccgaaatt aatacgactc actatanggga ggcgatcgcg cacgaggttt ttctgtctag        60
tgagcagtgt ccaacctcaa aagacaacat gtgtgacgac gatgtagcgg ctcttgtcgt       120
agacaatgga tccggtatgt gcaaagccgg tttcgcagga gatgacgcac cccgtgccgt       180 cttccctcg atcgtcggtc gcccaaggca tcaaggagtc atggtcggta tgggacaaaa       240
ggactcatac gtaggagatg aagcccaaag caaaagaggt atcctcacc tgaaataccc       300 catcgaacac ggtatcatca ccaactggga tgagtttaaa ccctctagct gctttacaaa       360
gtactggttc cctttccagc gggatgcttt atctaaacgc aatgagagag gtattcctca       420
ggccacatcg cttcctagtt ccgctgggat ccatcgttgg cggccgaagc cgccattcca       480
tagtgagttc tggcgcgcct catcccagtt ggtgatgata ccgtgttcga tggggtattt       540
cagggtgagg atacctcttt tgctttgggc ttcatctcct acgtatgagt cctttttgtcc       600 cataccgacc atgactcctt gatgccttgg gcgaccgacg atcgagggga agacggcacg       660
gggtgcgtca tctcctgcga aaccggcttt gcacataccg gatccattgt ctacgacaag       720
agccgctaca tcgtcgtcac acatgttgtc ttttgaggtt ggacactgct cactagacag       780
aaaaacctcg tgccggaccg aatacccggt ctgaacgagg gcggccgcgg tacccaagaa       840
gtacttagag ttaattaagg agttcaaaca tgaggatcac ccatgtcgaa gctcccacac       900
cctagcataa ccccttgggg cctctaaacg ggtcttgagg ggtttttttgc tgaaaggagg       960 aactatatcc ggatatccac aggacgggtg tggtcgccat gatcgcgtag tcgatagtgg      1020
ctccaagtag cgaagcgagc aggactgggc ggcgggcatg catcgtccat tccgacagca      1080
tcgccagtca ctatggcgtg ctgctagcgc tatatgcgtt gatgcaattt ctatgcgcac      1140
ccgttctcgg agcactgtcc gaccgctttg ccgccgccc agtcctgctc gcttcgctac      1200
ttggagccac tatcgactac gcgatcatgg cgaccacacc cgtcctgtgg atccagatct      1260
cgatcccgcg aaattaatac gactcactat agggagacca caacggtttc cctctagatc      1320
acaagtttgt acaaaaaagc aggctaagaa ggagatatac atatggcgtc taactttacc      1380
caattcgttc tggttgataa cggcggtacg ggtgacgtta ccgtagctcc gtccaacttc      1440
gccaacggtg ttgcggaatg gattagctct aacagccgct ctcaggccta caaagtcacg      1500
tgctccgttc gtcagtctag cgcgcagaat cgcaaataca ccatcaaagt tgaagtaccg      1560
aaagtcgcaa cgcagaccgt aggcggcgta gaactcccag ttgcggcctg gcgctcttac      1620
ctcaacatgg aactgactat tccgatttt gcgacgaact ccgactgcga actgattgtt      1680
aaggcaatgc agggcctgct gaaagacggt aatccgatcc catctgcaat cgctgctaac      1740
```

-continued

```
tctggcattt actaataagc ggacgcgctg ccaccgctga gcaataacta gcataacccc     1800
ttggggcctc taaacgggtc ttgaggggtt ttttgctgaa aggaggaact atatccggca     1860
tgcaccattc cttgcggcgg cggtgctcaa cggcctcaac ctactactgg gctgcttcct     1920
aatgcaggag tcgcataagg gagagcgtcg accgatgccc ttgagagcct tcaacccagt     1980
cagctccttc cggtgggcgc ggggcatgac tatcgtcgcc gcacttatga ctgtcttctt     2040
tatcatgcaa ctcgtaggac aggtgccggc agcgctctgg gtcattttcg gcgaggaccg     2100
ctttcgctgg agcgcgacga tgatcggcct gtcgcttgcg gtattcggaa tcttgcacgc     2160
cctcgctcaa gccttcgtca ctggtcccgc caccaaacgt ttcggcgaga agcaggccat     2220
tatcgccggc atggcggccg acgcgctggg ctacgtcttg ctggcgttcg ccatggtcgt     2280
cacagagctg gaagcggcag cgagaattat ccgcgatcgt ggcgcggtgc ccgcaggcat     2340
gacaaacatc gtaaatgccg cgtttcgtgt ggccgtggcc gcccaggacg tgtcagcgcc     2400
gccaccacct gcaccgaatc ggcagcagcg tcgcgcgtcg aaaaagcgca caggcggcaa     2460
gaagcgataa gctgcacgaa tacctgaaaa atgttgaacg ccccgtgagc ggtaactcac     2520
agggcgtcgg ctaaccccca gtccaaacct gggagaaagc gctcaaaaat gactctagcg     2580
gattcacgag acattgacac accggcctgg aaattttccg ctgatctgtt cgacacccat     2640
cccgagctcg cgctgcgatc acgtggctgg acgagcgaag accgccgcga attcctcgct     2700
cacctgggca gagaaaattt ccagggcagc aagacccgcg acttcgccag cgcttggatc     2760
aaagacccgg acacgggaga aacacagccg aagttatacc gagttggttc aaaatcgctt     2820
gcccggtgcc agtatgttgc tctgacgcac gcgcagcacg cagccgtgct tgtcctggac     2880
attgatgtgc cgagccacca ggccggcggg aaaatcgagc acgtaaaccc cgaggtctac     2940
gcgattttgg agcgctgggc acgcctggaa aaagcgccag cttggatcgg cgtgaatcca     3000
ctgagcggga aatgccagct catctggctc attgatccgg tgtatgccgc agcaggcatg     3060
agcagcccga atatgcgcct gctggctgca acgaccgagg aaatgacccg cgttttcggc     3120
gctgaccagg cttttttcaca taggctgagc cggtggccac tgcacgtctc cgacgatccc     3180
accgcgtacc gctggcatgc ccagcacaat cgcgtggatc gcctagctga tcttatggag     3240
gttgctcgca tgatctcagg cacagaaaaa cctaaaaaac gctatgagca ggagttttct     3300
agcggacggg cacgtatcga agcggcaaga aaagccactg cggaagcaaa agcacttgcc     3360
acgcttgaag caagcctgcc gagcgccgct gaagcgtctg gagagctgat cgacggcgtc     3420
cgtgtcctct ggactgctcc agggcgtgcc gcccgtgatg agacggcttt cgccacgct     3480 ttgactgtgg gataccagtt aaaagcggct ggtgagcgcc taaaagacac caagatcatc     3540
gacgcctacg agcgtgccta caccgtcgct caggcggtcg gagcagacgg ccgtgagcct     3600
gatctgccgc cgatgcgtga ccgccagacg atggcgcgac gtgtgcgcgg ctacgtcgct     3660
aaaggccagc cagtcgtccc tgctcgtcag acagagacgc agagcagccg agggcgaaaa     3720
gctctggcca ctatgggaag acgtggcggt aaaaaggccg cagaacgctg gaaagaccca     3780
aacagtgagt acgcccgagc acagcgagaa aaactagcta agtccagtca acgacaagct     3840
aggaaagcta aaggaaatcg cttgaccatt gcaggttggt ttatgactgt tgagggagag     3900
actggctcgt ggcgacaatc aatgaagcta tgtctgaatt tagcgtgtca cgtcagaccg     3960
tgaatagagc acttaagtct gcgggcattg aacttccacg aggacgccgt aaagcttccc     4020
agtaaatgtg ccatctcgta ggcagaaaac ggttccccc gtaggggtct ctctcttggc     4080
```

-continued

```
ctcctttcta ggtcgggctg attgctcttg aagctctcta gggggggctca caccataggc    4140 agataacggt tccccaccgg ctcacctcgt aagcgcacaa ggactgctcc caatgccgca    4200
agcactcagg gcgcaagggc tgctaaagga agcggaacac gtagaaagcc agtccgcaga    4260
aacggtgctg accccggatg aatgtcagct actgggctat ctggacaagg gaaaacgcaa    4320
gcgcaaagag aaagcaggta gcttgcagtg ggcttacatg gcgatagcta gactgggcgg    4380
ttttatggac agcaagcgaa ccggaattgc cagctggggc gccctctggt aaggttggga    4440
agccctgcaa agtaaactgg atggctttct tgccgccaag gatctgatgg cgcaggggat    4500
caagatctga tcaagagaca ggatgaggat cgtttcgcat gattgaacaa gatggattgc    4560
acgcaggttc tccggccgct tgggtggaga ggctattcgg ctatgactgg gcacaacaga    4620
caatcggctg ctctgatgcc gccgtgttcc ggctgtcagc gcaggggcgc ccggttcttt    4680
ttgtcaagac cgacctgtcc ggtgccctga atgaactcca agacgaggca gcgcggctat    4740
cgtggctggc cacgacgggc gttccttgcg cagctgtgct cgacgttgtc actgaagcgg    4800
gaagggactg gctgctattg ggcgaagtgc cggggcagga tctcctgtca tctcaccttg    4860
ctcctgccga gaaagtatcc atcatggctg atgcaatgcg gcggctgcat acgcttgatc    4920
cggctacctg cccattcgac caccaagcga aacatcgcat cgagcgagca cgtactcgga    4980
tggaagccgg tcttgtcgat caggatgatc tggacgaaga gcatcagggg ctcgcgccag    5040
ccgaactgtt cgccaggctc aaggcgcgga tgcccgacgg cgaggatctc gtcgtgaccc    5100
atggcgatgc ctgcttgccg aatatcatgg tggaaaatgg ccgcttttct ggattcatcg    5160
actgtggccg ctgggtgtg gcggaccgct atcaggacat agcgttggct acccgtgata    5220
ttgctgaaga gcttggcggc gaatgggctg accgcttcct cgtgctttac ggtatcgccg    5280
ctcccgattc gcagcgcatc gccttctatc gccttcttga cgagttcttc tgagcgggac    5340
tctggggttc gctagaggat cgatccttt taacccatca catatacctg ccgttcacta    5400
ttatttagtg aaatgagata ttatgatatt ttctgaattg tgattaaaaa ggcaacttta    5460
tgcccatgca acagaaacta taaaaaatac agagaatgaa aagaaacaga tagatttttt    5520
agttctttag gcccgtagtc tgcaaatcct tttatgattt tctatcaaac aaaagaggaa    5580
aatagaccag ttgcaatcca aacgagagtc taacgacgcg aggctggatg gccttcccca    5640
ttatgattct tctcgcttcc ggcggcatcg ggatgcccgc gttgcaggcc atgctgtcca    5700
ggcaggtaga tgacgaccat cagggacagc ttcaaggatc gctcgcggct cttaccagcc    5760
taacttcgat cattggaccg ctgatcgtca cggcgattta tgccgcctcg gcgagcacat    5820
ggaacgggtt ggcatggatt gtaggcgccg ccctatacct tgtctgcctc cccgcgttgc    5880
gtcgcggtgc atggagccgg gccacctcga cctgaatgga agccggcggc acctcgctaa    5940
cggattcacc actccaagaa ttggagccaa tcaattcttg cggagaactg tgaatgcgca    6000 aaccaacct tggcagaaca tatccatcgc gtccgccatc tccagcagcc gcacgcggcg    6060
catctcgggc agcgttgggt cctggccacg ggtgcgcatg atcgtgctcc tgtcgttgag    6120
gacccggcta ggctggcggg gttgccttac tggttagcag aatgaatcac cgatacgcga    6180
gcgaacgtga agcgactgct gctgcaaaac gtctgcgacc tgagcaacaa catgaatggt    6240
cttcggtttc cgtgtttcgt aaagtctgga aacgcggaag tcagcgccct gcaccattat    6300
gttccggatc tgcatcgcag gatgctgctg gctaccctgt ggaacaccta catctgtatt    6360
aacgaagcgc tggcattgac cctgagtgat ttttctctgg tcccgccgca tccataccgc    6420 cagttgtttta ccctcacaac gttccagtaa ccgggcatgt tcatcatcag taacccgtat    6480
```

-continued

```
cgtgagcatc ctctctcgtt tcatcggtat cattacccccc atgaacagaa atccccctta   6540
cacggaggca tcagtgacca aacaggaaaa aaccgcccctt aacatggccc gctttatcag   6600
aagccagaca ttaacgcttc tggagaaact caacgagctg gacgcggatg aacaggcaga   6660
catctgtgaa tcgcttcacg accacgctga tgagctttac cgcagctgcc tcgcgcgttt   6720
cggtgatgac ggtgaaaacc tctgacacat gcagctcccg gagacggtca cagcttgtct   6780
gtaagcggat gccgggagca gacaagcccg tcagggcgcg tcagcgggtg ttggcgggtg   6840
tcggggcgca gccatgaccc agtcacgtag cgatagcgga gtgtatactg gcttaactat   6900
gcggcatcag agcagattgt actgagagtg caccatatgc ggtgtgaaat accgcacaga   6960
tgcgtaagga gaaaataccg catcaggcgc tcttccgctt cctcgctcac tgactcgctg   7020
cgctcggtcg ttcggctgcg gcgagcggta tcagctcact caaaggcggt aatacggtta   7080
tccacagaat caggggataa cgcaggaaag aacatgtgag caaaaggcca gcaaaaggcc   7140
aggaaccgta aaaaggccgc gttgctggcg tttttccata ggctccgccc ccctgacgag   7200
catcacaaaa atcgacgctc aagtcagagg tggcgaaacc cgacaggact ataaagatac   7260
caggcgtttc ccccctggaag ctccctcgtg cgctctcctg ttccgacccct gccgcttacc   7320 ggatacctgt ccgcctttct cccttcggga agcgtggcgc tttctcatag ctcacgctgt   7380
aggtatctca gttcggtgta ggtcgttcgc tccaagctgg gctgtgtgca cgaaccccccc   7440 gttcagcccg accgctgcgc cttatccggt aactatcgtc ttgagtccaa cccggtaaga   7500
cacgacttat cgccactggc agcagccact ggtaacagga ttagcagagc gaggtatgta   7560
ggcggtgcta cagagttctt gaagtggtgg cctaactacg gctacactag aaggacagta   7620
tttggtatct gcgctctgct gaagccagtt accttcggaa aaagagttgg tagctcttga   7680
tccggcaaac aaaccaccgc tggtagcggt ggtttttttg tttgcaagca gcagattacg   7740
cgcagaaaaa aaggatctca agaagatcct ttgatctttt ctacggggtc tgacgctcag   7800
tggaacgaaa actcacgtta agggattttg gtcatgagat tatcaaaaag gatcttcacc   7860
tagatccttt taaattaaaa atgaagtttt aaatcaatct aaagtatata tgagtaaact   7920
tggtctgaca gttaccaatg cttaatcagt gaggcaccta tctcagcgat ctgtctattt   7980
cgttcatcca tagttgcctg actccccgtc gtgtagataa ctacgatacg ggagggctta   8040
ccatctggcc ccagtgctgc aatgataccg cgagacccac gctcaccggc tccagattta   8100
tcagcaataa accagccagc cggaagggcc gagcgcagaa gtggtcctgc aactttatcc   8160
gcctccatcc agtctattaa ttgttgccgg gaagctagat taagtagttc gccagttaat   8220
agtttgcgca acgttgttgc cattgctgca ggcatcgtgg tgtcacgctc gtcgtttggt   8280
atggcttcat tcagctccgg ttcccaacga tcaaggcgag ttacatgatc ccccatgttg   8340
tgcaaaaaag cggttagctc cttcggtcct ccgatcgttg tcagaagtaa gttggccgca   8400
gtgttatcac tcatggttat ggcagcactg cataattctc ttactgtcat gccatccgta   8460
agatgctttt ctgtgactgg tgagtactca accaagtcat tctgagaata gtgtatgcgg   8520
cgaccgagtt gctcttgccc ggcgtcaaca cgggataata ccgcgccaca tagcagaact   8580
ttaaaagtgc tcatcattgg aaaacgttct tcggggcgaa aactctcaag gatcttaccg   8640
ctgttgagat ccagttcgat gtaacccact cgtgcaccca actgatcttc agcatctttt   8700
actttcacca gcgtttctgg gtgagcaaaa acaggaaggc aaaatgccgc aaaaaaggga   8760
ataagggcga cacggaaatg ttgaatactc atactcttcc tttttcaata ttattgaagc   8820
```

-continued

```
atttatcagg gttattgtct catgagcgga tacatatttg aatgtatta gaaaaataaa      8880 caaataggg  ttccgcgcac atttccccga aaagtgccac ctgacgtcta agaaaccatt      8940
attatcatga cattaaccta taaaaatagg cgtatcacga ggccctttcg tcttcaagaa      9000
```

<210> SEQ ID NO 34
<211> LENGTH: 8198
<212> TYPE: DNA
<213> ORGANISM: Artificial Sequence
<220> FEATURE:
<223> OTHER INFORMATION: Recombinant plasmid pAPSE10433; beta actin
      hairpin - coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (41)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI site
<220> FEATURE:
<221> NAME/KEY: misc_feature
<222> LOCATION: (498)..(793)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: misc_feature
<222> LOCATION: (1470)..(4812)
<223> OTHER INFORMATION: bacteriophage T7 transcription terminator

<400> SEQUENCE: 34

```
ttccgaaatt aatacgactc actatagggga ggcgatcgcg cacgaggttt ttctgtctag       60
tgagcagtgt ccaacctcaa aagacaacat gtgtgacgac gatgtagcgg ctcttgtcgt      120
agacaatgga tccggtatgt gcaaagccgg tttcgcagga gatgacgcac cccgtgccgt      180
cttcccctcg atcgtcggtc gcccaaggca tcaaggagtc atggtcggta tgggacaaaa      240
ggactcatac gtaggagatg aagcccaaag caaaagaggg atcctcaccc tgaaataccc      300
catcgaacac ggtatcatca ccaactggga tgagtttaaa ccctctagct gctttacaaa      360
gtactggttc cctttccagc gggatgcttt atctaaacgc aatgagagag gtattcctca      420
ggccacatcg cttcctagtt ccgctgggat ccatcgttgg cggccgaagc cgccattcca      480
tagtgagttc tggcgcgcct catcccagtt ggtgatgata ccgtgttcga tggggtattt      540
cagggtgagg atacctcttt tgctttgggc ttcatctcct acgtatgagt ccttttgtcc      600
cataccgacc atgactcctt gatgccttgg cgaccgacg atcgagggga agacggcacg       660
gggtgcgtca tctcctgcga aaccggcttt gcacataccg gatccattgt ctacgacaag      720
agccgctaca tcgtcgtcac acatgttgtc ttttgaggtt ggacactgct cactagacag      780
aaaaacctcg tgccggaccg aatacccggt ctgaacgagg cggccgcgg tacccaagaa       840 gtacttagag ttaattaagg agttcaaaca tgaggatcac ccatgtcgaa gctcccacac      900
```

```
cctagcataa ccccttgggg cctctaaacg ggtcttgagg ggtttttttgc tgaaaggagg    960 aactatatcc ggatatccac aggacgggtg tggtcgccat gatcgcgtag tcgatagtgg   1020
ctccaagtag cgaagcgagc aggactgggc ggcgggcatg caccattcct tgcggcggcg   1080
gtgctcaacg gcctcaacct actactgggc tgcttcctaa tgcaggagtc gcataaggga   1140
gagcgtcgac cgatgccctt gagagccttc aacccagtca gctccttccg gtgggcgcgg   1200
ggcatgacta tcgtcgccgc acttatgact gtcttcttta tcatgcaact cgtaggacag   1260
gtgccggcag cgctctgggt cattttcggc gaggaccgct ttcgctggag cgcgacgatg   1320
atcggcctgt cgcttgcggt attcggaatc ttgcacgccc tcgctcaagc cttcgtcact   1380
ggtcccgcca ccaaacgttt cggcgagaag caggccatta tcgccggcat ggcggccgac   1440
gcgctgggct acgtcttgct ggcgttcgcc atggtcgtca cagagctgga agcggcagcg   1500
agaattatcc gcgatcgtgg cgcggtgccc gcaggcatga caaacatcgt aaatgccgcg   1560
tttcgtgtgg ccgtggccgc ccaggacgtg tcagcgccgc caccacctgc accgaatcgg   1620
cagcagcgtc gcgcgtcgaa aaagcgcaca ggcggcaaga agcgataagc tgcacgaata   1680
cctgaaaaat gttgaacgcc ccgtgagcgg taactcacag ggcgtcggct aaccccccagt   1740 ccaaacctgg gagaaagcgc tcaaaaatga ctctagcgga ttcacgagac attgacacac   1800
cggcctggaa attttccgct gatctgttcg acacccatcc cgagctcgcg ctgcgatcac   1860
gtggctggac gagcgaagac cgccgcgaat tcctcgctca cctgggcaga gaaaatttcc   1920
agggcagcaa gacccgcgac ttcgccagcg cttggatcaa agacccggac acgggagaaa   1980
cacagccgaa gttataccga gttggttcaa aatcgcttgc ccggtgccag tatgttgctc   2040
tgacgcacgc gcagcacgca gccgtgcttg tcctggacat tgatgtgccg agccaccagg   2100
ccggcgggaa aatcgagcac gtaaaccccg aggtctacgc gattttggag cgctgggcac   2160
gcctggaaaa agcgccagct tggatcggcg tgaatccact gagcgggaaa tgccagctca   2220
tctggctcat tgatccggtg tatgccgcag caggcatgag cagcccgaat atgcgcctgc   2280
tggctgcaac gaccgaggaa atgacccgcg ttttcggcgc tgaccaggct ttttcacata   2340
ggctgagccg gtggccactg cacgtctccg acgatcccac cgcgtaccgc tggcatgccc   2400
agcacaatcg cgtggatcgc ctagctgatc ttatggaggt tgctcgcatg atctcaggca   2460
cagaaaaacc taaaaaacgc tatgagcagg agttttctag cggacgggca cgtatcgaag   2520
cggcaagaaa agccactgcg gaagcaaaag cacttgccac gcttgaagca agcctgccga   2580
gcgccgctga agcgtctgga gagctgatcg acggcgtccg tgtcctctgg actgctccag   2640
ggcgtgccgc ccgtgatgag acggcttttc gccacgcttt gactgtggga taccagttaa   2700
aagcggctgg tgagcgccta aaagacacca agatcatcga cgcctacgag cgtgcctaca   2760
ccgtcgctca ggcggtcgga gcagacggcc gtgagcctga tctgccgccg atgcgtgacc   2820
gccagacgat ggcgcgacgt gtgcgcggct acgtcgctaa aggccagcca gtcgtccctg   2880
ctcgtcagac agagacgcag agcagccgag ggcgaaaagc tctggccact atgggaagac   2940
gtggcggtaa aaaggccgca gaacgctgga aagacccaaa cagtgagtac gcccgagcac   3000
agcgagaaaa actagctaag tccagtcaac gacaagctag gaaagctaaa ggaaatcgct   3060
tgaccattgc aggttggttt atgactgttg agggagagac tggctcgtgg cgacaatcaa   3120
tgaagctatg tctgaattta gcgtgtcacg tcagaccgtg aatagagcac ttaagtctgc   3180
gggcattgaa cttccacgag gacgccgtaa agcttcccag taaatgtgcc atctcgtagg   3240
cagaaaacgg ttccccccgt aggggtctct ctcttggcct cctttctagg tcgggctgat   3300
```

-continued

```
tgctcttgaa gctctctagg ggggctcaca ccataggcag ataacggttc cccaccggct   3360
cacctcgtaa gcgcacaagg actgctccca atgccgcaag cactcagggc gcaagggctg   3420
ctaaaggaag cggaacacgt agaaagccag tccgcagaaa cggtgctgac cccggatgaa   3480
tgtcagctac tgggctatct ggacaaggga aaacgcaagc gcaaagagaa agcaggtagc   3540
ttgcagtggg cttacatggc gatagctaga ctgggcggtt ttatggacag caagcgaacc   3600
ggaattgcca gctggggcgc cctctggtaa ggttgggaag ccctgcaaag taaactggat   3660
ggctttcttg ccgccaagga tctgatggcg cagggggatca agatctgatc aagagacagg   3720
atgaggatcg tttcgcatga ttgaacaaga tggattgcac gcaggttctc cggccgcttg   3780
ggtggagagg ctattcggct atgactgggc acaacagaca atcggctgct ctgatgccgc   3840
cgtgttccgg ctgtcagcgc aggggcgccc ggttcttttt gtcaagaccg acctgtccgg   3900
tgccctgaat gaactccaag acgaggcagc gcggctatcg tggctggcca cgacgggcgt   3960
tccttgcgca gctgtgctcg acgttgtcac tgaagcggga agggactggc tgctattggg   4020
cgaagtgccg gggcaggatc tcctgtcatc tcaccttgct cctgccgaga aagtatccat   4080
catggctgat gcaatgcggc ggctgcatac gcttgatccg gctacctgcc cattcgacca   4140
ccaagcgaaa catcgcatcg agcgagcacg tactcggatg gaagccggtc ttgtcgatca   4200
ggatgatctg gacgaagagc atcagggggct cgcgccagcc gaactgttcg ccaggctcaa   4260
ggcgcggatg cccgacggcg aggatctcgt cgtgacccat ggcgatgcct gcttgccgaa   4320
tatcatggtg gaaaatggcc gcttttctgg attcatcgac tgtggccggc tgggtgtggc   4380
ggaccgctat caggacatag cgttggctac ccgtgatatt gctgaagagc ttggcggcga   4440
atgggctgac cgcttcctcg tgctttacgg tatcgccgct cccgattcgc agcgcatcgc   4500
cttctatcgc cttcttgacg agttcttctg agcgggactc tggggttcgc tagaggatcg   4560
atccttttta acccatcaca tatacctgcc gttcactatt atttagtgaa atgagatatt   4620
atgatatttt ctgaattgtg attaaaaagg caactttatg cccatgcaac agaaactata   4680
aaaaatacag agaatgaaaa gaaacagata gattttttag ttctttaggc ccgtagtctg   4740
caaatccttt tatgattttc tatcaaacaa aagaggaaaa tagaccagtt gcaatccaaa   4800
cgagagtcta acgacgcgag gctggatggc cttccccatt atgattcttc tcgcttccgg   4860
cggcatcggg atgcccgcgt tgcaggccat gctgtccagg caggtagatg acgaccatca   4920
gggacagctt caaggatcgc tcgcggctct taccagccta acttcgatca ttggaccgct   4980
gatcgtcacg gcgatttatg ccgcctcggc gagcacatgg aacgggttgg catggattgt   5040
aggcgccgcc ctataccttg tctgcctccc cgcgttgcgt cgcggtgcat ggagccgggc   5100
cacctcgacc tgaatggaag ccggcggcac ctcgctaacg gattcaccac tccaagaatt   5160
ggagccaatc aattcttgcg gagaactgtg aatgcgcaaa ccaacccttg gcagaacata   5220
tccatcgcgt ccgccatctc cagcagccgc acgcggcgca tctcgggcag cgttgggtcc   5280
tggccacggg tgcgcatgat cgtgctcctg tcgttgagga cccggctagg ctggcggggt   5340
tgccttactg gttagcagaa tgaatcaccg atacgcgagc gaacgtgaag cgactgctgc   5400
tgcaaaacgt ctgcgacctg agcaacaaca tgaatggtct tcggtttccg tgtttcgtaa   5460
agtctggaaa cgcggaagtc agcgccctgc accattatgt tccggatctg catcgcagga   5520
tgctgctggc taccctgtgg aacacctaca tctgtattaa cgaagcgctg gcattgaccc   5580
tgagtgattt ttctctggtc ccgccgcatc cataccgcca gttgtttacc ctcacaacgt   5640
```

-continued

```
tccagtaacc gggcatgttc atcatcagta acccgtatcg tgagcatcct ctctcgtttc    5700
atcggtatca ttacccccat gaacagaaat cccccttaca cggaggcatc agtgaccaaa    5760
caggaaaaaa ccgcccttaa catggcccgc tttatcagaa gccagacatt aacgcttctg    5820
gagaaactca acgagctgga cgcggatgaa caggcagaca tctgtgaatc gcttcacgac    5880
cacgctgatg agctttaccg cagctgcctc gcgcgtttcg gtgatgacgg tgaaaacctc    5940
tgacacatgc agctcccgga gacggtcaca gcttgtctgt aagcggatgc cgggagcaga    6000
caagcccgtc agggcgcgtc agcgggtgtt ggcgggtgtc ggggcgcagc catgacccag    6060
tcacgtagcg atagcggagt gtatactggc ttaactatgc ggcatcagag cagattgtac    6120
tgagagtgca ccatatgcgg tgtgaaatac cgcacagatg cgtaaggaga aaataccgca    6180
tcaggcgctc ttccgcttcc tcgctcactg actcgctgcg ctcggtcgtt cggctgcggc    6240
gagcggtatc agctcactca aaggcggtaa tacggttatc cacagaatca ggggataacg    6300
caggaaagaa catgtgagca aaaggccagc aaaaggccag gaaccgtaaa aaggccgcgt    6360
tgctggcgtt tttccatagg ctccgccccc ctgacgagca tcacaaaaat cgacgctcaa    6420
gtcagaggtg gcgaaacccg acaggactat aaagatacca ggcgtttccc cctggaagct    6480
ccctcgtgcg ctctcctgtt ccgaccctgc cgcttaccgg atacctgtcc gcctttctcc    6540
cttcgggaag cgtggcgctt tctcatagct cacgctgtag gtatctcagt tcggtgtagg    6600
tcgttcgctc caagctgggc tgtgtgcacg aaccccccgt tcagcccgac cgctgcgcct    6660
tatccggtaa ctatcgtctt gagtccaacc cggtaagaca cgacttatcg ccactggcag    6720
cagccactgg taacaggatt agcagagcga ggtatgtagg cggtgctaca gagttcttga    6780
agtggtggcc taactacggc tacactagaa ggacagtatt tggtatctgc gctctgctga    6840
agccagttac cttcggaaaa agagttggta gctcttgatc cggcaaacaa accaccgctg    6900
gtagcggtgg tttttttgtt tgcaagcagc agattacgcg cagaaaaaaa ggatctcaag    6960
aagatccttt gatcttttct acggggtctg acgctcagtg gaacgaaaac tcacgttaag    7020
ggattttggt catgagatta tcaaaaagga tcttcaccta gatccttttta aattaaaaat    7080 gaagttttaa atcaatctaa agtatatatg agtaaacttg gtctgacagt taccaatgct    7140
taatcagtga ggcacctatc tcagcgatct gtctatttcg ttcatccata gttgcctgac    7200
tccccgtcgt gtagataact acgatacggg agggcttacc atctggcccc agtgctgcaa    7260
tgataccgcg agacccacgc tcaccggctc cagatttatc agcaataaac cagccagccg    7320
gaagggccga gcgcagaagt ggtcctgcaa ctttatccgc ctccatccag tctattaatt    7380
gttgccggga agctagagta agtagttcgc cagttaatag tttgcgcaac gttgttgcca    7440
ttgctgcagg catcgtggtg tcacgctcgt cgtttggtat ggcttcattc agctccggtt    7500
cccaacgatc aaggcgagtt acatgatccc ccatgttgtg caaaaaagcg gttagctcct    7560
tcggtcctcc gatcgttgtc agaagtaagt tggccgcagt gttatcactc atggttatgg    7620
cagcactgca taattctctt actgtcatgc catccgtaag atgcttttct gtgactggtg    7680
agtactcaac caagtcattc tgagaatagt gtatgcggcg accgagttgc tcttgcccgg    7740
cgtcaacacg ggataatacc gcgccacata gcagaacttt aaaagtgctc atcattggaa    7800
aacgttcttc ggggcgaaaa ctctcaagga tcttaccgct gttgagatcc agttcgatgt    7860
aacccactcg tgcacccaac tgatcttcag catcttttac tttcaccagc gtttctgggt    7920
gagcaaaaac aggaaggcaa aatgccgcaa aaaagggaat aagggcgaca cggaaatgtt    7980
gaatactcat actcttcctt tttcaatatt attgaagcat ttatcagggt tattgtctca    8040
```

-continued

```
tgagcggata catatttgaa tgtatttaga aaaataaaca aataggggtt ccgcgcacat      8100
ttccccgaaa agtgccacct gacgtctaag aaaccattat tatcatgaca ttaacctata      8160
aaaataggcg tatcacgagg ccctttcgtc ttcaagaa                              8198
```

```
<210> SEQ ID NO 35
<211> LENGTH: 9327
<212> TYPE: DNA
<213> ORGANISM: Artificial Sequence
<220> FEATURE:
<223> OTHER INFORMATION: Recombinant plasmid pAPSE10434; beta actin
      hairpin + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1602)..(1620)
<223> OTHER INFORMATION: bacteriophage T7 gene 1 promoter
<220> FEATURE:
<221> NAME/KEY: gene
<222> LOCATION: (1693)..(2082)
<223> OTHER INFORMATION: bacteriophage MS2 coat protein gene
<220> FEATURE:
<221> NAME/KEY: terminator
<222> LOCATION: (2115)..(2162)
<223> OTHER INFORMATION: bacteriophage T7 transcription terminator
<220> FEATURE:
<221> NAME/KEY: misc_feature
<222> LOCATION: (2599)..(5941)
<223> OTHER INFORMATION: synthetic DNA (SEQ ID NO: 30)

<400> SEQUENCE: 35
ttctcatgtt tgacagctta tcatcgataa gctttaatgc ggtagtttat cacagttaaa        60
ttgctaacgc agtcaggcac cgtgtatgaa atctaacaat gcgctcatcg tcatcctcgg       120
caccgtcacc ctggatgctg taggcatagg cttggttatg ccggtactgc cgggcctctt       180
gcgggatgaa ttcagatctc gatcccgcga aattaatacg actcactata gggagaccac       240
aacggtttcc ctctagatca caagtttgta caaaaaagca ggctaagaag gagatataca       300
tacgccggcc attcaaacat gaggattacc catgtattta atacccatg tccaggcgcg        360 ctccgcgatc gcgcacgagg tttttctgtc tagtgagcag tgtccaacct caaaagacaa       420
```

-continued

```
catgtgtgac  gacgatgtag  cggctcttgt  cgtagacaat  ggatccggta  tgtgcaaagc      480
cggtttcgca  ggagatgacg  caccccgtgc  cgtcttcccc  tcgatcgtcg  gtcgcccaag      540
gcatcaagga  gtcatggtcg  gtatgggaca  aaaggactca  tacgtaggag  atgaagccca      600
aagcaaaaga  ggtatcctca  ccctgaaata  ccccatcgaa  cacggtatca  tcaccaactg      660
ggatgagttt  aaaccctcta  gctgctttac  aaagtactgg  ttccctttcc  agcgggatgc      720
tttatctaaa  cgcaatgaga  gaggtattcc  tcaggccaca  tcgcttccta  gttccgctgg      780
gatccatcgt  tggcggccga  agccgccatt  ccatagtgag  ttctggcgcg  cctcatccca      840
gttggtgatg  ataccgtgtt  cgatggggta  tttcagggtg  aggatacctc  ttttgctttg      900
ggcttcatct  cctacgtatg  agtccttttg  tcccataccg  accatgactc  cttgatgcct      960
tgggcgaccg  acgatcgagg  ggaagacggc  acggggtgcg  tcatctcctg  cgaaaccggc     1020
tttgcacata  ccggatccat  tgtctacgac  aagagccgct  acatcgtcgt  cacacatgtt     1080
gtcttttgag  gttggacact  gctcactaga  cagaaaaacc  tcgtgccgga  ccgaataccc     1140
ggtctgaacg  agggcggccg  cggtacccaa  gaagtactta  gagttaatta  aggagttcaa     1200
acatgaggat  cacccatgtc  gaagctccca  caccctagca  taaccccttg  gggcctctaa     1260
acgggtcttg  aggggttttt  tgctgaaagg  aggaactata  tccgcacagg  acgggtgtgg     1320
tcgccatgat  cgcgtagtcg  atagtggctc  caagtagcga  agcgagcagg  actgggcggc     1380
gggcatgcat  cgtccattcc  gacagcatcg  ccagtcacta  tggcgtgctg  ctagcgctat     1440
atgcgttgat  gcaatttcta  tgcgcacccg  ttctcggagc  actgtccgac  cgctttggcc     1500
gccgcccagt  cctgctcgct  tcgctacttg  gagccactat  cgactacgcg  atcatggcga     1560
ccacacccgt  cctgtggatc  cagatctcga  tcccgcgaaa  ttaatacgac  tcactatagg     1620
gagaccacaa  cggtttccct  ctagatcaca  agtttgtaca  aaaaagcagg  ctaagaagga     1680
gatatacata  tggcgtctaa  ctttacccaa  ttcgttctgg  ttgataacgg  cggtacgggt     1740
gacgttaccg  tagctccgtc  caacttcgcc  aacggtgttg  cggaatggat  tagctctaac     1800
agccgctctc  aggcctacaa  agtcacgtgc  tccgttcgtc  agtctagcgc  gcagaatcgc     1860
aaatacacca  tcaaagttga  agtaccgaaa  gtcgcaacgc  agaccgtagg  cggcgtagaa     1920
ctcccagttg  cggcctggcg  ctcttacctc  aacatggaac  tgactattcc  gatttttgcg     1980
acgaactccg  actgcgaact  gattgttaag  gcaatgcagg  gcctgctgaa  agacggtaat     2040
ccgatcccat  ctgcaatcgc  tgctaactct  ggcatttact  aataagcgga  cgcgctgcca     2100
ccgctgagca  ataactagca  taaccccttg  gggcctctaa  acgggtcttg  aggggttttt     2160
tgctgaaagg  aggaactata  tccggcatgc  accattcctt  gcggcggcgg  tgctcaacgg     2220
cctcaaccta  ctactgggct  gcttcctaat  gcaggagtcg  cataagggag  agcgtcgacc     2280
gatgcccttg  agagccttca  acccagtcag  ctccttccgg  tgggcgcggg  gcatgactat     2340
cgtcgccgca  cttatgactg  tcttctttat  catgcaactc  gtaggacagg  tgccggcagc     2400
gctctgggtc  attttcggcg  aggaccgctt  tcgctggagc  gcgacgatga  tcggcctgtc     2460
gcttgcggta  ttcggaatct  tgcacgccct  cgctcaagcc  ttcgtcactg  gtcccgccac     2520
caaacgtttc  ggcgagaagc  aggccattat  cgccggcatg  gcggccgacg  cgctgggcta     2580
cgtcttgctg  gcgttcgcca  tggtcgtcac  agagctggaa  gcggcagcga  gaattatccg     2640
cgatcgtggc  gcggtgcccg  caggcatgac  aaacatcgta  aatgccgcgt  ttcgtgtggc     2700
cgtggccgcc  caggacgtgt  cagcgccgcc  accacctgca  ccgaatcggc  agcagcgtcg     2760
```

-continued

```
cgcgtcgaaa aagcgcacag gcggcaagaa gcgataagct gcacgaatac ctgaaaaatg    2820
ttgaacgccc cgtgagcggt aactcacagg gcgtcggcta acccccagtc caaacctggg    2880
agaaagcgct caaaaatgac tctagcggat tcacgagaca ttgacacacc ggcctggaaa    2940
ttttccgctg atctgttcga cacccatccc gagctcgcgc tgcgatcacg tggctggacg    3000
agcgaagacc gccgcgaatt cctcgctcac ctgggcagag aaaatttcca gggcagcaag    3060
acccgcgact tcgccagcgc ttggatcaaa gacccggaca cgggagaaac acagccgaag    3120
ttataccgag ttggttcaaa atcgcttgcc cggtgccagt atgttgctct gacgcacgcg    3180
cagcacgcag ccgtgcttgt cctggacatt gatgtgccga gccaccaggc cggcgggaaa    3240
atcgagcacg taaaccccga ggtctacgcg attttggagc gctgggcacg cctggaaaaa    3300
gcgccagctt ggatcggcgt gaatccactg agcgggaaat gccagctcat ctggctcatt    3360
gatccggtgt atgccgcagc aggcatgagc agcccgaata tgccgcctgct ggctgcaacg    3420 accgaggaaa tgacccgcgt tttcggcgct gaccaggctt tttcacatag gctgagccgg    3480
tggccactgc acgtctccga cgatcccacc gcgtaccgct ggcatgccca gcacaatcgc    3540
gtggatcgcc tagctgatct tatggaggtt gctcgcatga tctcaggcac agaaaaacct    3600
aaaaaacgct atgagcagga gttttctagc ggacgggcac gtatcgaagc ggcaagaaaa    3660
gccactgcgg aagcaaaagc acttgccacg cttgaagcaa gcctgccgag cgccgctgaa    3720
gcgtctggag agctgatcga cggcgtccgt gtcctctgga ctgctccagg gcgtgccgcc    3780
cgtgatgaga cggcttttcg ccacgctttg actgtgggat accagttaaa agcggctggt    3840
gagcgcctaa aagacaccaa gatcatcgac gcctacgagc gtgcctacac cgtcgctcag    3900
gcggtcggag cagacggccg tgagcctgat ctgccgccga tgcgtgaccg ccagacgatg    3960
gcgcgacgtg tgcgcggcta cgtcgctaaa ggccagccag tcgtccctgc tcgtcagaca    4020
gagacgcaga gcagccgagg gcgaaaagct ctggccacta tgggaagacg tggcggtaaa    4080
aaggccgcag aacgctggaa agacccaaac agtgagtacg cccgagcaca gcgagaaaaa    4140
ctagctaagt ccagtcaacg acaagctagg aaagctaaag gaaatcgctt gaccattgca    4200
ggttggttta tgactgttga gggagagact ggctcgtggc gacaatcaat gaagctatgt    4260
ctgaatttag cgtgtcacgt cagaccgtga atagagcact taagtctgcg ggcattgaac    4320
ttccacgagg acgccgtaaa gcttccagt aaatgtgcca tctcgtaggc agaaaacggt    4380 tcccccgta ggggtctctc tcttggcctc ctttctaggt cgggctgatt gctcttgaag    4440
ctctctaggg gggctcacac cataggcaga taacggttcc ccaccggctc acctcgtaag    4500
cgcacaagga ctgctcccaa tgccgcaagc actcagggcg caagggctgc taaaggaagc    4560
ggaacacgta gaaagccagt ccgcagaaac ggtgctgacc ccggatgaat gtcagctact    4620
gggctatctg gacaagggaa aacgcaagcg caaagagaaa gcaggtagct tgcagtgggc    4680
ttacatggcg atagctagac tgggcggtt tatggacagc aagcgaaccg gaattgccag    4740
ctggggcgcc ctctggtaag gttgggaagc cctgcaaagt aaactggatg gctttcttgc    4800
cgccaaggat ctgatggcgc aggggatcaa gatctgatca agagacagga tgaggatcgt    4860
ttcgcatgat tgaacaagat ggattgcacg caggttctcc ggccgcttgg gtggagaggc    4920
tattcggcta tgactgggca caacagacaa tcggctgctc tgatgccgcc gtgttccggc    4980
tgtcagcgca ggggcgcccg gttctttttg tcaagaccga cctgtccggt gccctgaatg    5040
aactccaaga cgaggcagcg cggctatcgt ggctggccac gacgggcgtt ccttgcgcag    5100
ctgtgctcga cgttgtcact gaagcgggaa gggactggct gctattgggc gaagtgccgg    5160
```

-continued

```
ggcaggatct cctgtcatct caccttgctc ctgccgagaa agtatccatc atggctgatg      5220
caatgcggcg gctgcatacg cttgatccgg ctacctgccc attcgaccac caagcgaaac      5280
atcgcatcga gcgagcacgt actcggatgg aagccggtct tgtcgatcag gatgatctgg      5340
acgaagagca tcaggggctc gcgccagccg aactgttcgc caggctcaag gcgcggatgc      5400
ccgacggcga ggatctcgtc gtgacccatg gcgatgcctg cttgccgaat atcatggtgg      5460
aaaatggccg cttttctgga ttcatcgact gtggccggct gggtgtggcg gaccgctatc      5520
aggacatagc gttggctacc cgtgatattg ctgaagagct tggcggcgaa tgggctgacc      5580
gcttcctcgt gctttacggt atcgccgctc ccgattcgca gcgcatcgcc ttctatcgcc      5640
ttcttgacga gttcttctga gcgggactct ggggttcgct agaggatcga tcctttttaa      5700
cccatcacat atacctgccg ttcactatta tttagtgaaa tgagatatta tgatattttc      5760
tgaattgtga ttaaaaaggc aactttatgc ccatgcaaca gaaactataa aaaatacaga      5820
gaatgaaaag aaacagatag attttttagt tctttaggcc cgtagtctgc aaatcctttt      5880
atgattttct atcaaacaaa agaggaaaat agaccagttg caatccaaac gagagtctaa      5940
cgacgcgagg ctggatggcc ttccccatta tgattcttct cgcttccggc ggcatcggga      6000
tgcccgcgtt gcaggccatg ctgtccaggc aggtagatga cgaccatcag gacagcttc       6060 aaggatcgct cgcggctctt accagcctaa cttcgatcat tggaccgctg atcgtcacgg       6120
cgatttatgc cgcctcggcg agcacatgga acgggttggc atggattgta ggcgccgccc       6180
tataccttgt ctgcctcccc gcgttgcgtc gcggtgcatg gagccgggcc acctcgacct       6240
gaatggaagc cggcggcacc tcgctaacgg attcaccact ccaagaattg gagccaatca       6300
attcttgcgg agaactgtga atgcgcaaac caacccttgg cagaacatat ccatcgcgtc       6360
cgccatctcc agcagccgca cgcggcgcat ctcgggcagc gttgggtcct ggccacgggt       6420
gcgcatgatc gtgctcctgt cgttgaggac ccggctaggc tggcggggtt gccttactgg       6480
ttagcagaat gaatcaccga tacgcgagcg aacgtgaagc gactgctgct gcaaaacgtc       6540
tgcgacctga gcaacaacat gaatggtctt cggtttccgt gtttcgtaaa gtctggaaac       6600
gcggaagtca gcgccctgca ccattatgtt ccggatctgc atcgcaggat gctgctggct       6660
accctgtgga acacctacat ctgtattaac gaagcgctgg cattgaccct gagtgatttt       6720
tctctggtcc cgccgcatcc ataccgccag ttgtttaccc tcacaacgtt ccagtaaccg       6780
ggcatgttca tcatcagtaa cccgtatcgt gagcatcctc tctcgtttca tcggtatcat       6840
tacccccatg aacagaaatc ccccttacac ggaggcatca gtgaccaaac aggaaaaaac       6900
cgcccttaac atggcccgct ttatcagaag ccagacatta acgcttctgg agaaactcaa       6960
cgagctggac gcggatgaac aggcagacat ctgtgaatcg cttcacgacc acgctgatga       7020
gctttaccgc agctgcctcg cgcgtttcgg tgatgacggt gaaaacctct gacacatgca       7080
gctcccggag acggtcacag cttgtctgta agcggatgcc gggagcagac aagcccgtca       7140
gggcgcgtca gcgggtgttg gcgggtgtcg gggcgcagcc atgacccagt cacgtagcga       7200
tagcggagtg tatactggct taactatgcg gcatcagagc agattgtact gagagtgcac       7260
catatgcggt gtgaaatacc gcacagatgc gtaaggagaa aataccgcat caggcgctct       7320
tccgcttcct cgctcactga ctcgctgcgc tcggtcgttc ggctgcggcg agcggtatca       7380
gctcactcaa aggcggtaat acggttatcc acagaatcag gggataacgc aggaaagaac       7440
atgtgagcaa aaggccagca aaaggccagg aaccgtaaaa aggccgcgtt gctggcgttt       7500
```

```
ttccataggc tccgcccccc tgacgagcat cacaaaaatc gacgctcaag tcagaggtgg    7560
cgaaacccga caggactata aagataccag gcgtttcccc ctggaagctc cctcgtgcgc    7620
tctcctgttc cgaccctgcc gcttaccgga tacctgtccg cctttctccc ttcgggaagc    7680
gtggcgcttt ctcatagctc acgctgtagg tatctcagtt cggtgtaggt cgttcgctcc    7740
aagctgggct gtgtgcacga accccccgtt cagcccgacc gctgcgcctt atccggtaac    7800
tatcgtcttg agtccaaccc ggtaagacac gacttatcgc cactggcagc agccactggt    7860
aacaggatta gcagagcgag gtatgtaggc ggtgctacag agttcttgaa gtggtggcct    7920
aactacggct acactagaag gacagtattt ggtatctgcg ctctgctgaa gccagttacc    7980
ttcggaaaaa gagttggtag ctcttgatcc ggcaaacaaa ccaccgctgg tagcggtggt    8040 tttttttgttt gcaagcagca gattacgcgc agaaaaaaag gatctcaaga agatcctttg    8100
atcttttcta cggggtctga cgctcagtgg aacgaaaact cacgttaagg gattttggtc    8160
atgagattat caaaaaggat cttcacctag atcctttaa attaaaaatg aagttttaaa    8220
tcaatctaaa gtatatatga gtaaacttgg tctgacagtt accaatgctt aatcagtgag    8280
gcacctatct cagcgatctg tctatttcgt tcatccatag ttgcctgact ccccgtcgtg    8340
tagataacta cgatacggga gggcttacca tctggcccca gtgctgcaat gataccgcga    8400
gacccacgct caccggctcc agatttatca gcaataaacc agccagccgg aagggccgag    8460
cgcagaagtg gtcctgcaac tttatccgcc tccatccagt ctattaattg ttgccgggaa    8520
gctagagtaa gtagttcgcc agttaatagt ttgcgcaacg ttgttgccat tgctgcaggc    8580
atcgtggtgt cacgctcgtc gtttggtatg gcttcattca gctccggttc ccaacgatca    8640
aggcgagtta catgatcccc catgttgtgc aaaaaagcgg ttagctcctt cggtcctccg    8700
atcgttgtca gaagtaagtt ggccgcagtg ttatcactca tggttatggc agcactgcat    8760
aattctctta ctgtcatgcc atccgtaaga tgcttttctg tgactggtga gtactcaacc    8820
aagtcattct gagaatagtg tatgcggcga ccgagttgct cttgcccggc gtcaacacgg    8880
gataataccg cgccacatag cagaacttta aaagtgctca tcattggaaa acgttcttcg    8940
gggcgaaaac tctcaaggat cttaccgctg ttgagatcca gttcgatgta acccactcgt    9000
gcacccaact gatcttcagc atcttttact ttcaccagcg tttctgggtg agcaaaaaca    9060
ggaaggcaaa atgccgcaaa aaagggaata agggcgacac ggaaatgttg aatactcata    9120
ctcttccttt ttcaatatta ttgaagcatt tatcagggtt attgtctcat gagcggatac    9180
atatttgaat gtatttagaa aaataaacaa ataggggttc cgcgcacatt tccccgaaaa    9240
gtgccacctg acgtctaaga aaccattatt atcatgacat taacctataa aaataggcgt    9300
atcacgaggc cctttcgtct tcaagaa                                        9327
```

<210> SEQ ID NO 36
<211> LENGTH: 8531
<212> TYPE: DNA
<213> ORGANISM: Artificial Sequence
<220> FEATURE:
<223> OTHER INFORMATION: Recombinant plasmid pAPSE10435; beta actin
      hairpin - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:

<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1803)..(5145)
<223> OTHER INFORMATION: synthetic DNA (SEQ ID NO: 30)

<400> SEQUENCE: 36
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttcccttttcc agcgggatgc     720 tttatctaaa cgcaatgaga gaggtattcc tcaggccaca tcgcttccta gttccgctgg     780
gatccatcgt tggcggccga agccgccatt ccatagtgag ttctggcgcg cctcatccca     840
gttggtgatg ataccgtgtt cgatgggta tttcagggtg aggatacctc ttttgctttg     900
ggcttcatct cctacgtatg agtccttttg tcccataccg accatgactc cttgatgcct     960
tgggcgaccg acgatcgagg ggaagacggc acggggtgcg tcatctcctg cgaaaccggc    1020
tttgcacata ccggatccat tgtctacgac aagagccgct acatcgtcgt cacacatgtt    1080
gtcttttgag gttggacact gctcactaga cagaaaaacc tcgtgccgga ccgaataccc    1140
ggtctgaacg agggcggccg cggtacccaa gaagtactta gagttaatta aggagttcaa    1200
acatgaggat cacccatgtc gaagctccca caccctagca taaccccttg gggcctctaa    1260
acgggtcttg aggggttttt tgctgaaagg aggaactata tccggatatc cacaggacgg    1320
gtgtggtcgc catgatcgcg tagtcgatag tggctccaag tagcgaagcg agcaggactg    1380
ggcggcgggc atgcaccatt ccttgcggcg gcggtgctca acggcctcaa cctactactg    1440
ggctgcttcc taatgcagga gtcgcataag ggagagcgtc gaccgatgcc cttgagagcc    1500

-continued

```
ttcaacccag tcagctcctt ccggtgggcg cggggcatga ctatcgtcgc cgcacttatg   1560
actgtcttct ttatcatgca actcgtagga caggtgccgg cagcgctctg ggtcattttc   1620
ggcgaggacc gctttcgctg gagcgcgacg atgatcggcc tgtcgcttgc ggtattcgga   1680
atcttgcacg ccctcgctca agccttcgtc actggtcccg ccaccaaacg tttcggcgag   1740
aagcaggcca ttatcgccgg catggcggcc gacgcgctgg gctacgtctt gctggcgttc   1800
gccatggtcg tcacagagct ggaagcggca gcgagaatta ccgcgatcg tggcgcggtg   1860 cccgcaggca tgacaaacat cgtaaatgcc gcgtttcgtg tggccgtggc cgcccaggac   1920
gtgtcagcgc cgccaccacc tgcaccgaat cggcagcagc gtcgcgcgtc gaaaaagcgc   1980
acaggcggca agaagcgata agctgcacga atacctgaaa aatgttgaac gccccgtgag   2040
cggtaactca cagggcgtcg gctaaccccc agtccaaacc tgggagaaag cgctcaaaaa   2100
tgactctagc ggattcacga gacattgaca caccggcctg gaaattttcc gctgatctgt   2160
tcgacaccca tcccgagctc gcgctgcgat cacgtggctg gacgagcgaa gaccgccgcg   2220
aattcctcgc tcacctgggc agagaaaatt tccagggcag caagacccgc gacttcgcca   2280
gcgcttggat caaagacccg gacacgggag aaacacagcc gaagttatac cgagttggtt   2340
caaaatcgct tgcccggtgc cagtatgttg ctctgacgca cgcgcagcac gcagccgtgc   2400
ttgtcctgga cattgatgtg ccgagccacc aggccggcgg gaaaatcgag cacgtaaacc   2460
ccgaggtcta cgcgattttg gagcgctggg cacgcctgga aaaagcgcca gcttggatcg   2520
gcgtgaatcc actgagcggg aaatgccagc tcatctggct cattgatccg gtgtatgccg   2580
cagcaggcat gagcagcccg aatatgcgcc tgctggctgc aacgaccgag gaaatgaccc   2640
gcgttttcgg cgctgaccag gcttttttcac ataggctgag ccggtggcca ctgcacgtct   2700
ccgacgatcc caccgcgtac cgctggcatg cccagcacaa tcgcgtggat cgcctagctg   2760
atcttatgga ggttgctcgc atgatctcag gcacagaaaa acctaaaaaa cgctatgagc   2820
aggagttttc tagcggacgg gcacgtatcg aagcggcaag aaaagccact gcggaagcaa   2880
aagcacttgc cacgcttgaa gcaagcctgc cgagcgccgc tgaagcgtct ggagagctga   2940
tcgacggcgt ccgtgtcctc tggactgctc cagggcgtgc cgcccgtgat gagacggctt   3000
ttcgccacgc tttgactgtg ggataccagt taaaagcggc tggtgagcgc ctaaaagaca   3060
ccaagatcat cgacgcctac gagcgtgcct acaccgtcgc tcaggcggtc ggagcagacg   3120
gccgtgagcc tgatctgccg ccgatgcgtg accgccagac gatggcgcga cgtgtgcgcg   3180
gctacgtcgc taaaggccag ccagtcgtcc ctgctcgtca gacagagacg cagagcagcc   3240
gagggcgaaa agctctggcc actatgggaa gacgtggcgg taaaaaggcc gcagaacgct   3300
ggaaagaccc aaacagtgag tacgcccgag cacagcgaga aaaactagct aagtccagtc   3360
aacgacaagc taggaaagct aaaggaaatc gcttgaccat tgcaggttgg tttatgactg   3420
ttgagggaga gactggctcg tggcgacaat caatgaagct atgtctgaat ttagcgtgtc   3480
acgtcagacc gtgaatagag cacttaagtc tgcgggcatt gaacttccac gaggacgccg   3540
taaagcttcc cagtaaatgt gccatctcgt aggcagaaaa cggttcccc cgtaggggtc   3600 tctctcttgg cctcctttct aggtcgggct gattgctctt gaagctctct aggggggctc   3660
acaccatagg cagataacgg ttccccaccg gctcacctcg taagcgcaca aggactgctc   3720
ccaatgccgc aagcactcag ggcgcaaggg ctgctaaagg aagcggaaca cgtagaaagc   3780
cagtccgcag aaacggtgct gaccccggat gaatgtcagc tactgggcta tctggacaag   3840
```

-continued

```
ggaaaacgca agcgcaaaga gaaagcaggt agcttgcagt gggcttacat ggcgatagct    3900
agactgggcg gttttatgga cagcaagcga accggaattg ccagctgggg cgccctctgg    3960
taaggttggg aagccctgca aagtaaactg gatggctttc ttgccgccaa ggatctgatg    4020
gcgcagggga tcaagatctg atcaagagac aggatgagga tcgtttcgca tgattgaaca    4080
agatggattg cacgcaggtt ctccggccgc ttgggtggag aggctattcg gctatgactg    4140
ggcacaacag acaatcggct gctctgatgc cgccgtgttc cggctgtcag cgcaggggcg    4200
cccggttctt tttgtcaaga ccgacctgtc cggtgccctg aatgaactcc aagacgaggc    4260
agcgcggcta tcgtggctgg ccacgacggg cgttccttgc gcagctgtgc tcgacgttgt    4320
cactgaagcg ggaagggact ggctgctatt gggcgaagtg ccggggcagg atctcctgtc    4380
atctcacctt gctcctgccg agaaagtatc catcatggct gatgcaatgc ggcggctgca    4440
tacgcttgat ccggctacct gcccattcga ccaccaagcg aaacatcgca tcgagcgagc    4500
acgtactcgg atggaagccg gtcttgtcga tcaggatgat ctggacgaag agcatcaggg    4560
gctcgcgcca gccgaactgt tcgccaggct caaggcgcgg atgcccgacg gcgaggatct    4620
cgtcgtgacc catggcgatg cctgcttgcc gaatatcatg gtggaaaatg gccgcttttc    4680
tggattcatc gactgtggcc ggctgggtgt ggcggaccgc tatcaggaca tagcgttggc    4740
tacccgtgat attgctgaag agcttggcgg cgaatgggct gaccgcttcc tcgtgcttta    4800
cggtatcgcc gctcccgatt cgcagcgcat cgccttctat cgccttcttg acgagttctt    4860
ctgagcggga ctctggggtt cgctagagga tcgatccttt ttaacccatc acatatacct    4920
gccgttcact attatttagt gaaatgagat attatgatat tttctgaatt gtgattaaaa    4980
aggcaacttt atgcccatgc aacagaaact ataaaaaata cagagaatga aaagaaacag    5040
atagattttt tagttcttta ggcccgtagt ctgcaaatcc ttttatgatt ttctatcaaa    5100
caaaagagga aaatagacca gttgcaatcc aaacgagagt ctaacgacgc gaggctggat    5160
ggccttcccc attatgattc ttctcgcttc cggcggcatc gggatgcccg cgttgcaggc    5220
catgctgtcc aggcaggtag atgacgacca tcagggacag cttcaaggat cgctcgcggc    5280
tcttaccagc ctaacttcga tcattggacc gctgatcgtc acggcgattt atgccgcctc    5340
ggcgagcaca tggaacgggt tggcatggat tgtaggcgcc gccctatacc ttgtctgcct    5400
ccccgcgttg cgtcgcggtg catggagccg ggccacctcg acctgaatgg aagccggcgg    5460
cacctcgcta acggattcac cactccaaga attggagcca atcaattctt gcggagaact    5520
gtgaatgcgc aaaccaaccc ttggcagaac atatccatcg cgtccgccat ctccagcagc    5580
cgcacgcggc gcatctcggg cagcgttggg tcctggccac gggtgcgcat gatcgtgctc    5640
ctgtcgttga ggacccggct aggctggcgg ggttgcctta ctggttagca gaatgaatca    5700
ccgatacgcg agcgaacgtg aagcgactgc tgctgcaaaa cgtctgcgac ctgagcaaca    5760
acatgaatgg tcttcggttt ccgtgtttcg taaagtctgg aaacgcggaa gtcagcgccc    5820
tgcaccatta tgttccggat ctgcatcgca ggatgctgct ggctaccctg tggaacacct    5880
acatctgtat taacgaagcg ctggcattga ccctgagtga ttttttctctg tcccgccgc    5940 atccataccg ccagttgttt accctcacaa cgttccagta accggcatg ttcatcatca    6000 gtaacccgta tcgtgagcat cctctctcgt ttcatcggta tcattacccc catgaacaga    6060
aatccccctt acacggaggc atcagtgacc aaacaggaaa aaaccgccct taacatggcc    6120
cgctttatca gaagccagac attaacgctt ctggagaaac tcaacgagct ggacgcggat    6180
gaacaggcag acatctgtga atcgcttcac gaccacgctg atgagcttta ccgcagctgc    6240
```

```
ctcgcgcgtt tcggtgatga cggtgaaaac ctctgacaca tgcagctccc ggagacggtc     6300
acagcttgtc tgtaagcgga tgccgggagc agacaagccc gtcagggcgc gtcagcgggt     6360
gttggcgggt gtcggggcgc agccatgacc cagtcacgta gcgatagcgg agtgtatact     6420
ggcttaacta tgcggcatca gagcagattg tactgagagt gcaccatatg cggtgtgaaa     6480
taccgcacag atgcgtaagg agaaaatacc gcatcaggcg ctcttccgct tcctcgctca     6540
ctgactcgct gcgctcggtc gttcggctgc ggcgagcggt atcagctcac tcaaaggcgg     6600
taatacggtt atccacagaa tcaggggata cgcaggaaa gaacatgtga gcaaaaggcc     6660
agcaaaaggc caggaaccgt aaaaaggccg cgttgctggc gtttttccat aggctccgcc     6720
cccctgacga gcatcacaaa aatcgacgct caagtcagag gtggcgaaac ccgacaggac     6780
tataaagata ccaggcgttt ccccctggaa gctccctcgt gcgctctcct gttccgaccc     6840
tgccgcttac cggatacctg tccgcctttc tcccttcggg aagcgtggcg ctttctcata     6900
gctcacgctg taggtatctc agttcggtgt aggtcgttcg ctccaagctg ggctgtgtgc     6960 acgaacccc cgttcagccc gaccgctgcg ccttatccgg taactatcgt cttgagtcca     7020
acccggtaag acacgactta tcgccactgg cagcagccac tggtaacagg attagcagag     7080
cgaggtatgt aggcggtgct acagagttct tgaagtggtg gcctaactac ggctacacta     7140
gaaggacagt atttggtatc tgcgctctgc tgaagccagt taccttcgga aaaagagttg     7200
gtagctcttg atccggcaaa caaaccaccg ctggtagcgg tggtttttt gtttgcaagc     7260 agcagattac gcgcagaaaa aaaggatctc aagaagatcc tttgatcttt tctacggggt     7320
ctgacgctca gtggaacgaa aactcacgtt aagggatttt ggtcatgaga ttatcaaaaa     7380
ggatcttcac ctagatcctt ttaaattaaa aatgaagttt taaatcaatc taaagtatat     7440
atgagtaaac ttggtctgac agttaccaat gcttaatcag tgaggcacct atctcagcga     7500
tctgtctatt tcgttcatcc atagttgcct gactccccgt cgtgtagata actacgatac     7560
gggagggctt accatctggc cccagtgctg caatgatacc gcgagaccca cgctcaccgg     7620
ctccagattt atcagcaata aaccagccag ccggaagggc cgagcgcaga agtggtcctg     7680
caactttatc cgcctccatc cagtctatta attgttgccg ggaagctaga gtaagtagtt     7740
cgccagttaa tagtttgcgc aacgttgttg ccattgctgc aggcatcgtg gtgtcacgct     7800
cgtcgtttgg tatggcttca ttcagctccg gttcccaacg atcaaggcga gttacatgat     7860
cccccatgtt gtgcaaaaaa gcggttagct ccttcggtcc tccgatcgtt gtcagaagta     7920
agttggccgc agtgttatca ctcatggtta tggcagcact gcataattct cttactgtca     7980
tgccatccgt aagatgcttt tctgtgactg gtgagtactc aaccaagtca ttctgagaat     8040
agtgtatgcg gcgaccgagt tgctcttgcc cggcgtcaac acgggataat accgcgccac     8100
atagcagaac tttaaaagtg ctcatcattg gaaaacgttc ttcggggcga aaactctcaa     8160
ggatcttacc gctgttgaga tccagttcga tgtaacccac tcgtgcaccc aactgatctt     8220
cagcatcttt tactttcacc agcgtttctg ggtgagcaaa aacaggaagg caaaatgccg     8280
caaaaaaggg aataagggcg acacggaaat gttgaatact catactcttc cttttttcaat     8340 attattgaag catttatcag ggttattgtc tcatgagcgg atacatattt gaatgtattt     8400
agaaaaataa acaaataggg gttccgcgca catttccccg aaaagtgcca cctgacgtct     8460
aagaaaccat tattatcatg acattaacct ataaaaatag gcgtatcacg aggccctttc     8520
gtcttcaaga a                                                          8531
```

<210> SEQ ID NO 37
<211> LENGTH: 9520
<212> TYPE: DNA
<213> ORGANISM: Artificial Sequence
<220> FEATURE:
<223> OTHER INFORMATION: Recombinant plasmid pAPSE10436; beta actin
      hairpin + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (665)..(672)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator
<220> FEATURE:
<221> NAME/KEY: misc_feature
<222> LOCATION: (2792)..(6134)
<223> OTHER INFORMATION: synthetic DNA (SEQ ID NO: 30)

<400> SEQUENCE: 37
ttctcatgtt tgacagctta tcatcgataa gctttaatgc ggtagtttat cacagttaaa        60
ttgctaacgc agtcaggcac cgtgtatgaa atctaacaat gcgctcatcg tcatcctcgg       120
caccgtcacc ctggatgctg taggcatagg cttggttatg ccggtactgc cgggcctctt       180
gcgggatgaa ttcagatctc gatcccgcga aattaatacg actcactata gggagaccac       240
aacggtttcc ctctagatca caagtttgta caaaaaagca ggctaagaag gagatataca       300
tacgccggcc attcaaacat gaggattacc catgtattta aatacccatg tccaggcgcg       360
ctccgcgatc gcgcacgagg tttttctgtc tagtgagcag tgtccaacct caaaagacaa       420
catgtgtgac gacgatgtag cggctcttgt cgtagacaat ggatccggta tgtgcaaagc       480

-continued

```
cggtttcgca ggagatgacg cacccgtgc  cgtcttcccc tcgatcgtcg gtcgcccaag      540
gcatcaagga gtcatggtcg gtatgggaca aaaggactca tacgtaggag atgaagccca      600
aagcaaaaga ggtatcctca ccctgaaata ccccatcgaa cacggtatca tcaccaactg      660
ggatgagttt aaaccctcta gctgctttac aaagtactgg ttccctttcc agcgggatgc      720
tttatctaaa cgcaacatga ggatcaccca tgtcgccaca tcgcttccta gttccgctgg      780
gatccatcgt tggcggccga agccgccatt ccatagtgag ttctggcgcg cctcatccca      840
gttggtgatg ataccgtgtt cgatggggta tttcagggtg aggatacctc ttttgctttg      900
ggcttcatct cctacgtatg agtccttttg tcccataccg accatgactc cttgatgcct      960
tgggcgaccg acgatcgagg ggaagacggc acggggtgcg tcatctcctg cgaaaccggc     1020
tttgcacata ccggatccat tgtctacgac aagagccgct acatcgtcgt cacacatgtt     1080
gtcttttgag gttggacact gctcactaga cagaaaaacc tcgtgccgga ccgaataccc     1140
ggtctgaacg agggcggccg cggtacccaa gaagtactta gagttaatta aggagttcaa     1200
acatgaggat cacccatgtc gaagctccca caccctagca taaccccttg gggcctctaa     1260
acgggtcttg aggggttttt tgctgaaagg aggaactata tccggatatc cacaggacgg     1320
gtgtggtcgc catgatcgcg tagtcgatag tggctccaag tagcgaagcg agcaggactg     1380
ggcggcgggc atgcatcgtc cattccgaca gcatcgccag tcactatggc gtgctgctag     1440
cgctatatgc gttgatgcaa tttctatgcg cacccgttct cggagcactg tccgaccgct     1500
ttggccgccg cccagtcctg ctcgcttcgc tacttggagc cactatcgac tacgcgatca     1560
tggcgaccac acccgtcctg tggatccaga tctcgatccc gcgaaattaa tacgactcac     1620
tatagggaga ccacaacggt ttccctctag atcacaagtt tgtacaaaaa agcaggctaa     1680
gaaggagata tacatatggc gtctaacttt acccaattcg ttctggttga taacggcggt     1740
acgggtgacg ttaccgtagc tccgtccaac ttcgccaacg gtgttgcgga atggattagc     1800
tctaacagcc gctctcaggc ctacaaagtc acgtgctccg ttcgtcagtc tagcgcgcag     1860
aatcgcaaat acaccatcaa agttgaagta ccgaaagtcg caacgcagac cgtaggcggc     1920
gtagaactcc cagttgcggc ctggcgctct tacctcaaca tggaactgac tattccgatt     1980
tttgcgacga actccgactg cgaactgatt gttaaggcaa tgcagggcct gctgaaagac     2040
ggtaatccga tccatctgc  aatcgctgct aactctggca tttactaata agcggacgcg     2100
ctgccaccgc tgagcaataa ctagcataac cccttggggc ctctaaacgg tcttgagggg     2160 gtttttttgct gaaaggagga actatatccg gcatgcatcg tccattccga cagcatcgcc     2220
agtcactatg gcgtgctgct agcgctatat gcgttgatgc aatttctatg cgcacccgtt     2280
ctcggagcac tgtccgaccg ctttggccgc cgcccagtcc tgctcgcttc gctacttgga     2340
gccactatcg actacgcgat catggcgacc acacccgtcc tgtaccattc cttgcggcgg     2400
cggtgctcaa cggcctcaac ctactactgg gctgcttcct aatgcaggag tcgcataagg     2460
gagagcgtcg accgatgccc ttgagagcct tcaacccagt cagctccttc cggtgggcgc     2520
ggggcatgac tatcgtcgcc gcacttatga ctgtcttctt tatcatgcaa ctcgtaggac     2580
aggtgccggc agcgctctgg gtcatttttcg gcgaggaccg cttttcgctgg agcgcgacga     2640 tgatcggcct gtcgcttgcg gtattcggaa tcttgcacgc cctcgctcaa gccttcgtca     2700
ctggtcccgc caccaaacgt ttcggcgaga gcaggccat  tatcgccggc atggcggccg     2760
acgcgctggg ctacgtcttg ctggcgttcg ccatggtcgt cacagagctg gaagcggcag     2820
cgagaattat ccgcgatcgt ggcgcggtgc ccgcaggcat gacaaacatc gtaaatgccg     2880
```

-continued

```
cgtttcgtgt ggccgtggcc gcccaggacg tgtcagcgcc gccaccacct gcaccgaatc    2940
ggcagcagcg tcgcgcgtcg aaaaagcgca caggcggcaa gaagcgataa gctgcacgaa    3000
tacctgaaaa atgttgaacg ccccgtgagc ggtaactcac agggcgtcgg ctaaccccca    3060
gtccaaacct gggagaaagc gctcaaaaat gactctagcg gattcacgag acattgacac    3120
accggcctgg aaattttccg ctgatctgtt cgacacccat cccgagctcg cgctgcgatc    3180
acgtggctgg acgagcgaag accgccgcga attcctcgct cacctgggca gagaaaattt    3240
ccagggcagc aagacccgcg acttcgccag cgcttggatc aaagacccgg acacgggaga    3300
aacacagccg aagttatacc gagttggttc aaaatcgctt gcccggtgcc agtatgttgc    3360
tctgacgcac gcgcagcacg cagccgtgct tgtcctggac attgatgtgc cgagccacca    3420
ggccggcggg aaaatcgagc acgtaaaccc cgaggtctac gcgattttgg agcgctgggc    3480
acgcctggaa aaagcgccag cttggatcgg cgtgaatcca ctgagcggga aatgccagct    3540
catctggctc attgatccgg tgtatgccgc agcaggcatg agcagcccga atatgcgcct    3600
gctggctgca acgaccgagg aaatgacccg cgtttttcggc gctgaccagg ctttttcaca    3660
taggctgagc cggtggccac tgcacgtctc cgacgatccc accgcgtacc gctggcatgc    3720
ccagcacaat cgcgtggatc gcctagctga tcttatggag gttgctcgca tgatctcagg    3780
cacagaaaaa cctaaaaaac gctatgagca ggagtttttct agcggacggg cacgtatcga    3840
agcggcaaga aaagccactg cggaagcaaa agcacttgcc acgcttgaag caagcctgcc    3900
gagcgccgct gaagcgtctg gagagctgat cgacggcgtc cgtgtcctct ggactgctcc    3960
agggcgtgcc gcccgtgatg agacggcttt tcgccacgct ttgactgtgg gataccagtt    4020
aaaagcggct ggtgagcgcc taaaagacac caagatcatc gacgcctacg agcgtgccta    4080
caccgtcgct caggcggtcg gagcagacgg ccgtgagcct gatctgccgc cgatgcgtga    4140
ccgccagacg atggcgcgac gtgtgcgcgg ctacgtcgct aaaggccagc cagtcgtccc    4200
tgctcgtcag acagagacgc agagcagccg agggcgaaaa gctctggcca ctatgggaag    4260
acgtggcggt aaaaaggccg cagaacgctg gaaagaccca aacagtgagt acgcccgagc    4320
acagcgagaa aaactagcta agtccagtca acgacaagct aggaaagcta aaggaaatcg    4380
cttgaccatt gcaggttggt ttatgactgt tgagggagag actggctcgt ggcgacaatc    4440
aatgaagcta tgtctgaatt tagcgtgtca cgtcagaccg tgaatagagc acttaagtct    4500
gcgggcattg aacttccacg aggacgccgt aaagcttccc agtaaatgtg ccatctcgta    4560
ggcagaaaac ggttccccccc gtaggggtct ctctcttggc ctcctttcta ggtcgggctg    4620
attgctcttg aagctctcta gggggggctca caccataggc agataacggt tccccaccgg    4680
ctcacctcgt aagcgcacaa ggactgctcc caatgccgca agcactcagg cgcaagggc    4740 tgctaaagga agcggaacac gtagaaagcc agtccgcaga aacggtgctg accccggatg    4800
aatgtcagct actgggctat ctggacaagg gaaaacgcaa gcgcaaagag aaagcaggta    4860
gcttgcagtg ggcttacatg gcgatagcta gactgggcgg ttttatggac agcaagcgaa    4920
ccggaattgc cagctggggc gccctctggt aaggttggga agccctgcaa agtaaactgg    4980
atggctttct tgccgccaag gatctgatgg cgcaggggat caagatctga tcaagagaca    5040
ggatgaggat cgtttcgcat gattgaacaa gatggattgc acgcaggttc tccggccgct    5100
tgggtggaga ggctattcgg ctatgactgg gcacaacaga caatcggctg ctctgatgcc    5160
gccgtgttcc ggctgtcagc gcaggggcgc ccggttcttt ttgtcaagac cgacctgtcc    5220
```

-continued

```
ggtgccctga atgaactcca agacgaggca gcgcggctat cgtggctggc cacgacgggc   5280
gttccttgcg cagctgtgct cgacgttgtc actgaagcgg gaagggactg gctgctattg   5340
ggcgaagtgc cggggcagga tctcctgtca tctcaccttg ctcctgccga gaaagtatcc   5400
atcatggctg atgcaatgcg gcggctgcat acgcttgatc cggctacctg cccattcgac   5460
caccaagcga aacatcgcat cgagcgagca cgtactcgga tggaagccgg tcttgtcgat   5520
caggatgatc tggacgaaga gcatcagggg ctcgcgccag ccgaactgtt cgccaggctc   5580
aaggcgcgga tgcccgacgg cgaggatctc gtcgtgaccc atggcgatgc ctgcttgccg   5640
aatatcatgg tggaaaatgg ccgcttttct ggattcatcg actgtggccg gctgggtgtg   5700
gcggaccgct atcaggacat agcgttggct acccgtgata ttgctgaaga gcttggcggc   5760
gaatgggctg accgcttcct cgtgctttac ggtatcgccg ctcccgattc gcagcgcatc   5820
gccttctatc gccttcttga cgagttcttc tgagcgggac tctggggttc gctagaggat   5880
cgatcctttt taacccatca catatacctg ccgttcacta ttatttagtg aaatgagata   5940
ttatgatatt ttctgaattg tgattaaaaa ggcaacttta tgcccatgca acagaaacta   6000
taaaaaatac agagaatgaa aagaaacaga tagatttttt agttctttag gcccgtagtc   6060
tgcaaatcct tttatgattt tctatcaaac aaaagaggaa aatagaccag ttgcaatcca   6120
aacgagagtc taacgacgcg aggctggatg gccttcccca ttatgattct tctcgcttcc   6180
ggcggcatcg ggatgcccgc gttgcaggcc atgctgtcca ggcaggtaga tgacgaccat   6240
cagggacagc ttcaaggatc gctcgcggct cttaccagcc taacttcgat cattggaccg   6300
ctgatcgtca cggcgattta tgccgcctcg gcgagcacat ggaacgggtt ggcatggatt   6360
gtaggcgccg ccctatacct tgtctgcctc cccgcgttgc gtcgcggtgc atggagccgg   6420
gccacctcga cctgaatgga agccggcggc acctcgctaa cggattcacc actccaagaa   6480
ttggagccaa tcaattcttg cggagaactg tgaatgcgca aaccaaccct tggcagaaca   6540
tatccatcgc gtccgccatc tccagcagcc gcacgcggcg catctcgggc agcgttgggt   6600
cctggccacg ggtgcgcatg atcgtgctcc tgtcgttgag gacccggcta ggctggcggg   6660
gttgccttac tggttagcag aatgaatcac cgatacgcga gcgaacgtga agcgactgct   6720
gctgcaaaac gtctgcgacc tgagcaacaa catgaatggt cttcggtttc cgtgtttcgt   6780
aaagtctgga aacgcggaag tcagcgccct gcaccattat gttccggatc tgcatcgcag   6840
gatgctgctg gctaccctgt ggaacaccta catctgtatt aacgaagcgc tggcattgac   6900
cctgagtgat ttttctctgg tcccgccgca tccataccgc cagttgttta ccctcacaac   6960
gttccagtaa ccgggcatgt tcatcatcag taacccgtat cgtgagcatc ctctctcgtt   7020
tcatcggtat cattaccccc atgaacagaa atccccctta cacggaggca tcagtgacca   7080
aacaggaaaa aaccgccctt aacatggccc gctttatcag aagccagaca ttaacgcttc   7140
tggagaaact caacgagctg gacgcggatg aacaggcaga catctgtgaa tcgcttcacg   7200
accacgctga tgagctttac cgcagctgcc tcgcgcgttt cggtgatgac ggtgaaaacc   7260
tctgacacat gcagctcccg gagacggtca cagcttgtct gtaagcggat gccgggagca   7320
gacaagcccg tcaggcgcgt cagcgggtg ttggcgggtg tcgggcgca gccatgaccc   7380 agtcacgtag cgatagcgga gtgtatactg gcttaactat gcggcatcag agcagattgt   7440
actgagagtg caccatatgc ggtgtgaaat accgcacaga tgcgtaagga gaaaataccg   7500
catcaggcgc tcttccgctt cctcgctcac tgactcgctg cgctcggtcg ttcggctgcg   7560
gcgagcggta tcagctcact caaaggcggt aatacggtta tccacagaat cagggggataa   7620
```

```
cgcaggaaag aacatgtgag caaaaggcca gcaaaaggcc aggaaccgta aaaaggccgc      7680
gttgctggcg tttttccata ggctccgccc ccctgacgag catcacaaaa atcgacgctc      7740
aagtcagagg tggcgaaacc cgacaggact ataaagatac caggcgtttc ccctggaag       7800 ctccctcgtg cgctctcctg ttccgaccct gccgcttacc ggatacctgt ccgcctttct      7860
cccttcggga agcgtggcgc tttctcatag ctcacgctgt aggtatctca gttcggtgta      7920
ggtcgttcgc tccaagctgg gctgtgtgca cgaacccccc gttcagcccg accgctgcgc      7980
cttatccggt aactatcgtc ttgagtccaa cccggtaaga cacgacttat cgccactggc      8040
agcagccact ggtaacagga ttagcagagc gaggtatgta ggcggtgcta cagagttctt      8100
gaagtggtgg cctaactacg gctacactag aaggacagta tttggtatct gcgctctgct      8160
gaagccagtt accttcggaa aaagagttgg tagctcttga tccggcaaac aaaccaccgc      8220
tggtagcggt ggtttttttg tttgcaagca gcagattacg cgcagaaaaa aaggatctca      8280
agaagatcct ttgatctttt ctacggggtc tgacgctcag tggaacgaaa actcacgtta      8340
agggattttg gtcatgagat tatcaaaaag gatcttcacc tagatccttt taaattaaaa      8400
atgaagtttt aaatcaatct aaagtatata tgagtaaact tggtctgaca gttaccaatg      8460
cttaatcagt gaggcaccta tctcagcgat ctgtctattt cgttcatcca tagttgcctg      8520
actccccgtc gtgtagataa ctacgatacg ggagggctta ccatctggcc ccagtgctgc      8580
aatgataccg cgagacccac gctcaccggc tccagattta tcagcaataa accagccagc      8640
cggaagggcc gagcgcagaa gtggtcctgc aactttatcc gcctccatcc agtctattaa      8700
ttgttgccgg gaagctagag taagtagttc gccagttaat agtttgcgca acgttgttgc      8760
cattgctgca ggcatcgtgg tgtcacgctc gtcgtttggt atggcttcat tcagctccgg      8820
ttcccaacga tcaaggcgag ttacatgatc ccccatgttg tgcaaaaaag cggttagctc      8880
cttcggtcct ccgatcgttg tcagaagtaa gttggccgca gtgttatcac tcatggttat      8940
ggcagcactg cataattctc ttactgtcat gccatccgta agatgctttt ctgtgactgg      9000
tgagtactca accaagtcat tctgagaata gtgtatgcgg cgaccgagtt gctcttgccc      9060
ggcgtcaaca cgggataata ccgcgccaca tagcagaact ttaaaagtgc tcatcattgg      9120
aaaacgttct cgggcgcaa aactctcaag gatcttaccg ctgttgagat ccagttcgat      9180
gtaacccact cgtgcaccca actgatcttc agcatctttt actttcacca gcgtttctgg      9240
gtgagcaaaa acaggaaggc aaaatgccgc aaaaaaggga ataagggcga cacggaaatg      9300
ttgaatactc atactcttcc tttttcaata ttattgaagc atttatcagg gttattgtct      9360
catgagcgga tacatatttg aatgtattta gaaaaataaa caaataggg ttccgcgcac       9420 atttccccga aaagtgccac ctgacgtcta agaaaccatt attatcatga cattaaccta      9480
taaaaatagg cgtatcacga ggccctttcg tcttcaagaa                            9520
```

<210> SEQ ID NO 38
<211> LENGTH: 8718
<212> TYPE: DNA
<213> ORGANISM: Artificial Sequence
<220> FEATURE:
<223> OTHER INFORMATION: Recombinant plasmid pAPSE10437; beta actin
      hairpin - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature

```
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1990)..(5332)
<223> OTHER INFORMATION: synthetic DNA (SEQ ID NO: 30)

<400> SEQUENCE: 38
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta atacccatg tccaggcgcg      360 ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccgtgc cgtcttcccc tcgatcgtcg gtcgcccaag      540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttccctttcc agcgggatgc     720
tttatctaaa cgcaacatga ggatcaccca tgtcgccaca tcgcttccta gttccgctgg     780
gatccatcgt tggcggccga agccgccatt ccatagtgag ttctggcgcg cctcatccca     840
gttggtgatg ataccgtgtt cgatggggta tttcagggtg aggataccctc ttttgctttg     900 ggcttcatct cctacgtatg agtccttttg tcccataccg accatgactc cttgatgcct     960
tgggcgaccg acgatcgagg ggaagacggc acggggtgcg tcatctcctg cgaaaccggc    1020
tttgcacata ccggatccat tgtctacgac aagagccgct acatcgtcgt cacacatgtt    1080
gtcttttgag gttggacact gctcactaga cagaaaaacc tcgtgccgga ccgaataccc    1140
ggtctgaacg agggcggccg cggtacccaa gaagtactta gagttaatta aggagttcaa    1200
acatgaggat cacccatgtc gaagctccca caccctagca taaccccttg gggcctctaa    1260
```

-continued

```
acgggtcttg aggggttttt tgctgaaagg aggaactata tccggatatc cacaggacgg    1320
gtgtggtcgc catgatcgcg tagtcgatag tggctccaag tagcgaagcg agcaggactg    1380
ggcggcgggc atgcatcgtc cattccgaca gcatcgccag tcactatggc gtgctgctag    1440
cgctatatgc gttgatgcaa tttctatgcg cacccgttct cggagcactg tccgaccgct    1500
ttggccgccg cccagtcctg ctcgcttcgc tacttggagc cactatcgac tacgcgatca    1560
tggcgaccac acccgtcctg taccattcct tgcggcggcg gtgctcaacg gcctcaacct    1620
actactgggc tgcttcctaa tgcaggagtc gcataaggga gagcgtcgac cgatgccctt    1680
gagagccttc aacccagtca gctccttccg gtgggcgcgg ggcatgacta tcgtcgccgc    1740
acttatgact gtcttcttta tcatgcaact cgtaggacag gtgccggcag cgctctgggt    1800
cattttcggc gaggaccgct ttcgctggag cgcgacgatg atcggcctgt cgcttgcggt    1860
attcggaatc ttgcacgccc tcgctcaagc cttcgtcact ggtcccgcca ccaaacgttt    1920
cggcgagaag caggccatta tcgccggcat ggcggccgac gcgctgggct acgtcttgct    1980
ggcgttcgcc atggtcgtca cagagctgga agcggcagcg agaattatcc gcgatcgtgg    2040
cgcggtgccc gcaggcatga caaacatcgt aaatgccgcg tttcgtgtgg ccgtggccgc    2100
ccaggacgtg tcagcgccgc caccacctgc accgaatcgg cagcagcgtc gcgcgtcgaa    2160
aaagcgcaca ggcggcaaga agcgataagc tgcacgaata cctgaaaaat gttgaacgcc    2220
ccgtgagcgg taactcacag ggcgtcggct aacccccagt ccaaacctgg gagaaagcgc    2280
tcaaaaatga ctctagcgga ttcacgagac attgacacac cggcctggaa attttccgct    2340
gatctgttcg acacccatcc cgagctcgcg ctgcgatcac gtggctggac gagcgaagac    2400
cgccgcgaat cctcgctca cctgggcaga gaaaatttcc agggcagcaa gacccgcgac    2460
ttcgccagcg cttggatcaa agacccggac acgggagaaa cacagccgaa gttataccga    2520
gttggttcaa aatcgcttgc ccggtgccag tatgttgctc tgacgcacgc gcagcacgca    2580
gccgtgcttg tcctggacat tgatgtgccg agccaccagg ccggcgggaa aatcgagcac    2640
gtaaaccccg aggtctacgc gattttggag cgctgggcac gcctggaaaa agcgccagct    2700
tggatcggcg tgaatccact gagcgggaaa tgccagctca tctggctcat tgatccggtg    2760
tatgccgcag caggcatgag cagcccgaat atgcgcctgc tggctgcaac gaccgaggaa    2820
atgacccgcg ttttcggcgc tgaccaggct ttttcacata ggctgagccg gtggccactg    2880
cacgtctccg acgatcccac cgcgtaccgc tggcatgccc agcacaatcg cgtggatcgc    2940
ctagctgatc ttatggaggt tgctcgcatg atctcaggca cagaaaaacc taaaaaacgc    3000
tatgagcagg agttttctag cggacgggca cgtatcgaag cggcaagaaa agccactgcg    3060
gaagcaaaag cacttgccac gcttgaagca agcctgccga gcgccgctga agcgtctgga    3120
gagctgatcg acggcgtccg tgtcctctgg actgctccag ggcgtgccgc ccgtgatgag    3180
acggcttttc gccacgcttt gactgtggga taccagttaa aagcggctgg tgagcgccta    3240
aaagacacca agatcatcga cgcctacgag cgtgcctaca ccgtcgctca ggcggtcgga    3300
gcagacggcc gtgagcctga tctgccgccg atgcgtgacc gccagacgat ggcgcgacgt    3360
gtgcgcggct acgtcgctaa aggccagcca gtcgtccctg ctcgtcagac agagacgcag    3420
agcagccgag ggcgaaaagc tctggccact atgggaagac gtggcggtaa aaaggccgca    3480
gaacgctgga aagacccaaa cagtgagtac gcccgagcac agcgagaaaa actagctaag    3540
tccagtcaac gacaagctag gaaagctaaa ggaaatcgct tgaccattgc aggttggttt    3600
atgactgttg agggagagac tggctcgtgg cgacaatcaa tgaagctatg tctgaattta    3660
```

```
gcgtgtcacg tcagaccgtg aatagagcac ttaagtctgc gggcattgaa cttccacgag    3720
gacgccgtaa agcttcccag taaatgtgcc atctcgtagg cagaaaacgg ttcccccgt     3780 aggggtctct ctcttggcct cctttctagg tcgggctgat tgctcttgaa gctctctagg    3840
ggggctcaca ccataggcag ataacggttc cccaccggct cacctcgtaa gcgcacaagg    3900
actgctccca atgccgcaag cactcagggc gcaagggctg ctaaaggaag cggaacacgt    3960
agaaagccag tccgcagaaa cggtgctgac cccggatgaa tgtcagctac tgggctatct    4020
ggacaaggga aaacgcaagc gcaaagagaa agcaggtagc ttgcagtggg cttacatggc    4080
gatagctaga ctgggcggtt ttatggacag caagcgaacc ggaattgcca gctggggcgc    4140
cctctggtaa ggttgggaag ccctgcaaag taaactggat ggctttcttg ccgccaagga    4200
tctgatggcg caggggatca agatctgatc aagagacagg atgaggatcg tttcgcatga    4260
ttgaacaaga tggattgcac gcaggttctc cggccgcttg ggtggagagg ctattcggct    4320
atgactgggc acaacagaca atcggctgct ctgatgccgc cgtgttccgg ctgtcagcgc    4380
aggggcgccc ggttcttttt gtcaagaccg acctgtccgg tgccctgaat gaactccaag    4440
acgaggcagc gcggctatcg tggctggcca cgacgggcgt tccttgcgca gctgtgctcg    4500
acgttgtcac tgaagcggga agggactggc tgctattggg cgaagtgccg gggcaggatc    4560
tcctgtcatc tcaccttgct cctgccgaga aagtatccat catggctgat gcaatgcggc    4620
ggctgcatac gcttgatccg gctacctgcc cattcgacca ccaagcgaaa catcgcatcg    4680
agcgagcacg tactcggatg gaagccggtc ttgtcgatca ggatgatctg gacgaagagc    4740
atcaggggct cgcgccagcc gaactgttcg ccaggctcaa ggcgcggatg cccgacggcg    4800
aggatctcgt cgtgacccat ggcgatgcct gcttgccgaa tatcatggtg gaaaatggcc    4860
gcttttctgg attcatcgac tgtggccggc tgggtgtggc ggaccgctat caggacatag    4920
cgttggctac ccgtgatatt gctgaagagc ttggcggcga atgggctgac cgcttcctcg    4980
tgctttacgg tatcgccgct cccgattcgc agcgcatcgc cttctatcgc cttcttgacg    5040
agttcttctg agcgggactc tggggttcgc tagaggatcg atccttttta acccatcaca    5100
tatacctgcc gttcactatt atttagtgaa atgagatatt atgatatttt ctgaattgtg    5160
attaaaaagg caactttatg cccatgcaac agaaactata aaaaatacag agaatgaaaa    5220
gaaacagata gattttttag ttctttaggc ccgtagtctg caaatccttt tatgattttc    5280
tatcaaacaa aagaggaaaa tagaccagtt gcaatccaaa cgagagtcta acgacgcgag    5340
gctggatggc cttccccatt atgattcttc tcgcttccgg cggcatcggg atgcccgcgt    5400
tgcaggccat gctgtccagg caggtagatg acgaccatca gggacagctt caaggatcgc    5460
tcgcggctct taccagccta acttcgatca ttggaccgct gatcgtcacg gcgatttatg    5520
ccgcctcggc gagcacatgg aacgggttgg catggattgt aggcgccgcc ctataccttg    5580
tctgcctccc cgcgttgcgt cgcggtgcat ggagccgggc cacctcgacc tgaatggaag    5640
ccggcggcac ctcgctaacg gattcaccac tccaagaatt ggagccaatc aattcttgcg    5700
gagaactgtg aatgcgcaaa ccaacccttg gcagaacata tccatcgcgt ccgccatctc    5760
cagcagccgc acgcggcgca tctcgggcag cgttgggtcc tggccacggg tgcgcatgat    5820
cgtgctcctg tcgttgagga cccggctagg ctggcggggt tgccttactg gttagcagaa    5880
tgaatcaccg atacgcgagc gaacgtgaag cgactgctgc tgcaaaacgt ctgcgacctg    5940
agcaacaaca tgaatggtct tcggtttccg tgtttcgtaa agtctggaaa cgcggaagtc    6000
```

-continued

```
agcgccctgc accattatgt tccggatctg catcgcagga tgctgctggc taccctgtgg      6060
aacacctaca tctgtattaa cgaagcgctg gcattgaccc tgagtgattt ttctctggtc      6120
ccgccgcatc cataccgcca gttgtttacc ctcacaacgt tccagtaacc gggcatgttc      6180
atcatcagta acccgtatcg tgagcatcct ctctcgtttc atcggtatca ttaccccat       6240 gaacagaaat cccccttaca cggaggcatc agtgaccaaa caggaaaaaa ccgcccttaa      6300
catggcccgc tttatcagaa gccagacatt aacgcttctg gagaaactca acgagctgga      6360
cgcggatgaa caggcagaca tctgtgaatc gcttcacgac cacgctgatg agctttaccg      6420
cagctgcctc gcgcgtttcg gtgatgacgg tgaaaacctc tgacacatgc agctcccgga      6480
gacggtcaca gcttgtctgt aagcggatgc cgggagcaga caagcccgtc agggcgcgtc      6540
agcgggtgtt ggcgggtgtc ggggcgcagc catgacccag tcacgtagcg atagcggagt      6600
gtatactggc ttaactatgc ggcatcagag cagattgtac tgagagtgca ccatatgcgg      6660
tgtgaaatac cgcacagatg cgtaaggaga aaataccgca tcaggcgctc ttccgcttcc      6720
tcgctcactg actcgctgcg ctcggtcgtt cggctgcggc gagcggtatc agctcactca      6780
aaggcggtaa tacggttatc cacagaatca ggggataacg caggaaagaa catgtgagca      6840
aaaggccagc aaaaggccag gaaccgtaaa aaggccgcgt tgctggcgtt tttccatagg      6900
ctccgccccc ctgacgagca tcacaaaaat cgacgctcaa gtcagaggtg cgaaacccg       6960 acaggactat aaagatacca ggcgtttccc cctggaagct ccctcgtgcg ctctcctgtt      7020
ccgaccctgc cgcttaccgg atacctgtcc gcctttctcc cttcgggaag cgtggcgctt      7080
tctcatagct cacgctgtag gtatctcagt tcggtgtagg tcgttcgctc caagctgggc      7140
tgtgtgcacg aaccccccgt tcagcccgac cgctgcgcct tatccggtaa ctatcgtctt      7200
gagtccaacc cggtaagaca cgacttatcg ccactggcag cagccactgg taacaggatt      7260
agcagagcga ggtatgtagg cggtgctaca gagttcttga agtggtggcc taactacggc      7320
tacactagaa ggacagtatt tggtatctgc gctctgctga agccagttac cttcggaaaa      7380
agagttggta gctcttgatc cggcaaacaa accaccgctg gtagcggtgg tttttttgtt      7440
tgcaagcagc agattacgcg cagaaaaaaa ggatctcaag aagatccttt gatcttttct      7500
acggggtctg acgctcagtg gaacgaaaac tcacgttaag ggattttggt catgagatta      7560
tcaaaaagga tcttcaccta gatccttta aattaaaaat gaagttttaa atcaatctaa       7620
agtatatatg agtaaacttg gtctgacagt taccaatgct taatcagtga ggcacctatc      7680
tcagcgatct gtctatttcg ttcatccata gttgcctgac tccccgtcgt gtagataact      7740
acgatacggg agggcttacc atctggcccc agtgctgcaa tgataccgcg agacccacgc      7800
tcaccggctc cagatttatc agcaataaac cagccagccg gaagggccga gcgcagaagt      7860
ggtcctgcaa ctttatccgc ctccatccag tctattaatt gttgccggga agctagagta      7920
agtagttcgc cagttaatag tttgcgcaac gttgttgcca ttgctgcagg catcgtggtg      7980
tcacgctcgt cgtttggtat ggcttcattc agctccggtt cccaacgatc aaggcgagtt      8040
acatgatccc ccatgttgtg caaaaaagcg gttagctcct tcggtcctcc gatcgttgtc      8100
agaagtaagt tggccgcagt gttatcactc atggttatgg cagcactgca taattctctt      8160
actgtcatgc catccgtaag atgctttct gtgactggtg agtactcaac caagtcattc       8220
tgagaatagt gtatgcggcg accgagttgc tcttgcccgg cgtcaacacg ggataatacc      8280
gcgccacata gcagaacttt aaaagtgctc atcattggaa aacgttcttc ggggcgaaaa      8340
ctctcaagga tcttaccgct gttgagatcc agttcgatgt aacccactcg tgcacccaac      8400
```

```
tgatcttcag catcttttac tttcaccagc gtttctgggt gagcaaaaac aggaaggcaa      8460
aatgccgcaa aaaagggaat aagggcgaca cggaaatgtt gaatactcat actcttcctt      8520
tttcaatatt attgaagcat ttatcagggt tattgtctca tgagcggata catatttgaa      8580
tgtatttaga aaaataaaca aatagggggtt ccgcgcacat ttccccgaaa agtgccacct      8640
gacgtctaag aaaccattat tatcatgaca ttaacctata aaaataggcg tatcacgagg      8700
ccctttcgtc ttcaagaa                                                    8718
```

```
<210> SEQ ID NO 39
<211> LENGTH: 7250
<212> TYPE: DNA
<213> ORGANISM: Artificial Sequence
<220> FEATURE:
<223> OTHER INFORMATION: Recombinant plasmid pAPSE10439; beta actin
      hairpin - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional prmoter
<220> FEATURE:
<221> NAME/KEY: misc_feature
<222> LOCATION: (2844)..(2851)
<223> OTHER INFORMATION: restriction endonuclease AsiSI recognition
      sequence
<220> FEATURE:
<221> NAME/KEY: misc_feature
<222> LOCATION: (2852)..(3146)
<223> OTHER INFORMATION: beta actin sense gene fragment
<220> FEATURE:
<221> NAME/KEY: misc_feature
<222> LOCATION: (3146)..(3153)
<223> OTHER INFORMATION: restriction endonuclease PmeI recognition site
<220> FEATURE:
<221> NAME/KEY: misc_feature
<222> LOCATION: (3311)..(3605)
<223> OTHER INFORMATION: beta actin antisense strand gene fragment
<220> FEATURE:
<221> NAME/KEY: terminator
<222> LOCATION: (3657)..(3846)
<223> OTHER INFORMATION: yeast CYC1 terminator
<220> FEATURE:
<221> NAME/KEY: misc_feature
<222> LOCATION: (5840)..(7182)
<223> OTHER INFORMATION: yeast 2 micron ori

<400> SEQUENCE: 39
tcgcgcgttt cggtgatgac ggtgaaaacc tctgacacat gcagctcccg gagacggtca        60
cagcttgtct gtaagcggat gccgggagca gacaagcccg tcaggcgcg tcagcgggtg       120 ttggcgggtg tcgggctgg cttaactatg cggcatcaga gcagattgta ctgagagtgc       180
accataaacg acattactat atatataata taggaagcat ttaatagaca gcatcgtaat      240
atatgtgtac tttgcagtta tgacgccaga tggcagtagt ggaagatatt ctttattgaa      300
```

-continued

```
aaatagcttg tcaccttacg tacaatcttg atccggagct tttctttttt tgccgattaa      360
gaattaattc ggtcgaaaaa agaaaaggag agggccaaga gggagggcat tggtgactat      420
tgagcacgtg agtatacgtg attaagcaca caaaggcagc ttggagtatg tctgttatta      480
atttcacagt tagttctggt ccattggtga aagtttgcgg cttgcagagc acagaggccg      540
cagaatgtgc tctagattcc gatgctgact tgctgggtat tatatgtgtg cccaatagaa      600
agagaacaat tgacccggtt attgcaagga aaatttcaag tcttgtaaaa gcatataaaa      660
atagttcagg cactccgaaa tacttggttg gcgtgtttcg taatcaacct aaggaggatg      720
ttttggctct ggtcaatgat tacggcattg atatcgtcca actgcatgga gatgagtcgt      780
ggcaagaata ccaagagttc ctcggtttgc cagttattaa aagactcgta tttccaaaag      840
actgcaacat actactcagt gcagcttcac agaaacctca ttcgtttatt cccttgtttg      900
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgg tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa tttttgttaa atcagctcat tttttaacca ataggccgaa     1320
atcggcaaaa tcccttataa atcaaaagaa tagaccgaga tagggttgag tgttgttcca     1380
gtttggaaca agagtccact attaaagaac gtggactcca acgtcaaagg gcgaaaaacc     1440
gtctatcagg gcgatggccc actacgtgaa ccatcaccct aatcaagttt tttggggtcg     1500
aggtgccgta aagcactaaa tcggaaccct aaagggagcc cccgatttag agcttgacgg     1560
ggaaagccgg cgaacgtggc gagaaaggaa gggaagaaag cgaaaggagc gggcgctagg     1620
gcgctggcaa gtgtagcggt cacgctgcgc gtaaccacca cacccgccgc gcttaatgcg     1680
ccgctacagg gcgcgtcgcg ccattcgcca ttcaggctgc gcaactgttg ggaagggcga     1740
tcggtgcggg cctcttcgct attacgccag ctgaattgga cgacctcat gctatacctg      1800 agaaagcaac ctgacctaca ggaaagagtt actcaagaat aagaattttc gttttaaaac     1860
ctaagagtca ctttaaaatt tgtatacact tatttttttt ataacttatt taataataaa     1920
aatcataaat cataagaaat tcgcttattt agaagtgtca acaacgtatc taccaacgat     1980
ttgacccttt tccatctttt cgtaaatttc tggcaaggta gacaagccga caaccttgat     2040
tggagacttg accaaacctc tggcgaagaa ttgttaatta agagctcaga tcttatcgtc     2100
gtcatccttg taatccatcg atactagtgc ggccgcccct tagtgagggt tgaattcgaa     2160
ttttcaaaaa ttcttacttt tttttggat ggacgcaaag aagtttaata atcatattac      2220
atggcattac caccatatac atatccatat acatatccat atctaatctt acttatatgt     2280
tgtggaaatg taaagagccc cattatctta gcctaaaaaa accttctctt tggaactttc     2340
agtaatacgc ttaactgctc attgctatat tgaagtacgg attagaagcc gccgagcggg     2400
tgacagccct ccgaaggaag actctcctcc gtgcgtcctc gtcttcaccg gtcgcgttcc     2460
tgaaacgcag atgtgcctcg cgccgcactg ctccgaacaa taaagattct acaatactag     2520
cttttatggt tatgaagagg aaaaattggc agtaacctgg ccccacaaac cttcaaatga     2580
acgaatcaaa ttaacaacca taggatgata atgcgattag ttttttagcc ttatttctgg     2640
ggtaattaat cagcgaagcg atgatttttg atctattaac agatatataa atgcaaaaac     2700
```

-continued

```
tgcataacca ctttaactaa tactttcaac attttcggtt tgtattactt cttattcaaa      2760
tgtaataaaa gtatcaacaa aaaattgtta atatacctct atactttaac gtcaaggaga      2820
aaaaaccccg gatccattta aatgcgatcg cgcacgaggt ttttctgtct agtgagcagt      2880
gtccaacctc aaaagacaac atgtgtgacg acgatgtagc ggctcttgtc gtagacaatg      2940
gatccggtat gtgcaaagcc ggtttcgcag gagatgacgc accccgtgcc gtcttcccct      3000
cgatcgtcgg tcgcccaagg catcaaggag tcatggtcgg tatgggacaa aaggactcat      3060
acgtaggaga tgaagcccaa agcaaaagag gtatcctcac cctgaaatac cccatcgaac      3120
acggtatcat caccaactgg gatgagttta aaccctctag ctgctttaca aagtactggt      3180 tcccttttcca gcgggatgct ttatctaaac gcaatgagag aggtattcct caggccacat      3240
cgcttcctag ttccgctggg atccatcgtt ggcggccgaa gccgccattc catagtgagt      3300
tctggcgcgc ctcatcccag ttggtgatga taccgtgttc gatggggtat ttcagggtga      3360
ggatacctct tttgctttgg gcttcatctc ctacgtatga gtccttttgt cccataccga      3420
ccatgactcc ttgatgcctt gggcgaccga cgatcgaggg gaagacggca cggggtgcgt      3480
catctcctgc gaaaccggct ttgcacatac cggatccatt gtctacgaca agagccgcta      3540
catcgtcgtc acacatgttg tcttttgagg ttggacactg ctcactagac agaaaaacct      3600
cgtgccggac cgaatacccg gtctgaacga gggcggccgc ccgcgggcta gctaagatcc      3660
gctctaaccg aaaaggaagg agttagacaa cctgaagtct aggtccctat ttattttttt      3720
atagttatgt tagtattaag aacgttattt atatttcaaa tttttctttt ttttctgtac      3780
agacgcgtgt acgcatgtaa cattatactg aaaaccttgc ttgagaaggt tttgggacgc      3840
tcgaagatcc agctgcatta atgaatcggc caacgcgcgg ggagaggcgg tttgcgtatt      3900
gggcgctctt ccgcttcctc gctcactgac tcgctgcgct cggtcgttcg gctgcggcga      3960
gcggtatcag ctcactcaaa ggcggtaata cggttatcca cagaatcagg ggataacgca      4020
ggaaagaaca tgtgagcaaa aggccagcaa aaggccagga accgtaaaaa ggccgcgttg      4080
ctggcgtttt tccataggct ccgcccccct gacgagcatc acaaaaatcg acgctcaagt      4140
cagaggtggc gaaacccgac aggactataa agataccagg cgtttccccc tggaagctcc      4200
ctcgtgcgct ctcctgttcc gaccctgccg cttaccggat acctgtccgc ctttctccct      4260
tcgggaagcg tggcgctttc tcatagctca cgctgtaggt atctcagttc ggtgtaggtc      4320
gttcgctcca gctgggctg tgtgcacgaa ccccccgttc agcccgaccg ctgcgcctta      4380
tccggtaact atcgtcttga gtccaacccg gtaagacacg acttatcgcc actggcagca      4440
gccactggta acaggattag cagagcgagg tatgtaggcg gtgctacaga gttcttgaag      4500
tggtggccta actacggcta cactagaagg acagtatttg gtatctgcgc tctgctgaag      4560
ccagttacct tcggaaaaag agttggtagc tcttgatccg gcaaacaaac caccgctggt      4620
agcggtggtt ttttgtttg caagcagcag attacgcgca gaaaaaaagg atctcaagaa      4680
gatcctttga tcttttctac ggggtctgac gctcagtgga acgaaaactc acgttaaggg      4740
attttggtca tgagattatc aaaaaggatc ttcacctaga tccttttaaa ttaaaaatga      4800
agttttaaat caatctaaag tatatatgag taaacttggt ctgacagtta ccaatgctta      4860
atcagtgagg cacctatctc agcgatctgt ctatttcgtt catccatagt tgcctgactc      4920
cccgtcgtgt agataactac gatacgggag ggcttaccat ctggccccag tgctgcaatg      4980
ataccgcgag acccacgctc accggctcca gatttatcag caataaacca gccagccgga      5040
```

-continued

```
agggccgagc gcagaagtgg tcctgcaact ttatccgcct ccatccagtc tattaattgt     5100
tgccgggaag ctagagtaag tagttcgcca gttaatagtt tgcgcaacgt tgttgccatt     5160
gctacaggca tcgtggtgtc acgctcgtcg tttggtatgg cttcattcag ctccggttcc     5220
caacgatcaa ggcgagttac atgatccccc atgttgtgca aaaaagcggt tagctccttc     5280
ggtcctccga tcgttgtcag aagtaagttg gccgcagtgt tatcactcat ggttatggca     5340
gcactgcata attctcttac tgtcatgcca tccgtaagat gcttttctgt gactggtgag     5400
tactcaacca agtcattctg agaatagtgt atgcggcgac cgagttgctc ttgcccggcg     5460
tcaatacggg ataataccgc gccacatagc agaactttaa aagtgctcat cattggaaaa     5520
cgttcttcgg ggcgaaaact ctcaaggatc ttaccgctgt tgagatccag ttcgatgtaa     5580
cccactcgtg cacccaactg atcttcagca tcttttactt tcaccagcgt ttctgggtga     5640
gcaaaaacag gaaggcaaaa tgccgcaaaa aagggaataa gggcgacacg gaaatgttga     5700
atactcatac tcttcctttt tcaatattat tgaagcattt atcagggtta ttgtctcatg     5760
agcggataca tatttgaatg tatttagaaa aataaacaaa taggggttcc gcgcacattt     5820
ccccgaaaag tgccacctga acgaagcatc tgtgcttcat tttgtagaac aaaaatgcaa     5880
cgcgagagcg ctaatttttc aaacaaagaa tctgagctgc atttttacag aacagaaatg     5940
caacgcgaaa gcgctatttt accaacgaag aatctgtgct tcatttttgt aaaacaaaaa     6000
tgcaacgcga gagcgctaat ttttcaaaca agaatctga gctgcatttt tacagaacag     6060
aaatgcaacg cgagagcgct attttaccaa caaagaatct atacttcttt tttgttctac     6120
aaaaatgcat cccgagagcg ctattttct aacaaagcat cttagattac ttttttttctc     6180 ctttgtgcgc tctataatgc agtctcttga taacttttg cactgtaggt ccgttaaggt      6240
tagaagaagg ctactttggt gtctatttc tcttccataa aaaaagcctg actccacttc      6300
ccgcgtttac tgattactag cgaagctgcg ggtgcatttt ttcaagataa aggcatcccc     6360
gattatattc tataccgatg tggattgcgc atacttgtg aacagaaagt gatagcgttg      6420
atgattcttc attggtcaga aaattatgaa cggtttcttc tattttgtct ctatatacta     6480
cgtataggaa atgtttacat tttcgtattg ttttcgattc actctatgaa tagttcttac     6540
tacaattttt ttgtctaaag agtaatacta gagataaaca taaaaaatgt agaggtcgag     6600
tttagatgca agttcaagga gcgaaaggtg gatgggtagg ttatataggg atatagcaca     6660
gagatatata gcaaagagat acttttgagc aatgtttgtg gaagcggtat tcgcaatatt     6720
ttagtagctc gttacagtcc ggtgcgtttt tggttttttg aaagtgcgtc ttcagagcgc     6780
ttttggtttt caaaagcgct ctgaagttcc tatactttct agagaatagg aacttcggaa     6840
taggaacttc aaagcgtttc cgaaaacgag cgcttccgaa aatgcaacgc gagctgcgca     6900
catacagctc actgttcacg tcgcacctat atctgcgtgt tgcctgtata tatatataca     6960
tgagaagaac ggcatagtgc gtgtttatgc ttaaatgcgt acttatatgc gtctatttat     7020
gtaggatgaa aggtagtcta gtacctcctg tgatattatc ccattccatg cggggtatcg     7080
tatgcttcct tcagcactac cctttagctg ttctatatgc tgccactcct caattggatt     7140
agtctcatcc ttcaatgcta tcatttcctt tgatattgga tcatattaag aaaccattat     7200
tatcatgaca ttaacctata aaaataggcg tatcacgagg cccttttcgtc              7250
```

<210> SEQ ID NO 40
<211> LENGTH: 7582
<212> TYPE: DNA
<213> ORGANISM: Artificial Sequence
<220> FEATURE:
<223> OTHER INFORMATION: Recombinant plasmid pAPSE1440; beta actin
     hairpin + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3183)
<223> OTHER INFORMATION: restriction endonuclease AsiSI recognition
     sequence
<220> FEATURE:
<221> NAME/KEY: misc_feature
<222> LOCATION: (3185)..(3478)
<223> OTHER INFORMATION: beta actin sense gene fragment
<220> FEATURE:
<221> NAME/KEY: misc_feature
<222> LOCATION: (3478)..(3485)
<223> OTHER INFORMATION: restriction endonuclease PmeI recognition site
<220> FEATURE:
<221> NAME/KEY: misc_feature
<222> LOCATION: (3643)..(3937)
<223> OTHER INFORMATION: beta actin antisense strand gene fragment
<220> FEATURE:
<221> NAME/KEY: terminator
<222> LOCATION: (3989)..(4178)
<223> OTHER INFORMATION: yeast CYC1 terminator
<220> FEATURE:
<221> NAME/KEY: misc_feature
<222> LOCATION: (6172)..(7514)
<223> OTHER INFORMATION: yeast 2 micron ori

<400> SEQUENCE: 40
tcgcgcgttt cggtgatgac ggtgaaaacc tctgacacat gcagctcccg gagacggtca        60
cagcttgtct gtaagcggat gccgggagca gacaagcccg tcaggcgcg tcagcgggtg        120 ttggcgggtg tcggggctgg cttaactatg cggcatcaga gcagattgta ctgagagtgc       180
accataaacg acattactat atatataata taggaagcat ttaatagaca gcatcgtaat       240
atatgtgtac tttgcagtta tgacgccaga tggcagtagt ggaagatatt ctttattgaa       300
aaatagcttg tcaccttacg tacaatcttg atccggagct tttctttttt tgccgattaa       360
gaattaattc ggtcgaaaaa agaaaaggag agggccaaga gggagggcat tggtgactat       420
tgagcacgtg agtatacgtg attaagcaca caaaggcagc ttggagtatg tctgttatta      480
atttcacagg tagttctggt ccattggtga aagtttgcgg cttgcagagc acagaggccg      540
cagaatgtgc tctagattcc gatgctgact tgctgggtat tatatgtgtg cccaatagaa      600
agagaacaat tgacccggtt attgcaagga aaatttcaag tcttgtaaaa gcatataaaa      660
atagttcagg cactccgaaa tacttggttg gcgtgtttcg taatcaacct aaggaggatg      720

-continued

```
ttttggctct ggtcaatgat tacggcattg atatcgtcca actgcatgga gatgagtcgt      780
ggcaagaata ccaagagttc ctcggtttgc cagttattaa aagactcgta tttccaaaag      840
actgcaacat actactcagt gcagcttcac agaaacctca ttcgtttatt cccttgtttg      900
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgg tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa ttttttgttaa atcagctcat ttttttaacca ataggccgaa     1320 atcggcaaaa tcccttataa atcaaaagaa tagaccgaga tagggttgag tgttgttcca     1380
gtttggaaca agagtccact attaaagaac gtggactcca acgtcaaagg gcgaaaaacc     1440
gtctatcagg gcgatggccc actacgtgaa ccatcaccct aatcaagttt tttggggtcg     1500
aggtgccgta aagcactaaa tcggaaccct aaagggagcc cccgatttag agcttgacgg     1560
ggaaagccgg cgaacgtggc gagaaaggaa gggaagaaag cgaaaggagc gggcgctagg     1620
gcgctggcaa gtgtagcggt cacgctgcgc gtaaccacca cacccgccgc gcttaatgcg     1680
ccgctacagg gcgcgtcgcg ccattcgcca ttcaggctgc gcaactgttg ggaagggcga     1740
tcggtgcggg cctcttcgct attacgccag ctgaattgga gcgacctcat gctatacctg     1800
agaaagcaac ctgacctaca ggaaagagtt actcaagaat aagaattttc gttttaaaac     1860
ctaagagtca ctttaaaatt tgtatacact tattttttttt ataacttatt taataataaa     1920
aatcataaat cataagaaat tcgcttattt agaagtgtca acaacgtatc taccaacgat     1980
ttgacccttt tccatctttt cgtaaatttc tggcaaggta gacaagccga caaccttgat     2040
tggagacttg accaaacctc tggcgaagaa ttgttaatta agagctctta ttagtaaatg     2100
ccagagttag cagcgattgc agatgggatc ggattaccgt ctttcagcag gccctgcatt     2160
gccttaacaa tcagttcgca gtcggagttc gtcgcaaaaa tcggaatagt cagttccatg     2220
ttgaggtaag agcgccaggc cgcaactggg agttctacgc cgcctacggt ctgcgttgcg     2280
actttcggta cttcaacttt gatggtgtat ttgcgattct gcgcgctaga ctgacgaacg     2340
gagcacgtga ctttgtaggc ctgagagcgg ctgttagagc taatccattc cgcaacaccg     2400
ttggcgaagt tggacggagc tacggtaacg tcacccgtac cgccgttatc aaccagaacg     2460
aattgggtaa agttagacgc catgaattcg aattttcaaa aattcttact tttttttttgg     2520 atggacgcaa agaagtttaa taatcatatt acatggcatt accaccatat acatatccat     2580
atacatatcc atatctaatc ttacttatat gttgtggaaa tgtaaagagc cccattatct     2640
tagcctaaaa aaaccttctc tttggaactt tcagtaatac gcttaactgc tcattgctat     2700
attgaagtac ggattagaag ccgccgagcg ggtgacagcc ctccgaagga agactctcct     2760
ccgtgcgtcc tcgtcttcac cggtcgcgtt cctgaaacgc agatgtgcct cgcgccgcac     2820
tgctccgaac aataaagatt ctacaatact agctttatg gttatgaaga ggaaaaattg     2880
gcagtaacct ggccccacaa accttcaaat gaacgaatca aattaacaac cataggatga     2940
taatgcgatt agttttttag ccttatttct ggggtaatta atcagcgaag cgatgatttt     3000
tgatctatta acagatatat aaatgcaaaa actgcataac cactttaact aatactttca     3060
acattttcgg tttgtattac ttcttattca aatgtaataa aagtatcaac aaaaaattgt     3120
```

-continued

```
taatatacct ctatacttta acgtcaagga gaaaaaaccc cggatccatt taaatgcgat    3180
cgcgcacgag gttttttctgt ctagtgagca gtgtccaacc tcaaaagaca acatgtgtga   3240
cgacgatgta gcggctcttg tcgtagacaa tggatccggt atgtgcaaag ccggtttcgc    3300
aggagatgac gcacccgtg ccgtcttccc ctcgatcgtc ggtcgcccaa ggcatcaagg    3360
agtcatggtc ggtatgggac aaaaggactc atacgtagga gatgaagccc aaagcaaaag    3420
aggtatcctc accctgaaat accccatcga acacggtatc atcaccaact gggatgagtt    3480
taaaccctct agctgcttta caaagtactg gttcccttc cagcgggatg ctttatctaa     3540
acgcaatgag agaggtattc ctcaggccac atcgcttcct agttccgctg ggatccatcg    3600
ttggcggccg aagccgccat tccatagtga gttctggcgc gcctcatccc agttggtgat    3660
gataccgtgt tcgatggggt atttcaggg gaggatacct ctttttgcttt gggcttcatc    3720 tcctacgtat gagtccttt gtcccatacc gaccatgact ccttgatgcc ttgggcgacc    3780
gacgatcgag gggaagacgg cacggggtgc gtcatctcct gcgaaaccgg ctttgcacat    3840
accggatcca ttgtctacga caagagccgc tacatcgtcg tcacacatgt tgtctttttga   3900 ggttggcacac tgctcactag acagaaaaac ctcgtgccgg accgaatacc cggtctgaac    3960
gagggcggcc gcccgcgggc tagctaagat ccgctctaac cgaaaaggaa ggagttagac    4020
aacctgaagt ctaggtccct atttattttt ttatagttat gttagtatta agaacgttat    4080
ttatatttca aattttttctt tttttctgt acagacgcgt gtacgcatgt aacattatac    4140
tgaaaacctt gcttgagaag gttttgggac gctcgaagat ccagctgcat taatgaatcg    4200
gccaacgcgc ggggagaggc ggtttgcgta ttgggcgctc ttccgcttcc tcgctcactg    4260
actcgctgcg ctcggtcgtt cggctgcggc gagcggtatc agctcactca aaggcggtaa    4320
tacggttatc cacagaatca ggggataacg caggaaagaa catgtgagca aaaggccagc    4380
aaaaggccag gaaccgtaaa aaggccgcgt tgctggcgtt tttccatagg ctccgccccc    4440
ctgacgagca tcacaaaaat cgacgctcaa gtcagaggtg gcgaaacccg acaggactat    4500
aaagatacca ggcgtttccc cctggaagct ccctcgtgcg ctctcctgtt ccgaccctgc    4560
cgcttaccgg atacctgtcc gcctttctcc cttcgggaag cgtggcgctt tctcatagct    4620
cacgctgtag gtatctcagt tcggtgtagg tcgttcgctc caagctgggc tgtgtgcacg    4680 aacccccgt tcagcccgac cgctgcgcct tatccggtaa ctatcgtctt gagtccaacc    4740
cggtaagaca cgacttatcg ccactggcag cagccactgg taacaggatt agcagagcga    4800
ggtatgtagg cggtgctaca gagttcttga agtggtggcc taactacggc tacactagaa    4860
ggacagtatt tggtatctgc gctctgctga gccagttac cttcggaaaa agagttggta     4920
gctcttgatc cggcaaacaa accaccgctg gtagcggtgg tttttttgtt tgcaagcagc    4980
agattacgcg cagaaaaaaa ggatctcaag aagatccttt gatctttct acggggtctg     5040 acgctcagtg gaacgaaaac tcacgttaag ggattttggt catgagatta tcaaaaagga    5100
tcttcaccta gatccttta aattaaaaat gaagttttaa atcaatctaa agtatatatg     5160
agtaaacttg gtctgacagt taccaatgct taatcagtga ggcacctatc tcagcgatct    5220
gtctatttcg ttcatccata gttgcctgac tccccgtcgt gtagataact acgatacggg    5280
agggcttacc atctggcccc agtgctgcaa tgataccgcg agacccacgc tcaccggctc    5340
cagatttatc agcaataaac cagccagccg gaagggccga gcgcagaagt ggtcctgcaa    5400
ctttatccgc ctccatccag tctattaatt gttgccggga agctagagta agtagttcgc    5460
```

```
cagttaatag tttgcgcaac gttgttgcca ttgctacagg catcgtggtg tcacgctcgt    5520
cgtttggtat ggcttcattc agctccggtt cccaacgatc aaggcgagtt acatgatccc    5580
ccatgttgtg caaaaaagcg gttagctcct tcggtcctcc gatcgttgtc agaagtaagt    5640
tggccgcagt gttatcactc atggttatgg cagcactgca taattctctt actgtcatgc    5700
catccgtaag atgcttttct gtgactggtg agtactcaac caagtcattc tgagaatagt    5760
gtatgcggcg accgagttgc tcttgcccgg cgtcaatacg ggataatacc gcgccacata    5820
gcagaacttt aaaagtgctc atcattggaa aacgttcttc ggggcgaaaa ctctcaagga    5880
tcttaccgct gttgagatcc agttcgatgt aacccactcg tgcacccaac tgatcttcag    5940
catcttttac tttcaccagc gtttctgggt gagcaaaaac aggaaggcaa aatgccgcaa    6000
aaaagggaat aagggcgaca cggaaatgtt gaatactcat actcttcctt tttcaatatt    6060
attgaagcat ttatcagggt tattgtctca tgagcggata catatttgaa tgtatttaga    6120
aaaataaaca aataggggtt ccgcgcacat ttccccgaaa agtgccacct gaacgaagca    6180
tctgtgcttc attttgtaga acaaaaatgc aacgcgagag cgctaatttt tcaaacaaag    6240
aatctgagct gcatttttac agaacagaaa tgcaacgcga aagcgctatt ttaccaacga    6300
agaatctgtg cttcattttt gtaaacaaa aatgcaacgc gagagcgcta atttttcaaa    6360
caaagaatct gagctgcatt tttacagaac agaaatgcaa cgcgagagcg ctattttacc    6420
aacaaagaat ctatacttct tttttgttct acaaaaatgc atcccgagag cgctattttt    6480
ctaacaaagc atcttagatt actttttttc tcctttgtgc gctctataat gcagtctctt    6540
gataactttt tgcactgtag gtccgttaag gttagaagaa ggctactttg gtgtctattt    6600
tctcttccat aaaaaaagcc tgactccact tcccgcgttt actgattact agcgaagctg    6660
cgggtgcatt ttttcaagat aaaggcatcc ccgattatat tctataccga tgtggattgc    6720
gcatactttg tgaacagaaa gtgatagcgt tgatgattct tcattggtca gaaaattatg    6780
aacggtttct tctattttgt ctctatatac tacgtatagg aaatgtttac attttcgtat    6840
tgttttcgat tcactctatg aatagttctt actacaattt ttttgtctaa agagtaatac    6900
tagagataaa cataaaaaat gtagaggtcg agtttagatg caagttcaag gagcgaaagg    6960
tggatgggta ggttatatag ggatatagca cagagatata tagcaaagag atacttttga    7020
gcaatgtttg tggaagcggt attcgcaata ttttagtagc tcgttacagt ccggtgcgtt    7080
tttggttttt tgaaagtgcg tcttcagagc gcttttggtt ttcaaaagcg ctctgaagtt    7140
cctatacttt ctagagaata ggaacttcgg aataggaact tcaaagcgtt tccgaaaacg    7200
agcgcttccg aaaatgcaac gcgagctgcg cacatacagc tcactgttca cgtcgcacct    7260
atatctgcgt gttgcctgta tatatatata catgagaaga acggcatagt gcgtgtttat    7320
gcttaaatgc gtacttatat gcgtctattt atgtaggatg aaaggtagtc tagtacctcc    7380
tgtgatatta tcccattcca tgcggggtat cgtatgcttc cttcagcact acccttttagc    7440 tgttctatat gctgccactc ctcaattgga ttagtctcat ccttcaatgc tatcatttcc    7500
tttgatattg gatcatatta agaaaccatt attatcatga cattaaccta taaaaatagg    7560
cgtatcacga ggccctttcg tc                                            7582
```

<210> SEQ ID NO 41
<211> LENGTH: 7269
<212> TYPE: DNA
<213> ORGANISM: Artificial Sequence
<220> FEATURE:
<223> OTHER INFORMATION: Recombinant plasmid pAPSE10441; beta actin stem -continued

```
        loop - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional promoter
<220> FEATURE:
<221> NAME/KEY: misc_feature
<222> LOCATION: (2844)..(2851)
<223> OTHER INFORMATION: restriction endonuclease AsiSI recognition
        sequence
<220> FEATURE:
<221> NAME/KEY: misc_feature
<222> LOCATION: (2852)..(3146)
<223> OTHER INFORMATION: beta actin sense gene fragment
<220> FEATURE:
<221> NAME/KEY: misc_feature
<222> LOCATION: (3146)..(3153)
<223> OTHER INFORMATION: restriction endonuclease PmeI recognition site
<220> FEATURE:
<221> NAME/KEY: misc_feature
<222> LOCATION: (3311)..(3605)
<223> OTHER INFORMATION: beta actin antisense strand gene fragment
<220> FEATURE:
<221> NAME/KEY: misc_feature
<222> LOCATION: (3641)..(3659)
<223> OTHER INFORMATION: bacteriophage MS2 pac sequence
<220> FEATURE:
<221> NAME/KEY: terminator
<222> LOCATION: (3676)..(3865)
<223> OTHER INFORMATION: yeast CYC1 terminator
<220> FEATURE:
<221> NAME/KEY: misc_feature
<222> LOCATION: (5859)..(7201)
<223> OTHER INFORMATION: yeast 2 micron ori

<400> SEQUENCE: 41
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg  cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga aagtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
```

-continued

```
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat ttttttaacca ataggccgaa   1320 atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tattttttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctcaga tcttatcgtc   2100
gtcatccttg taatccatcg atactagtgc ggccgccctt tagtgagggt tgaattcgaa   2160
ttttcaaaaa ttcttacttt ttttttggat ggacgcaaag aagtttaata atcatattac   2220
atggcattac caccatatac atatccatat acatatccat atctaatctt acttatatgt   2280
tgtggaaatg taaagagccc cattatctta gcctaaaaaa accttctctt tggaactttc   2340
agtaatacgc ttaactgctc attgctatat tgaagtacgg attagaagcc gccgagcggg   2400
tgacagccct ccgaaggaag actctcctcc gtgcgtcctc gtcttcaccg gtcgcgttcc   2460
tgaaacgcag atgtgcctcg cgccgcactg ctccgaacaa taaagattct acaatactag   2520
cttttatggt tatgaagagg aaaaattggc agtaacctgg ccccacaaac cttcaaatga   2580
acgaatcaaa ttaacaacca taggatgata atgcgattag ttttttagcc ttatttctgg   2640
ggtaattaat cagcgaagcg atgattttg atctattaac agatatataa atgcaaaaac   2700
tgcataacca ctttaactaa tactttcaac attttcggtt tgtattactt cttattcaaa   2760
tgtaataaaa gtatcaacaa aaaattgtta atatacctct atactttaac gtcaaggaga   2820
aaaaaccccg gatccattta aatgcgatcg cgcacgaggt ttttctgtct agtgagcagt   2880
gtccaacctc aaaagacaac atgtgtgacg acgatgtagc ggctcttgtc gtagacaatg   2940
gatccggtat gtgcaaagcc ggtttcgcag agatgacgc accccgtgcc gtcttcccct    3000
cgatcgtcgg tcgcccaagg catcaaggag tcatggtcgg tatgggacaa aaggactcat   3060
acgtaggaga tgaagcccaa agcaaaagag gtatcctcac cctgaaatac cccatcgaac   3120
acggtatcat caccaactgg gatgagttta aaccctctag ctgctttaca aagtactggt   3180
```

-continued

```
tcccttttcca gcgggatgct ttatctaaac gcaatgagag aggtattcct caggccacat    3240
cgcttcctag ttccgctggg atccatcgtt ggcggccgaa gccgccattc catagtgagt    3300
tctggcgcgc ctcatcccag ttggtgatga taccgtgttc gatggggtat ttcagggtga    3360
ggatacctct tttgctttgg gcttcatctc ctacgtatga gtcctttgt cccataccga    3420 ccatgactcc ttgatgcctt gggcgaccga cgatcgaggg gaagacggca cggggtgcgt    3480
catctcctgc gaaaccggct ttgcacatac cggatccatt gtctacgaca agagccgcta    3540
catcgtcgtc acacatgttg tcttttgagg ttggacactg ctcactagac agaaaaacct    3600
cgtgccggac cgaatacccg gtctgaacga gggcggccgc acatgaggat cacccatgtc    3660
cgcgggctag ctaagatccg ctctaaccga aaaggaagga gttagacaac ctgaagtcta    3720
ggtccctatt tatttttta tagttatgtt agtattaaga acgttattta tatttcaaat    3780
ttttcttttt tttctgtaca gacgcgtgta cgcatgtaac attatactga aaaccttgct    3840
tgagaaggtt ttgggacgct cgaagatcca gctgcattaa tgaatcggcc aacgcgcggg    3900
gagaggcggt ttgcgtattg ggcgctcttc cgcttcctcg ctcactgact cgctgcgctc    3960
ggtcgttcgg ctgcggcgag cggtatcagc tcactcaaag gcggtaatac ggttatccac    4020
agaatcaggg gataacgcag gaaagaacat gtgagcaaaa ggccagcaaa aggccaggaa    4080
ccgtaaaaag gccgcgttgc tggcgttttt ccataggctc cgcccccctg acgagcatca    4140
caaaaatcga cgctcaagtc agaggtggcg aaacccgaca ggactataaa gataccaggc    4200
gtttccccct ggaagctccc tcgtgcgctc tcctgttccg accctgccgc ttaccggata    4260
cctgtccgcc tttctccctt cgggaagcgt ggcgctttct catagctcac gctgtaggta    4320
tctcagttcg gtgtaggtcg ttcgctccaa gctgggctgt gtgcacgaac cccccgttca    4380
gcccgaccgc tgcgccttat ccggtaacta tcgtcttgag tccaacccgg taagacacga    4440
cttatcgcca ctggcagcag ccactggtaa caggattagc agagcgaggt atgtaggcgg    4500
tgctacagag ttcttgaagt ggtggcctaa ctacggctac actagaagga cagtatttgg    4560
tatctgcgct ctgctgaagc cagttacctt cggaaaaaga gttggtagct cttgatccgg    4620
caaacaaacc accgctggta gcggtggttt ttttgtttgc aagcagcaga ttacgcgcag    4680
aaaaaaagga tctcaagaag atcctttgat cttttctacg gggtctgacg ctcagtggaa    4740
cgaaaactca cgttaaggga ttttggtcat gagattatca aaaaggatct tcacctagat    4800
ccttttaaat taaaaatgaa gttttaaatc aatctaaagt atatatgagt aaacttggtc    4860
tgacagttac caatgcttaa tcagtgaggc acctatctca gcgatctgtc tatttcgttc    4920
atccatagtt gcctgactcc ccgtcgtgta gataactacg atacgggagg gcttaccatc    4980
tggccccagt gctgcaatga taccgcgaga cccacgctca ccggctccag atttatcagc    5040
aataaaccag ccagccggaa gggccgagcg cagaagtggt cctgcaactt tatccgcctc    5100
catccagtct attaattgtt gccgggaagc tagagtaagt agttcgccag ttaatagttt    5160
gcgcaacgtt gttgccattg ctacaggcat cgtggtgtca cgctcgtcgt ttggtatggc    5220
ttcattcagc tccggttccc aacgatcaag gcgagttaca tgatccccca tgttgtgcaa    5280
aaaagcggtt agctccttcg gtcctccgat cgttgtcaga agtaagttgg ccgcagtgtt    5340
atcactcatg gttatggcag cactgcataa ttctcttact gtcatgccat ccgtaagatg    5400
cttttctgtg actggtgagt actcaaccaa gtcattctga atagtgta tgcggcgacc    5460 gagttgctct tgcccggcgt caatacggga taataccgcg ccacatagca gaactttaaa    5520
```

```
agtgctcatc attggaaaac gttcttcggg gcgaaaactc tcaaggatct taccgctgtt      5580
gagatccagt tcgatgtaac ccactcgtgc acccaactga tcttcagcat cttttacttt      5640
caccagcgtt tctgggtgag caaaaacagg aaggcaaaat gccgcaaaaa agggaataag      5700
ggcgacacgg aaatgttgaa tactcatact cttcctttt caatattatt gaagcattta       5760
tcagggttat tgtctcatga gcggatacat atttgaatgt atttagaaaa ataaacaaat      5820
aggggttccg cgcacatttc cccgaaaagt gccacctgaa cgaagcatct gtgcttcatt      5880
ttgtagaaca aaaatgcaac gcgagagcgc taattttca aacaaagaat ctgagctgca       5940
tttttacaga acagaaatgc aacgcgaaag cgctatttta ccaacgaaga atctgtgctt      6000 cattttgta aaacaaaaat gcaacgcgag agcgctaatt tttcaaacaa agaatctgag       6060 ctgcatttt acagaacaga aatgcaacgc gagagcgcta ttttaccaac aaagaatcta       6120
tacttctttt ttgttctaca aaaatgcatc ccgagagcgc tattttttcta acaaagcatc     6180 ttagattact tttttctcc tttgtgcgct ctataatgca gtctcttgat aactttttgc       6240
actgtaggtc cgttaaggtt agaagaaggc tactttggtg tctattttct cttccataaa      6300
aaaagcctga ctccacttcc cgcgtttact gattactagc gaagctgcgg gtgcattttt      6360
tcaagataaa ggcatccccg attatattct ataccgatgt ggattgcgca ctttgtgtga     6420
acagaaagtg atagcgttga tgattcttca ttggtcagaa aattatgaac ggtttcttct      6480
attttgtctc tatatactac gtataggaaa tgtttacatt ttcgtattgt tttcgattca      6540
ctctatgaat agttcttact acaattttt tgtctaaaga gtaatactag agataaacat        6600
aaaaaatgta gaggtcgagt ttagatgcaa gttcaaggag cgaaaggtgg atgggtaggt      6660
tatataggga tatagcacag agatatatag caaagagata cttttgagca atgtttgtgg      6720
aagcggtatt cgcaatattt tagtagctcg ttacagtccg gtgcgttttt ggttttttga      6780
aagtgcgtct tcagagcgct tttggttttc aaaagcgctc tgaagttcct atactttcta      6840
gagaatagga acttcggaat aggaacttca aagcgtttcc gaaaacgagc gcttccgaaa      6900
atgcaacgcg agctgcgcac atacagctca ctgttcacgt cgcacctata tctgcgtgtt      6960
gcctgtatat atatatacat gagaagaacg gcatagtgcg tgtttatgct taaatgcgta      7020
cttatatgcg tctatttatg taggatgaaa ggtagtctag tacctcctgt gatattatcc      7080
cattccatgc ggggtatcgt atgcttcctt cagcactacc ctttagctgt tctatatgct      7140
gccactcctc aattggatta gtctcatcct tcaatgctat catttccttt gatattggat      7200
catattaaga aaccattatt atcatgacat taacctataa aaataggcgt atcacgaggc      7260
cctttcgtc                                                              7269
```

```
<210> SEQ ID NO 42
<211> LENGTH: 7601
<212> TYPE: DNA
<213> ORGANISM: Artificial Sequence
<220> FEATURE:
<223> OTHER INFORMATION: Recombinant plasmid pAPSE10442; beta actin
      hairpin + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
```

```
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3183)
<223> OTHER INFORMATION: restriction endonuclease AsiSI recognition
      sequence
<220> FEATURE:
<221> NAME/KEY: misc_feature
<222> LOCATION: (3185)..(3478)
<223> OTHER INFORMATION: beta actin sense gene fragment
<220> FEATURE:
<221> NAME/KEY: misc_feature
<222> LOCATION: (3478)..(3485)
<223> OTHER INFORMATION: restriction endonuclease PmeI recognition site
<220> FEATURE:
<221> NAME/KEY: misc_feature
<222> LOCATION: (3643)..(3937)
<223> OTHER INFORMATION: beta actin antisense strand gene fragment
<220> FEATURE:
<221> NAME/KEY: misc_feature
<222> LOCATION: (3973)..(3991)
<223> OTHER INFORMATION: bacteriophage MS2 pac sequence
<220> FEATURE:
<221> NAME/KEY: terminator
<222> LOCATION: (4008)..(4197)
<223> OTHER INFORMATION: yeast CYC1 terminator
<220> FEATURE:
<221> NAME/KEY: misc_feature
<222> LOCATION: (6191)..(7533)
<223> OTHER INFORMATION: yeast 2 micron ori

<400> SEQUENCE: 42
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga aagtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
ggcaagaata ccaagagttc ctcggtttgc cagttattaa aagactcgta tttccaaaag     840
actgcaacat actactcagt gcagcttcac agaaacctca ttcgtttatt cccttgtttg     900
attcagaagc aggtgggaca ggtgaacttt tggattggaa ctcgatttct gactgggttg     960
gaaggcaaga gagccccgaa agcttacatt ttatgttagc tggtggactg acgccagaaa    1020
```

-continued

```
atgttggtga tgcgcttaga ttaaatggcg ttattggtgt tgatgtaagc ggaggtgtgg    1080
agacaaatgg tgtaaaagac tctaacaaaa tagcaaattt cgtcaaaaat gctaagaaat    1140
aggttattac tgagtagtat ttatttaagt attgtttgtg cacttgccta tgcggtgtga    1200
aataccgcac agatgcgtaa ggagaaaata ccgcatcagg aaattgtaaa cgttaatatt    1260
ttgttaaaat tcgcgttaaa ttttttgttaa atcagctcat tttttaacca ataggccgaa    1320
atcggcaaaa tcccttataa atcaaaagaa tagaccgaga tagggttgag tgttgttcca    1380
gtttggaaca agagtccact attaaagaac gtggactcca acgtcaaagg gcgaaaaacc    1440
gtctatcagg gcgatggccc actacgtgaa ccatcaccct aatcaagttt tttggggtcg    1500
aggtgccgta aagcactaaa tcggaaccct aaagggagcc cccgatttag agcttgacgg    1560
ggaaagccgg cgaacgtggc gagaaaggaa gggaagaaag cgaaaggagc gggcgctagg    1620
gcgctggcaa gtgtagcggt cacgctgcgc gtaaccacca cacccgccgc gcttaatgcg    1680
ccgctacagg gcgcgtcgcg ccattcgcca ttcaggctgc gcaactgttg ggaagggcga    1740
tcggtgcggg cctcttcgct attacgccag ctgaattgga gcgacctcat gctatacctg    1800
agaaagcaac ctgacctaca ggaaagagtt actcaagaat aagaattttc gttttaaaac    1860
ctaagagtca ctttaaaatt tgtatacact tattttttt ataacttatt taataataaa    1920
aatcataaat cataagaaat tcgcttattt agaagtgtca acaacgtatc taccaacgat    1980
ttgacccttt tccatctttt cgtaaatttc tggcaaggta gacaagccga caaccttgat    2040
tggagacttg accaaacctc tggcgaagaa ttgttaatta agagctctta ttagtaaatg    2100
ccagagttag cagcgattgc agatgggatc ggattaccgt ctttcagcag gccctgcatt    2160
gccttaacaa tcagttcgca gtcggagttc gtcgcaaaaa tcggaatagt cagttccatg    2220
ttgaggtaag agcgccaggc cgcaactggg agttctacgc cgcctacggt ctgcgttgcg    2280
actttcggta cttcaacttt gatggtgtat ttgcgattct gcgcgctaga ctgacgaacg    2340
gagcacgtga ctttgtaggc ctgagagcgg ctgttagagc taatccattc cgcaacaccg    2400
ttggcgaagt tggacggagc tacggtaacg tcacccgtac cgccgttatc aaccagaacg    2460
aattgggtaa agttagacgc catgaattcg aattttcaaa aattcttact ttttttttgg    2520
atggacgcaa agaagtttaa taatcatatt acatggcatt accaccatat acatatccat    2580
atacatatcc atatctaatc ttacttatat gttgtggaaa tgtaaagagc cccattatct    2640
tagcctaaaa aaaccttctc tttggaactt tcagtaatac gcttaactgc tcattgctat    2700
attgaagtac ggattagaag ccgccgagcg ggtgacagcc ctccgaagga agactctcct    2760
ccgtgcgtcc tcgtcttcac cggtcgcgtt cctgaaacgc agatgtgcct cgcgccgcac    2820
tgctccgaac aataaagatt ctacaatact agctttatg gttatgaaga ggaaaaattg    2880
gcagtaacct ggccccacaa accttcaaat gaacgaatca aattaacaac cataggatga    2940
taatgcgatt agttttttag ccttatttct ggggtaatta atcagcgaag cgatgatttt    3000
tgatctatta acagatatat aaatgcaaaa actgcataac cactttaact aatactttca    3060
acattttcgg tttgtattac ttcttattca aatgtaataa aagtatcaac aaaaaattgt    3120
taatatacct ctatacttta acgtcaagga gaaaaaaccc cggatccatt taaatgcgat    3180
cgcgcacgag gtttttctgt ctagtgagca gtgtccaacc tcaaaagaca acatgtgtga    3240
cgacgatgta gcggctcttg tcgtagacaa tggatccggt atgtgcaaag ccggtttcgc    3300
aggagatgac gcacccgtg ccgtcttccc ctcgatcgtc ggtcgcccaa ggcatcaagg    3360
agtcatggtc ggtatgggac aaaaggactc atacgtagga gatgaagccc aaagcaaaag    3420
```

-continued

```
aggtatcctc accctgaaat accccatcga acacggtatc atcaccaact gggatgagtt   3480
taaaccctct agctgcttta caaagtactg gttccctttc cagcgggatg ctttatctaa   3540
acgcaatgag agaggtattc ctcaggccac atcgcttcct agttccgctg ggatccatcg   3600
ttggcggccg aagccgccat tccatagtga gttctggcgc gcctcatccc agttggtgat   3660
gataccgtgt tcgatggggt atttcagggt gaggatacct cttttgcttt gggcttcatc   3720
tcctacgtat gagtcctttt gtcccatacc gaccatgact ccttgatgcc ttgggcgacc   3780
gacgatcgag gggaagacgg cacggggtgc gtcatctcct gcgaaaccgg ctttgcacat   3840
accggatcca ttgtctacga caagagccgc tacatcgtcg tcacacatgt tgtcttttga   3900
ggttggacac tgctcactag acagaaaaac ctcgtgccgg accgaatacc cggtctgaac   3960
gagggcggcc gcacatgagg atcacccatg tccgcgggct agctaagatc cgctctaacc   4020
gaaaaggaag gagttagaca acctgaagtc taggtcccta tttatttttt tatagttatg   4080
ttagtattaa gaacgttatt tatatttcaa atttttcttt tttttctgta cagacgcgtg   4140
tacgcatgta acattatact gaaaaccttg cttgagaagg ttttgggacg ctcgaagatc   4200
cagctgcatt aatgaatcgg ccaacgcgcg gggagaggcg gtttgcgtat tgggcgctct   4260
tccgcttcct cgctcactga ctcgctgcgc tcggtcgttc ggctgcggcg agcggtatca   4320
gctcactcaa aggcggtaat acggttatcc acagaatcag gggataacgc aggaaagaac   4380
atgtgagcaa aaggccagca aaaggccagg aaccgtaaaa aggccgcgtt gctggcgttt   4440
ttccataggc tccgcccccc tgacgagcat cacaaaaatc gacgctcaag tcagaggtgg   4500
cgaaacccga caggactata aagataccag gcgtttcccc ctggaagctc cctcgtgcgc   4560
tctcctgttc cgaccctgcc gcttaccgga tacctgtccg cctttctccc ttcgggaagc   4620
gtggcgcttt ctcatagctc acgctgtagg tatctcagtt cggtgtaggt cgttcgctcc   4680
aagctgggct gtgtgcacga acccccc gtt cagcccgacc gctgcgcctt atccggtaac   4740
tatcgtcttg agtccaaccc ggtaagacac gacttatcgc cactggcagc agccactggt   4800
aacaggatta gcagagcgag gtatgtaggc ggtgctacag agttcttgaa gtggtggcct   4860
aactacggct acactagaag gacagtattt ggtatctgcg ctctgctgaa gccagttacc   4920
ttcggaaaaa gagttggtag ctcttgatcc ggcaaacaaa ccaccgctgg tagcggtggt   4980
ttttttgttt gcaagcagca gattacgcgc agaaaaaaag gatctcaaga agatcctttg   5040 atctttteta cggggtctga cgctcagtgg aacgaaaact cacgttaagg gattttggtc   5100
atgagattat caaaaaggat cttcacctag atccttttaa attaaaaatg aagttttaaa   5160
tcaatctaaa gtatatatga gtaaacttgg tctgacagtt accaatgctt aatcagtgag   5220
gcacctatct cagcgatctg tctatttcgt tcatccatag ttgcctgact ccccgtcgtg   5280
tagataacta cgatacggga gggcttacca tctggcccca gtgctgcaat gataccgcga   5340
gacccacgct caccggctcc agatttatca gcaataaacc agccagccgg aagggccgag   5400
cgcagaagtg gtcctgcaac tttatccgcc tccatccagt ctattaattg ttgccgggaa   5460
gctagagtaa gtagttcgcc agttaatagt ttgcgcaacg ttgttgccat tgctacaggc   5520
atcgtggtgt cacgctcgtc gtttggtatg gcttcattca gctccggttc ccaacgatca   5580
aggcgagtta catgatcccc catgttgtgc aaaaaagcgg ttagctcctt cggtcctccg   5640
atcgttgtca gaagtaagtt ggccgcagtg ttatcactca tggttatggc agcactgcat   5700
aattctctta ctgtcatgcc atccgtaaga tgcttttctg tgactggtga gtactcaacc   5760
```

-continued

```
aagtcattct gagaatagtg tatgcggcga ccgagttgct cttgcccggc gtcaatacgg    5820
gataataccg cgccacatag cagaacttta aaagtgctca tcattggaaa acgttcttcg    5880
gggcgaaaac tctcaaggat cttaccgctg ttgagatcca gttcgatgta acccactcgt    5940
gcacccaact gatcttcagc atcttttact ttcaccagcg tttctgggtg agcaaaaaca    6000
ggaaggcaaa atgccgcaaa aaagggaata agggcgacac ggaaatgttg aatactcata    6060
ctcttccttt ttcaatatta ttgaagcatt tatcagggtt attgtctcat gagcggatac    6120
atatttgaat gtatttagaa aaataaacaa ataggggttc cgcgcacatt tccccgaaaa    6180
gtgccacctg aacgaagcat ctgtgcttca ttttgtagaa caaaaatgca acgcgagagc    6240
gctaattttt caaacaaaga atctgagctg catttttaca gaacagaaat gcaacgcgaa    6300
agcgctattt taccaacgaa gaatctgtgc ttcatttttg taaaacaaaa atgcaacgcg    6360
agagcgctaa tttttcaaac aaagaatctg agctgcattt ttacagaaca gaaatgcaac    6420
gcgagagcgc tattttacca acaaagaatc tatacttctt ttttgttcta caaaaatgca    6480
tcccgagagc gctattttc taacaaagca tcttagatta ctttttttct cctttgtgcg    6540
ctctataatg cagtctcttg ataacttttt gcactgtagg tccgttaagg ttagaagaag    6600
gctactttgg tgtctatttt ctcttccata aaaaaagcct gactccactt cccgcgttta    6660
ctgattacta gcgaagctgc gggtgcattt tttcaagata aaggcatccc cgattatatt    6720
ctataccgat gtggattgcg catactttgt gaacagaaag tgatagcgtt gatgattctt    6780
cattggtcag aaaattatga acggtttctt ctattttgtc tctatatact acgtatagga    6840
aatgtttaca ttttcgtatt gttttcgatt cactctatga atagttctta ctacaattt    6900 tttgtctaaa gagtaatact agagataaac ataaaaaatg tagaggtcga gtttagatgc    6960
aagttcaagg agcgaaaggt ggatgggtag gttatatagg gatatagcac agagatatat    7020
agcaaagaga tacttttgag caatgtttgt ggaagcggta ttcgcaatat tttagtagct    7080
cgttacagtc cggtgcgttt ttggtttttt gaaagtgcgt cttcagagcg cttttggttt    7140
tcaaaagcgc tctgaagttc ctatactttc tagagaatag gaacttcgga ataggaactt    7200
caaagcgttt ccgaaaacga gcgcttccga aaatgcaacg cgagctgcgc acatacagct    7260
cactgttcac gtcgcaccta tatctgcgtg ttgcctgtat atatatatac atgagaagaa    7320
cggcatagtg cgtgtttatg cttaaatgcg tacttatatg cgtctatta tgtaggatga    7380 aaggtagtct agtacctcct gtgatattat cccattccat gcggggtatc gtatgcttcc    7440
ttcagcacta ccctttagct gttctatatg ctgccactcc tcaattggat tagtctcatc    7500
cttcaatgct atcatttcct ttgatattgg atcatattaa gaaaccatta ttatcatgac    7560
attaacctat aaaaataggc gtatcacgag gcccttcgt c    7601
```

```
<210> SEQ ID NO 43
<211> LENGTH: 7288
<212> TYPE: DNA
<213> ORGANISM: Artificial Sequence
<220> FEATURE:
<223> OTHER INFORMATION: Recombinant plasmid pAPSE10443; beta actin stem
      loop - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
```

<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional promoter
<220> FEATURE:
<221> NAME/KEY: misc_feature
<222> LOCATION: (2844)..(2862)
<223> OTHER INFORMATION: bacteriophage MS2 pac sequence
<220> FEATURE:
<221> NAME/KEY: misc_feature
<222> LOCATION: (2863)..(2870)
<223> OTHER INFORMATION: restriction endonuclease AsiSI recognition
      sequence
<220> FEATURE:
<221> NAME/KEY: misc_feature
<222> LOCATION: (2872)..(3165)
<223> OTHER INFORMATION: beta actin sense gene fragment
<220> FEATURE:
<221> NAME/KEY: misc_feature
<222> LOCATION: (3165)..(3172)
<223> OTHER INFORMATION: restriction endonuclease PmeI recognition site
<220> FEATURE:
<221> NAME/KEY: misc_feature
<222> LOCATION: (3329)..(3624)
<223> OTHER INFORMATION: beta actin antisense strand gene fragment
<220> FEATURE:
<221> NAME/KEY: misc_feature
<222> LOCATION: (3660)..(3678)
<223> OTHER INFORMATION: bacteriophage MS2 pac sequence
<220> FEATURE:
<221> NAME/KEY: terminator
<222> LOCATION: (3695)..(3884)
<223> OTHER INFORMATION: yeast CYC1 terminator
<220> FEATURE:
<221> NAME/KEY: misc_feature
<222> LOCATION: (5878)..(7220)
<223> OTHER INFORMATION: yeast 2 micron ori

<400> SEQUENCE: 43
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcggggctgg cttaactatg cggcatcaga gcagattgta ctgagagtgc      180
accataaacg acattactat atatataata taggaagcat ttaatagaca gcatcgtaat      240
atatgtgtac tttgcagtta tgacgccaga tggcagtagt ggaagatatt ctttattgaa      300
aaatagcttg tcaccttacg tacaatcttg atccggagct tttctttttt tgccgattaa      360
gaattaattc ggtcgaaaaa agaaaaggag agggccaaga gggagggcat tggtgactat      420
tgagcacgtg agtatacgtg attaagcaca caaaggcagc ttggagtatg tctgttatta      480
atttcacagg tagttctggt ccattggtga aagtttgcgg cttgcagagc acagaggccg      540
cagaatgtgc tctagattcc gatgctgact tgctgggtat tatatgtgtg cccaatagaa      600
agagaacaat tgacccggtt attgcaagga aaatttcaag tcttgtaaaa gcatataaaa      660
atagttcagg cactccgaaa tacttggttg gcgtgtttcg taatcaacct aaggaggatg      720
ttttggctct ggtcaatgat tacggcattg atatcgtcca actgcatgga gatgagtcgt      780
ggcaagaata ccaagagttc ctcggtttgc cagttattaa aagactcgta tttccaaaag      840
actgcaacat actactcagt gcagcttcac agaaacctca ttcgtttatt cccttgtttg      900
attcagaagc aggtgggaca ggtgaacttt tggattggaa ctcgatttct gactgggttg      960

-continued

```
gaaggcaaga gagccccgaa agcttacatt ttatgttagc tggtggactg acgccagaaa      1020
atgttggtga tgcgcttaga ttaaatggcg ttattggtgt tgatgtaagc ggaggtgtgg      1080
agacaaatgg tgtaaaagac tctaacaaaa tagcaaattt cgtcaaaaat gctaagaaat      1140
aggttattac tgagtagtat ttatttaagt attgtttgtg cacttgccta tgcggtgtga      1200
aataccgcac agatgcgtaa ggagaaaata ccgcatcagg aaattgtaaa cgttaatatt      1260
ttgttaaaat tcgcgttaaa ttttttgttaa atcagctcat ttttttaacca ataggccgaa      1320 atcggcaaaa tcccttataa atcaaaagaa tagaccgaga tagggttgag tgttgttcca      1380
gtttggaaca agagtccact attaaagaac gtggactcca acgtcaaagg gcgaaaaacc      1440
gtctatcagg gcgatggccc actacgtgaa ccatcaccct aatcaagttt tttggggtcg      1500
aggtgccgta aagcactaaa tcggaaccct aaagggagcc cccgatttag agcttgacgg      1560
ggaaagccgg cgaacgtggc gagaaaggaa gggaagaaag cgaaaggagc gggcgctagg      1620
gcgctggcaa gtgtagcggt cacgctgcgc gtaaccacca cacccgccgc gcttaatgcg      1680
ccgctacagg gcgcgtcgcg ccattcgcca ttcaggctgc gcaactgttg ggaagggcga      1740
tcggtgcggg cctcttcgct attacgccag ctgaattgga gcgacctcat gctatacctg      1800
agaaagcaac ctgacctaca ggaaagagtt actcaagaat aagaatttttc gttttaaaac      1860 ctaagagtca ctttaaaatt tgtatacact tattttttttt ataacttatt taataataaa      1920
aatcataaat cataagaaat tcgcttattt agaagtgtca acaacgtatc taccaacgat      1980
ttgacccttt tccatctttt cgtaaatttc tggcaaggta gacaagccga caaccttgat      2040
tggagacttg accaaacctc tggcgaagaa ttgttaatta agagctcaga tcttatcgtc      2100
gtcatccttg taatccatcg atactagtgc ggccgccctt tagtgagggt tgaattcgaa      2160
ttttcaaaaa ttcttacttt ttttttggat ggacgcaaag aagtttaata atcatattac      2220
atggcattac caccatatac atatccatat acatatccat atctaatctt acttatatgt      2280
tgtggaaatg taaagagccc cattatctta gcctaaaaaa accttctctt tggaactttc      2340
agtaatacgc ttaactgctc attgctatat tgaagtacgg attagaagcc gccgagcggg      2400
tgacagccct ccgaaggaag actctcctcc gtgcgtcctc gtcttcaccg gtcgcgttcc      2460
tgaaacgcag atgtgcctcg cgccgcactg ctccgaacaa taaagattct acaatactag      2520
cttttatggt tatgaagagg aaaaattggc agtaacctgg ccccacaaac cttcaaatga      2580
acgaatcaaa ttaacaacca taggatgata atgcgattag ttttttttagcc ttatttctgg      2640 ggtaattaat cagcgaagcg atgatttttg atctattaac agatatataa atgcaaaaac      2700
tgcataacca ctttaactaa tactttcaac attttcggtt tgtattactt cttattcaaa      2760
tgtaataaaa gtatcaacaa aaaattgtta atatacctct atactttaac gtcaaggaga      2820
aaaaaccccg gatccattta aatacatgag gattacccat gtgcgatcgc gcacgaggtt      2880
tttctgtcta gtgagcagtg tccaacctca aaagacaaca tgtgtgacga cgatgtagcg      2940
gctcttgtcg tagacaatgg atccggtatg tgcaaagccg gtttcgcagg agatgacgca      3000
ccccgtgccg tcttcccctc gatcgtcggt cgcccaaggc atcaaggagt catggtcggt      3060
atgggacaaa aggactcata cgtaggagat gaagcccaaa gcaaaagagg tatcctcacc      3120
ctgaaatacc ccatcgaaca cggtatcatc accaactggg atgagtttaa accctctagc      3180
tgctttacaa agtactggtt ccctttccag cgggatgctt tatctaaacg caatgagaga      3240
ggtattcctc aggccacatc gcttcctagt tccgctggga tccatcgttg gcggccgaag      3300
ccgccattcc atagtgagtt ctggcgcgcc tcatcccagt tggtgatgat accgtgttcg      3360
```

-continued

```
atggggtatt tcagggtgag gatacctctt ttgctttggg cttcatctcc tacgtatgag       3420 tcctttttgtc ccataccgac catgactcct tgatgccttg ggcgaccgac gatcgagggg      3480
aagacggcac ggggtgcgtc atctcctgcg aaaccggctt tgcacatacc ggatccattg       3540
tctacgacaa gagccgctac atcgtcgtca cacatgttgt cttttgaggt tggacactgc       3600
tcactagaca gaaaaacctc gtgccggacc gaatacccgg tctgaacgag ggcggccgca       3660
catgaggatc acccatgtcc gcgggctagc taagatccgc tctaaccgaa aaggaaggag       3720
ttagacaacc tgaagtctag gtccctattt attttttat agttatgtta gtattaagaa        3780
cgttatttat atttcaaatt tttctttttt ttctgtacag acgcgtgtac gcatgtaaca       3840
ttatactgaa aaccttgctt gagaaggttt tgggacgctc gaagatccag ctgcattaat       3900
gaatcggcca acgcgcgggg agaggcggtt tgcgtattgg gcgctcttcc gcttcctcgc      3960
tcactgactc gctgcgctcg gtcgttcggc tgcggcgagc ggtatcagct cactcaaagg       4020
cggtaatacg gttatccaca gaatcagggg ataacgcagg aaagaacatg tgagcaaaag       4080
gccagcaaaa ggccaggaac cgtaaaaagg ccgcgttgct ggcgtttttc cataggctcc       4140
gcccccctga cgagcatcac aaaaatcgac gctcaagtca gaggtggcga acccgacag       4200 gactataaag ataccaggcg tttccccctg gaagctccct cgtgcgctct cctgttccga       4260
ccctgccgct taccggatac ctgtccgcct ttctcccttc gggaagcgtg cgctttctc       4320 atagctcacg ctgtaggtat ctcagttcgg tgtaggtcgt tcgctccaag ctgggctgtg       4380
tgcacgaacc ccccgttcag cccgaccgct gcgccttatc cggtaactat cgtcttgagt       4440
ccaacccggt aagacacgac ttatcgccac tggcagcagc cactggtaac aggattagca       4500
gagcgaggta tgtaggcggt gctacagagt tcttgaagtg gtggcctaac tacggctaca       4560
ctagaaggac agtatttggt atctgcgctc tgctgaagcc agttaccttc ggaaaaagag       4620
ttggtagctc ttgatccggc aaacaaacca ccgctggtag cggtggtttt tttgtttgca       4680
agcagcagat tacgcgcaga aaaaaggat ctcaagaaga tcctttgatc ttttctacgg        4740
ggtctgacgc tcagtggaac gaaaactcac gttaagggat tttggtcatg agattatcaa       4800
aaaggatctt cacctagatc cttttaaatt aaaaatgaag ttttaaatca atctaaagta       4860
tatatgagta aacttggtct gacagttacc aatgcttaat cagtgaggca cctatctcag       4920
cgatctgtct atttcgttca tccatagttg cctgactccc cgtcgtgtag ataactacga       4980
tacgggaggg cttaccatct ggccccagtg ctgcaatgat accgcgagac ccacgctcac       5040
cggctccaga tttatcagca ataaaccagc cagccggaag ggccgagcgc agaagtggtc      5100
ctgcaacttt atccgcctcc atccagtcta ttaattgttg ccgggaagct agagtaagta       5160
gttcgccagt taatagtttg cgcaacgttg ttgccattgc tacaggcatc gtggtgtcac      5220
gctcgtcgtt tggtatggct tcattcagct ccggttccca acgatcaagg cgagttacat      5280
gatcccccat gttgtgcaaa aaagcggtta gctccttcgg tcctccgatc gttgtcagaa       5340
gtaagttggc cgcagtgtta tcactcatgg ttatggcagc actgcataat tctcttactg      5400
tcatgccatc cgtaagatgc ttttctgtga ctggtgagta ctcaaccaag tcattctgag       5460
aatagtgtat gcggcgaccg agttgctctt gcccggcgtc aatacgggat aataccgcgc       5520
cacatagcag aactttaaaa gtgctcatca ttggaaaacg ttcttcgggg cgaaaactct       5580
caaggatctt accgctgttg agatccagtt cgatgtaacc cactcgtgca cccaactgat       5640
cttcagcatc ttttactttc accagcgttt ctgggtgagc aaaaacagga aggcaaaatg       5700
```

-continued

```
ccgcaaaaaa gggaataagg gcgacacgga aatgttgaat actcatactc ttcctttttc   5760
aatattattg aagcatttat cagggttatt gtctcatgag cggatacata tttgaatgta   5820
tttagaaaaa taaacaaata ggggttccgc gcacatttcc ccgaaaagtg ccacctgaac   5880
gaagcatctg tgcttcattt tgtagaacaa aaatgcaacg cgagagcgct aatttttcaa   5940
acaaagaatc tgagctgcat ttttacagaa cagaaatgca acgcgaaagc gctattttac   6000
caacgaagaa tctgtgcttc attttttgtaa aacaaaaatg caacgcgaga cgctaatttt   6060
ttcaaacaaa gaatctgagc tgcatttta cagaacagaa atgcaacgcg agagcgctat   6120
tttaccaaca aagaatctat acttcttttt tgttctacaa aaatgcatcc cgagagcgct   6180 attttttctaa caaagcatct tagattactt tttttctcct ttgtgcgctc tataatgcag   6240
tctcttgata acttttttgca ctgtaggtcc gttaaggtta gaagaaggct actttggtgt   6300
ctattttctc ttccataaaa aaagcctgac tccacttccc gcgtttactg attactagcg   6360
aagctgcggg tgcattttttt caagataaag gcatccccga ttatattcta taccgatgtg   6420
gattgcgcat actttgtgaa cagaaagtga tagcgttgat gattcttcat tggtcagaaa   6480
attatgaacg gtttcttcta ttttgtctct atatactacg tataggaaat gtttacattt   6540
tcgtattgtt ttcgattcac tctatgaata gttcttacta caattttttt gtctaaagag   6600
taatactaga gataaacata aaaaatgtag aggtcgagtt tagatgcaag ttcaaggagc   6660
gaaaggtgga tgggtaggtt atatagggat atagcacaga gatatatagc aaagagatac   6720
ttttgagcaa tgtttgtgga agcggtattc gcaatatttt agtagctcgt tacagtccgg   6780
tgcgtttttg gttttttgaa agtgcgtctt cagagcgctt ttggtttttca aaagcgctct   6840 gaagttccta tactttctag agaataggaa cttcggaata ggaacttcaa agcgtttccg   6900
aaaacgagcg cttccgaaaa tgcaacgcga gctgcgcaca tacagctcac tgttcacgtc   6960
gcacctatat ctgcgtgttg cctgtatata tatatacatg agaagaacgg catagtgcgt   7020
gtttatgctt aaatgcgtac ttatatgcgt ctatttatgt aggatgaaag gtagtctagt   7080
acctcctgtg atattatccc attccatgcg gggtatcgta tgcttccttc agcactaccc   7140
tttagctgtt ctatatgctg ccactcctca attggattag tctcatcctt caatgctatc   7200
atttcctttg atattggatc atattaagaa accattatta tcatgacatt aacctataaa   7260
aataggcgta tcacgaggcc ctttcgtc                                       7288
```

```
<210> SEQ ID NO 44
<211> LENGTH: 7620
<212> TYPE: DNA
<213> ORGANISM: Artificial Sequence
<220> FEATURE:
<223> OTHER INFORMATION: Recombinant plasmid pAPSE10444; beta actin stem
      loop + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
```

-continued

```
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3194)
<223> OTHER INFORMATION: bacteriophage MS2 pac sequence
<220> FEATURE:
<221> NAME/KEY: misc_feature
<222> LOCATION: (3195)..(3202)
<223> OTHER INFORMATION: restriction endonuclease AsiSI recognition
      sequence
<220> FEATURE:
<221> NAME/KEY: misc_feature
<222> LOCATION: (3204)..(3497)
<223> OTHER INFORMATION: beta actin sense gene fragment
<220> FEATURE:
<221> NAME/KEY: misc_feature
<222> LOCATION: (3497)..(3504)
<223> OTHER INFORMATION: restriction endonuclease PmeI recognition site
<220> FEATURE:
<221> NAME/KEY: misc_feature
<222> LOCATION: (3661)..(3957)
<223> OTHER INFORMATION: beta actin antisense strand gene fragment
<220> FEATURE:
<221> NAME/KEY: misc_feature
<222> LOCATION: (3992)..(4010)
<223> OTHER INFORMATION: bacteriophage MS2 pac sequence
<220> FEATURE:
<221> NAME/KEY: terminator
<222> LOCATION: (4027)..(4216)
<223> OTHER INFORMATION: yeast CYC1 terminator
<220> FEATURE:
<221> NAME/KEY: misc_feature
<222> LOCATION: (6210)..(7552)
<223> OTHER INFORMATION: yeast 2 micron ori

<400> SEQUENCE: 44
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accataaacg acattactat atatataata taggaagcat ttaatagaca gcatcgtaat       240
atatgtgtac tttgcagtta tgacgccaga tggcagtagt ggaagatatt ctttattgaa       300
aaatagcttg tcaccttacg tacaatcttg atccggagct tttctttttt tgccgattaa       360
gaattaattc ggtcgaaaaa agaaaaggag agggccaaga gggagggcat tggtgactat       420
tgagcacgtg agtatacgtg attaagcaca caaaggcagc ttggagtatg tctgttatta       480
atttcacagg tagttctggt ccattggtga agtttgcgg cttgcagagc acagaggccg       540
cagaatgtgc tctagattcc gatgctgact tgctgggtat tatatgtgtg cccaatagaa       600
agagaacaat tgacccggtt attgcaagga aaatttcaag tcttgtaaaa gcatataaaa       660
atagttcagg cactccgaaa tacttggttg gcgtgtttcg taatcaacct aaggaggatg       720
ttttggctct ggtcaatgat tacggcattg atatcgtcca actgcatgga gatgagtcgt       780
ggcaagaata ccaagagttc ctcggtttgc cagttattaa aagactcgta tttccaaaag       840
actgcaacat actactcagt gcagcttcac agaaacctca ttcgtttatt cccttgtttg       900
attcagaagc aggtgggaca ggtgaacttt tggattggaa ctcgatttct gactgggttg       960
gaaggcaaga gagccccgaa agcttacatt ttatgttagc tggtggactg acgccagaaa      1020
atgttggtga tgcgcttaga ttaaatggcg ttattggtgt tgatgtaagc ggaggtgtgg      1080
```

-continued

```
agacaaatgg tgtaaaagac tctaacaaaa tagcaaattt cgtcaaaaat gctaagaaat    1140
aggttattac tgagtagtat ttatttaagt attgtttgtg cacttgccta tgcggtgtga    1200
aataccgcac agatgcgtaa ggagaaaata ccgcatcagg aaattgtaaa cgttaatatt    1260
ttgttaaaat tcgcgttaaa ttttttgttaa atcagctcat tttttaacca ataggccgaa    1320
atcggcaaaa tcccttataa atcaaaagaa tagaccgaga tagggttgag tgttgttcca    1380
gtttggaaca agagtccact attaaagaac gtggactcca acgtcaaagg gcgaaaaacc    1440
gtctatcagg gcgatggccc actacgtgaa ccatcaccct aatcaagttt tttggggtcg    1500
aggtgccgta aagcactaaa tcggaaccct aaagggagcc cccgatttag agcttgacgg    1560
ggaaagccgg cgaacgtggc gagaaaggaa gggaagaaag cgaaaggagc gggcgctagg    1620
gcgctggcaa gtgtagcggt cacgctgcgc gtaaccacca cacccgccgc gcttaatgcg    1680
ccgctacagg gcgcgtcgcg ccattcgcca ttcaggctgc gcaactgttg ggaagggcga    1740
tcggtgcggg cctcttcgct attacgccag ctgaattgga gcgacctcat gctatacctg    1800
agaaagcaac ctgacctaca ggaaagagtt actcaagaat aagaattttc gttttaaaac    1860
ctaagagtca ctttaaaatt tgtatacact tatttttttt ataacttatt taataataaa    1920
aatcataaat cataagaaat tcgcttattt agaagtgtca acaacgtatc taccaacgat    1980
ttgacccttt tccatctttt cgtaaatttc tggcaaggta gacaagccga caaccttgat    2040
tggagacttg accaaacctc tggcgaagaa ttgttaatta agagctctta ttagtaaatg    2100
ccagagttag cagcgattgc agatgggatc ggattaccgt ctttcagcag gccctgcatt    2160
gccttaacaa tcagttcgca gtcggagttc gtcgcaaaaa tcggaatagt cagttccatg    2220
ttgaggtaag agcgccaggc cgcaactggg agttctacgc cgcctacggt ctgcgttgcg    2280
actttcggta cttcaacttt gatggtgtat ttgcgattct gcgcgctaga ctgacgaacg    2340
gagcacgtga ctttgtaggc ctgagagcgg ctgttagagc taatccattc cgcaacaccg    2400
ttggcgaagt tggacggagc tacggtaacg tcacccgtac cgccgttatc aaccagaacg    2460
aattgggtaa agttagacgc catgaattcg aattttcaaa aattcttact ttttttttgg    2520
atggacgcaa agaagtttaa taatcatatt acatggcatt accaccatat acatatccat    2580
atacatatcc atatctaatc ttacttatat gttgtggaaa tgtaaagagc cccattatct    2640
tagcctaaaa aaaccttctc tttggaactt tcagtaatac gcttaactgc tcattgctat    2700
attgaagtac ggattagaag ccgccgagcg ggtgacagcc ctccgaagga agactctcct    2760
ccgtgcgtcc tcgtcttcac cggtcgcgtt cctgaaacgc agatgtgcct cgcgccgcac    2820
tgctccgaac aataaagatt ctacaatact agctttatg gttatgaaga ggaaaaattg    2880
gcagtaacct ggccccacaa accttcaaat gaacgaatca aattaacaac cataggatga    2940
taatgcgatt agttttttag ccttatttct ggggtaatta atcagcgaag cgatgatttt    3000
tgatctatta acagatatat aaatgcaaaa actgcataac cactttaact aatactttca    3060
acattttcgg tttgtattac ttcttattca aatgtaataa aagtatcaac aaaaaattgt    3120
taatatacct ctatacttta acgtcaagga gaaaaaaccc cggatccatt taaatacatg    3180
aggattaccc atgtgcgatc gcgcacgagg tttttctgtc tagtgagcag tgtccaacct    3240
caaaagacaa catgtgtgac gacgatgtag cggctcttgt cgtagacaat ggatccggta    3300
tgtgcaaagc cggtttcgca ggagatgacg cacccgtgc cgtcttcccc tcgatcgtcg    3360
gtcgcccaag gcatcaagga gtcatggtcg gtatgggaca aaaggactca tacgtaggag    3420
atgaagccca aagcaaaaga ggtatcctca ccctgaaata ccccatcgaa cacggtatca    3480
```

-continued

```
tcaccaactg ggatgagttt aaaccctcta gctgctttac aaagtactgg ttcccttttcc      3540 agcgggatgc tttatctaaa cgcaatgaga gaggtattcc tcaggccaca tcgcttccta      3600
gttccgctgg gatccatcgt tggcggccga agccgccatt ccatagtgag ttctggcgcg      3660
cctcatccca gttggtgatg ataccgtgtt cgatggggta tttcagggtg aggatacctc      3720
ttttgctttg ggcttcatct cctacgtatg agtccttttg tcccataccg accatgactc      3780
cttgatgcct tgggcgaccg acgatcgagg ggaagacggc acggggtgcg tcatctcctg      3840
cgaaaccggc tttgcacata ccggatccat tgtctacgac aagagccgct acatcgtcgt      3900
cacacatgtt gtctttgag gttggacact gctcactaga cagaaaaacc tcgtgccgga       3960
ccgaataccc ggtctgaacg agggcggccg cacatgagga tcacccatgt ccgcgggcta      4020
gctaagatcc gctctaaccg aaaaggaagg agttagacaa cctgaagtct aggtccctat      4080
ttattttttt atagttatgt tagtattaag aacgttattt atatttcaaa ttttttcttt      4140
ttttctgtac agacgcgtgt acgcatgtaa cattatactg aaaaccttgc ttgagaaggt      4200
tttgggacgc tcgaagatcc agctgcatta atgaatcggc caacgcgcgg ggagaggcgg      4260
tttgcgtatt gggcgctctt ccgcttcctc gctcactgac tcgctgcgct cggtcgttcg      4320
gctgcggcga gcggtatcag ctcactcaaa ggcggtaata cggttatcca cagaatcagg      4380
ggataacgca ggaaagaaca tgtgagcaaa aggccagcaa aaggccagga accgtaaaaa      4440
ggccgcgttg ctggcgtttt tccataggct ccgcccccct gacgagcatc acaaaaatcg      4500
acgctcaagt cagaggtggc gaaacccgac aggactataa agataccagg cgtttccccc      4560
tggaagctcc ctcgtgcgct ctcctgttcc gaccctgccg cttaccggat acctgtccgc      4620
ctttctccct tcgggaagcg tggcgctttc tcatagctca cgctgtaggt atctcagttc      4680
ggtgtaggtc gttcgctcca agctgggctg tgtgcacgaa ccccccgttc agcccgaccg      4740
ctgcgcctta tccggtaact atcgtcttga gtccaacccg gtaagacacg acttatcgcc      4800
actggcagca gccactggta acaggattag cagagcgagg tatgtaggcg gtgctacaga      4860
gttcttgaag tggtggccta actacggcta cactagaagg acagtatttg gtatctgcgc      4920
tctgctgaag ccagttacct tcggaaaaag agttggtagc tcttgatccg gcaaacaaac      4980
caccgctggt agcggtggtt tttttgtttg caagcagcag attacgcgca gaaaaaaagg      5040
atctcaagaa gatcctttga tcttttctac ggggtctgac gctcagtgga acgaaaactc      5100
acgttaaggg attttggtca tgagattatc aaaaaggatc ttcacctaga tccttttaaa      5160
ttaaaaatga agttttaaat caatctaaag tatatatgag taaacttggt ctgacagtta      5220
ccaatgctta atcagtgagg cacctatctc agcgatctgt ctatttcgtt catccatagt      5280
tgcctgactc cccgtcgtgt agataactac gatacgggag gcttaccat ctggccccag       5340 tgctgcaatg ataccgcgag acccacgctc accggctcca gatttatcag caataaacca      5400
gccagccgga agggccgagc gcagaagtgg tcctgcaact ttatccgcct ccatccagtc      5460
tattaattgt tgccgggaag ctagagtaag tagttcgcca gttaatagtt tgcgcaacgt      5520
tgttgccatt gctacaggca tcgtggtgtc acgctcgtcg tttggtatgg cttcattcag      5580
ctccggttcc caacgatcaa ggcgagttac atgatccccc atgttgtgca aaaaagcggt      5640
tagctccttc ggtcctccga tcgttgtcag aagtaagttg gccgcagtgt tatcactcat      5700
ggttatggca gcactgcata attctcttac tgtcatgcca tccgtaagat gcttttctgt      5760
gactggtgag tactcaacca agtcattctg agaatagtgt atgcggcgac cgagttgctc      5820
```

```
ttgcccggcg tcaatacggg ataataccgc gccacatagc agaactttaa aagtgctcat    5880
cattggaaaa cgttcttcgg ggcgaaaact ctcaaggatc ttaccgctgt tgagatccag    5940
ttcgatgtaa cccactcgtg cacccaactg atcttcagca tcttttactt tcaccagcgt    6000
ttctgggtga gcaaaaacag gaaggcaaaa tgccgcaaaa aagggaataa gggcgacacg    6060
gaaatgttga atactcatac tcttcctttt tcaatattat tgaagcattt atcagggtta    6120
ttgtctcatg agcggataca tatttgaatg tatttagaaa aataaacaaa taggggttcc    6180
gcgcacattt ccccgaaaag tgccacctga acgaagcatc tgtgcttcat tttgtagaac    6240
aaaaatgcaa cgcgagagcg ctaatttttc aaacaaagaa tctgagctgc atttttacag    6300
aacagaaatg caacgcgaaa gcgctatttt accaacgaag aatctgtgct tcattttgt     6360 aaaacaaaaa tgcaacgcga gagcgctaat ttttcaaaca aagaatctga gctgcatttt    6420
tacagaacag aaatgcaacg cgagagcgct attttaccaa caaagaatct atacttcttt    6480
tttgttctac aaaaatgcat cccgagagcg ctatttttct aacaaagcat cttagattac    6540
tttttttctc ctttgtgcgc tctataatgc agtctcttga taactttttg cactgtaggt    6600
ccgttaaggt tagaagaagg ctactttggt gtctattttc tcttccataa aaaaagcctg    6660
actccacttc ccgcgtttac tgattactag cgaagctgcg ggtgcatttt ttcaagataa    6720
aggcatcccc gattatattc tataccgatg tggattgcgc atactttgtg aacagaaagt    6780
gatagcgttg atgattcttc attggtcaga aaattatgaa cggtttcttc tattttgtct    6840
ctatatacta cgtataggaa atgtttacat tttcgtattg ttttcgattc actctatgaa    6900
tagttcttac tacaattttt ttgtctaaag agtaatacta gagataaaca taaaaaatgt    6960
agaggtcgag tttagatgca agttcaagga gcgaaaggtg gatgggtagg ttatataggg    7020
atatagcaca gagatatata gcaaagagat acttttgagc aatgtttgtg gaagcggtat    7080
tcgcaatatt ttagtagctc gttacagtcc ggtgcgtttt tggttttttg aaagtgcgtc    7140
ttcagagcgc ttttggtttt caaaagcgct ctgaagttcc tatactttct agagaatagg    7200
aacttcggaa taggaacttc aaagcgtttc cgaaaacgag cgcttccgaa aatgcaacgc    7260
gagctgcgca catacagctc actgttcacg tcgcacctat atctgcgtgt tgcctgtata    7320
tatatataca tgagaagaac ggcatagtgc gtgtttatgc ttaaatgcgt acttatatgc    7380
gtctatttat gtaggatgaa aggtagtcta gtacctcctg tgatattatc ccattccatg    7440
cggggtatcg tatgcttcct tcagcactac cctttagctg ttctatatgc tgccactcct    7500
caattggatt agtctcatcc ttcaatgcta tcatttcctt tgatattgga tcatattaag    7560
aaaccattat tatcatgaca ttaacctata aaaataggcg tatcacgagg ccctttcgtc    7620
```

```
<210> SEQ ID NO 45
<211> LENGTH: 7288
<212> TYPE: DNA
<213> ORGANISM: Artificial Sequence
<220> FEATURE:
<223> OTHER INFORMATION: Recpmbinant plasmid pAPSE10445; beta actin stem
      loop - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
```

```
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: misc_feature
<222> LOCATION: (2162)..(2826)
<223> OTHER INFORMATION: yeast GAL1, 10 bidirectional prmoter
<220> FEATURE:
<221> NAME/KEY: misc_feature
<222> LOCATION: (2844)..(2862)
<223> OTHER INFORMATION: bacteriophage MS2 pac sequence
<220> FEATURE:
<221> NAME/KEY: misc_feature
<222> LOCATION: (2863)..(2870)
<223> OTHER INFORMATION: restriction endonuclease AsiSI recognition
      sequence
<220> FEATURE:
<221> NAME/KEY: misc_feature
<222> LOCATION: (2872)..(3165)
<223> OTHER INFORMATION: beta actin sense gene fragment
<220> FEATURE:
<221> NAME/KEY: misc_feature
<222> LOCATION: (3165)..(3172)
<223> OTHER INFORMATION: restriction endonuclease PmeI recognition site
<220> FEATURE:
<221> NAME/KEY: misc_feature
<222> LOCATION: (3233)..(3251)
<223> OTHER INFORMATION: bacteriophage MS2 pac sequence
<220> FEATURE:
<221> NAME/KEY: misc_feature
<222> LOCATION: (3329)..(3624)
<223> OTHER INFORMATION: beta actin antisense strand gene fragment
<220> FEATURE:
<221> NAME/KEY: misc_feature
<222> LOCATION: (3660)..(3678)
<223> OTHER INFORMATION: bacteriophage MS2 pac sequence
<220> FEATURE:
<221> NAME/KEY: terminator
<222> LOCATION: (3695)..(3884)
<223> OTHER INFORMATION: yeast CYC1 terminator
<220> FEATURE:
<221> NAME/KEY: misc_feature
<222> LOCATION: (5878)..(7220)
<223> OTHER INFORMATION: yeast 2 micron ori

<400> SEQUENCE: 45
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc       180
accataaacg acattactat atatataata taggaagcat ttaatagaca gcatcgtaat       240
atatgtgtac tttgcagtta tgacgccaga tggcagtagt ggaagatatt ctttattgaa       300
aaatagcttg tcaccttacg tacaatcttg atccggagct tttctttttt tgccgattaa       360
gaattaattc ggtcgaaaaa agaaaaggag agggccaaga gggagggcat tggtgactat       420
tgagcacgtg agtatacgtg attaagcaca caaaggcagc ttggagtatg tctgttatta       480
atttcacagg tagttctggt ccattggtga aagtttgcgg cttgcagagc acagaggccg       540
cagaatgtgc tctagattcc gatgctgact tgctgggtat tatatgtgtg cccaatagaa       600
agagaacaat tgacccggtt attgcaagga aaatttcaag tcttgtaaaa gcatataaaa       660
atagttcagg cactccgaaa tacttggttg gcgtgtttcg taatcaacct aaggaggatg       720
ttttggctct ggtcaatgat tacggcattg atatcgtcca actgcatgga gatgagtcgt       780
ggcaagaata ccaagagttc ctcggtttgc cagttattaa aagactcgta tttccaaaag       840
actgcaacat actactcagt gcagcttcac agaaacctca ttcgtttatt cccttgtttg       900
```

-continued

```
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgg tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa ttttttgttaa atcagctcat tttttaacca ataggccgaa     1320
atcggcaaaa tcccttataa atcaaaagaa tagaccgaga tagggttgag tgttgttcca     1380
gtttggaaca agagtccact attaaagaac gtggactcca acgtcaaagg gcgaaaaacc     1440
gtctatcagg gcgatggccc actacgtgaa ccatcaccct aatcaagttt tttggggtcg     1500
aggtgccgta aagcactaaa tcggaaccct aaagggagcc cccgatttag agcttgacgg     1560
ggaaagccgg cgaacgtggc gagaaaggaa gggaagaaag cgaaaggagc gggcgctagg     1620
gcgctggcaa gtgtagcggt cacgctgcgc gtaaccacca cacccgccgc gcttaatgcg     1680
ccgctacagg gcgcgtcgcg ccattcgcca ttcaggctgc gcaactgttg ggaagggcga     1740
tcggtgcggg cctcttcgct attacgccag ctgaattgga gcgacctcat gctatacctg     1800
agaaagcaac ctgacctaca ggaaagagtt actcaagaat aagaattttc gttttaaaac     1860
ctaagagtca ctttaaaatt tgtatacact tattttttttt ataacttatt taataataaa     1920
aatcataaat cataagaaat tcgcttattt agaagtgtca acaacgtatc taccaacgat     1980
ttgacccttt tccatctttt cgtaaatttc tggcaaggta gacaagccga caaccttgat     2040
tggagacttg accaaacctc tggcgaagaa ttgttaatta agagctcaga tcttatcgtc     2100
gtcatccttg taatccatcg atactagtgc ggccgccctt tagtgagggt tgaattcgaa     2160
ttttcaaaaa ttcttacttt tttttttggat ggacgcaaag aagtttaata atcatattac     2220
atggcattac caccatatac atatccatat acatatccat atctaatctt acttatatgt     2280
tgtggaaatg taaagagccc cattatctta gcctaaaaaa accttctctt tggaactttc     2340
agtaatacgc ttaactgctc attgctatat tgaagtacgg attagaagcc gccgagcggg     2400
tgacagccct ccgaaggaag actctcctcc gtgcgtcctc gtcttcaccg gtcgcgttcc     2460
tgaaacgcag atgtgcctcg cgccgcactg ctccgaacaa taaagattct acaatactag     2520
cttttatggt tatgaagagg aaaaattggc agtaacctgg ccccacaaac cttcaaatga     2580
acgaatcaaa ttaacaacca taggatgata atgcgattag ttttttagcc ttatttctgg     2640
ggtaattaat cagcgaagcg atgatttttg atctattaac agatatataa atgcaaaaac     2700
tgcataacca ctttaactaa tactttcaac attttcggtt tgtattactt cttattcaaa     2760
tgtaataaaa gtatcaacaa aaaattgtta atatacctct atactttaac gtcaaggaga     2820
aaaaaccccg gatccattta aatacatgag gattacccat gtgcgatcgc gcacgaggtt     2880
tttctgtcta gtgagcagtg tccaacctca aaagacaaca tgtgtgacga cgatgtagcg     2940
gctcttgtcg tagacaatgg atccggtatg tgcaaagccg gtttcgcagg agatgacgca     3000
ccccgtgccg tcttcccctc gatcgtcggt cgcccaaggc atcaaggagt catggtcggt     3060
atgggacaaa aggactcata cgtaggagat gaagcccaaa gcaaaagagg tatcctcacc     3120
ctgaaatacc ccatcgaaca cggtatcatc accaactggg atgagtttaa accctctagc     3180
tgctttacaa agtactggtt cccttttccag cgggatgctt tatctaaacg caacatgagg     3240
atcacccatg tcgccacatc gcttcctagt tccgctggga tccatcgttg gcggccgaag     3300
```

-continued

```
ccgccattcc atagtgagtt ctggcgcgcc tcatcccagt tggtgatgat accgtgttcg      3360
atggggtatt tcagggtgag gatacctctt ttgctttggg cttcatctcc tacgtatgag      3420
tccttttgtc ccataccgac catgactcct tgatgccttg ggcgaccgac gatcgagggg      3480
aagacggcac ggggtgcgtc atctcctgcg aaaccggctt tgcacatacc ggatccattg      3540
tctacgacaa gagccgctac atcgtcgtca cacatgttgt cttttgaggt tggacactgc      3600
tcactagaca gaaaaacctc gtgccggacc gaatacccgg tctgaacgag ggcggccgca      3660
catgaggatc acccatgtcc gcgggctagc taagatccgc tctaaccgaa aaggaaggag      3720
ttagacaacc tgaagtctag gtccctattt attttttat agttatgtta gtattaagaa      3780
cgttatttat atttcaaatt tttctttttt ttctgtacag acgcgtgtac gcatgtaaca      3840
ttatactgaa aaccttgctt gagaaggttt tgggacgctc gaagatccag ctgcattaat      3900
gaatcggcca acgcgcgggg agaggcggtt tgcgtattgg gcgctcttcc gcttcctcgc      3960
tcactgactc gctgcgctcg gtcgttcggc tgcggcgagc ggtatcagct cactcaaagg      4020
cggtaatacg gttatccaca gaatcagggg ataacgcagg aaagaacatg tgagcaaaag      4080
gccagcaaaa ggccaggaac cgtaaaaagg ccgcgttgct ggcgtttttc cataggctcc      4140
gcccccctga cgagcatcac aaaaatcgac gctcaagtca gaggtggcga acccgacag      4200 gactataaag ataccaggcg tttccccctg gaagctccct cgtgcgctct cctgttccga      4260
ccctgccgct taccggatac ctgtccgcct ttctcccttc gggaagcgtg gcgctttctc      4320
atagctcacg ctgtaggtat ctcagttcgg tgtaggtcgt tcgctccaag ctgggctgtg      4380
tgcacgaacc ccccgttcag cccgaccgct gcgccttatc cggtaactat cgtcttgagt      4440
ccaacccggt aagacacgac ttatcgccac tggcagcagc cactggtaac aggattagca      4500
gagcgaggta tgtaggcggt gctacagagt tcttgaagtg gtggcctaac tacggctaca      4560
ctagaaggac agtatttggt atctgcgctc tgctgaagcc agttaccttc ggaaaaagag      4620
ttggtagctc ttgatccggc aaacaaacca ccgctggtag cggtggtttt tttgtttgca      4680
agcagcagat tacgcgcaga aaaaaaggat ctcaagaaga tcctttgatc ttttctacgg      4740
ggtctgacgc tcagtggaac gaaaactcac gttaagggat tttggtcatg agattatcaa      4800
aaaggatctt cacctagatc cttttaaatt aaaaatgaag ttttaaatca atctaaagta      4860
tatatgagta aacttggtct gacagttacc aatgcttaat cagtgaggca cctatctcag      4920
cgatctgtct atttcgttca tccatagttg cctgactccc cgtcgtgtag ataactacga      4980
tacgggaggg cttaccatct ggccccagtg ctgcaatgat accgcgagac ccacgctcac      5040
cggctccaga tttatcagca ataaaccagc cagccggaag ggccgagcgc agaagtggtc      5100
ctgcaacttt atccgcctcc atccagtcta ttaattgttg ccgggaagct agagtaagta      5160
gttcgccagt taatagtttg cgcaacgttg ttgccattgc tacaggcatc gtggtgtcac      5220
gctcgtcgtt tggtatggct tcattcagct ccggttccca acgatcaagg cgagttacat      5280
gatcccccat gttgtgcaaa aaagcggtta gctccttcgg tcctccgatc gttgtcagaa      5340
gtaagttggc cgcagtgtta tcactcatgg ttatggcagc actgcataat tctcttactg      5400
tcatgccatc cgtaagatgc ttttctgtga ctggtgagta ctcaaccaag tcattctgag      5460
aatagtgtat gcggcgaccg agttgctctt gcccggcgtc aatacgggat aataccgcgc      5520
cacatagcag aactttaaaa gtgctcatca ttggaaaacg ttcttcgggg cgaaaactct      5580
caaggatctt accgctgttg agatccagtt cgatgtaacc cactcgtgca cccaactgat      5640
```

```
cttcagcatc ttttactttc accagcgttt ctgggtgagc aaaaacagga aggcaaaatg    5700
ccgcaaaaaa gggaataagg gcgacacgga aatgttgaat actcatactc ttccttttc     5760 aatattattg aagcatttat cagggttatt gtctcatgag cggatacata tttgaatgta    5820
tttagaaaaa taaacaaata ggggttccgc gcacatttcc ccgaaaagtg ccacctgaac    5880
gaagcatctg tgcttcattt tgtagaacaa aaatgcaacg cgagagcgct aatttttcaa    5940
acaaagaatc tgagctgcat ttttacagaa cagaaatgca acgcgaaagc gctattttac    6000
caacgaagaa tctgtgcttc atttttgtaa aacaaaatg caacgcgaga gcgctaattt    6060
ttcaaacaaa gaatctgagc tgcattttta cagaacagaa atgcaacgcg agagcgctat    6120
tttaccaaca aagaatctat acttcttttt tgttctacaa aaatgcatcc cgagagcgct    6180
atttttctaa caaagcatct tagattactt tttttctcct ttgtgcgctc tataatgcag    6240
tctcttgata acttttttgca ctgtaggtcc gttaaggtta gaagaaggct actttggtgt    6300
ctattttctc ttccataaaa aaagcctgac tccacttccc gcgtttactg attactagcg    6360
aagctgcggg tgcatttttt caagataaag gcatccccga ttatattcta taccgatgtg    6420
gattgcgcat actttgtgaa cagaaagtga tagcgttgat gattcttcat tggtcagaaa    6480
attatgaacg gtttcttcta ttttgtctct atatactacg tataggaaat gtttacattt    6540
tcgtattgtt ttcgattcac tctatgaata gttcttacta caattttttt gtctaaagag    6600
taatactaga gataaacata aaaaatgtag aggtcgagtt tagatgcaag ttcaaggagc    6660
gaaaggtgga tgggtaggtt atatagggat atagcacaga gatatatagc aaagagatac    6720
ttttgagcaa tgtttgtgga agcggtattc gcaatatttt agtagctcgt tacagtccgg    6780
tgcgtttttg gttttttgaa agtgcgtctt cagagcgctt ttggttttca aaagcgctct    6840
gaagttccta tactttctag agaataggaa cttcggaata ggaacttcaa agcgtttccg    6900
aaaacgagcg cttccgaaaa tgcaacgcga gctgcgcaca tacagctcac tgttcacgtc    6960
gcacctatat ctgcgtgttg cctgtatata tatatacatg agaagaacgg catagtgcgt    7020
gtttatgctt aaatgcgtac ttatatgcgt ctatttatgt aggatgaaag gtagtctagt    7080
acctcctgtg atattatccc attccatgcg gggtatcgta tgcttccttc agcactaccc    7140
tttagctgtt ctatatgctg ccactcctca attggattag tctcatcctt caatgctatc    7200
atttcctttg atattggatc atattaagaa accattatta tcatgacatt aacctataaa    7260
aataggcgta tcacgaggcc ctttcgtc                                       7288
```

```
<210> SEQ ID NO 46
<211> LENGTH: 7620
<212> TYPE: DNA
<213> ORGANISM: Artificial Sequence
<220> FEATURE:
<223> OTHER INFORMATION: Recombinant plasmid pAPSE10446; beta actin stem
      loop + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
```

```
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3194)
<223> OTHER INFORMATION: bacteriophage MS2 pac sequence
<220> FEATURE:
<221> NAME/KEY: misc_feature
<222> LOCATION: (3195)..(3202)
<223> OTHER INFORMATION: restriction endonuclease AsiSI recognition
      sequence
<220> FEATURE:
<221> NAME/KEY: misc_feature
<222> LOCATION: (3204)..(3497)
<223> OTHER INFORMATION: beta actin sense gene fragment
<220> FEATURE:
<221> NAME/KEY: misc_feature
<222> LOCATION: (3497)..(3504)
<223> OTHER INFORMATION: restriction endonuclease PmeI recognition site
<220> FEATURE:
<221> NAME/KEY: misc_feature
<222> LOCATION: (3565)..(3583)
<223> OTHER INFORMATION: bacteriophage MS2 pac sequence
<220> FEATURE:
<221> NAME/KEY: misc_feature
<222> LOCATION: (3662)..(3956)
<223> OTHER INFORMATION: beta actin antisense strand gene fragment
<220> FEATURE:
<221> NAME/KEY: misc_feature
<222> LOCATION: (3992)..(4010)
<223> OTHER INFORMATION: bacteriophage MS2 pac sequence
<220> FEATURE:
<221> NAME/KEY: terminator
<222> LOCATION: (4027)..(4216)
<223> OTHER INFORMATION: yeast CYC1 terminator
<220> FEATURE:
<221> NAME/KEY: misc_feature
<222> LOCATION: (6210)..(7552)
<223> OTHER INFORMATION: yeast 2 micron ori

<400> SEQUENCE: 46
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttcttttt tgccgattaa     360 gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga aagtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
ggcaagaata ccaagagttc ctcggtttgc cagttattaa aagactcgta tttccaaaag     840
actgcaacat actactcagt gcagcttcac agaaacctca ttcgtttatt cccttgtttg     900
```

-continued

```
attcagaagc aggtgggaca ggtgaacttt tggattggaa ctcgatttct gactgggttg     960
gaaggcaaga gagccccgaa agcttacatt ttatgttagc tggtggactg acgccagaaa    1020
atgttggtga tgcgcttaga ttaaatggcg ttattggtgt tgatgtaagc ggaggtgtgg    1080
agacaaatgg tgtaaaagac tctaacaaaa tagcaaattt cgtcaaaaat gctaagaaat    1140
aggttattac tgagtagtat ttatttaagt attgtttgtg cacttgccta tgcggtgtga    1200
aataccgcac agatgcgtaa ggagaaaata ccgcatcagg aaattgtaaa cgttaatatt    1260
ttgttaaaat tcgcgttaaa tttttgttaa atcagctcat tttttaacca ataggccgaa    1320
atcggcaaaa tcccttataa atcaaaagaa tagaccgaga tagggttgag tgttgttcca    1380
gtttggaaca agagtccact attaaagaac gtggactcca acgtcaaagg gcgaaaaacc    1440
gtctatcagg gcgatggccc actacgtgaa ccatcaccct aatcaagttt tttggggtcg    1500
aggtgccgta aagcactaaa tcggaaccct aaagggagcc cccgatttag agcttgacgg    1560
ggaaagccgg cgaacgtggc gagaaaggaa gggaagaaag cgaaaggagc gggcgctagg    1620
gcgctggcaa gtgtagcggt cacgctgcgc gtaaccacca cacccgccgc gcttaatgcg    1680
ccgctacagg gcgcgtcgcg ccattcgcca ttcaggctgc gcaactgttg ggaagggcga    1740
tcggtgcggg cctcttcgct attacgccag ctgaattgga gcgacctcat gctatacctg    1800
agaaagcaac ctgacctaca ggaaagagtt actcaagaat aagaattttc gttttaaaac    1860
ctaagagtca ctttaaaatt tgtatacact tatttttttt ataacttatt taataataaa    1920
aatcataaat cataagaaat tcgcttattt agaagtgtca acaacgtatc taccaacgat    1980
ttgacccttt tccatctttt cgtaaatttc tggcaaggta gacaagccga caaccttgat    2040
tggagacttg accaaacctc tggcgaagaa ttgttaatta agagctctta ttagtaaatg    2100
ccagagttag cagcgattgc agatgggatc ggattaccgt ctttcagcag gccctgcatt    2160
gccttaacaa tcagttcgca gtcggagttc gtcgcaaaaa tcggaatagt cagttccatg    2220
ttgaggtaag agcgccaggc cgcaactggg agttctacgc cgcctacggt ctgcgttgcg    2280
actttcggta cttcaacttt gatggtgtat ttgcgattct gcgcgctaga ctgacgaacg    2340
gagcacgtga ctttgtaggc ctgagagcgg ctgttagagc taatccattc cgcaacaccg    2400
ttggcgaagt tggacggagc tacggtaacg tcacccgtac cgccgttatc aaccagaacg    2460
aattgggtaa agttagacgc catgaattcg aattttcaaa aattcttact tttttttttgg    2520 atggacgcaa agaagtttaa taatcatatt acatggcatt accaccatat acatatccat    2580
atacatatcc atatctaatc ttacttatat gttgtggaaa tgtaaagagc cccattatct    2640
tagcctaaaa aaaccttctc tttggaactt tcagtaatac gcttaactgc tcattgctat    2700
attgaagtac ggattagaag ccgccgagcg ggtgacagcc ctccgaagga agactctcct    2760
ccgtgcgtcc tcgtcttcac cggtcgcgtt cctgaaacgc agatgtgcct cgcgccgcac    2820
tgctccgaac aataaagatt ctacaatact agctttatg gttatgaaga ggaaaaattg     2880
gcagtaacct ggccccacaa accttcaaat gaacgaatca aattaacaac cataggatga    2940
taatgcgatt agttttttag ccttatttct ggggtaatta atcagcgaag cgatgatttt    3000
tgatctatta acagatatat aaatgcaaaa actgcataac cactttaact aatactttca    3060
acattttcgg tttgtattac ttcttattca aatgtaataa aagtatcaac aaaaaattgt    3120
taatatacct ctatacttta acgtcaagga gaaaaaaccc cggatccatt taaatacatg    3180
aggattaccc atgtgcgatc gcgcacgagg tttttctgtc tagtgagcag tgtccaacct    3240
caaaagacaa catgtgtgac gacgatgtag cggctcttgt cgtagacaat ggatccggta    3300
```

-continued

```
tgtgcaaagc cggtttcgca ggagatgacg cacccgtgc cgtcttcccc tcgatcgtcg    3360
gtcgcccaag gcatcaagga gtcatggtcg gtatgggaca aaaggactca tacgtaggag    3420
atgaagccca aagcaaaaga ggtatcctca ccctgaaata ccccatcgaa cacggtatca    3480
tcaccaactg ggatgagttt aaaccctcta gctgctttac aaagtactgg ttcccttttcc   3540 agcgggatgc tttatctaaa cgcaacatga ggatcaccca tgtcgccaca tcgcttccta    3600
gttccgctgg gatccatcgt tggcggccga agccgccatt ccatagtgag ttctggcgcg    3660
cctcatccca gttggtgatg ataccgtgtt cgatggggta tttcagggtg aggatacctc    3720
ttttgctttg ggcttcatct cctacgtatg agtccttttg tcccataccg accatgactc     3780
cttgatgcct tgggcgaccg acgatcgagg ggaagacggc acggggtgcg tcatctcctg    3840
cgaaaccggc tttgcacata ccggatccat tgtctacgac aagagccgct acatcgtcgt    3900
cacacatgtt gtcttttgag gttggacact gctcactaga cagaaaaacc tcgtgccgga    3960
ccgaataccc ggtctgaacg agggcggccg cacatgagga tcacccatgt ccgcgggcta    4020
gctaagatcc gctctaaccg aaaaggaagg agttagacaa cctgaagtct aggtccctat    4080
ttattttttt atagttatgt tagtattaag aacgttattt atatttcaaa tttttcttttt   4140 ttttctgtac agacgcgtgt acgcatgtaa cattatactg aaaaccttgc ttgagaaggt    4200
tttgggacgc tcgaagatcc agctgcatta atgaatcggc caacgcgcgg ggagaggcgg    4260
tttgcgtatt gggcgctctt ccgcttcctc gctcactgac tcgctgcgct cggtcgttcg    4320
gctgcggcga gcggtatcag ctcactcaaa ggcggtaata cggttatcca cagaatcagg    4380
ggataacgca ggaaagaaca tgtgagcaaa aggccagcaa aaggccagga accgtaaaaa    4440
ggccgcgttg ctggcgtttt tccataggct ccgcccccct gacgagcatc acaaaaatcg    4500
acgctcaagt cagaggtggc gaaacccgac aggactataa agataccagg cgtttccccc    4560
tggaagctcc ctcgtgcgct ctcctgttcc gaccctgccg cttaccggat acctgtccgc    4620
ctttctccct tcgggaagcg tggcgctttc tcatagctca cgctgtaggt atctcagttc    4680
ggtgtaggtc gttcgctcca agctgggctg tgtgcacgaa ccccccgttc agcccgaccg    4740
ctgcgcctta tccggtaact atcgtcttga gtccaacccg gtaagacacg acttatcgcc    4800
actggcagca gccactggta acaggattag cagagcgagg tatgtaggcg gtgctacaga    4860
gttcttgaag tggtggccta actacggcta cactagaagg acagtatttg gtatctgcgc    4920
tctgctgaag ccagttacct tcggaaaaag agttggtagc tcttgatccg gcaaacaaac    4980
caccgctggt agcggtggtt tttttgtttg caagcagcag attacgcgca gaaaaaaagg    5040
atctcaagaa gatcctttga tcttttctac ggggtctgac gctcagtgga acgaaaactc    5100
acgttaaggg attttggtca tgagattatc aaaaaggatc ttcacctaga tccttttaaa    5160
ttaaaaatga agttttaaat caatctaaag tatatatgag taaacttggt ctgacagtta    5220
ccaatgctta atcagtgagg cacctatctc agcgatctgt ctatttcgtt catccatagt    5280
tgcctgactc cccgtcgtgt agataactac gatacgggag ggcttaccat ctggccccag    5340
tgctgcaatg ataccgcgag acccacgctc accggctcca gatttatcag caataaacca    5400
gccagccgga agggccgagc gcagaagtgg tcctgcaact ttatccgcct ccatccagtc    5460
tattaattgt tgccgggaag ctagagtaag tagttcgcca gttaatagtt tgcgcaacgt    5520
tgttgccatt gctacaggca tcgtggtgtc acgctcgtcg tttggtatgg cttcattcag    5580
ctccggttcc caacgatcaa ggcgagttac atgatccccc atgttgtgca aaaaagcggt    5640
```

-continued

```
tagctccttc ggtcctccga tcgttgtcag aagtaagttg gccgcagtgt tatcactcat    5700
ggttatggca gcactgcata attctcttac tgtcatgcca tccgtaagat gcttttctgt    5760
gactggtgag tactcaacca agtcattctg agaatagtgt atgcggcgac cgagttgctc    5820
ttgcccggcg tcaatacggg ataataccgc gccacatagc agaactttaa aagtgctcat    5880
cattggaaaa cgttcttcgg ggcgaaaact ctcaaggatc ttaccgctgt tgagatccag    5940
ttcgatgtaa cccactcgtg cacccaactg atcttcagca tcttttactt tcaccagcgt    6000
ttctgggtga gcaaaaacag gaaggcaaaa tgccgcaaaa aagggaataa gggcgacacg    6060
gaaatgttga atactcatac tcttcctttt tcaatattat tgaagcattt atcagggtta    6120
ttgtctcatg agcggataca tatttgaatg tatttagaaa aataaacaaa taggggttcc    6180
gcgcacattt ccccgaaaag tgccacctga acgaagcatc tgtgcttcat tttgtagaac    6240
aaaaatgcaa cgcgagagcg ctaatttttc aaacaaagaa tctgagctgc attttttacag   6300 aacagaaatg caacgcgaaa gcgctatttt accaacgaag aatctgtgct tcatttttgt    6360
aaaacaaaaa tgcaacgcga gagcgctaat ttttcaaaca aagaatctga gctgcatttt    6420
tacagaacag aaatgcaacg cgagagcgct attttaccaa caaagaatct atacttcttt    6480
tttgttctac aaaaatgcat cccgagagcg ctatttttct aacaaagcat cttagattac    6540 ttttttctc ctttgtgcgc tctataatgc agtctcttga taactttttg cactgtaggt     6600
ccgttaaggt tagaagaagg ctactttggt gtctattttc tcttccataa aaaaagcctg    6660
actccacttc ccgcgtttac tgattactag cgaagctgcg ggtgcatttt ttcaagataa    6720
aggcatcccc gattatattc tataccgatg tggattgcgc atactttgtg aacagaaagt    6780
gatagcgttg atgattcttc attggtcaga aaattatgaa cggtttcttc tattttgtct    6840
ctatatacta cgtataggaa atgtttacat tttcgtattg ttttcgattc actctatgaa    6900
tagttcttac tacaattttt ttgtctaaag agtaatacta gagataaaca taaaaaatgt    6960
agaggtcgag tttagatgca agttcaagga gcgaaaggtg gatgggtagg ttatataggg    7020
atatagcaca gagatatata gcaaagagat acttttgagc aatgtttgtg gaagcggtat    7080
tcgcaatatt ttagtagctc gttacagtcc ggtgcgtttt tggttttttg aaagtgcgtc    7140
ttcagagcgc ttttggtttt caaaagcgct ctgaagttcc tatactttct agagaatagg    7200
aacttcggaa taggaacttc aaagcgtttc cgaaaacgag cgcttccgaa aatgcaacgc    7260
gagctgcgca catacagctc actgttcacg tcgcacctat atctgcgtgt tgcctgtata    7320
tatatataca tgagaagaac ggcatagtgc gtgtttatgc ttaaatgcgt acttatatgc    7380
gtctatttat gtaggatgaa aggtagtcta gtacctcctg tgatattatc ccattccatg    7440
cggggtatcg tatgcttcct tcagcactac cctttagctg ttctatatgc tgccactcct    7500
caattggatt agtctcatcc ttcaatgcta tcatttcctt tgatattgga tcatattaag    7560
aaaccattat tatcatgaca ttaacctata aaaataggcg tatcacgagg ccctttcgtc    7620
```